US009133474B2

(12) United States Patent
DeFramond et al.

(10) Patent No.: US 9,133,474 B2
(45) **Date of Patent: *Sep. 15, 2015**

(54) CORN EVENT 5307

(75) Inventors: Annick Jeanne DeFramond, Research Triangle Park, NC (US); Moez Rajabali Meghji, St. Louis, MO (US); Stephen L. New, Cary, NC (US); Anna Underwood Prairie, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 994 days.

This patent is subject to a terminal disclaimer.

(21) Appl. No.: 13/140,429

(22) PCT Filed: Dec. 14, 2009

(86) PCT No.: PCT/US2009/067873
§ 371 (c)(1),
(2), (4) Date: Aug. 26, 2011

(87) PCT Pub. No.: WO2010/077816
PCT Pub. Date: Jul. 8, 2010

(65) Prior Publication Data

US 2012/0042407 A1 Feb. 16, 2012

Related U.S. Application Data

(60) Provisional application No. 61/122,885, filed on Dec. 16, 2008.

(51) Int. Cl.
*A01H 5/10* (2006.01)
*C12N 15/82* (2006.01)
*C07K 14/415* (2006.01)

(52) U.S. Cl.
CPC .......... *C12N 15/8286* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 5,736,131 | A | 4/1998 | Bosch et al. | |
| 8,466,346 | B2 * | 6/2013 | DeFramond et al. | 800/302 |
| 2006/0141495 | A1 | 6/2006 | Wu et al. | |
| 2010/0017914 | A1 | 1/2010 | Hart et al. | |

FOREIGN PATENT DOCUMENTS

| | | | |
|---|---|---|---|
| EP | 0942985 | B1 | 9/2004 |
| WO | WO9822595 | | 5/1998 |
| WO | 2007/142840 | A2 | 12/2007 |
| WO | WO2007142840 | A2 | 12/2007 |
| WO | WO2008121633 | A1 | 9/2008 |
| WO | WO2011041256 | A2 | 4/2011 |

OTHER PUBLICATIONS

GenBank. Accession AC125584. 2002.*

Song, Rentao and Messing, Joachim, Gene expression of a gene family in maize based on noncollinear haplotypes, Proceedings of the National Academy of Sciences of the United States of America (PNAS), Jul. 22, 2003, vol. 100, No. 15, pp. 9055-9060, ISSN: 0027-8424.

Genbank AC125584.2. Rattus norvegicus cloe CH230-1F2. 9Oc2002. [Retrieved from the Internet Apr. 6, 2010:<URL://www.ncbi.nlm.nih.gov/nuccore/2326310>] in entirety.

Grimanelli et al., "Timing of the Maternal-to-Zygotic Transition during Early Seed Development in Maize," The Plant Cell, vol. 17, 1061-1072, Apr. 2005, Supplementary Table 1.

Corresponding to GenBank/EMBL Accession No. T14727 [Retrieved from the internet Oct. 18, 2013:<URL:http://ftp.gramene.org/archives/release26/data/maps/ibm2n04.tab] in entirety, 59 pp.

Genbank AC202540.4. Zea mays chromosome 3 clone ZMMBBb-133C10; ZMMBBb0133c10, * Sequencing in Progress *, 4 unordered pieces. Jun. 27, 2008. [Retrieved from the internet Oct. 5, 2011:<URL://www.ncbi.nlm.nih.gov/nuccore/160688634>] in entirety.

Genbank AC208695.3. *Zea mays chromosome* 4 clone ZMMBBb-318B2; ZMMBBb0318B02, * Sequencing in Progress *, 4 unordered pieces. Jun. 27, 2008 [Retrieved from the internet Oct. 5, 2011:<URL://www.ncbi.nlm.nih.gov/nuccore/189908068>] in entirety.

* cited by examiner

*Primary Examiner* — David H Kruse
(74) *Attorney, Agent, or Firm* — Yoshimi D. Barron

(57) ABSTRACT

A novel transgenic corn event designated 5307, is disclosed. The invention relates to DNA sequences of the recombinant constructs inserted into the corn genome and of genomic sequences flanking the insertion site that resulted in the 5307 event. The invention further relates to assays for detecting the presence of the DNA sequences of 5307, to corn plants and corn seeds comprising the genotype of and to methods for producing a corn plant by crossing a corn plant comprising the 5307 genotype with itself or another corn variety.

5 Claims, 2 Drawing Sheets

Plasmid map of pSYN12274.

Insert map of Event 5307.

CORN EVENT 5307

STATEMENT REGARDING ELECTRONIC SUBMISSION OF A SEQUENCE LISTING

A Sequence Listing in ASCII test format, submitted under 37 C.F.R. 1.821, entitled "71922USPCT_WOPCT_Sequence_Listing_ST25.txt", 446 kilobytes in size, generated on Mar. 14, 2012 and filed via EFS-Web is provided in lieu of a paper copy. This sequence listing is hereby incorporated by reference into the specification for its disclosure.

FIELD OF THE INVENTION

The invention relates generally to the field of plant molecular biology, plant transformation, and plant breeding. More specifically, the invention relates to insect resistant transgenic corn plants comprising a novel transgenic genotype and to methods of detecting the presence of the corn plant DNA in a sample and compositions thereof.

BACKGROUND

Plant pests are a major factor in the loss of the world's important agricultural crops. About $8 billion are lost every year in the U.S. alone due to infestations of non-mammalian pests including insects. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

The expression of foreign genes in plants can to be influenced by their chromosomal position, perhaps due to chromatin structure or the proximity of transcriptional regulation elements close to the integration site (See for example, Weising et al., 1988, "Foreign Genes in Plants," Ann. Rev. Genet. 22:421-477). Therefore, it is common to produce hundreds of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, for example. It is possible to detect the presence of a transgene by any well-known nucleic acid detection method including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods may not be useful for discriminating between different events, particularly those produced using the same DNA construct unless the sequence of chromosomal DNA adjacent to the inserted heterologous DNA ("flanking DNA") is known.

The invention includes an insect resistant transgenic corn event that has incorporated into its genome a FR8a gene, disclosed in International Publication No. WO 08/121,633, published Oct. 9, 2008, which is herein incorporated by reference, encoding a FR8a insecticidal toxin, useful in controlling *Diabrotica* spp. insect pests. The transgenic corn event also has incorporated in its genome a PMI gene, encoding a phosphomannose isomerase enzyme (PMI), disclosed in U.S. Pat. No. 5,767,378, which is herein incorporated by reference, useful as a selectable marker, which allows the plant to utilize mannose as a carbon source. The invention further includes novel isolated nucleic acid sequences which are unique to the transgenic corn event, useful for identifying the transgenic corn event and for detecting nucleic acids from the transgenic corn event in a biological sample, as well as kits comprising the reagents necessary for use in detecting these nucleic acids in a biological sample.

SUMMARY

The invention is drawn to a transgenic corn event, designated 5307, comprising a novel transgenic genotype that comprises a FR8a gene and a PMI gene which confers insect resistance and the ability to utilize mannose as a carbon source, respectively, to the 5307 corn event and progeny thereof. The invention also provides transgenic corn plants comprising the genotype of the invention, seed from transgenic corn plants comprising the genotype of the invention, and to methods for producing a transgenic corn plant comprising the genotype of the invention by crossing a corn inbred comprising the genotype of the invention with itself or another corn line of a different genotype. The transgenic corn plants of the invention may have essentially all of the morphological and physiological characteristics of the corresponding isogenic non-transgenic corn plant in addition to those conferred upon the corn plant by the novel genotype of the invention. The invention also provides compositions and methods for detecting the presence of nucleic acids from event 5307 based on the DNA sequence of the recombinant expression cassettes inserted into the corn genome that resulted in the 5307 event and of genomic sequences flanking the insertion site. The 5307 event can be further characterized by analyzing expression levels of FR8a and PMI proteins as well as by testing efficacy against corn rootworm.

According to one aspect, the invention provides a preferably isolated nucleic acid molecule comprising at least 10 contiguous nucleotides of a heterologous DNA sequence inserted into the corn plant genome of corn event 5307 and at least 10 contiguous nucleotides of a corn plant genome DNA flanking the point of insertion of a heterologous DNA sequence inserted into the corn plant genome of corn event 5307. The preferably isolated nucleic acid molecule according to this aspect may comprise at least 20 or at least 50 contiguous nucleotides of a heterologous DNA sequence inserted into the corn plant genome of corn event 5307 and at least 20 or at least 50 contiguous nucleotides of a corn plant genome DNA flanking the point of insertion of a heterologous DNA sequence inserted into the corn plant genome of corn event 5307.

According to another aspect, the invention provides a preferably isolated nucleic acid molecule comprising at least one junction sequence of event 5307 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the 5307 event.

According to another aspect, the invention provides a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and complements thereof.

According to another aspect, the invention provides a preferably isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting event 5307 are provided. Such flanking sequence primers comprise a preferably isolated nucleic acid sequence comprising at least 10-15 contiguous nucleotides from nucleotides 1-1348 as set forth in SEQ ID NO: 5 (arbitrarily designated herein as the 5' flanking sequence), or the complements thereof, also disclosed as SEQ ID NO: 111. In one embodiment of this aspect the flanking sequence primers are selected from the group consisting of SEQ ID NO: 9 through SEQ ID NO: 14, and complements thereof.

In another aspect of the invention, the flanking sequences primers comprise a preferably isolated nucleic acid sequence comprising at least 10-15 contiguous nucleotides from nucleotides 1-1093 as set forth in SEQ ID NO: 6 (arbitrarily designated herein as the 3' flanking sequence), or the complements thereof. In one embodiment of this aspect the flanking sequence primers are selected from the group consisting of SEQ ID NO: 69 through SEQ ID NO: 72, and complements thereof.

According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 5, or SEQ ID NO: 6) and a second primer comprising a nucleotide sequence of at least 10-15 contiguous nucleotides of heterologous DNA inserted into the event 5307 genome. The second primer preferably comprises a nucleotide sequence which is or is complementary to the insert sequence adjacent to the plant genomic flanking DNA sequence as set forth in SEQ ID NO: 7. In one embodiment of this aspect the insert sequence primers are selected from the group consisting of SEQ ID NO: 15 through SEQ ID NO: 68, and complements thereof.

According to another aspect of the invention, methods of detecting the presence of DNA corresponding to event 5307 in a biological sample are provided. Such methods comprise: (a) contacting the sample comprising DNA with a pair of primers that, when used in a nucleic acid amplification reaction with genomic DNA from corn event 5307; produces an amplicon that is diagnostic for corn event 5307; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, and complements thereof.

According to another aspect, the invention provides methods of detecting the presence of a DNA corresponding to the 5307 event in a biological sample. Such methods comprise: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. The detected hybridized DNA sequence includes at least one polynucleotide sequence comprising SEQ ID NO: 1, SEQ ID NO: 2, SEQ ID NO: 3, SEQ ID NO: 4, SEQ ID NO: 5, SEQ ID NO: 6, and complements thereof.

According to another aspect of the invention, a kit is provided for the detection of event 5307 nucleic acids in a biological sample. The kit includes at least one DNA sequence comprising a sufficient length of polynucleotides which is or is complementary to SEQ ID NO: 1, SEQ ID NO: 2, SEQ ID NO: 3, SEQ ID NO: 4, SEQ ID NO: 5 or SEQ ID NO: 6, wherein the DNA sequences are useful as primers or probes that hybridize to isolated DNA from event 5307, and which, upon amplification of or hybridization to a nucleic acid sequence in a sample followed by detection of the amplicon or hybridization to the target sequence, are diagnostic for the presence of nucleic acid sequences from event 5307 in the sample. The kit further includes other materials necessary to enable nucleic acid hybridization or amplification methods.

In another aspect, the invention provides a method of detecting corn event 5307 protein in a biological sample comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

In another aspect, the invention provides a biological sample derived from a event 5307 corn plant, tissue, or seed, wherein the sample comprises a nucleic acid comprising a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the invention provides an extract derived from a event 5307 corn plant, tissue, or seed comprising a nucleotide sequence which is or is complementary to a nucleotide sequence selected from the group consisting of SEQ ID NO: 1 and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided. In one embodiment of the invention, a deposit of event 5307 corn seed was made to the American Type Culture Collection (ATCC) in accordance with the Budapest Treaty on 15 Oct. 2008. An example of said seed being deposited as ATCC Accession No: PTA-9561.

According to another aspect, the invention provides a method for producing a corn plant resistant to at least corn rootworm infestation comprising: (a) sexually crossing a first parent corn plant with a second parent corn plant, wherein first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO: 3 and SEQ ID NO: 4.

According to yet another aspect, the invention provides a method for producing corn seed comprising crossing a first parent corn plant with a second parent corn plant and harvesting the resultant first generation corn seed, wherein the first or second parent corn plant is an inbred corn plant of the invention.

According to another aspect, the invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

According to another aspect of the invention, the invention provides a method of selecting corn plants and seeds comprising the nucleic acid molecules of event 5307 on chromosome 5. In one embodiment of the invention, polymorphic markers are used to select or track the sequences specific to the 5307 corn event. The invention provides a method of selecting sequences specific to the 5307 corn event comprising the steps of: (a) detecting a polymorphic marker sequence; (b) designing an assay for the purposes of detecting the marker; (c) running the assay on corn nucleic acid sequences from many corn lines, and (d) selecting corn lines based upon the sequences with nucleotides specific to corn event 5307.

According to another aspect of the invention, the invention provides a site on chromosome 5 for targeted integration of a heterologous nucleic acid. The invention provides a method of selecting sequences specific to the 5307 corn event for targeted integration comprising the steps of: (a) designing homologous sequences based on the insertion site or vector sequence; (b) using these homologous sequences at a target locus; (c) using zinc finger nucleases to create a break in the target locus, and (d) inserting a heterologous donor molecule within nucleotides specific to corn event 5307 or the vector sequence of pSYN12274. An example of this technique is demonstrated in Shukla et al. (Nature vol. 459, 21 May 2009).

The foregoing and other aspects of the invention will become more apparent from the following detailed description.

DESCRIPTION OF THE SEQUENCES IN THE SEQUENCE LISTING

SEQ ID NO: 1 is the 5' genome-insert junction.

SEQ ID NO: 2 is the 3' insert-genome junction.

SEQ ID NO: 3 is the 5' genome+insert sequence.

SEQ ID NO: 4 is the 3' insert+genome sequence.

SEQ ID NO: 5 is the 5' genome+insert sequence.

SEQ ID NO: 6 is the 3' corn genome flanking sequence.

SEQ ID NO: 7 is the event 5307 full length insert.

SEQ ID Nos: 8-14 are 5' flanking sequence primers useful in the invention.

SEQ ID Nos: 15-68 are 5307 transgene insert primers useful in the invention.

SEQ ID Nos: 69-72 are 3' flanking sequence primers useful in the invention.

SEQ ID Nos: 73-75 are FR8a TAQMAN primers and probe.

SEQ ID Nos: 76-78 are PMI TAQMAN primers and probe.

SEQ ID Nos: 79-81 are ZmAdh TAQMAN primers and probe.

SEQ ID Nos: 82-90 are 5307 event specific primers and probes useful in the invention.

SEQ ID Nos: 91-102 are corn genomic primers and probes useful in the invention.

SEQ ID NO: 103 is the AC202955 Chromosome 5 Sequence, where N is any base "A", "T", "G" or "C".

SEQ ID NO: 104 is the umc1475 marker region.

SEQ ID Nos: 105-106 are umc1475 primers.

SEQ ID NO: 107 is the uaz190 marker region.

SEQ ID NOs: 108-109 are uaz190 primers

SEQ ID NO: 110 is the reverse complement of SEQ ID NO: 103, AC202955 Chromosome 5 Sequence, where N is any base "A", "T", "G" or "C".

SEQ ID NO: 111 is the 5' corn genome flanking sequence.

DEFINITIONS

Figure 1:
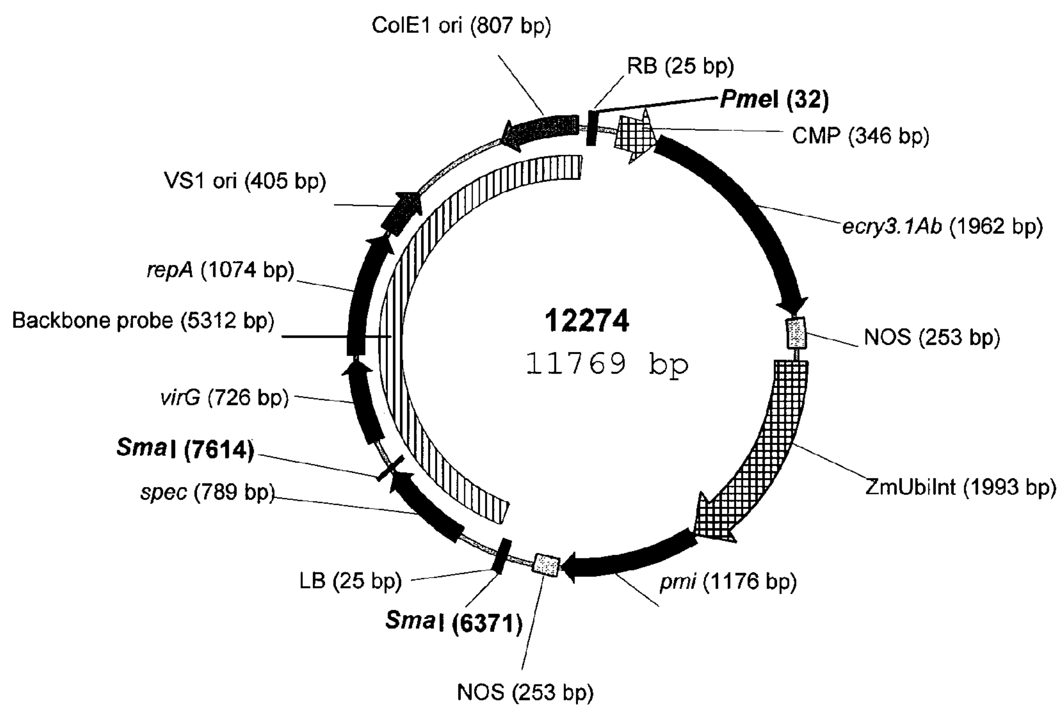
FIG. 1 illustrates a plant expression vector designated pSYN12274. The plasmid map identifies the SmaI and PmeI restriction sites used for Southern analysis.
Figure 2:
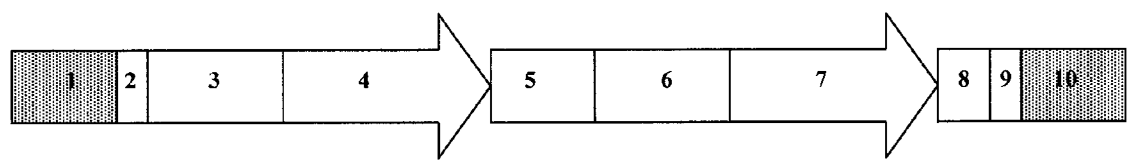
FIG. 2 is a graphical map illustrating the organization of the elements comprising the heterologous nucleic acid sequences inserted into the genome of corn to create event 5307 and sets forth the relative positions at which the inserted nucleic acid sequences are linked to corn genomic DNA sequences which flank the ends of the inserted heterologous DNA sequences. 1=5' flanking plant genome (SEQ ID NO: 5); 2=right border region; 3=CMP promoter; 4=FR8a gene; 5=NOS terminator; 6=ZmUbINT promoter; 7=PMI gene; 8=NOS terminator; 9=left border region (sections 2 through 9 are contained within SEQ ID NO: 7); and 10=3' flanking plant genome (SEQ ID NO: 6).

The following definitions and methods are provided to better define the invention and to guide those of ordinary skill in the art in the practice of the invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, 5$^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

A "biological sample" is a plant, plant material or products comprising plant material. The term "plant" is intended to encompass corn (*Zea mays*) plant tissues, at any stage of maturity, as well as cells, tissues, organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the invention, such biological sample are tested for the presence of nucleic acids specific to corn event 5307, implying the presence of nucleic acids in the samples. Thus, the methods referred to herein for identifying corn event 5307 in biological samples, relate to the identification in biological samples of nucleic acids which from an event 5307 corn plant and are diagnostic for event 5307.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

"Detection kit" as used herein refers to a kit used to detect the presence or absence of DNA from event 5307 corn plants in a sample comprising nucleic acid probes and primers of the invention, which hybridize specifically under high stringency conditions to a target DNA sequence, and other materials necessary to enable nucleic acid hybridization or amplification methods.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event 5307", "5307 event" or "5307" as used herein, means the original 5307 transformant and/or progeny of the 5307 transformant, including any plant derived therefrom.

"Expression cassette" as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent corn plants not all of which is necessarily expressed in the descendant corn plants. The 5307 genotype refers to the heterologous genetic material transformed into the genome of a plant as well as the genetic material flanking the inserted sequence.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

The term "isolated" when used in relation to a nucleic acid refers to a nucleic acid sequence that is identified and separated from at least one contaminant nucleic acid with which it is ordinarily associated in its natural source. An isolated nucleic acid is present in a form or setting that is different from that in which it is found in nature. In contrast, a nonisolated nucleic acids such as DNA and RNA found in the state they exist in nature. An isolated nucleic acid may be in a transgenic plant and still be considered "isolated".

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

"Primers" as used herein are isolated nucleic acids that are annealed to a complimentary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other conventional nucleic-acid amplification methods.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the invention, to a strand of genomic DNA from corn event, M5307. The genomic DNA of event 5307 can be from a corn plant or from a sample that includes DNA from the event. Probes according to the invention include not only deoxyribonucleic or ribonucleic acids but also polyamides and other probe materials that bind specifically to a target DNA sequence and can be used to detect the presence of that target DNA sequence.

Primers and probes are generally between 10 and 15 nucleotides or more in length, Primers and probes can also be at least 20 nucleotides or more in length, or at least 25 nucleotides or more, or at least 30 nucleotides or more in length. Such primers and probes hybridize specifically to a target sequence under high stringency hybridization conditions. Primers and probes according to the invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* ($5^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C. The sequences of the invention may be detected using all the above conditions. For the purposes of defining the invention, the high stringency conditions are used.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule. As used herein, "transgenic" refers to a plant, plant cell, or multitude of structured or unstructured plant cells having integrated, via well known techniques of genetic manipulation and gene insertion, a nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. §1.822 is used herein.

DETAILED DESCRIPTION

This invention relates to a genetically improved line of corn that produces the insect control protein, FR8a, and a phosphomannose isomerase enzyme (PMI) that allows the plant to utilize mannose as a carbon source. The invention is particularly drawn to a transgenic corn event designated event 5307 comprising a novel genotype, as well as to compositions and methods for detecting nucleic acids from this event in a biological sample. The invention is further drawn to corn plants comprising the event 5307 genotype, to transgenic seed from the corn plants, and to methods for producing a corn plant comprising the event 5307 genotype by crossing a corn inbred comprising the event 5307 genotype with itself or another corn line. Corn plants comprising the event 5307 genotype of the invention are useful in controlling coleopteran insect pests including *Diabrotica virgifera virgifera*, the western corn rootworm, *D. virgifera zeae*, the Mexican corn rootworm, and *D. longicornis barberi*, the northern corn rootworm. Corn plants comprising the event 5307 genotype of the invention are also able to utilize mannose as a carbon source.

In one embodiment, the invention encompasses a transgenic corn seed of an event 5307 corn plant. An example of said seed being deposited as ATCC Accession No: PTA-9561. The transgenic seed of event 5307 comprises SEQ ID NO: 1, SEQ ID NO: 2, SEQ ID NO: 3, SEQ ID NO: 4, SEQ ID NO: 5, or SEQ ID NO: 6, and complements thereof. These sequences define a point of insertion of a heterologous DNA sequence inserted into the corn plant genome of corn event 5307. In another embodiment, the invention encompasses a preferably isolated nucleic acid molecule comprising SEQ ID NO: 1, SEQ ID NO: 2, SEQ ID NO: 3 or SEQ ID NO: 4. In another embodiment, the invention encompasses a preferably isolated nucleic acid molecule, wherein the nucleic acid molecule is comprised in a corn seed deposited as ATCC Accession No. PTA-9561

In one embodiment, the invention encompasses a nucleic acid molecule, preferably isolated, comprising at least 10 or more (for example 15, 20, 25, or 50) contiguous nucleotides of a heterologous DNA sequence inserted into the corn plant genome of corn event 5307 and at least 10 or more (for example 15, 20, 25, or 50) contiguous nucleotides of a corn plant genome DNA flanking the point of insertion of a heterologous DNA sequence inserted into the corn plant genome of corn event 5307. Also included are nucleotide sequences that comprise 10 or more nucleotides of contiguous insert sequence from event 5307 and at lease one nucleotide of flanking DNA from event 5307 adjacent to the insert sequence. Such nucleotide sequences are diagnostic for event 5307. Nucleic acid amplification of genomic DNA from the 5307 event produces an amplicon comprising such diagnostic nucleotide sequences.

In another embodiment, the invention encompasses a nucleic acid molecule, preferably isolated, comprising a nucleotide sequence which comprises at least one junction sequence of event 5307 selected from the group consisting of SEQ ID NO: 1, SEQ ID NO: 2, SEQ ID NO: 3, SEQ ID NO: 4, and complements thereof, wherein a junction sequence spans the junction between a heterologous expression cassette inserted into the corn genome and DNA from the corn genome flanking the insertion site and is diagnostic for the event.

In another embodiment, the invention encompasses a preferably isolated nucleic acid linking a heterologous DNA molecule to the corn plant genome in corn event 5307 comprising a sequence of from about 11 to about 20 contiguous nucleotides selected from the group consisting of SEQ ID NO: 1, SEQ ID NO: 2, and the complements thereof.

In another embodiment, the invention encompasses an nucleic acid molecule, preferably isolated, comprising a nucleotide sequence selected from the group consisting of SEQ ID NO: 1, SEQ ID NO: 2, SEQ ID NO: 3, SEQ ID NO: 4, and complements thereof.

In one embodiment of the invention, an amplicon comprising a nucleotide sequence selected from the group consisting of SEQ ID NO: 1, SEQ ID NO: 2, SEQ ID NO: 3, SEQ ID NO: 4, and the complements thereof is provided.

In another embodiment, the invention encompasses flanking sequence primers for detecting event 5307. Such flanking sequence primers comprise an isolated nucleic acid sequence comprising at least 10-15 contiguous nucleotides from nucleotides 1-1348 of SEQ ID NO: 5 (arbitrarily designated herein as the 5' flanking sequence), or the complements thereof, also disclosed as SEQ ID NO: 111. In one aspect of this embodiment the flanking sequence primers are selected from the group consisting of SEQ ID NO: 8 through SEQ ID NO: 14, and complements thereof. The flanking sequences can be extended to include chromosome 5 sequences, with specific emphasis on nucleotide comprised with SEQ ID NO: 103, useful in detecting sequences associated with the 5307 corn event. In the context of SEQ ID NO: 103, an "N" is defined as any base "A", "T", "G", or "C". SEQ ID NO: 110 is the reverse complement of this sequence. In the context of SEQ ID NO: 110, an "N" is defined as any base "A", "T", "G", or "C".

In another embodiment, the invention encompasses flanking sequence primers that comprise at least 10-15 contiguous nucleotides from nucleotides 1-1093 of SEQ ID NO: 6 (arbitrarily designated herein as the 3' flanking sequence), or the complements thereof. In one aspect of this embodiment the flanking sequence primers are selected from the group consisting of SEQ ID NO: 69 through SEQ ID NO: 72, and complements thereof.

In still another embodiment, the invention encompasses a pair of polynucleotide primers comprising a first polynucleotide primer and a second polynucleotide primer which function together in the presence of a corn event 5307 DNA template in a sample to produce an amplicon diagnostic for the corn event 5307, wherein the first primer sequence is or is complementary to a corn plant genome flanking the point of insertion of a heterologous DNA sequence inserted into the corn plant genome of corn event 5307, and the second polynucleotide primer sequence is or is complementary to the heterologous DNA sequence inserted into the corn plant genome of the corn event 5307.

In one aspect of this embodiment the first polynucleotide primer comprises at least 10 contiguous nucleotides from position 1-1348 of SEQ ID NO: 5 or complements thereof. In a further aspect of this embodiment, the first polynucleotide primer comprises the nucleotide sequence set forth in SEQ ID NO: 8 through SEQ ID NO: 14, or the complements thereof. In another aspect of this embodiment the first polynucleotide primer least 10 contiguous nucleotides from position 1-1093 of SEQ ID NO: 6 or complements thereof. In another aspect of this embodiment, the first polynucleotide primer comprises the nucleotide sequence set forth in SEQ ID NO: 69 through SEQ ID NO: 72, or the complements thereof. In yet another aspect of this embodiment, the second polynucleotide primer comprises at least 10 contiguous nucleotides of SEQ ID NO: 7, or the complements thereof. In still a further aspect of this embodiment, the second polynucleotide primer comprises the nucleotide sequence set forth in SEQ ID NO: 15 to SEQ ID NO: 68, or the complements thereof.

In another aspect of this embodiment, the first polynucleotide primer, which is set forth in SEQ ID NO: 8, and the second polynucleotide primer which is set forth in SEQ ID NO: 41, function together in the presence of a corn event 5307 DNA template in a sample to produce an amplicon diagnostic for the corn event 5307 as described in Example 4. In another aspect of this embodiment, the first polynucleotide primer, which is set forth in SEQ ID NO: 69, and the second polynucleotide primer which is set forth in SEQ ID NO: 72, function together in the presence of a corn event 5307 DNA template in a sample to produce an amplicon diagnostic for the corn event 5307 as described in Example 4.

It is well within the skill in the art to obtain additional sequence further out into the genome sequence flanking either end of the inserted heterologous DNA sequences for use as a primer sequence that can be used in such primer pairs for amplifying the sequences that are diagnostic for the 5307 event. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 3 or SEQ ID NO: 4 depending upon the nature of the product desired to be obtained through the use of the nested set of primers intended for use in amplifying a particular flanking sequence containing the junction between the genomic DNA sequence and the inserted heterologous DNA sequence. Further more, one skilled in the art would be able to design primers for a multitude of native corn genes for the purposes of designing a positive control. One such example is the corn Adh1 gene, where examples of suitable primers for producing an amplicon by nucleic acid amplification are set forth as SEQ ID NO: 79 and SEQ ID NO: 80.

In another embodiment, the invention encompasses a method of detecting the presence of DNA corresponding to the event 5307 in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. In one aspect of this embodiment the amplicon comprises a nucleotide sequence selected from the group consisting of SEQ ID NO: 1, SEQ ID NO: 2, SEQ ID NO: 3, SEQ ID NO: 4, and complements thereof.

In another embodiment, the invention encompasses a method of detecting the presence of a DNA corresponding to the 5307 event in a biological sample, wherein the method comprises: (a) contacting the sample comprising DNA with a probe that hybridizes under high stringency conditions with genomic DNA from corn event 5307 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the 5307 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the invention encompasses a kit for detecting the presence of event 5307 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for event 5307, and other materials necessary to enable nucleic acid hybridization or amplification. A variety of detection methods can be used including TAQMAN (Perkin Elmer), thermal amplification, ligase chain reaction, southern hybridization, ELISA methods, and colorimetric and fluorescent detection methods. In particular the invention provides for kits for detecting the presence of the target sequence, i.e., at least one of the junctions of the insert DNA with the genomic DNA of the corn plant in event 5307, in a sample containing genomic nucleic acid from event 5307. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in event 5307, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the invention encompasses a method for detecting event 5307 protein in a biological sample, the method comprising: (a) extracting protein from a sample of corn event 5307 tissue; (b) assaying the extracted protein using an immunological method comprising antibody specific for the insecticidal or selectable marker protein produced by the 5307 event; and (c) detecting the binding of said antibody to the insecticidal or selectable marker protein.

Another embodiment of the invention encompasses a corn plant, or parts thereof, comprising the genotype of the transgenic event 5307, wherein the genotype comprises the nucleotide sequence set forth in SEQ ID NO: 1, SEQ ID NO: 2, SEQ ID NO: 3, SEQ ID NO: 4, or the complements thereof. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP948, NP934, NP982, NP991, NP993, NP2010, NP2013, NP2015, NP2017, NP2029, NP2031, NP2034, NP2045, NP2052, NP2138, NP2151, NP2105, NP2161, NP2171, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the event 5307 genotype can be introgressed into any plant variety that can be bred with corn, including wild maize species, and thus the preferred inbred lines of this embodiment are not meant to be limiting.

In another embodiment, the invention encompasses a corn plant comprising at least a first and a second DNA sequence linked together to form a contiguous nucleotide sequence, wherein the first DNA sequence is within a junction sequence and comprises at least about 10-15 contiguous nucleotides selected from the group consisting of nucleotides SEQ ID NO: 5, SEQ ID NO: 6, and complements thereof, wherein the second DNA sequence is within the heterologous insert DNA sequence selected from the group consisting of SEQ ID NO: 15 through SEQ ID NO: 68, and complements thereof; and wherein the first and the second DNA sequences are useful as nucleotide primers or probes for detecting the presence of corn event 5307 nucleic acid sequences in a biological sample. In one aspect of this embodiment, the nucleotide primers are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2

Corn plants of the invention can be further characterized in that digesting the plant's genomic DNA with the restriction endonucleases SmaI and PmeI results in a single hybridizing band using a full length probe under high stringency conditions. Exemplified herein is a full length probe comprising a nucleotide sequence set forth in SEQ ID NO: 7.

In one embodiment, the invention provides a corn plant, wherein the event 5307 genotype confers upon the corn plant resistance to insects or the ability to utilize mannose. In one aspect of this embodiment, the genotype conferring resistance to insects upon the corn plant comprises a FR8a gene. In another aspect of this embodiment, the genotype conferring upon the corn plant the ability to utilize mannose comprises a PMI gene.

In one embodiment, the invention provides a biological sample derived from a event 5307 corn plant, tissue, or seed, wherein the sample comprises a nucleotide sequence which is or is complementary to a sequence selected from the group consisting of SEQ ID NO: 1, SEQ ID NO: 2, SEQ ID NO: 3 and SEQ ID NO: 4, and wherein the sequence is detectable in the sample using a nucleic acid amplification or nucleic acid hybridization method. Thus, the genetic sequence functions a means of detection. In one aspect of this embodiment, the sample is selected from corn flour, corn meal, corn syrup, corn oil, corn starch, and cereals manufactured in whole or in part to contain corn products.

In another embodiment, the invention provides an extract derived from a event 5307 corn plant, tissue, or seed comprising a nucleotide sequence which is or is complementary to a nucleotide sequence selected from the group consisting of SEQ ID NO: 1, SEQ ID NO: 2, SEQ ID NO: 3 and SEQ ID NO: 4. An example of such seed is deposited at the ATCC under Accession No. PTA-9561. In one aspect of this embodiment, the sequence is detected in the extract using a nucleic acid amplification or nucleic acid hybridization method. In another aspect of this embodiment, the sample is selected from corn flour, corn syrup, corn oil, cornstarch, and cereals manufactured in whole or in part to contain corn products.

In yet another embodiment, the invention provides a method for producing a corn plant resistant to at least corn rootworm infestation comprising: (a) sexually crossing a first parent corn plant with a second parent corn plant, wherein said first or second parent corn plant comprises corn event 5307 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; and (d) selecting from the second generation progeny plants, a plant that is at least resistant to corn rootworm infestation; wherein the second generation progeny plants comprise a nucleotide sequence selected from the group consisting of SEQ ID NO: 1, SEQ ID NO: 2, SEQ ID NO:3 and SEQ ID NO: 4.

In another embodiment, the invention provides a method of producing hybrid corn seeds comprising: (a) planting seeds of a first inbred corn line comprising a nucleotide sequence selected from the group consisting of SEQ ID NO: 1, SEQ ID NO: 2, SEQ ID NO: 3, and SEQ ID NO: 4, and seeds of a second inbred line having a different genotype; (b) cultivating corn plants resulting from said planting until time of flowering; (c) emasculating said flowers of plants of one of the corn inbred lines; (d) sexually crossing the two different inbred lines with each other; and (e) harvesting the hybrid seed produced thereby. In one aspect of this embodiment, the first inbred corn line provides the female parents. In another aspect of this embodiment, the first inbred corn line provides the male parents. The invention also encompasses the hybrid seed produced by the embodied method and hybrid plants grown from the seed.

In another embodiment, the invention provides a method of selecting markers associated with corn event 5307 comprising: (a) screening corn event 5307 chromosome 5 sequences, (b) comparing these with a non-transgenic NP2222 sequences, (c) comparing the sequences for the purpose of detecting sequence variations, (d) using these sequence variations as a means to develop markers associated with corn event 5307, (e) using the markers to screen lines, and (f) detecting marker confirming the presence of corn event 5307 sequences on chromosome 5.

One skilled in the art will recognize that the transgenic genotype of the invention can be introgressed by breeding into other corn lines comprising different transgenic genotypes. For example, a corn inbred comprising the transgenic genotype of the invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the invention include, the glyphosate herbicide tolerant events GA21 and NK603, the glyphosate tolerant/lepidopteran insect resistant MON802 event, the lepidopteran insect resistant event DBT418, the lepidopteran insect resistant event DAS-06275-8, the lepidopteran insect resistant event MIR162, the male sterile event MS3, the phosphinothricin tolerant event B16, the lepidopteran insect resistant event MON 80100, the phosphinothricin herbicide tolerant events T14 and T25, the lepidopteran insect resistant event 176, the coleopteran insect resistant event MIR604 and the coleopteran insect resistant event MON863, all of which are known in the art. It will be further recognized that other combinations can be made with the transgenic genotype of the invention and thus these examples should not be viewed as limiting.

One skilled in the art will also recognize that transgenic corn seed comprising the transgenic genotype of the invention can be treated with various seed-treatment chemicals, including insecticides, to augment or synergize the insecticidal activity of the FR8a protein. For example, the transgenic corn seed of the invention can be treated with the commercial insecticide Cruiser®. Such a combination may be used to increase the spectrum of activity and to increase the efficacy of the expressed protein and chemical.

Breeding

The transgenic genotype of the invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, marker assisted selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

As is readily apparent to one skilled in the art, the foregoing are only some of the various ways by which the inbred of the invention can be obtained by those looking to introgress the transgenic genotype of the invention into other corn lines. Other means are available, and the above examples are illustrative only.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual,* 3*d Ed*., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1

Transformation and Selection of the 5307 Event

The 5307 event was produced by *Agrobacterium*-mediated transformation of the inbred corn (*Zea mays*) line NP2222. Immature embryos were transformed essentially as described in Negrotto et al. (Plant Cell Reports 19: 798-803, 2000), incorporated herein by reference, using a DNA fragment from plasmid pSYN12274 (FIG. 1). pSYN12274 contains a nucleotide sequence comprising tandem expression cassettes. The first expression cassette is comprised of a CMP promoter sequence (U.S. Pat. No. 7,166,770) operably linked to a FR8a coding sequence further operably linked to a nopaline synthase 3' end transcription termination and polyadenylation sequence. The second expression cassette is comprised of a maize ubiquitin promoter (ZmUbiInt) (Christensen et al. 1992 PMB 18: 675) operably linked to a PMI coding sequence further operably linked to a nopaline synthase 3' end transcription termination and polyadenylation sequence.

Immature embryos were excised from 8-12 day old ears and rinsed with fresh medium in preparation for transformation. Embryos were mixed with the suspension of *Agrobacterium* cells harboring the transformation vector pSYN12274, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. Embryos were transferred to culture medium supplemented with ticarcillin (100 mg/ml) and silver nitrate (1.6 mg/l) and incubated in the dark for 10 days. Embryos producing embryogenic callus were transferred to cell culture medium containing mannose.

Regenerated plantlets were tested by TAQMAN® PCR analysis (see Example 2) for the presence of both the PMI and FR8a genes, as well as for the absence of the antibiotic resistance spectinomycin (spec) gene. Plants positive for both transgenes, and negative for the spec gene, were transferred to the greenhouse for further propagation. Positive events were identified and screened using insect bioassays against corn rootworm. Insecticidal events were characterized for copy number by TAQMAN analysis. Event 5307 was chosen for further analysis based on having a single copy of the transgenes, good protein expression as identified by ELISA, and better insecticidal activity against corn rootworm when compared to other events made with the same construct.

The $T_0$ 5307 event was backcrossed to inbred corn line NP2460, creating the $T_1$ population. The $T_1$ plants were self-pollinated to create the $T_2$ generation, and this process was repeated to create a $T_3$ generation. Progeny testing of the $T_3$ plants was employed to identify homozygous (converted) families. The event 5307-converted NP2460 inbred was crossed to other elite inbred lines to create hybrids used in further studies.

Example 2

Event 5307 Detection by TAQMAN PCR

TAQMAN analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 Mm Tris-HCl, pH 8.0, 1 mM EDTA).

TAQMAN PCR reactions were carried out in 96-well plates. For the endogenous corn gene control, primers and probes were designed specific to the *Zea mays* alcohol dehydrogenase (Adh) gene (Genbank accession no. AF044295). It will be recognized by the skilled person that other corn genes can be used as endogenous controls. Reactions were multiplexed to simultaneously amplify FR8a and Adh or PMI and Adh. For each sample, a master mixture was generated by combining 20 μL extracted genomic DNA with 35 μL 2× TAQMAN Universal PCR Master Mix (Applied Biosystems) supplemented with primers to a final concentration of 900 nM each, probes to a final concentration of 100 nM each, and water to a 700 μL final volume. This mixture was distributed into three replicates of 20 μL each in 96-well amplification plates and sealed with optically clear heat seal film (Marsh Bio Products). PCR was run in the ABI Prism 7700 instrument using the following amplification parameters: 2 min at 50° C. and 10 min at 95° C., followed by 35 cycles of 15 s at 95° C. and 1 min at 60° C.

Results of the TAQMAN analysis demonstrated that event 5307 had one copy of the FR8a gene and one copy of the PMI gene.

Examples of suitable primer/probe sequence combinations which were used are:

| Primer Name | Primer Sequence | SEQ ID NO: |
|---|---|---|
| FR8a-forward | 5'-TACGAGAGCTGGGTGAACTTCA-3' | SEQ ID NO: 73 |
| FR8a-reverse | 5'-CGATCAGGTCCAGCACGG-3' | SEQ ID NO: 74 |
| FR8a-probe | 5'-CCGCTACCGCCGCGAGATGA-3' (5' label = FAM, 3' label = TAMRA) | SEQ ID NO: 75 |
| PMI-forward | 5'-CCGGGTGAATCAGCGTTT-3' | SEQ ID NO: 76 |
| PMI-reverse | 5'-GCCGTGGCCTTTGACAGT-3' | SEQ ID NO: 77 |
| PMI-probe | 5'-TGCCGCCAACGAATCACCGG-3' (5' label = FAM, 3' label = TAMRA) | SEQ ID NO: 78 |
| ZmADH-267 forward | 5'-GAACGTGTGTTGGGTTTGCAT-3' | SEQ ID NO: 79 |
| ZmADH-337 reverse | 5'-TCCAGCAATCCTTGCACCTT-3' | SEQ ID NO: 80 |
| ZmADH-316 probe | 5'-TGCAGCCTAACCATGCGCAGGGTA-3' (5' label = TET, 3' label = TAMRA) | SEQ ID NO: 81 |

The PM1271, MIC5307a and MIC5307b TAQMAN assays are designed as an event specific assay, which covers the 3' junction sequence.

Examples of suitable primer/probe sequence combinations which were used are:

| Primer Name | Primer Sequence | SEQ ID NO: |
|---|---|---|
| PM1277-forward | 5'-GCCGTATCCGCAATGTGTTA-3' | SEQ ID NO: 82 |
| PM1277-reverse | 5'-GGCCCAGGGAAGAGGGTATAT-3' | SEQ ID NO: 83 |
| PM1277-probe | 5'-AAGTTGTCTAAGCGTCAAT-3' (5' label = TET, 3' label = TAMRA) | SEQ ID NO: 84 |
| MIC5307a-forward | 5'-TGTCTAAGCGTCAATTTGTTTACACC-3' | SEQ ID NO: 82 |
| MIC5307a-reverse | 5'-TTTGCCAGTGGGCCCA-3' | SEQ ID NO: 83 |
| MIC5307a-probe | 5'-ACAATATACCCTCTTCCCTGGGCCAGG-3' (5' label = TET, 3' label = TAMRA) | SEQ ID NO: 84 |

-continued

| Primer Name | Primer Sequence | SEQ ID NO: |
|---|---|---|
| MIC5307b-forward | 5'-GCCGTATCCGCAATGTGTTA-3' | SEQ ID NO: 82 |
| MIC5307b-reverse | 5'-AAGTTGTCTAAGCGTCAAT-3' | SEQ ID NO: 83 |
| MIC5307b-probe | 5'-GGCCCAGGGAAGAGGGTATAT-3' (5' label = TET, 3' label = TAMRA) | SEQ ID NO: 84 |

Example 3

Event 5307 Detection by Southern Blot

Genomic DNA used for southern analysis was isolated from pooled leaf tissue of ten plants representing the back-cross six (BC6) generation of event 5307 using essentially the method of Thomas et al. (Theor. Appl. Genet. 86:173-180, 1993), incorporated herein by reference. All plants used for DNA isolation were individually analyzed using TAQMAN PCR (as described in Example 2) to confirm the presence of a single copy of the FR8a gene and the PMI gene. For the negative segregant controls, DNA was isolated from pooled leaf tissue of five plants representing the BC4 generation of event 5307. These negative segregant plants were individually analyzed using TAQMAN PCR and the assays were negative for the presence of the FR8a gene and the PMI gene, but were, as expected, positive for the assay internal control, the endogenous maize Adh gene.

Southern analysis was carried out using conventional molecular biology techniques. Genomic DNA (7.5 μg) was doubly digested with SmaI and PmeI restriction enzymes, which have single recognition sites within the event 5307 T-DNA insert from plasmid pSYN12274 (FIG. 1). This approach allows for determination of the number of copies of the elements, corresponding to the specific probe used for each Southern, which have been incorporated into event 5307. This results in one hybridization band per copy of the element present in event 5307. This results in one hybridization band per copy of the element present in event 5307. Following agarose gel electrophoresis and alkaline transfer to a Nytran® membrane, hybridizations were carried out using element-specific full-length PCR-generated probes. The full length probe used in the Southern blots comprises the nucleotide sequences set forth in SEQ ID NO: 7. The probe was labeled with $^{32}P$ via random priming using the Rediprime™ II system (Amersham Biosciences, Cat. No. RPN1633).

The following high stringency hybridization conditions were used: 1-2 million cpm/ml are added to PerfectHyb (Sigma) supplemented with 100 μg/ml Calf Thymus DNA (Invitrogen) pre-warmed to 65° C. Pre-hybridization takes place in the same solution as above, at the same temp overnight or for at least one hour. Hybridization was carried out at 65° C. for 3 hours followed by washing 2× in 2×SSC, 0.1% SDS for 20 minutes at 65° C. and 2× in 0.1×SSC, 0.1% SDS for 20 minutes at 65° C.

Included on each Southern were three control samples: (1) DNA from a negative (non-transformed) segregant used to identify any endogenous *Zea mays* sequences that may cross-hybridize with the element-specific probe; (2) DNA from a negative segregant into which is introduced an amount of SmaI-PmeI digested pSYN12274 that is equal to one copy number based on probe length, to demonstrate the sensitivity of the experiment in detecting a single gene copy within the *Zea mays* genome; and (3) SmaI-PmeI digested pSYN12274 plasmid that is equal to one copy number based on probe length, as a positive control for hybridization as well as to demonstrate the sensitivity of the experiment.

The hybridization data provide confirmatory evidence to support the TAQMAN PCR analysis that event 5307 contains a single copy of the FR8a and PMI genes, and that 5307 event does not contain any of the vector backbone sequences present in pSYN12274. As expected for both the FR8a and PMI probes, the SmaI-PmeI digest resulted in a single hybridization band of the correct size, demonstrating that a single copy of each gene is present in the 5307 event. Additionally, for the backbone probe lack of hybridization demonstrates the absence of any pSYN12274 vector backbone sequences being incorporated into event 5307 during the transformation process.

Example 4

T-DNA Insert Sequencing

The nucleotide sequence of the entire transgene DNA insert present in event 5307 was determined to demonstrate overall integrity of the insert, contiguousness of the functional elements and to detect any individual basepair changes. The event 5307 insert was PCR amplified from DNA derived from the BC5 generation as two individual overlapping fragments. Each fragment was amplified using one polynucleotide primer homologous to plant genomic sequences flanking the event 5307 insert and one polynucleotide primer homologous to the FR8a gene. To generate the 5' fragment, a first polynucleotide primer homologous to the 5' flanking sequence, SEQ ID NO: 8 through SEQ ID NO: 15, was combined with a second polynucleotide primer homologous to the inserted DNA the FR8a gene, SEQ ID NO: 33 through SEQ ID NO: 41, the Ubiquitin promoter, SEQ ID NO: 42 through SEQ ID NO: 53 or the PMI gene, SEQ ID NO: 54 through SEQ ID NO: 60. To generate the 3' fragment, a first polynucleotide primer homologous to the 3' flanking sequence, SEQ ID NO: 69 through SEQ ID NO: 72, was combined with a second polynucleotide primer homologous to the inserted DNA within the FR8a gene, SEQ ID NO: 9 through SEQ ID NO: 17, the Ubiquitin promoter, SEQ ID NO: 18 through SEQ ID NO: 26 or the PMI gene, SEQ ID NO: 27 through SEQ ID NO: 32.

PCR amplification was carried out using the Expand High Fidelity PCR system (Roche, Cat. No. 1732650) and the following amplification parameters: 2 min at 94° C. for 1 cycle, followed by 10 cycles of 15 s at 94° C., 30 s at 55-65° C. and 5 min at 68° C., followed by 20 cycles of 15 s 94° C., 30 s at 55-65° C., and 5 min+5 s/cyc of 72° C., followed by 1 cycle of 7 min at 72° C.

The amplicon resulting from the PCR amplification using SEQ ID NO: 8 and SEQ ID NO: 41 comprised the 5' junction sequence (SEQ ID NO: 1). The amplicon resulting from the PCR amplification using SEQ ID NO: 69 and SEQ ID NO: 72 comprised the 3' junction sequence (SEQ ID NO: 2). Each sequencing fragment was individually cloned into the pCR®-XL-TOPO vector (Invitrogen, Cat. No. K4700-20) and three separate clones for each fragment were identified and sequenced. Sequencing was carried out using the ABI3730XL analyzer using ABI BigDye® 1.1 or Big Dye 3.1 dGTP (for GC rich templates) chemistry. The sequence analysis was done using the Phred, Phrap, and Consed package from the University of Washington and was carried out to an error rate of less than 1 in 10,000 bases (Ewing and Green, 1998). The final consensus sequence was determined by combining the sequence data from the six individual clones (three for each sequencing fragment) to generate one consensus sequence of the event 5307 insert. To further validate any individual basepair discrepancies between the event 5307 insert and the pSYN12274 plasmid, small (approximately 300-500 bp) PCR products specific to any regions where a basepair discrepancy was seen in the initial consensus sequence were amplified using the same methodology above. For all putative basepair discrepancies in the event 5307 insert, direct PCR product sequencing resulted in single clear peaks at all basepairs in question, indicating these discrepancies are likely present in the event 5307 insert. Alignment was performed using the ClustalW program with the following parameters: scoring matrix blosum55, gap opening penalty 15, gap extension penalty 6.66 (Thompson et al, 1994, Nucleic Acids Research, 22, 4673-4680).

The consensus sequence data for the event 5307 T-DNA insert demonstrates that the overall integrity of the insert and contiguousness of the functional elements within the insert as intended in pSYN12274 have been maintained.

Example 5

Analysis of Flanking DNA Sequence

Corn genome DNA sequence flanking the heterologous DNA inserted into the corn plant genome of event 5307 was obtained using OmniPlex™ Technology essentially as described in Kamberov et al (Proceedings of SPIE, *Tools for Molecular Analysis and High-Throughput Screening,* 4626: 1-12, 2002), incorporated herein by reference.

The 5' and 3' flanking sequences and junction sequences were confirmed using standard PCR procedures. The 5' flanking and junction sequences were confirmed using a first polynucleotide primer set forth in SEQ ID NO: 8 through SEQ ID NO: 14 combined with a second polynucleotide primer set forth in SEQ ID NO: 33 through SEQ ID NO: 41. The 3' flanking and junction sequences were confirmed using a first polynucleotide primer set forth in SEQ ID NO: 69 through SEQ ID NO: 72 combined with a second polynucleotide primer set forth in SEQ ID NO: 27 through SEQ ID NO: 32. It will be recognized by the skilled person that other primer sequences can be used to confirm the flanking and junction sequences.

The event 5307 insert was found to be flanked on the right border (5' flanking sequence) by the corn genomic sequence shown in SEQ ID NO: 5 and flanked on the left border (3' flanking sequence) by the corn genomic sequence shown in SEQ ID NO: 6. The 5' junction sequence is set forth in SEQ ID NO: 1. The 3' junction sequence is set forth in SEQ ID NO: 2. The integration site of the pSYN12274 vector insertion is comprised within SEQ ID NO: 103 or its reverse complement SEQ ID NO: 110, depending on the orientation of the nucleic acid used.

Example 6

Detection of Event 5307 Protein via ELISA

To characterize the range of expression of FR8a (the active insecticidal principle) and phosphomannose isomerase (PMI) (the selectable marker) proteins in event 5307 plants, the concentrations of FR8a protein and PMI were determined by ELISA in several plant tissues. The hybrids were hemizygous for the transgenes in event 5307, whereas the inbred was homozygous for the transgenes.

Whole plants and individual parts (except pollen) were reduced to a fine powder by processing using either a coffee grinder, blender, Grindomix™ grinder (Brinkmann Instruments; Westbury, N.Y., USA), mortar with a pestle or mill, or a combination of these devices. All processing was done in the presence of either dry ice or liquid nitrogen. Samples were mixed well to ensure homogeneity. The entire plant tissue sample, or a representative sub-sample, was retained for analysis, allowing sufficient sample size for archival storage of reserve plant tissue samples. The percent dry weight of each sample was determined and the processed samples were stored at ca. −80° C. until lyophilization.

Fresh tissue (except pollen and silage) and whole-plant samples were extracted. For each sample analyzed, a 1.0 g aliquot of the powdered fresh material was weighed into a 15-ml polypropylene tube, suspended in 3 ml extraction buffer [50 mM CAPS, 0.1 M NaCl, 2 mM EDTA, 1 mM dithiothreitol, 1 mM 4-(1-aminoethyl)benzenesulfonyl fluoride HCl, 1 mM leupeptin, pH 10], and extracted using an Autogizer® homogenizer (Tomtek; Hamden, Conn., USA). After centrifugation for 15 min at 10,000×g at 4° C., the supernatant was used for FR8a and PMI analysis by ELISA. After treatment with iodoacetamide as described by Hill and Straka (1988), total protein in the extracts was quantitated using the BCA™ Protein Assay Reagent (Pierce; Rockford, Ill., USA).

Pollen extracts were prepared by suspending pollen 1:30 (w/v) in extraction buffer. After 30 min on ice, the pollen suspensions were disrupted by three passages through a French pressure cell at ca. 15,000 psi, followed by centrifugation at 14,000×g for 5 min at 4° C. Cry3A055 and PMI analyses by ELISA were performed on the supernatants as described below. Total protein was quantitated as described above.

Silage extracts were prepared by suspending silage 1:25 (w/v) in 2× extraction buffer. After 30 min on ice, the silage suspensions were extracted using a Brinkmann Polytron® Homogenizer (Brinkmann; Westbury, N.Y., USA). After centrifugation for 15 min at 10,000×g at 4° C., the supernatant was used for FR8a and PMI analysis by ELISA. Total protein was quantitated as described above.

FR8a Quantification

The extracts prepared as described above were quantitatively analyzed for FR8a by ELISA (Tijssen, 1985) using immuno-affinity purified monoclonal, anti-mCry3A antibody and immuno-affinity purified polyclonal anti-Cry1Ab antibody. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

Quantifiable levels of FR8a protein were detected in all event 5307-derived plant tissues. In most cases, results are presented as means of the five replicate tissue samples. Control sample levels were below the limit of quantification for all tissues.

Across all growth stages, mean FR8a levels measured in leaves, roots and pollen ranged from ca. 18-29 μg/g fresh wt. (77-113 μg/g dry wt.), ca. 1.8-4.1 μg/g fresh wt. (22-41 μg/g dry wt.) and ca. <LOD-0.15 μg/g fresh wt. (<LOD-0.15 μg/g dry wt.) respectively. [limit of detection (LOD)=0.08 μg/g fresh wt., 0.08 μg/g dry wt.].

The levels of FR8a were generally similar among the inbred and hybrid genotypes for each tissue type at each time point PMI Quantification The extracts prepared as described above were quantitatively analyzed for PMI by ELISA (Tjissen, 1985) using Protein A-purified polyclonal rabbit and immunoaffinity-purified polyclonal goat antibodies specific for PMI. The lower limit of quantification of the double-sandwich ELISA was estimated based on the lowest concentration of pure reference protein lying on the linear portion of the standard curve, the maximum volume of a control extract that could be analyzed without background interference, and the corresponding weight of the sample that the aliquot represented.

PMI protein was detected in most of the event 5307-derived plant tissues analyzed. In most cases, results are presented as means of the five replicate tissue samples. Control sample levels were below the limit of quantification for all stages and tissues.

Across all plant stages, mean PMI levels measured in leaves, roots and pollen ranged from ca. 0.4 to ca. 0.6 μg/g fresh wt. (1.5-2.3 μg/g dry wt.), ca. 0.1-0.2 μg/g fresh wt. (0.9-1.5 μg/g dry wt.) and ca. 16.7-30.6 μg/g fresh wt. (17.1-31.1 μg/g dry wt.) respectively. [limit of detection (LOD) =0.08 μg/g fresh wt., 0.08 μg/g dry wt.].

The levels of PMI were generally similar among the inbred and hybrid genotypes for each tissue type at each time point.

Example 7

Field Efficacy of Event 5307

Western and Northern Corn Rootworm

Event 5307 plants were tested for efficacy against western and northern corn rootworm at 12 locations in the United States. Event 5307 was tested with and without the addition of the insecticidal seed treatment Crusier®. Control groups consisted of seed treated with two different rates of Cruiser® and an untreated check. Treatments consisted of four replications of two 17.5-20 foot rows spaced 30" on center designed in a randomized complete block. Ten plants per treatment were chosen at random and evaluated for efficacy using a 0-3 scale wherein 0=No feeding damage (lowest rating that can be given); 1=One node (circle of roots), or the equivalent of an entire node, eaten back within approximately two inches of the stalk (soil line on the $7^{th}$ node); 2=Two complete nodes eaten; 3=Three or more nodes eaten (highest rating that can be given). Damage in between complete nodes eaten was noted as the percentage of the node missing, i.e. 1.50=1½ nodes eaten, 0.25=¼ of one node eaten.

Event 5307 efficacy was compared with commercial granular insecticide standards applied in-furrow. The experimental design was as described above. Results in Table 2 demonstrate that the efficacy of event 5307 was comparable to the commercial standards in protecting plants against corn rootworm feeding damage.

TABLE 2

Comparison of efficacy of event 5307 with commercial insecticides applied in-furrow.

| Treatment | Root Damage Rating (0-3 CRW Scale) |
|---|---|
| 5307 | 0.06 |
| Force ® 3G | 0.23 |
| MIR604 | 0.13 |
| Untreated Check | 2.05 |

Mexican Corn Rootworm

Event 5307 plants were evaluated for resistance to the Mexican corn rootworm at two locations in Texas. Experimental design was essentially the same as described above.

A clear rate response was evident. Results shown in Table 3 demonstrate that the efficacy of event 5307 was comparable to the commercial standards in protecting plants against Mexican corn rootworm feeding damage.

TABLE 3

Efficacy of event 5307 compared with commercial insecticides applied in-furrow against Mexican corn rootworm.

| Treatment | Root Damage Rating (0-3 CRW Scale) |
|---|---|
| Event 5307 | 0.025 |
| Force ® 3G | 0.084 |
| MIR604 with Cruiser ® | 0.104 |
| Untreated Check | 0.710 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the invention.

Example 8

Use of Event 5307 Insertion Site for Targeted Integration in Maize

The event 5307 flanking sequences disclosed in SEQ ID NO: 5 and SEQ ID NO: 6 were used to search maize genome databases. Identical matches to both flanking sequences where found on a BAC clone, ZMMBBc0077H14, of chromosome 5 (NCBI Accession No. AC202955). More specifically, the event 5307 insert lies between a 5' marker, designated herein as the public molecular marker umc1475 (SEQ ID No: 104), and a 3' marker, designated herein as the public molecular marker uaz190 (SEQ ID No: 107). Using this information, it was determined that the heterologous DNA inserted into event 5307 displaced 38 nucleotides of maize genomic DNA, which lies between the 5' flanking sequence (upstream of the deleted sequence) and the 3' flanking sequence (down stream of the deleted sequence). Primers useful for identifying molecular marker uaz190 are set forth as SEQ ID NO: 108 and 109. Primers useful for identifying molecular marker umc1475 are set forth as SEQ ID NO: 105 and 106. Further markers were developed for the purposes of fine mapping the insertion site. These markers are designated as SM1108C, SM0584B, SM0377D and SM0501D. Primers and probes useful for detecting these markers are as follows: SM1108C, SEQ ID NO: 91 through SEQ ID NO: 93; SM0584B, SEQ ID NO: 94 through SEQ ID: 96; SM0377D, SEQ ID NO: 97 through SEQ ID NO: 99; and SM0501D, SEQ ID NO: 100 through SEQ ID NO: 102.

Consistent agronomic performance of the transgene of event 5307 over several generations under field conditions suggests that these identified regions around the event 5307 insertion site provide good genomic locations for the targeted integration of other transgenic genes of interest. Such targeted integration overcomes the problems with so-called "positions effects," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the above disclosed teaching, the skilled person is able to use methods know in the art to target transgenes to the same insertion site as that in event 5307 or to a site in close proximity to the insertion site in 5307. One such method is disclosed in US Patent Application Publication No. 20060253918, herein incorporated by reference in its entirety. Briefly, up to 20 Kb of the genomic sequence flanking 5' to the insertion site (SEQ ID NO: 5) and up to 20 Kb of the genomic sequence flanking 3' to the insertion site (SEQ ID NO: 6) are used to flank the gene or genes of interest that are intended to be inserted into a genomic location on Chromosome 5 via homologous recombination. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression without detrimental effects on the plant. The DNA vectors containing the gene or genes of interest and flanking sequences can be delivered into plant cells via one of the several methods known to those skilled in the art, including but not limited to *Agrobacterium*-mediated transformation. The insertion of the DNA vector into the event 5307 target site can be further enhanced by one of the several methods, including but not limited to the co-expression or up-regulation of recombination enhancing genes or down-regulation of endogenous recombination suppression genes. Furthermore, it is known in the art that cleavage of specific sequences in the genome can be used to increase homologous recombination frequency, therefore insertion into the event 5307 insertion site and its flanking regions can be enhanced by expression of natural or designed sequence-specific endonucleases for cleaving these sequences.

An example of this technique is demonstrated in Shukla et al. (Nature vol. 459, 21 May 2009). This method uses zinc finger nucleases for the purposes of targeting heterologous sequences to a specific locus based upon the use of homologous sequences within the target plant. One skilled in the art could use the event 5307 insert between a 5' marker, designated herein as the public molecular marker umc1475 (SEQ ID No: 104), and a 3' marker, designated herein as the public molecular marker uaz190 (SEQ ID No: 107) to create a locus for targeted insertion.

Example 9

Use of Event 5307 Insertion Site and Flanking Sequences for Stabilization of Gene Expression The genomic sequences flanking the event 5307 insertion site may also be used to stabilize expression of other gene(s) of interest when inserted as a transgene in other genomic locations in maize and other crops. Specifically, up to 20 Kb of the genomic sequence flanking 5' to the insertion site (SEQ ID NO: 5) and up to 20 Kb of the genomic sequence flanking 3' to the insertion site (SEQ OD NO: 6) are used to flank the gene or genes of interest that are intended to be inserted into the genome of plants. These sequences can be further flanked by T-DNA border repeats such as the left border (LB) and right border (RB) repeat sequences and other booster sequences for enhancing T-DNA delivery efficiency. The gene or genes of interest can be placed exactly as in the event 5307 insertion site or can be placed anywhere within the 20 Kb regions around the event 5307 insertion sites to confer consistent level of transgene expression. The DNA vectors containing the gene or genes of interest and event 5307 insertion site flanking sequence can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. The DNA vectors containing the gene(s) of interest and the event 5307 insertion site flanking sequences can be delivered into plant cells. Thus, by surrounding a gene or genes of interest with the genomic sequence flanking the event 5307 insertion site, the expression of such genes are stabilized in a transgenic host plant such as a dicot plant or a monocot plant like corn.

DEPOSIT

Applicants have made a deposit of corn seed of event 5307 disclosed above on 15 Oct. 2008 in accordance with the Budapest Treaty at the American Type Culture Collection (ATCC), 10801 University Boulevard, Manassas, Va. 20110-2209 under ATCC Accession No. PTA-9561. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, applicants have no authority to waive any restrictions imposed by law on the transfer of biological material or its transportation in commerce.

All publications and published patent documents cited in this specification are incorporated herein by reference to the same extent as if each individual publication or patent document was specifically and individually indicated to be incorporated by reference.

What is claimed is:

1. A seed of a transgenic corn plant comprising insect control event 5307, wherein a representative sample of said seed has been deposited with the American Type Culture Collection as ATCC Accession No. PTA-9561.

2. A transgenic corn plant, cells and tissues thereof, comprising insect control event 5307 and further comprising SEQ ID NO: 1 or SEQ ID NO: 2.

3. A nucleic acid molecule comprising SEQ ID NO: 1, SEQ ID NO: 3 or SEQ ID NO: 4.

4. A nucleic acid molecule comprising SEQ ID NO: 1, SEQ ID NO: 3 or SEQ ID NO: 4, wherein the nucleic acid molecule is derived from transgenic corn cells comprising insect control event 5307.

5. An amplicon comprising the nucleic acid molecule of claim 3 or 4.

* * * * *

SEQUENCE LISTING

```
<160> NUMBER OF SEQ ID NOS: 111

<210> SEQ ID NO 1
<211> LENGTH: 20
<212> TYPE: DNA
<213> ORGANISM: Artificial
<220> FEATURE:
<223> OTHER INFORMATION: 5' genome-insert juction

<400> SEQUENCE: 1

caactcacga actgatagtt                                                  20


<210> SEQ ID NO 2
<211> LENGTH: 20
<212> TYPE: DNA
<213> ORGANISM: Artificial
<220> FEATURE:
<223> OTHER INFORMATION: 3' insert-genome junction

<400> SEQUENCE: 2

ccacaatata ccctcttccc                                                  20


<210> SEQ ID NO 3
<211> LENGTH: 200
<212> TYPE: DNA
<213> ORGANISM: Artificial
<220> FEATURE:
<223> OTHER INFORMATION: 5' genome + insert sequence

<400> SEQUENCE: 3

gtcgactcaa acggctagtt ctgacagcta gccgttggac agatggcata ccggacagtc      60

cgatacgctg tccggtgtgc ctctaaaatt caactcacga actgatagtt taaactgaag     120

gcgggaaacg acaatctgat catgagcgga gaattaaggg agtcacgtta tgacccccgc     180

cgatgacgcg ggacaagccg                                                 200


<210> SEQ ID NO 4
<211> LENGTH: 200
<212> TYPE: DNA
<213> ORGANISM: Artificial
<220> FEATURE:
<223> OTHER INFORMATION: 3' insert + genome sequence

<400> SEQUENCE: 4

gccctgcagg aaatttaccg gtgcccgggc ggccagcatg gccgtatccg caatgtgtta      60

ttaagttgtc taagcgtcaa tttgtttaca ccacaatata ccctcttccc tgggccaggc     120

tgggcccact ggcaaagggt gcaccggaca gtccggtgcc ccaaagccag aaaccctagc     180

ttctgttttg tgctgttttt                                                 200


<210> SEQ ID NO 5
<211> LENGTH: 1548
<212> TYPE: DNA
<213> ORGANISM: Artificial
<220> FEATURE:
<223> OTHER INFORMATION: 5' genome + insert sequence

<400> SEQUENCE: 5

tacaagaata ttgagacgtg agtacatagc attggcattt tcattagcaa gcatttcaaa      60

agaatttaat tttctcatag caatgtgata tctctcctca cgctcaattc tagttccttc     120

atgtagagca catatgtcca tccacaaatc atgacaattt ttatggtttc taactctatt     180

aaacacatct ttgcaaaggc ctctaaaaag ggtgtttttg gccttagcat tccatttctc     240
```

```
atagttcaac tcttcaccta caagatttgt gggatctcta ggttcgggga atctttgtgt    300
ggcggctttg tagacaccaa tgtctatagc ctctaaatat gcttccatac gaattttcca    360
atatggaaaa tcgtcaccat aaaaaacggg agaaggtcca tccccaccgg acatcgttac    420
tctagcggtt aagctaatct aagagcaaca aggctcttat accaattgaa aggatcacga    480
tgcccaagag ggggggttga attgggcttt tctaaaaatc aacactaact aaaatctaag    540
caagagccca acttcacccc gacaactagc actaagagaa taatactaga aatacaacaa    600
tgctaagata atacttcaaa tacttgctaa acaaatacac aatgtaaaat acttgaatta    660
agtgcggaat gtaaagcaag gtttagaaga ctcctccaat ttttctagag gtatcaaaga    720
gtcggcactc tcccctagtc ctcgttggag cacctgcgta agggtatcgc tctcccttgg    780
tcatcgcaag aaccaagtgc tcacaacgag atgatccttt gccactccgg cgcggtggat    840
ccctcacgac cgcttacaaa cttgagtcgg gtcaccaaca agatctccac ggtgatcacc    900
gagctcccaa cgccaccaag ccgtctaggt gatgccgatc accaagagta ataagccata    960
gactttcact tgaccaagag aagcctaatg catgcggtgt gtgctctagg tggctctcgc   1020
tagcgttaat gaggtccaaa tgcgggatta agattctcaa gtcacctcac taggctttgt   1080
ggtgcttgca atgctctacc aatgtgtagg agtaaatgtg ggcagcaaga ccatcaatat   1140
ggtaggtgga tggggtataa atagccctca cccaccaact agccattacc aggaatctgc   1200
tgcgcatggg cgcaccggac agtccggtgt gccaccggtg cgccaacggt cgactcaaac   1260
ggctagttct gacagctagc cgttggacag atggcatacc ggacagtccg atacgctgtc   1320
cggtgtgcct ctaaaattca actcacgaac tgatagttta aactgaaggc gggaaacgac   1380
aatctgatca tgagcggaga attaagggag tcacgttatg acccccgccg atgacgcggg   1440
acaagccgtt ttacgtttgg aactgacaga accgcaacgc tgcaggaatt ggccgcagct   1500
gccatttaaa tcaattgggc gcgccgaatt cgagctcggt acaagctt                1548
```

<210> SEQ ID NO 6
<211> LENGTH: 1093
<212> TYPE: DNA
<213> ORGANISM: Zea mays

<400> SEQUENCE: 6

```
ccctcttccc tgggccaggc tgggcccact ggcaaagggt gcaccggaca gtccggtgcc     60
ccaaagccag aaaccctagc ttctgttttg tgctgttttt tcaatttggt tttgttcta     120
acttgtgagt atgttctaga gttacaccta gcactatatg tgagtgtgaa tatgcaccaa    180
cactacacta gaactctttt ggtcaaacta cttatcgaca acccctcttt atagtacggc    240
taaaacaaaa taaaagacct aactatatca cgagtgtccg caactccttg acactcggaa    300
tacgaagacc ttcacttttt gtttcgtcgc tttagccgtt gcttcaagtt tttatctccg    360
ggattgtttt caccattgta gtacatctac ctgtaatgcg acctaactta ccatttgcct    420
ctgcaaaaca catgttagtc acatataaaa ttacgttgtc attaatcact aaaaccaacc    480
aggggcctag atgctttcta gtttaaatcc ccaacaagtc aaaattcttt ctattttttt    540
ttgcaagttc caattgacat ctgaaaggtt gtaaggtaca cgtttggctc tcattgataa    600
cgggggaaag atacagtgca aaccaccata taatgaccca cttctaatcg aatggacctg    660
taacgacgaa ataccctgtg agaactatgg ttcactcatg ttaattcatt gaaattgttg    720
tagtgaattg acatggttgg gagcctgctt agagagtata gattgtcact tttttttgga    780
```

```
ccgcaactta tttttaaaag atattgcgat cgcttgttta gtagctgttt caggccccaa    840

tgcagtttct atcgtgatcc atttaagtca ctcaacattc tcatacttct cattttgcat    900

taattcattc caatctccac tactataaaa tactagcttc gatggtcgtc atacgccatg    960

cacgaagcat gtagatcaat ccgcatacca gtgggcatct atagataggc tgtgaaaacc   1020

acccaaatcc ctactagtgg acattttatc tatagatgga ccgtgagaaa ccacacaagt   1080

ctaacacgac agg                                                      1093


<210> SEQ ID NO 7
<211> LENGTH: 6206
<212> TYPE: DNA
<213> ORGANISM: Artificial
<220> FEATURE:
<223> OTHER INFORMATION: Vector insert

<400> SEQUENCE: 7

ctggcagaca aagtggcaga catactgtcc cacaaatgaa gatggaatct gtaaaagaaa     60

acgcgtgaaa taatgcgtct gacaaaggtt aggtcggctg cctttaatca ataccaaagt    120

ggtccctacc acgatggaaa aactgtgcag tcggtttggc tttttctgac gaacaaataa    180

gattcgtggc cgacaggtgg gggtccacca tgtgaaggca tcttcagact ccaataatgg    240

agcaatgacg taagggctta cgaaataagt aagggtagtt tgggaaatgt ccactcaccc    300

gtcagtctat aaatacttag cccctccctc attgttaagg gagcaaggat ccaccatgac    360

tagtaacggc cgccagtgtg ctggtattcg cccttatgac ggccgacaac aacaccgagg    420

cctggacagc agcaccacca aggacgtgat ccagaagggc atcagcgtgg tgggcgacct    480

gctgggcgtg gtgggcttcc ccttcggcgg cgccctggtg agcttctaca ccaacttcct    540

gaacaccatc tggcccagcg aggacccctg gaaggccttc atggagcagg tggaggccct    600

gatggaccag aagatcgccg actacgccaa gaacaaggca ctggccgagc tacagggcct    660

ccagaacaac gtggaggact atgtgagcgc cctgagcagc tggcagaaga accccgctgc    720

accgttccgc aacccccaca gccagggccg catccgcgag ctgttcagcc aggccgagag    780

ccacttccgc aacagcatgc ccagcttcgc catcagcggc tacgaggtgc tgttcctgac    840

cacctacgcc caggccgcca acacccacct gttcctgctg aaggacgccc aaatctacgg    900

agaggagtgg ggctacgaga aggaggacat cgccgagttc tacaagcgcc agctgaagct    960

gacccaggag tacaccgacc actgcgtgaa gtggtacaac gtgggtctag acaagctccg   1020

cggcagcagc tacgagagct gggtgaactt caaccgctac cgccgcgaga tgaccctgac   1080

cgtgctggac ctgatcgccc tgttccccct gtacgacgtg cgcctgtacc ccaaggaggt   1140

gaagaccgag ctgacccgcg acgtgctgac cgaccccatc gtgggcgtga acaacctgcg   1200

cggctacggc accaccttca gcaacatcga gaactacatc cgcaagcccc acctgttcga   1260

ctacctgcac cgcatccagt tccacacgcg tttccagccc ggctactacg gcaacgacag   1320

cttcaactac tggagcggca actacgtgag cacccgcccc agcatcggca gcaacgacat   1380

catcaccagc cccttctacg gcaacaagag cagcgagccc gtgcagaacc ttgagttcaa   1440

cggcgagaag gtgtaccgcg ccgtggctaa caccaacctg gccgtgtggc cctctgcagt   1500

gtacagcggc gtgaccaagg tggagttcag ccagtacaac gaccagaccg acgaggccag   1560

cacccagacc tacgacagca agcgcaacgt gggcgccgtg agctgggaca gcatcgacca   1620

gctgcccccc gagaccaccg acgagcccct ggagaagggc tacagccacc agctgaacta   1680

cgtgatgtgc ttcctgatgc agggcagccg cggcaccatc cccgtgctga cctggaccca   1740
```

```
caagagcgtc gacttcttca acatgatcga cagcaagaag atcacccagc tgcccctgac   1800
caagagcacc aacctgggca gcggcaccag cgtggtgaag ggccccggct tcaccggcgg   1860
cgacatcctg cgccgcacca gccccggcca gatcagcacc ctgcgcgtga acatcaccgc   1920
cccccctgagc cagcgctacc gcgtccgcat ccgctacgcc agcaccacca acctgcagtt   1980
ccacaccagc atcgacggcc gccccatcaa ccagggcaac ttcagcgcca ccatgagcag   2040
cggcagcaac ctgcagagcg gcagcttccg caccgtgggc ttcaccaccc ccttcaactt   2100
cagcaacggc agcagcgtgt tcaccctgag cgcccacgtg ttcaacagcg gcaacgaggt   2160
gtacatcgac cgcatcgagt tcgtgcccgc cgaggtgacc ttcgaggccg agtacgacct   2220
ggagagggct cagaaggccg tgaacgagct gttcaccagc agcaaccaga tcggcctgaa   2280
gaccgacgtg accgactacc acatcgatca ggtgtaggag ctgagctcta gatccccgaa   2340
tttccccgat cgttcaaaca tttggcaata aagtttctta agattgaatc ctgttgccgg   2400
tcttgcgatg attatcatat aatttctgtt gaattacgtt aagcatgtaa taattaacat   2460
gtaatgcatg acgttattta tgagatgggt ttttatgatt agagtcccgc aattatacat   2520
ttaatacgcg atagaaaaca aaatatagcg cgcaaactag gataaattat cgcgcgcggt   2580
gtcatctatg ttactagatc gggaattggg taccagcttg catgcctgca gtgcagcgtg   2640
acccggtcgt gcccctctct agagataatg agcattgcat gtctaagtta taaaaaatta   2700
ccacatattt tttttgtcac acttgtttga agtgcagttt atctatcttt atacatatat   2760
ttaaacttta ctctacgaat aatataatct atagtactac aataatatca gtgttttaga   2820
gaatcatata aatgaacagt tagacatggt ctaaaggaca attgagtatt ttgacaacag   2880
gactctacag ttttatcttt ttagtgtgca tgtgttctcc ttttttttttg caaatagctt   2940
cacctatata atacttcatc cattttatta gtacatccat ttagggttta gggttaatgg   3000
tttttataga ctaatttttt tagtacatct attttattct attttagcct ctaaattaag   3060
aaaactaaaa ctctatttta gtttttttat ttaataattt agatataaaa tagaataaaa   3120
taaagtgact aaaaattaaa caaataccct ttaagaaatt aaaaaaacta aggaaacatt   3180
tttcttgttt cgagtagata atgccagcct gttaaacgcc gtcgacgagt ctaacggaca   3240
ccaaccagcg aaccagcagc gtcgcgtcgg gccaagcgaa gcagacggca cggcatctct   3300
gtcgctgcct ctggacccct ctcgagagtt ccgctccacc gttggacttg ctccgctgtc   3360
ggcatccaga aattgcgtgg cggagcggca gacgtgagcc ggcacggcag gcggcctcct   3420
cctcctctca cggcaccggc agctacgggg gattcctttc ccaccgctcc ttcgctttcc   3480
cttcctcgcc cgccgtaata aatagacacc ccctccacac cctctttccc caacctcgtg   3540
ttgttcggag cgcacacaca cacaaccaga tctcccccaa atccacccgt cggcacctcc   3600
gcttcaaggt acgccgctcg tcctcccccc cccccccctct ctaccttctc tagatcggcg   3660
ttccggtcca tggttagggc ccggtagttc tacttctgtt catgtttgtg ttagatccgt   3720
gtttgtgtta gatccgtgct gctagcgttc gtacacggat gcgacctgta cgtcagacac   3780
gttctgattg ctaacttgcc agtgtttctc tttggggaat cctgggatgg ctctagccgt   3840
tccgcagacg ggatcgattt catgattttt tttgtttcgt tgcatagggt ttggtttgcc   3900
cttttccttt atttcaatat atgccgtgca cttgtttgtc gggtcatctt ttcatgcttt   3960
tttttgtctt ggttgtgatg atgtggtctg gttgggcggt cgttctagat cggagtagaa   4020
ttctgtttca aactacctgg tggatttatt aattttggat ctgtatgtgt gtgccataca   4080
```

```
tattcatagt tacgaattga agatgatgga tggaaatatc gatctaggat aggtatacat   4140

gttgatgcgg gttttactga tgcatataca gagatgcttt ttgttcgctt ggttgtgatg   4200

atgtggtgtg gttgggcggt cgttcattcg ttctagatcg gagtagaata ctgtttcaaa   4260

ctacctggtg tatttattaa ttttggaact gtatgtgtgt gtcatacatc ttcatagtta   4320

cgagtttaag atggatggaa atatcgatct aggataggta tacatgttga tgtgggtttt   4380

actgatgcat atacatgatg gcatatgcag catctattca tatgctctaa ccttgagtac   4440

ctatctatta taataaacaa gtatgtttta taattatttt gatcttgata tacttggatg   4500

atggcatatg cagcagctat atgtggattt ttttagccct gccttcatac gctatttatt   4560

tgcttggtac tgtttctttt gtcgatgctc accctgttgt ttggtgttac ttctgcaggg   4620

atccccgatc atgcaaaaac tcattaactc agtgcaaaac tatgcctggg gcagcaaaac   4680

ggcgttgact gaactttatg gtatggaaaa tccgtccagc cagccgatgg ccgagctgtg   4740

gatgggcgca catccgaaaa gcagttcacg agtgcagaat gccgccggag atatcgtttc   4800

actgcgtgat gtgattgaga gtgataaatc gactctgctc ggagaggccg ttgccaaacg   4860

ctttggcgaa ctgcctttcc tgttcaaagt attatgcgca gcacagccac tctccattca   4920

ggttcatcca aacaaacaca attctgaaat cggttttgcc aaagaaaatg ccgcaggtat   4980

cccgatggat gccgccgagc gtaactataa agatcctaac cacaagccgg agctggtttt   5040

tgcgctgacg cctttccttg cgatgaacgc gtttcgtgaa ttttccgaga ttgtctccct   5100

actccagccg gtcgcaggtg cacatccggc gattgctcac tttttacaac agcctgatgc   5160

cgaacgttta agcgaactgt tcgccagcct gttgaatatg cagggtgaag aaaaatcccg   5220

cgcgctggcg attttaaaat cggccctcga tagccagcag ggtgaaccgt ggcaaacgat   5280

tcgtttaatt tctgaatttt acccggaaga cagcggtctg ttctccccgc tattgctgaa   5340

tgtggtgaaa ttgaaccctg gcgaagcgat gttcctgttc gctgaaacac cgcacgctta   5400

cctgcaaggc gtggcgctgg aagtgatggc aaactccgat aacgtgctgc gtgcgggtct   5460

gacgcctaaa tacattgata ttccggaact ggttgccaat gtgaaattcg aagccaaacc   5520

ggctaaccag ttgttgaccc agccggtgaa acaaggtgca gaactggact tcccgattcc   5580

agtggatgat tttgccttct cgctgcatga ccttagtgat aaagaaacca ccattagcca   5640

gcagagtgcc gccattttgt tctgcgtcga aggcgatgca acgttgtgga aaggttctca   5700

gcagttacag cttaaaccgg gtgaatcagc gtttattgcc gccaacgaat caccggtgac   5760

tgtcaaaggc cacggccgtt tagcgcgtgt ttacaacaag ctgtaagagc ttactgaaaa   5820

aattaacatc tcttgctaag ctgggagctc gatccgtcga cctgcagatc gttcaaacat   5880

ttggcaataa agtttcttaa gattgaatcc tgttgccggt cttgcgatga ttatcatata   5940

atttctgttg aattacgtta agcatgtaat aattaacatg taatgcatga cgttatttat   6000

gagatgggtt tttatgatta gagtcccgca attatacatt taatacgcga tagaaaacaa   6060

aatatagcgc gcaaactagg ataaattatc gcgcgcggtg tcatctatgt tactagatct   6120

gctagccctg caggaaattt accggtgccc gggcggccag catggccgta tccgcaatgt   6180

gttattaagt tgtctaagcg tcaatt                                         6206
```

<210> SEQ ID NO 8
<211> LENGTH: 28
<212> TYPE: DNA
<213> ORGANISM: Artificial
<220> FEATURE:
<223> OTHER INFORMATION: Primer

<400> SEQUENCE: 8
cacgaccgct tacaaacttg agttgggt 28

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ctcccaacgc caccaagccg t 21

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
cctcactagg ctttgtggtg cttgc 25

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
gagtaaatgt gggcagcaag acca 24

<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12
cccaccaact agccattacc agga 24

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
aaacggctag ttctgacagc tag 23

<210> SEQ ID NO 14
<211> LENGTH: 21
<212> TYPE: DNA
<213> ORGANISM: Artificial
<220> FEATURE:
<223> OTHER INFORMATION: Primer

<400> SEQUENCE: 14
atacgctgtc cggtgtgcct c 21

<210> SEQ ID NO 15

<211> LENGTH: 18
<212> TYPE: DNA
<213> ORGANISM: Artificial
<220> FEATURE:
<223> OTHER INFORMATION: Primer

<400> SEQUENCE: 15
ggtagtttgg gaaatgtc 18

<210> SEQ ID NO 16
<211> LENGTH: 18
<212> TYPE: DNA
<213> ORGANISM: Artificial
<220> FEATURE:
<223> OTHER INFORMATION: Primer

<400> SEQUENCE: 16
atacttagcc cctccctc 18

<210> SEQ ID NO 17
<211> LENGTH: 17
<212> TYPE: DNA
<213> ORGANISM: Artificial
<220> FEATURE:
<223> OTHER INFORMATION: Primer

<400> SEQUENCE: 17
atgactagta acggccg 17

<210> SEQ ID NO 18
<211> LENGTH: 18
<212> TYPE: DNA
<213> ORGANISM: Artificial
<220> FEATURE:
<223> OTHER INFORMATION: Primer

<400> SEQUENCE: 18
gccgacaaca acaccgag 18

<210> SEQ ID NO 19
<211> LENGTH: 17
<212> TYPE: DNA
<213> ORGANISM: Artificial
<220> FEATURE:
<223> OTHER INFORMATION: Primer

<400> SEQUENCE: 19
ctacgccaag aacaagg 17

<210> SEQ ID NO 20
<211> LENGTH: 17
<212> TYPE: DNA
<213> ORGANISM: Artificial
<220> FEATURE:
<223> OTHER INFORMATION: Primer

<400> SEQUENCE: 20
gagaggagtg gggctac 17

<210> SEQ ID NO 21
<211> LENGTH: 17
<212> TYPE: DNA
<213> ORGANISM: Artificial
<220> FEATURE:
<223> OTHER INFORMATION: Primer

<400> SEQUENCE: 21
ccaccttcag caacatc 17

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
agttcagcca gtacaacg 18

<210> SEQ ID NO 23
<211> LENGTH: 17
<212> TYPE: DNA
<213> ORGANISM: Artificial
<220> FEATURE:
<223> OTHER INFORMATION: Primer

<400> SEQUENCE: 23
agaagatcac ccagctg 17

<210> SEQ ID NO 24
<211> LENGTH: 17
<212> TYPE: DNA
<213> ORGANISM: Artificial
<220> FEATURE:
<223> OTHER INFORMATION: Primer

<400> SEQUENCE: 24
ccttcaactt cagcaac 17

<210> SEQ ID NO 25
<211> LENGTH: 17
<212> TYPE: DNA
<213> ORGANISM: Artificial
<220> FEATURE:
<223> OTHER INFORMATION: Primer

<400> SEQUENCE: 25
aggtgtagga gctgagc 17

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
tctagatccc cgaatttc 18

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27
cccctctcta gagataatg 19

<210> SEQ ID NO 28
<211> LENGTH: 18
<212> TYPE: DNA

<213> ORGANISM: Artificial
<220> FEATURE:
<223> OTHER INFORMATION: Primer

<400> SEQUENCE: 28
tttgcaaata gcttcacc 18

<210> SEQ ID NO 29
<211> LENGTH: 17
<212> TYPE: DNA
<213> ORGANISM: Artificial
<220> FEATURE:
<223> OTHER INFORMATION: Primer

<400> SEQUENCE: 29
atgccagcct gttaaac 17

<210> SEQ ID NO 30
<211> LENGTH: 17
<212> TYPE: DNA
<213> ORGANISM: Artificial
<220> FEATURE:
<223> OTHER INFORMATION: Primer

<400> SEQUENCE: 30
cctcctcctc ctctcac 17

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
tctgttcatg tttgtgttag 20

<210> SEQ ID NO 32
<211> LENGTH: 18
<212> TYPE: DNA
<213> ORGANISM: Artificial
<220> FEATURE:
<223> OTHER INFORMATION: Primer

<400> SEQUENCE: 32
gatgatgtgg tctggttg 18

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
tgtttcaaac tacctggtgt 20

<210> SEQ ID NO 34
<211> LENGTH: 17
<212> TYPE: DNA
<213> ORGANISM: Artificial
<220> FEATURE:
<223> OTHER INFORMATION: Primer

<400> SEQUENCE: 34
tagccctgcc ttcatac 17

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
tcattaactc agtgcaaaac 20

<210> SEQ ID NO 36
<211> LENGTH: 18
<212> TYPE: DNA
<213> ORGANISM: Artificial
<220> FEATURE:
<223> OTHER INFORMATION: Primer

<400> SEQUENCE: 36
tccgaaaagc agttcacg 18

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
aaacacaatt ctgaaatcgg 20

<210> SEQ ID NO 38
<211> LENGTH: 17
<212> TYPE: DNA
<213> ORGANISM: Artificial
<220> FEATURE:
<223> OTHER INFORMATION: Primer

<400> SEQUENCE: 38
aatcggccct cgatagc 17

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
tggttgccaa tgtgaaattc 20

<210> SEQ ID NO 40
<211> LENGTH: 19
<212> TYPE: DNA
<213> ORGANISM: Artificial
<220> FEATURE:
<223> OTHER INFORMATION: Primer

<400> SEQUENCE: 40
aacgaatcac cggtgactg 19

<210> SEQ ID NO 41
<211> LENGTH: 17
<212> TYPE: DNA
<213> ORGANISM: Artificial
<220> FEATURE:

<223> OTHER INFORMATION: Primer

<400> SEQUENCE: 41
gtcataaggg cgaatac 17

<210> SEQ ID NO 42
<211> LENGTH: 19
<212> TYPE: DNA
<213> ORGANISM: Artificial
<220> FEATURE:
<223> OTHER INFORMATION: Primer

<400> SEQUENCE: 42
acgctgatgc ccttctgga 19

<210> SEQ ID NO 43
<211> LENGTH: 17
<212> TYPE: DNA
<213> ORGANISM: Artificial
<220> FEATURE:
<223> OTHER INFORMATION: Primer

<400> SEQUENCE: 43
ccttgttctt ggcgtag 17

<210> SEQ ID NO 44
<211> LENGTH: 17
<212> TYPE: DNA
<213> ORGANISM: Artificial
<220> FEATURE:
<223> OTHER INFORMATION: Primer

<400> SEQUENCE: 44
tagaactcgg cgatgtc 17

<210> SEQ ID NO 45
<211> LENGTH: 17
<212> TYPE: DNA
<213> ORGANISM: Artificial
<220> FEATURE:
<223> OTHER INFORMATION: Primer

<400> SEQUENCE: 45
gatgttgctg aaggtgg 17

<210> SEQ ID NO 46
<211> LENGTH: 17
<212> TYPE: DNA
<213> ORGANISM: Artificial
<220> FEATURE:
<223> OTHER INFORMATION: Primer

<400> SEQUENCE: 46
ctgtacactg cagaggg 17

<210> SEQ ID NO 47
<211> LENGTH: 17
<212> TYPE: DNA
<213> ORGANISM: Artificial
<220> FEATURE:
<223> OTHER INFORMATION: Primer

<400> SEQUENCE: 47
gctgggtgat cttcttg 17

<210> SEQ ID NO 48
<211> LENGTH: 17
<212> TYPE: DNA
<213> ORGANISM: Artificial
<220> FEATURE:
<223> OTHER INFORMATION: Primer

<400> SEQUENCE: 48
ttgctgaagt tgaaggg 17

<210> SEQ ID NO 49
<211> LENGTH: 17
<212> TYPE: DNA
<213> ORGANISM: Artificial
<220> FEATURE:
<223> OTHER INFORMATION: Primer

<400> SEQUENCE: 49
gtcacgtcgg tcttcag 17

<210> SEQ ID NO 50
<211> LENGTH: 20
<212> TYPE: DNA
<213> ORGANISM: Artificial
<220> FEATURE:
<223> OTHER INFORMATION: Primer

<400> SEQUENCE: 50
gccaaatgtt tgaacgatcg 20

<210> SEQ ID NO 51
<211> LENGTH: 21
<212> TYPE: DNA
<213> ORGANISM: Artificial
<220> FEATURE:
<223> OTHER INFORMATION: Primer

<400> SEQUENCE: 51
caatgctcat tatctctaga g 21

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
gtgacaaaaa aaatatgtgg 20

<210> SEQ ID NO 53
<211> LENGTH: 18
<212> TYPE: DNA
<213> ORGANISM: Artificial
<220> FEATURE:
<223> OTHER INFORMATION: Primer

<400> SEQUENCE: 53
ctgcacttca aacaagtg 18

<210> SEQ ID NO 54
<211> LENGTH: 22
<212> TYPE: DNA
<213> ORGANISM: Artificial
<220> FEATURE:
<223> OTHER INFORMATION: Primer

<400> SEQUENCE: 54
tgaagtatta tataggtgaa gc 22

<210> SEQ ID NO 55
<211> LENGTH: 19
<212> TYPE: DNA
<213> ORGANISM: Artificial
<220> FEATURE:
<223> OTHER INFORMATION: Primer

<400> SEQUENCE: 55
acaggctggc attatctac 19

<210> SEQ ID NO 56
<211> LENGTH: 17
<212> TYPE: DNA
<213> ORGANISM: Artificial
<220> FEATURE:
<223> OTHER INFORMATION: Primer

<400> SEQUENCE: 56
gttagactcg tcgacgg 17

<210> SEQ ID NO 57
<211> LENGTH: 17
<212> TYPE: DNA
<213> ORGANISM: Artificial
<220> FEATURE:
<223> OTHER INFORMATION: Primer

<400> SEQUENCE: 57
ctatttatta cggcggg 17

<210> SEQ ID NO 58
<211> LENGTH: 17
<212> TYPE: DNA
<213> ORGANISM: Artificial
<220> FEATURE:
<223> OTHER INFORMATION: Primer

<400> SEQUENCE: 58
gacgtacagg tcgcatc 17

<210> SEQ ID NO 59
<211> LENGTH: 20
<212> TYPE: DNA
<213> ORGANISM: Artificial
<220> FEATURE:
<223> OTHER INFORMATION: Primer

<400> SEQUENCE: 59
ggtagtttga aacagaattc 20

<210> SEQ ID NO 60
<211> LENGTH: 23
<212> TYPE: DNA
<213> ORGANISM: Artificial
<220> FEATURE:
<223> OTHER INFORMATION: Primer

<400> SEQUENCE: 60
gtaactatga agatgtatga cac 23

<210> SEQ ID NO 61
<211> LENGTH: 17

<212> TYPE: DNA
<213> ORGANISM: Artificial
<220> FEATURE:
<223> OTHER INFORMATION: Primer

<400> SEQUENCE: 61
acaacagggt gagcatc 17

<210> SEQ ID NO 62
<211> LENGTH: 17
<212> TYPE: DNA
<213> ORGANISM: Artificial
<220> FEATURE:
<223> OTHER INFORMATION: Primer

<400> SEQUENCE: 62
agtcaacgcc gttttgc 17

<210> SEQ ID NO 63
<211> LENGTH: 17
<212> TYPE: DNA
<213> ORGANISM: Artificial
<220> FEATURE:
<223> OTHER INFORMATION: Primer

<400> SEQUENCE: 63
aggaaaggca gttcgcc 17

<210> SEQ ID NO 64
<211> LENGTH: 17
<212> TYPE: DNA
<213> ORGANISM: Artificial
<220> FEATURE:
<223> OTHER INFORMATION: Primer

<400> SEQUENCE: 64
aggctggcga acagttc 17

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
gcaaccagtt ccggaatatc 20

<210> SEQ ID NO 66
<211> LENGTH: 19
<212> TYPE: DNA
<213> ORGANISM: Artificial
<220> FEATURE:
<223> OTHER INFORMATION: Primer

<400> SEQUENCE: 66
agcttgttgt aaacacgcg 19

<210> SEQ ID NO 67
<211> LENGTH: 18
<212> TYPE: DNA
<213> ORGANISM: Artificial
<220> FEATURE:
<223> OTHER INFORMATION: Primer

<400> SEQUENCE: 67
ccagcttagc aagagatg 18

<210> SEQ ID NO 68
<211> LENGTH: 17
<212> TYPE: DNA
<213> ORGANISM: Artificial
<220> FEATURE:
<223> OTHER INFORMATION: Primer

<400> SEQUENCE: 68
taacacattg cggatac 17

<210> SEQ ID NO 69
<211> LENGTH: 21
<212> TYPE: DNA
<213> ORGANISM: Artificial
<220> FEATURE:
<223> OTHER INFORMATION: Primer

<400> SEQUENCE: 69
gcctggccca gggaagaggg t 21

<210> SEQ ID NO 70
<211> LENGTH: 25
<212> TYPE: DNA
<213> ORGANISM: Artificial
<220> FEATURE:
<223> OTHER INFORMATION: Primer

<400> SEQUENCE: 70
cagcacaaaa cagaagctag ggttt 25

<210> SEQ ID NO 71
<211> LENGTH: 26
<212> TYPE: DNA
<213> ORGANISM: Artificial
<220> FEATURE:
<223> OTHER INFORMATION: Primer

<400> SEQUENCE: 71
ccgagtgtca aggagttgcg gacact 26

<210> SEQ ID NO 72
<211> LENGTH: 26
<212> TYPE: DNA
<213> ORGANISM: Artificial
<220> FEATURE:
<223> OTHER INFORMATION: Primer

<400> SEQUENCE: 72
cttgaagcaa cggctaaagc gacgaa 26

<210> SEQ ID NO 73
<211> LENGTH: 22
<212> TYPE: DNA
<213> ORGANISM: Artificial
<220> FEATURE:
<223> OTHER INFORMATION: Primer

<400> SEQUENCE: 73
tacgagagct gggtgaactt ca 22

<210> SEQ ID NO 74
<211> LENGTH: 18
<212> TYPE: DNA
<213> ORGANISM: Artificial

<220> FEATURE:
<223> OTHER INFORMATION: Primer

<400> SEQUENCE: 74
cgatcaggtc cagcacgg 18

<210> SEQ ID NO 75
<211> LENGTH: 20
<212> TYPE: DNA
<213> ORGANISM: Artificial
<220> FEATURE:
<223> OTHER INFORMATION: Probe

<400> SEQUENCE: 75
ccgctaccgc cgcgagatga 20

<210> SEQ ID NO 76
<211> LENGTH: 18
<212> TYPE: DNA
<213> ORGANISM: Artificial
<220> FEATURE:
<223> OTHER INFORMATION: Primer

<400> SEQUENCE: 76
ccgggtgaat cagcgttt 18

<210> SEQ ID NO 77
<211> LENGTH: 18
<212> TYPE: DNA
<213> ORGANISM: Artificial
<220> FEATURE:
<223> OTHER INFORMATION: Primer

<400> SEQUENCE: 77
gccgtggcct ttgacagt 18

<210> SEQ ID NO 78
<211> LENGTH: 20
<212> TYPE: DNA
<213> ORGANISM: Artificial
<220> FEATURE:
<223> OTHER INFORMATION: Probe

<400> SEQUENCE: 78
tgccgccaac gaatcaccgg 20

<210> SEQ ID NO 79
<211> LENGTH: 21
<212> TYPE: DNA
<213> ORGANISM: Artificial
<220> FEATURE:
<223> OTHER INFORMATION: Primer

<400> SEQUENCE: 79
gaacgtgtgt tgggtttgca t 21

<210> SEQ ID NO 80
<211> LENGTH: 24
<212> TYPE: DNA
<213> ORGANISM: Artificial
<220> FEATURE:
<223> OTHER INFORMATION: Primer

<400> SEQUENCE: 80
tgcagcctaa ccatgcgcag ggta 24

<210> SEQ ID NO 81
<211> LENGTH: 20
<212> TYPE: DNA
<213> ORGANISM: Artificial
<220> FEATURE:
<223> OTHER INFORMATION: Probe

<400> SEQUENCE: 81
tccagcaatc cttgcacctt 20

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
gccgtatccg caatgtgtta 20

<210> SEQ ID NO 83
<211> LENGTH: 21
<212> TYPE: DNA
<213> ORGANISM: Artificial
<220> FEATURE:
<223> OTHER INFORMATION: Primer

<400> SEQUENCE: 83
ggcccaggga agagggtata t 21

<210> SEQ ID NO 84
<211> LENGTH: 19
<212> TYPE: DNA
<213> ORGANISM: Artificial
<220> FEATURE:
<223> OTHER INFORMATION: Probe

<400> SEQUENCE: 84
aagttgtcta agcgtcaat 19

<210> SEQ ID NO 85
<211> LENGTH: 26
<212> TYPE: DNA
<213> ORGANISM: Artificial
<220> FEATURE:
<223> OTHER INFORMATION: Primer

<400> SEQUENCE: 85
tgtctaagcg tcaatttgtt tacacc 26

<210> SEQ ID NO 86
<211> LENGTH: 16
<212> TYPE: DNA
<213> ORGANISM: Artificial
<220> FEATURE:
<223> OTHER INFORMATION: Primer

<400> SEQUENCE: 86
tttgccagtg ggccca 16

<210> SEQ ID NO 87
<211> LENGTH: 27
<212> TYPE: DNA
<213> ORGANISM: Artificial
<220> FEATURE:
<223> OTHER INFORMATION: Probe

<400> SEQUENCE: 87
acaatatacc ctcttccctg ggccagg 27

<210> SEQ ID NO 88
<211> LENGTH: 20
<212> TYPE: DNA
<213> ORGANISM: Artificial
<220> FEATURE:
<223> OTHER INFORMATION: Primer

<400> SEQUENCE: 88
gccgtatccg caatgtgtta 20

<210> SEQ ID NO 89
<211> LENGTH: 19
<212> TYPE: DNA
<213> ORGANISM: Artificial
<220> FEATURE:
<223> OTHER INFORMATION: Primer

<400> SEQUENCE: 89
aagttgtcta agcgtcaat 19

<210> SEQ ID NO 90
<211> LENGTH: 21
<212> TYPE: DNA
<213> ORGANISM: Artificial
<220> FEATURE:
<223> OTHER INFORMATION: Probe

<400> SEQUENCE: 90
ggcccaggga agagggtata t 21

<210> SEQ ID NO 91
<211> LENGTH: 25
<212> TYPE: DNA
<213> ORGANISM: Artificial
<220> FEATURE:
<223> OTHER INFORMATION: Primer

<400> SEQUENCE: 91
ccccacgatt aaatgtcaaa ctgat 25

<210> SEQ ID NO 92
<211> LENGTH: 25
<212> TYPE: DNA
<213> ORGANISM: Artificial
<220> FEATURE:
<223> OTHER INFORMATION: Primer

<400> SEQUENCE: 92
gctcagcctt gtttttgtac attca 25

<210> SEQ ID NO 93
<211> LENGTH: 20
<212> TYPE: DNA
<213> ORGANISM: Artificial
<220> FEATURE:
<223> OTHER INFORMATION: Probe

<400> SEQUENCE: 93
aattttcata gctttttgtg 20

<210> SEQ ID NO 94

<211> LENGTH: 27
<212> TYPE: DNA
<213> ORGANISM: Artificial
<220> FEATURE:
<223> OTHER INFORMATION: Primer

<400> SEQUENCE: 94
cgctcttaag tctgctgttt gtttact 27

<210> SEQ ID NO 95
<211> LENGTH: 24
<212> TYPE: DNA
<213> ORGANISM: Artificial
<220> FEATURE:
<223> OTHER INFORMATION: Primer

<400> SEQUENCE: 95
cacacgccac ttcttgtctt ctat 24

<210> SEQ ID NO 96
<211> LENGTH: 13
<212> TYPE: DNA
<213> ORGANISM: Artificial
<220> FEATURE:
<223> OTHER INFORMATION: Probe

<400> SEQUENCE: 96
cgcgagctca tgc 13

<210> SEQ ID NO 97
<211> LENGTH: 25
<212> TYPE: DNA
<213> ORGANISM: Artificial
<220> FEATURE:
<223> OTHER INFORMATION: Primer

<400> SEQUENCE: 97
gctgcagctc acttgaaggt ataat 25

<210> SEQ ID NO 98
<211> LENGTH: 20
<212> TYPE: DNA
<213> ORGANISM: Artificial
<220> FEATURE:
<223> OTHER INFORMATION: Primer

<400> SEQUENCE: 98
ggcaccaccc tgtaaaagca 20

<210> SEQ ID NO 99
<211> LENGTH: 17
<212> TYPE: DNA
<213> ORGANISM: Artificial
<220> FEATURE:
<223> OTHER INFORMATION: Probe

<400> SEQUENCE: 99
aaccattaga tgcttcc 17

<210> SEQ ID NO 100
<211> LENGTH: 16
<212> TYPE: DNA
<213> ORGANISM: Artificial
<220> FEATURE:
<223> OTHER INFORMATION: Primer

<400> SEQUENCE: 100
ccgtcgacga ggcgaa 16

<210> SEQ ID NO 101
<211> LENGTH: 16
<212> TYPE: DNA
<213> ORGANISM: Artificial
<220> FEATURE:
<223> OTHER INFORMATION: Primer

<400> SEQUENCE: 101
gcggcgagct gttcag 16

<210> SEQ ID NO 102
<211> LENGTH: 16
<212> TYPE: DNA
<213> ORGANISM: Artificial
<220> FEATURE:
<223> OTHER INFORMATION: Probe

<400> SEQUENCE: 102
tctgagcttc ggatac 16

<210> SEQ ID NO 103
<211> LENGTH: 161748
<212> TYPE: DNA
<213> ORGANISM: Zea mays
<220> FEATURE:
<221> NAME/KEY: misc_feature
<222> LOCATION: (2151)..(2250)
<223> OTHER INFORMATION: n is a, c, g, or t
<220> FEATURE:
<221> NAME/KEY: misc_feature
<222> LOCATION: (6108)..(6207)
<223> OTHER INFORMATION: n is a, c, g, or t
<220> FEATURE:
<221> NAME/KEY: misc_feature
<222> LOCATION: (9770)..(9869)
<223> OTHER INFORMATION: n is a, c, g, or t
<220> FEATURE:
<221> NAME/KEY: misc_feature
<222> LOCATION: (18125)..(18224)
<223> OTHER INFORMATION: n is a, c, g, or t
<220> FEATURE:
<221> NAME/KEY: misc_feature
<222> LOCATION: (33520)..(33619)
<223> OTHER INFORMATION: n is a, c, g, or t
<220> FEATURE:
<221> NAME/KEY: misc_feature
<222> LOCATION: (44173)..(44272)
<223> OTHER INFORMATION: n is a, c, g, or t
<220> FEATURE:
<221> NAME/KEY: misc_feature
<222> LOCATION: (67063)..(67162)
<223> OTHER INFORMATION: n is a, c, g, or t
<220> FEATURE:
<221> NAME/KEY: misc_feature
<222> LOCATION: (91565)..(91664)
<223> OTHER INFORMATION: n is a, c, g, or t
<220> FEATURE:
<221> NAME/KEY: misc_feature
<222> LOCATION: (136173)..(136272)
<223> OTHER INFORMATION: n is a, c, g, or t
<220> FEATURE:
<221> NAME/KEY: misc_feature
<222> LOCATION: (148532)..(148631)
<223> OTHER INFORMATION: n is a, c, g, or t
<220> FEATURE:
<221> NAME/KEY: misc_feature
<222> LOCATION: (154026)..(154125)
<223> OTHER INFORMATION: n is a, c, g, or t
<220> FEATURE:
<221> NAME/KEY: misc_feature
<222> LOCATION: (158039)..(158138)

<223> OTHER INFORMATION: n is a, c, g, or t

<400> SEQUENCE: 103

```
cccggccgct gatgaatcag cttgattcgt tctgttatca cgggtggtca ctcaacgagc     60
aggtccaaag gaaaggtact caggaaaata gcctgagtct cctaaagtgc cataagaaca    120
tcatcgtaat cataataaca acatcatatc ataaatattc gcatcatgtt tgttgattaa    180
agtggagcaa tagcttgaag cttaccataa taacccaaaa ggtaaacaag gacaagataa    240
atacagacta gtcaaacctt aggtttcaat taagtaaagg gggacagtga attatgaagt    300
aagtaggaca taataggtca gaggacactt gccttcacca ggttgttgcc caggaagatc    360
ttcggcaaca cactcaggaa ccatagactg cttgttgtct acgcaaagcg atcatgcatt    420
caacacattt cgataatgat aaagaaacaa tacaccaaaa atatacaatc aagtgaacac    480
taattcaaaa gaaagtaaca aactcaagcg aagcctaggg tctagggtgg accaatacac    540
atataggttt gtggttctct aagtattact tatctcaata gattacataa cttaatttca    600
tttatcttaa tgagacaaaa gaattatacc agggataggt tcatatatta catattatta    660
acccacaaag ttaaacatct aactaccatt atggttttcc ttttatcctt cttattaata    720
aataagccat cagttacact aacctatagt ctaggcataa aattagcaca tgcagacagt    780
aaaaggttat aatttaaaca ggtagagaat aaccttacaa acattttgca atttgaatca    840
ctcaatttgg agttcatatg caaaagatat gaaataaaca agttttggaa ttcaaaatac    900
aaaactaggt ctaattatgt gataacctaa aagattaggg gcctttctgc aaaagtacag    960
gggcatgcgt gcgaaaacca gggacgatgg gttgattctc agaaagccga gggccttttt   1020
aacaaaacta ccacgcaaag gggtatcagc tgatctcgac tgcatgatca cagatcaacg   1080
gccaggatta gatttgagcg cgagcacgag cacgagctaa caggtgggcc aggatagtca   1140
gcgacctagg ggcgaggcgg actgtctggc cgggcctagc tgcagggcgc gggtgaggtg   1200
gcggatccga gtggccagat ctccatcgga cagctgggat cagatcgagt ttaattgaag   1260
ccaggtcgtt agatctcaga tggatgcctg aaatctgatg gcaagctcgg gcggggttgc   1320
taggctgctc atggcgccgc cgcccaattt cgcggcgtgg cgcggccatg gtgagggtct   1380
gggcgctggg aaaaggctca ggcgagctca gggtgacacg gcgggctcag ccatgggcac   1440
gacaccggcg tagaggcacc agagagcacg gtccgaggca aagcagcccc acggcggcgc   1500
agcttaactc tggcgagcga ttgcatggac aacagggcag taaatgggaa attaagggca   1560
tgggtgggtt ggttacgtcg agagatgact ctagagcgct tgagcaacgg cgaggacacc   1620
gcgagggccc tggtggacgg tggcggagac tcggctgcat ggtgataggt ccggtgagcg   1680
aaccaaggga aatagagggg ctggggaaaa ccagagggtg tctcgtgttg ctggcgagga   1740
ggcgaagatc agtagggcaa tggacgcgac aggaactcga cgacggccac ggaacggacg   1800
gtggactacg gcagtgctcc acggctgtgc gctcggtgcg agagagaggt gcgagggggt   1860
cggctgtggg acgctactga gcgaggggag tgagcgagtg agtgtgggct ccaaaaaagt   1920
caggcgcgtg gggggagtgg ccgaaaaaca cgcgacatgt gtgcatccac ggcggggtgc   1980
gcgagcgggt ggttagggaa aggggaggtg gctgacaggt ggggtccgct tgccagcgag   2040
ggtgaatacg cgaacgagcg gttctgcgct gacaggccga cccaccgagg caaaaaggag   2100
cgggcgtgtt gcgtgaaaga aaccggcacc gacaaaccgg cctccgcgcg nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnnnnn ctgcgggtac cacgttctac aaggtttgat   2280
```

```
gatagtgagg aaggaagaat ttctggcact gaagcaaggg cccctgtctg tcagtgagta   2340
catggacaaa ttcctgcaac tatctcacaa tgcacccgag gatgtcaaca ttgatgctaa   2400
gaggtactac aggtttccga gagggttggt tgacccctgc actactagtt gatgaaccac   2460
acattcccta ccttccaaca tctgattgat agggcaataa tgactgagag gaagcgccag   2520
gagatggaag accaaaagcg caagattggt ggaccctagg ccaggagcag cagtcgtctc   2580
ccgtttctgg caatccaccc tagcagttca agtagatcca ccctcaggga taccaacacc   2640
agaaccaatg ttcgcaccag tagcaattcc agaggcagtt ccctcaacag cagcatgtca   2700
cacccgggtt ttaggggtcc aaaacccagg cgcgaaattc accaagtgct gggatcgagt   2760
ctcacacata tgatgactca tggtatagaa acaaatgtca catctttact atataataga   2820
agttctgcac aaaataacta aataattaca tcatacgatg acgacgatcc atcaacccaa   2880
agtttactgt gagacgacgg cctagacctc tcatgaactc atcgcgacat ccttcatgct   2940
cctcatcttg cggtacctgt tcttgaccag gggatttga gtacagcaag ggtgagctca    3000
catacgttca tcgctcaaca agttgtgggg aataatgtgt atgaactcac caaaggtggg   3060
agctcatgtg aagtgtaagg cttaccaaag gagatgggta aagatgagca tgacttttaa   3120
agttggtcaa aattttatta gcagttacta agtataagta gataccgacc caaataaata   3180
agagattaaa ttaataacaa cacccacaat gcaatgcata tgacaattta agtttagttc   3240
cataatttac tcatgtgagg gtccgagctg ctcatgaccg tgagcacggc tgatataaca   3300
gttttacagt ctgcacaggt tgcacatctt tacccacaag tcatgttacc tatttgccaa   3360
gggatcgcga cttctcattc atctctaccg agaagacaag gtaggttacc actacgaggc   3420
ctttacaaac ttccactagc ttccgaaaac ccgctacggt ttctaagaag gaaaatatag   3480
gaatccctcg tccaaaaagc catcgcagca tgatcgactc gagaacctcc ctatacgcat   3540
gctcctctac cgcccttgcc cctttcgggt aaggtagtct tccactagct ttcttaatta   3600
gtcagccaag ggcgtcccat accacccttg tggtagcact gttttcctgg gtggttgctc   3660
catgttccaa ttaacatagc aatcttatca tgaacaataa ttaaaataac aaaagaattg   3720
taacatgatc ataatgtaac attaatttcc caaaaccagg tagagcaata gcaatactac   3780
ccaatagtgc ttttgtttgc aaggtagggg ataaacaata ctaggaaaac ctattgggtc   3840
ccatcaaatt aacctgagca tgtcacagtg attaatagga acattattag gtaaagaaaa   3900
gtgatcaagg gcacaacttg gctgagactc aagattccta ggtaccagct tggtcttcaa   3960
gattctcgta acctcgctgc taatcatagc aatacaaaca aacatggtat aggcaaaatt   4020
aacatcacac caaacataaa gaacaaactg cataataatg atctacgcac cacaacgaga   4080
tcctaggttc gagaaccact aaattcggag ttacggttaa caagatgtgg ttttcggaag   4140
acctatgtga ttaaatatga gactaggtct ttatgttgat tttataaatt atgtgataaa   4200
gatattaaag aaataacttt aatctacatc atactagagt agacataata ttttagttac   4260
cttataatca tagacaaact aactttgatt agtaggaata atctactaag catatattaa   4320
atgaatattt attttttgga aacatgctat ttgctaaaat aattttacag aagcgtaggc   4380
aaaattatta cgaagctaac gcaacatgaa tacattaaat cagagttaaa atgaaagaga   4440
tatgtattta ttaagtttta ggatttaatt ctataattat taaatatttc tggattgggg   4500
acactattct ataaaagatc agggggctcc atataatatt taggacttat ccgcaatgat   4560
ttctacctat acccggactg cgggctgatt tgcaagaagt ctggggtctc ttttataagt   4620
```

```
tagtcacggt gaaggggtac acgtgactaa ttccttggat catcagccaa gcgcccagag   4680
tagaagattt gcccgccgaa ccggtacgca tcctagatcg tcggatctac gataaacggc   4740
ccacgcttaa aataatagag atcgatcctc atatgcaaga tccagatcag acgacccgga   4800
tcgattcgga tgaaacgtta cgtgtgatct aatcacagcc gatacctccc agatccacgg   4860
ttcacgcgag gcccagccat gccctgatcg tgatcgctca cccatgatct aacggctgct   4920
gcatttcctt ccacctcacg acggaaagca gagcactggt gcgggcacgc cgcggccatg   4980
ccccaccaca ccaccagtga tatcccgccc ggctccccat ttcctagtat cgagcgtggg   5040
tacgtgaatc acggagagga ggaggctcca agtatgctag ggctgttctt accaaggatc   5100
acggtgtttc aagtgttgac cccaccacgc agttgctccg tggcgccgcg ggtcaccagc   5160
gaagcatgca ctggtcgttg ttctcgcacg aggtgccttc tagaatcctg cacgcgtccc   5220
acggatgacc caacccgacg ccgagaccgc aataccggcg tgcccgggaa cccccgtcgg   5280
tggcaattca ccccctgtgt tctccttctc ccttacgacg atggtgatgg cgccttctct   5340
cccgatcggc agaccgagcg tagcccacga tgctgaagga gaggaaacta gagctgcacc   5400
catggccgag gttggagcgt ccgttatata tggccagggg tacggctagc agtgggcggg   5460
tgcaccatgg cacgaaggtc gttgcacagt ttacaggagg cgagcttgca gcggacgagc   5520
aggatcgcca tggggaggat agacttgacg gccatggccc acatgccaga cgcggctgca   5580
ggcgcgagag tgggcaggag cgggctgcgc cggagcaggg aaatagagtt gggcccgcta   5640
acgaaggaaa gaaactgggc cgagaagcca gagatccggc ccatagcgca gaaagcttcc   5700
ccttttttctt tattctttaa tgattttctg ttttatcttc cctttcatat ttctttccct   5760
tattttaaac tctaatctaa atgctcaatc caaaactccg gcatgatatg caataattac   5820
atatatctgt ttagttttgt ttattttatc caaatatttt aagtatgcaa tgcacacaca   5880
tagagtaaaa attacttctt tgaatgtata gtccatttaa aattatgttc ataattttta   5940
agatagagga tttttttgtg tgtatagtat ttattaaggt tttttaagct taattctttt   6000
ggagaatatc tctaatcatg ttattcaaca agggttggtt taaattatat gagggtcttt   6060
tatttaatct ctcattataa aagacttcta tttaaatctt ggaattcnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnggg ggtttttctt tatctcgtgc gtggttatcc   6240
atctaatcac gtgggagttt gttggctatc tcttaggaaa aggtccagac ctcctcccct   6300
ataaatataa aggggtacgg ccgattgaga acccccgaac acattccaat cgaaccaatt   6360
accttattta cttttcctgc cctaggagta gatgtagcat agttctagtt gtagtcttcc   6420
acatatccac ctccacccct attcaactct acgtcgtcta gatccgtctt gggtggcctg   6480
ccgatcccaa gacgacccta ggatctcacc cctcccgggg ggcaagatct agttgtccat   6540
ccaagacttc ttcctcgatt tgatctctta attcctaggc gactccacgt cgtctgggga   6600
cgccccgggt gacctgtcga cccggagcac cttaagatct ttccccccag gggacgagat   6660
ctagattcca gcaaggagta ggaagacgac cctgtcgcca ggtcgcggac cgtccggccc   6720
agagctgcgg accgtccggt gtgacgcagg gaagacaccg ctcctgcgcc caggtcgcgg   6780
accgtccggc ccaaggctgc ggaccgtccg gcccaaggct gcggaccgtc cgcgcctgac   6840
cagagggcac cgccacggtt cttgttgagt gtttggcgct ccaaaaaggc gtcaacatac   6900
tttttggcga ctccgctggg gaagaagttg cagatctaca aaatcaggct tacatggccg   6960
attctaaaga tctcaacagt gcttctccaa acagcaacac aaggctgact aatttatcgg   7020
```

```
ccgctgagca taaaaaatta gaagatgaca tgaagaaaat agacgaggag gcccaccgac   7080
aaaaggatca ggtgctcaag gtggcggaca agtggtacct ctcgcacttc aaggtagact   7140
gccaccagaa gaccgtccaa gagagggaga taaacgccga gtatatgtta gccgtgctgc   7200
aacagctccc cacaataggt gatgccaggt cagccgatga tattccatct attaaaattt   7260
cttttgataa tcggattaaa agtatcacgg aggatataga gaggatgaca catgcattag   7320
gaaaaactca catgcctaat tttttatcac ataaattagg cgatgaaaca attgcgccaa   7380
acacatcggc ggcaaatggg tttccccagc catattctgg tatgccgatg gactcatatc   7440
taggacgacc gtcatcacca tctttgctaa atggtgagtc aaccctgggc acagccggac   7500
cgtccgcaca caattgcgga ccgtccggcc ctctgtcgga ccgtccggca ccctacgccg   7560
gacagtctgg agttacacag agcccaccac aagggtcaca ggtgttgcct gacgtgaccg   7620
gactgtccga ggatagtacc ggaccgtccg atccacccgc agaccgtccg actgtgcaag   7680
tcggaccgtc cggggcacca gaagtcacct gtgatccacc tagtgcggaa ggccgacata   7740
aatataatcg gccacccaag ccccaagaac taaaaaagtc acatgtccct gagcttgttt   7800
ggcccactaa ggccaaacct tctgttcgct cttacccgca ctcgaaacaa aaggaaaagg   7860
ttaagttcac atttaatatt actaaatgtg ataaaatatt tgatgagttg cttaaacatg   7920
gtaatattaa attgtcacat gtaattcctc cggttgaaca attaaaaggg cgtgtttatt   7980
gcaaatggca tggctccttt ctccataaca ccaatgattg tgccgtcttc cgtcggcaaa   8040
tacaatcggc tataaacgaa ggccggttga ggtttcaaaa agaggtgaaa attgacaggc   8100
cacctgttcc tgtcaccaca ttagagccca tgagcaaaaa ggccataatt cggccttgtg   8160
cggccgataa aagtaaaaat aaaaatatcg tcattggtga tcctcgcaca ccaaatatgt   8220
cacgcagaat ggttactctg aaggctccgg acaaaagaaa gaccggaggc accgggggc   8280
aagcacgatc ggacacccga tcacggtcgc ctgtcatgcg tacgccggac gatccgggta   8340
ctaaggccga acagtccgag acaggcgcgg acagtccggc tatgatggcc ggacggtccg   8400
cagatggtca gaagcagcaa cctcagacca tcggaccaca acgttccaac acaagtgtta   8460
ggaaacaaaa cactactaag acgtctggac gactcagtag agtcggccct acttttggtc   8520
agttgcttgc caaatatatg aagaaggccg ttccacacaa ccggccaata aaacaaacaa   8580
agtcaatagg gcgatctgtg cgaaagcaaa agccgactaa acggacccaa agggtagcac   8640
aaccaatatc gccttatcat cctcctccag ggatagcatg gtgcgtccca ttctatccat   8700
cgccgatgtg ttgtcctact catgtgtggg gtggtacggc gatgaatttg tattactggc   8760
ccaatccgtt tgcttatttg ggctgggggg caccacaagt tttgcctat tgacaggttg   8820
atcagataga catggctgaa gaggatgcga tccgaaacgg cctctgtgca ttaaagtccc   8880
atcaagtatt tatattatct gatcgcaaga gccgatgact tgcatcgagc tgagtcctta   8940
cttcggaaaa aaaaacctca tgaggtcaat tgtttccgaa gttttcgcta atgcttttgg   9000
ttcgccatgc tccaccaaaa ggcagggggg catatgttgg acaccaaaat gagcggacgg   9060
tccggcccat gggcccggac ggtccgcgtg tcccgagatt agattaactc ggatgtttat   9120
ccttatctcg tgcgtggtta tccatctaat cacgtgggag tttgttggct atctcttagg   9180
aaaaggtcca gacctcctcc cctataaata taaaggggta cggccgattg agaaccccccg   9240
aacacattcc aatcgaacca attaccttat ttacttttcc tgccctagga gtagatgtag   9300
catagttcta gttgtagtct tccacatatc cacctccacc cctattcaac tctacgtcgt   9360
```

```
ctagatccgt cttgggtggc ctgccgatcc caagacgacc ctaggatctc acccctccgg   9420
ggggcaagat ctagttgtcc atccaagact tcttcctcga tttgatctct taattcctag   9480
gcgactccac gtcgtctggg gacgccccgg gtgacctgtc gacccggagc accttaagat   9540
ctttccccca ggggacgaga tctagattcc agcaaggagt aggaagacga ccctgtcgcc   9600
aggtcgcgga cgtccggccc agagctgcgg acgtccggtg tgacgcaggg aagacaccgc   9660
tcctcgccca ggtcgcggac cgtccgaccc aaggctcgga cgtccgccca aggctgggac   9720
cgtccgcgcc tgaccagagc acgccacggt ctgtgaggtt gcaagatgcn nnnnnnnnnn   9780
nnnnnnnnnn nnnnnnnnnn nnnnnnnnnn nnnnnnnnnn nnnnnnnnnn nnnnnnnnnn   9840
nnnnnnnnnn nnnnnnnnnn nnnnnnnnnt aatctataca gacgatctga gattcgtctc   9900
attttgagcc cgtctcaaga atccctttaa tgtctcttgg gttagagatt tttcctgtaa   9960
aaagaatacc caagtgaagc gagaataatc atccacaata actagacagt acttactccc  10020
gccgatactt atgtaagcga tcgggccgaa taaatccatg tggaggagct ccagtggcct  10080
gtcacttgtc attatgttct tgtgtggatg atgagtgcca acttgcttcc cggcttggca  10140
tgcgctacaa atcctgtctt tctcaaaatg aacatttgtt aatcctaaaa tgtgttctcc  10200
ctttagaagc ttatgaagat tcttcatccc aacatgggct agtcggcggt gccagagcca  10260
acccatgtta gtcttggcaa ttaagcatgt gtcgagttca gctctatcaa aatctactaa  10320
gtatagctga ccctctaaca caccccttaaa tgctattgaa tcgtcacttc ttctaaagac  10380
agtgacacct acatcagtaa aaagacagtt gtagcccatt tgacacaatt gggaaacaga  10440
aagcaagttg taatctaatg aatcaacaag aaaaacattg gaaatagtat ggtcaggtga  10500
tatagcaatt ttacccaatc ctttgaccaa acctcgattt ccatccccga atgtgatagc  10560
tcgttgggga tcttggtttt tctcatatga ggagaacatc cttttctccc cggtcatgtg  10620
ggtttgtgca cccgctgtcg agtatccaac ttgagccccc ggatgcataa acctacaaaa  10680
acaaatttag ttcttgactt taggtaccca aatggttttg ggtcctttgg cattagacac  10740
aataactttg ggtacccaaa cacaagtctt tgaccccttg tgcttgcccc caacatattt  10800
ggcaactact ttgccggatt tgtttgtaag cacataagaa gcatcaaaag ttttaaatga  10860
aatagcatga tcatttgatg caataggagt tttctttcta ggcaacttgg cacgggttgg  10920
ttgcctagag ctagatgtct caccccttata cataaaagca tgattagggc cagagtgaga  10980
cttcctagaa tgaattttcc taattttgct ctcgggataa ccggcagggt acaaaatgta  11040
accctcgtta tcctgaggca tgggagcctt gcccttaaca aagttagaca agtttttaag  11100
aggggcatta agtttgacat tgtctcccct ttggaagcca atgccatcct taatgtcagg  11160
gcgtctccca ttataaagca tgctacgagc aaatttaaat ttctcattct ctaggttgtg  11220
ctcggcaatt ttagcatcta attttgctat atgatcattt tgttgtttaa ttaaagccat  11280
atgatcaaga atagcattaa catcaacatc tctacatcta gtacaaatag atacatgctc  11340
atcaatagat gtagagggtt tgcaagaatt aagttcaaca atcttagcat gaagaatatc  11400
attcttatct ctaagatcgg aaattgtaac tttgcaaaca tcaaaatctt tagccttagc  11460
aatcaaattt tcattctcta atctaaggct agcaagagaa atgtttaatt cttcaatcct  11520
agcaagcaac tcatcattat tatctctagg attgggaatt gaaacattac aaatatgaga  11580
atcaacctta gcatttaaac tagcattttc atttctaagg ttgtcaatca tctcacggca  11640
agtgcttagc tcactagaca atttttcaca tttctcaact tctagagcat aagcctttct  11700
aaccttaaca tgtttcttgt tttctttaat tagacaatcc tcttgggaat ccaaaaggtc  11760
```

```
atccttttca tgaatagcac tgactaattc atttaatttt tccttttgag ctatgttaag  11820
gttggcaaag aggatacgca aattttcctc ctcatcacta gcattatcat cactagacga  11880
ttcatattta gtggaggagt tggatttaac cttcttcttt ttgccgtcct ttgccatgag  11940
gcacttgtgg ccgacgttgg ggaagagaag tcccttggtg acggcgatgt tggcggcatc  12000
ctcgtcgtcg gaggagtcgc ttgagctctc gtcggagtcc catttgcgac aaacatgggc  12060
atcgccgccc ttcttcttgt aatacctctt cttctccttt cttctcccct tcttgtcgtc  12120
gcctcggtca ctgtcactag atattggaca tttagcaata aaatgaccgg gcttaccaca  12180
tttgtagcaa accttcttgg agcgggactt gtagtctttc cccctccttt gtttgaggat  12240
ttggcggaag ctcttaatga cgagcgccat ctcctcattg tcaagcttgg aggcgtctat  12300
tggttgtcga cttggtgtag actcctcctt cttctcctcc gttgccttga atgcaacggg  12360
ttgggcttcg gatgagtcgc caagctcgtt gattttcctc gagccttcta tcatgcactc  12420
aaaacttaca aaatgcccga taacttcctc gggggtcatt ttagtatatc taggattacc  12480
acgaatcaat tgaacttgag tgggattaag aaaaatgaga gatcttaaaa taacatttac  12540
cacttcgtga tcgtcccact tcttgctccc gaggttgcgc acttggttca ccaaagtctt  12600
gagccggttg tacatgtgtt gtggctcctc tcctttgtga agccggaacc gaccgagctc  12660
cccctcgatc gtttcccgct tggtgatctt ggtgagctcg tctccctcgt gcgcggtttt  12720
gagtacatcc caaatctcct tggcgctctt caacccttgt actttgttat actcctctct  12780
acttagagag gcgaggagta ttgttgttgc ttgagagttg aagtgctcga tttgggccac  12840
ctcatcctca tcatagtcct catcccctac ggatggtacc tgcgcgccaa actcaacaac  12900
atcccatatg cttttgtgga gcgaggttag atgaaatcgc attaaatcgc tccacctagc  12960
gtaatcttca ccatcaaaag ttggtggttt gcctaatggg acggaaagta aaggtgtatg  13020
tttggaaatg cgagggtagc gtagggggat cttactatac ttcttgcgct cttggcgctt  13080
agaagtgacg gagggcgcat cggagtcgga ggtcgatgtt gatgaagtgt cggtctcgta  13140
gtagaccacc ttcctcatcc ttttgtgctt gtcgcctttc cgatgcggct tgtgggaaga  13200
agatttttcc ttcttctctt tgtggtgaga agaagatttc ttctccttcc ctttgttgga  13260
ggagctcttc ttcttctccc tccttttggt gcgagactct tccgatgaag tgctcccgtg  13320
gcttgtagtg ggcctttcgc cggtctccat ctccttcttg gcgtgatctc ccgacatcac  13380
ttcgagcggt taggctctaa tgaagcaccg ggctccgata ccaattgata gtcgcctaga  13440
ggggggtgaa tagggcgaaa ctgaaatttg caaatataaa cacaactaca agccggggtt  13500
agcgttagta ataaggaatg agtccgcaag agagggcgca aaacaaatcc caagcgaatg  13560
agcaagtgag acacggagat ttgttttacc gaggttcggt tcttgcaaac ctactccccg  13620
ttgaggaggc cacaaaggcc gggtctcttt caacccttcc ctctctcaaa cgatccacgg  13680
atcgagtgag cttctcttct caaatcaaag ccgggaacaa aacttccccg caagggccac  13740
cacacaattg gtgcctcttg ccttgattac aatggagttt tgatctcaag aacaagtgag  13800
aaagaaaaga agcaatccaa gcgcaagagc tcaaatgaac acgacaaatc actctcacta  13860
gtcactaggg ctttgtgatg aattggagag gatttgatct ctttgtatgt gtctagaatt  13920
gaatgcctag ctcttgtagt agttgggaag tggaaaactt ggatgctatg aatggtgggg  13980
tggttggggt atttatagcc ccaaccacca aacttgaccg ttggctggag gcgtctgctc  14040
gatggcgcac cggacagtcc ggtgcacacc ggacagtccg gtgcccctgc cacgtcatca  14100
```

```
ctgccgttgg attctagccg ttgaagcttc cgacttgtgg gcccgcctgg gtgtccggtg  14160
cacaccggac atgtactgtt tgatgtccgg tgcaccggta tgggcgtgcc tggcgtctgc  14220
gcgcgctgcg cgcgcattaa atgcaccgca gggagccgtt ggcgccgcag ggagccgttg  14280
ctccgctggc acaccggaca gtccggtgca caccggacag tccggtgaat tttagcggag  14340
cggctgccgc gcgaacccga ggctagcgag ttcctgaggc cgacctccct tggcgcaccg  14400
gacactgtcc ggtgtacacc ggacagtccg gtgaattata gccgagtcgc cttagaaatt  14460
cccgaaggtg gcgagtttga gtctgagtcc cctggtgcac cggacaggta ctgttcactg  14520
tccggtggca caccggacag tccggtgcgc cagaccaggg gtgccttcgg ttgccccttt  14580
gctcttttgt tgaatccaaa acttggtctt tttattggct gagtgtgaac cttttactcc  14640
tgtatacact atacacttgg gcaaacaagt tagtccaaaa gatttgtgtt gggcaattca  14700
accaccaaaa ttatttagga actaggtgta agcctaattc cctttcaatc tccccctttt  14760
tggtgattga tgccaacaca aaccaaagca aatatagaag tgcataattg aactagtttg  14820
cataatgtaa gtgtaaaggt tgcttggaat tgagccaata taactactta caagatatgc  14880
atggaatgtt tctttcttta tttagcattt tggaccacgt ttgcaccaca tgttttgttt  14940
ttgcaaattc ttttgtaagt ccatttcaaa gatcttttgc aaatagtcaa aggtgaatga  15000
ataagatttt tgcaaagcat tttcaagatt ttgaagtttt ctccccctgt ttcaaatgct  15060
tttcctttga ctaaacaaaa ctccccctaa attaaatcct cctcttagtg ttcaagaggg  15120
ttttgatata tcatttttga aatactactt tctccccctt ttgaacacga taggatgcca  15180
attgataaat atttcttgga aaacactaag tttttgaaat tggtggtggt gcggtccttt  15240
tgctttgggc tcctttctcc ccctttttgg catgaatcgc caaaaacgga atcattagag  15300
ccctcgaagt aatttcttct cctttggtca taagtaaatg agttaagatt ataccaaaga  15360
cgaagtcctt ttctttgatg ctcatttctc ccccaaagaa tagagagatg gttggagtga  15420
tggcgaagga tgagttacgg agtggaagcc tttgtcttcg ccgaagactc caattccctt  15480
ccaatatacc tatgacttgg tttgaaatag acttgaaaac acattagtca tagcatataa  15540
aagagatatg atcaagggta ttcaaatgag ctatgtgtgc aagctagcaa aagaaatttc  15600
tagaatcaag aatattgagc tcatgcctaa gtctggtaaa agattgttca tcaagtggct  15660
tggtaaagat atcggctaat tgatctttag tattaatgta agaaatctcg atatccccct  15720
tttgttggtg atccctaaga aaatgatacc gaatggctat gtgcttagtg cggctatgct  15780
cgacgggatt gtcggccatt ttgattgcac tctcattatc acatagcaaa gggactttgg  15840
ttaatttgta accatagtcc cgcagggttt gcctcatcca gagcaattgc gcgcaacaat  15900
gtcctgcggc aatgtactcg gcttcggcgg tggaaagagc gaccgagttt tgcttctttg  15960
aagcccaaga caccaaggat cttcccaaga actggcaagt ccccgatgtg ctcttcctat  16020
taattttgca ccccgcccaa tcggcatccg aataaccaat caaatcaaac gtggatcccc  16080
gagggtacca aagcccaaac ttaggtgtat aagccaaata tctcaagatt cgttttacgg  16140
ccgtaaggtg ggattcctta gggtcggatt ggaatcttgc acacatgcaa acggagagca  16200
taatgtccgg tcgagatgca cataaataaa gcaatgaacc aatcatcgac cggtatacct  16260
tttgatccac ggacttacct cccgtgtcga ggtcgagatg cccattggtt cccatgggtg  16320
ttttgatggg cttggcatcc ttcattccaa acttgcttag gatgtcttga gtgtactttg  16380
tttggctaat gaaagtgccc tcttggagtt gctttacttg aaatcttaag aaatacttca  16440
actcccccat catagacatc tcgaatttct gtgtcataat cctactaaac tcttcacatg  16500
```

```
tagactcgtt agtagaccca aatataatat catcaacata aatttggcat acaaacaagt  16560
cattttcaag agttttagta aagagtgtag gatcggcctt gccgactttg aagctattag  16620
aaataaggaa atctcttagg cattcatacc atgctcttgg ggcttgcttg agcccataaa  16680
gcgccttaga gagcctatag acatggttag ggtactcact gtcttcaaag ccgggaggtt  16740
gctcaacata gacctcttcc ttgattggtc cattgaggaa ggcacttttc acgtccattt  16800
gataaagctt aaagccatgg taagtagcat atgccaataa aatgcgaatt gactcaagcc  16860
tagctacggg tgcataggtt tcaccgaaat ccaaaccttc gacttgggag tatcccttgg  16920
ccacaagtcg agctttgttc cttgtcacca caccatgctc atcttgcttg ttgcggaaga  16980
cccatttggt tcctacaaca ttttggttag gacgtggaac caaatgccat acctcattcc  17040
ttgtgaagtt gttgagctcc tcttgcattg ccaccaccca atccgaatct tgtagtgctt  17100
cctctaccct gtgtggctca atagaggaaa caaacgagta atgttcacaa aaatgtgcaa  17160
tacgagatct agttgttacc cccttatgaa tgtcgccgag gatggtgtcg acggggtgat  17220
ctcgttgtat tgcttggtgg actcttgggt gtggcgccct tggttcttgc tcatcctcct  17280
tttcttgatt atttgcatct ccccttgat cattgccatc atcttgaggt ggctcatttg  17340
attgatcttc ttcttcatcg acttgagctt cttcctcatc ttgagttggt ggagatgctt  17400
gcatggagga ggatggttga tcttgtgcat ttggaggctc ttcggattcc ttaggacaca  17460
catccccaat ggacatgttc cttaatgcga tgcatggagc ctcttcatca cctatctcat  17520
caagatcaac ttgctctact tgagagccgt tagtttcatc aaacacaacg tcacatgaga  17580
cttcaactag tccagtggac ttgttaaaga ccctatatgc ccttgtgttt gagtcataac  17640
caagtaaaaa accttctaca gttttaggag caaatttaga ttttctacct cttttaacaa  17700
gaataaagca tttgctacca aaaactctaa agtatgaaat gttgggcttt ttaccggtta  17760
ggagttcata tgatgtcttc ttgaggattc ggtgtagata caatcggttg atggcgtagc  17820
aggcggtgtt gaccgcctcg gcccaaaacc gatccgaagt tttgtactca tcgagcatgg  17880
tccttgccat gtccaataga gttcgattct tcctctccac tacaccattt tgttgagggg  17940
tgtagggaga agagaactca tgcttgattc cctcttcctc aagaaagctt tcaatttgag  18000
agttcttgaa ctccgttccg ttgtcgcttc ttattttctt gacccttaag ccgaactcat  18060
tttgagcccg tctcaagaat ccctttaatg tctcttgggt ttgaggacga attttctaag  18120
aattnnnnnn nnnnnnnnnn nnnnnnnnnn nnnnnnnnnn nnnnnnnnnn nnnnnnnnnn  18180
nnnnnnnnnn nnnnnnnnnn nnnnnnnnnn nnnnnnnnnn nnnnttttca actctgagaa  18240
tcagcttgat tcgttcttct ggcatggctt ctactggcca actgctctct aggagggagc  18300
cgagttggtg aagtcctgcg aagcatgtca gtttcatgca aagcagacac acacacacac  18360
cagctcaggc tctgcaaatg attccaccct cttggccatt cgccgtatgg ggggtggata  18420
tcctgggacc atttcctagg gctgtcggcg ggtaccgttt tctctttgtc gccatctaca  18480
aattcataaa gtggtcggag gccaccccta tggtcagtat cacccaaggt gctgctgttg  18540
ccttcctcaa ttcgattgta tgcagatttg gggtcccaag ccatatcatt acggacaatg  18600
ggacccagtt caaaagtcga ctcttccaag agtattgcga gggcattggc acccagctct  18660
gctttacatc tgtgtctcat cccaggagca acgaccaggc tgagagggca aacacagaaa  18720
tccttagggg actcaaggca cacacctacg actgcttaaa aaagcatggt gccaattggg  18780
ccaatgagct tccgtccgta ctatggggga accggaccac acccagccga gctaccgggg  18840
```

```
agaccccgtt cttcttggtc tacggggccg aagcctgcct tctcccggaa atcattatgg  18900
gctccccatg agtccagtct ttcgatgagt ctatgcagga atagctacga cgtgaggaca  18960
tggacttcat cgacgaacgc agatggcaag cggtgatccg aaatgcacgg tacaaccaag  19020
cgctcaggcg ctaccaccaa cggtttgtgc atagtaggga gctcagggtc ggggacctag  19080
tcctaaggcg agtactgaac cgagaagggc tccacaaact ctcccccagt tgggaaggac  19140
ccttcaaggt gacagaaata tgccgaccat ggtgtgtccg ccttgccaca acagaaggag  19200
tgcctcttcc caatccctgg aatatagagc atctctgtaa gttctatcca taatagcaaa  19260
actggggggt tgagttttct tcctttgtaa ctaggttacg catatgtgta tgtcaattcg  19320
gtgaggcccg ccctcgtaag cccatctgtt ggtctacacc catgtatatc gagttataag  19380
gaaaggattt acccccctaga tgtgattttg tgatggtttt attctacttc ggtttacatg  19440
cattattttt tatctaaccc acccatatag tttcccaccc ttgttggtat gatgacatcc  19500
gaattgagta gacaggcttg cagttcaaga cccctttact gctacagggg gtccggcaaa  19560
ctgcggacca gttctagaga atgggcgcta gcctcctgga ggggtccgga gttgtgtagc  19620
cgcttagcat ggttccgtac cctaagcctg catgctccac cactctataa cgggtgccct  19680
agtatttgga actgtgatcc tatgggtcca ggcatacggc ttggcttccc aggctaaatc  19740
ctgcaggtcc tgttgcataa atcaaaggat ggcagatacc agacgatgga tcctatggtg  19800
tgctcctaac actttaaagc cgaagctgtg tacaagtcca ggtcccagtc cagtagtagg  19860
tagtctcaaa ctgtagagac tacctcctag gggccggacc accaatttta tctttggtat  19920
actggtatcc agcctcgaca cgtcgagcct acctcccagg gggccaagta ccaaggggaa  19980
gttgatgaca ctacacataa caaggacaaa taacatacaa ataagtttaa gttccaatgc  20040
tacctcatta gcggttctta taatatctta caaaatcaaa agttattaca accgcttccc  20100
agtggaaccc ttgctttgtc tctataggtc gtcagcagga tcgtgctgga agcgctcggc  20160
caccagctcc acggcgtctt gtacactctc ccaggcggcg tcttctatgg cggctaccgg  20220
accagcgatc actagcgcca aggatatggt ggggtcgtga ctccggaagc atgttaggac  20280
ttattcaacc actgcccgac agagcttgct gccctctgcc tctaggcggg ccccgaggat  20340
ctgatccagg cgacggaggc gatcggcggt agagtccagc accgggagcg catcagagat  20400
cgacgctggt agctccgaca ttgggatggg gctcatccct agtggcacta gtgccgtgct  20460
tgcctcgccg gcccacgcga caatacactg gacctcgacg cggtgctccg cttggagatc  20520
ttcaagggcc ttcctggtgg cctccatcgc ttggggaccc ggtgccgcct gcgctgcatt  20580
gaactagcgg atctgctcct ccagcttcct ctctttctcc tctgcctcga gcttgtgctt  20640
ggccagcaac tcgcctcgcc gggtgagcat ttcttccctg aagctgagat ccgtctcttg  20700
cctggcgagg tccgtctccc accggtccaa ggactgctcc ttcgccttaa gatttcctc  20760
ggcgagggtg gcattgctag ccttgccctc gagctcctgc taccactttt gcagcctctc  20820
cacgaccctg acctgctggg cccgctgggc ttccagagtc tggtccaggg cactcagctt  20880
ggcctggtac tctgttgtga gggtctcccg ctgggtcacg acctcctcct tcctggtcac  20940
cttcttctcc ctccgggacg cctccagctc cctggcgcac accctctgga ggtccctctt  21000
gtactcctta tggtcctgct cgagttggga ccgctcggag atgaattgtt gggacgccgt  21060
tctggtgcgc tcctccagtt gggtgcgcca gtcacttagg cgctggtgct cagcctcaag  21120
cgcctcccac tcccgcaaga ttgctgcccc agtgtcacta aggacctagt gggcacgaga  21180
cattatgcga gggaggggga ctggcgccgc ttcttgctcg gcacccgacc ggagtcgccg  21240
```

```
cccaaacacc acctccatct cctccggagc aggcgggggg ttggagctgg acatgcctac  21300
tgcgtcaccc ccagtgtcga gagcgggcgc ggatccccca gctgggacct ccttcgccac  21360
tgcgacgccg cctgacgctg ccaccggacc cccggctggg gcatgagaag ccgctggtgc  21420
tgtcttggca gcagctgggg gtgggccgcc ggcaccactc tcagcaggtt cctgctgttg  21480
agagccagac ccgtcggtgg gcctggtatc tggtggagga ggcatgacct tgggagcggc  21540
gaaggaagaa gccctagcga acagatgatg ggttaaaact ggtcggcatg atgattagac  21600
tcatggaaaa ggggctacgc ttacttgggg ccctagactt tctagtgacc ctggaagcgg  21660
ggcgatcacc gctcctgctg ttgctatcgc tgttgctgtt gctgttgctg ctgctggtgc  21720
ccctgggggt gaggactgac gcgcctctgc gcgccgtggg cctgggagct agcttcctcg  21780
gccccacctg cagccctctg acgcttctgg ggggggctcc gaaatgagcg acccatcagc  21840
gcgacatggc ctgcgttgcc tctcctcctc cgaccccctc ggagctacct ggggcggagg  21900
cactgctcgc agcccctttg cctttgtcca aggggctagg ggccacggcg gggttggtgc  21960
tgggagccgc accagtgggc tgggaacctc caatcggtgc attagaaatc tggatcccac  22020
ggagggggtc ccggccaccg gtctagcgaa ccgccatgcc gctctcgtcg agggtcggca  22080
acgtggccaa gatcaccatc ctcaggcctg gatcgtcgca gagcgcaggg atgttctggg  22140
ggagtatcag ggactcaggg acaaaagttt ccccaataat ccctcccatc aggactgcta  22200
gctcgtccca ggacagaacg gtgcccggcc tgcgttggat cctatcgatg tcgtttgggc  22260
cggtgaacca acagcacata cgcggtctcc tctgcagcgg cgcgatccgg tgcttcagga  22320
gatcgccgac cacgtgcatt gatggcaggc cgcccgtagc caagcccttg attctgtcca  22380
atacaggcag gaactctagc aagagggacg gcttagtcct ccactgcttg cggtcgagcg  22440
ctggcccatc gctcggcagg acgaggcggt cgttggcctc ggcgctggca atcacccaat  22500
cgttgcgcca gttttcccac ctcgcaccgc caaaggtggg gatgtatacg acggctggat  22560
ctggcctcgt ctggaagtag taggcaccga tgtggtccct agtcttcccg aacttgacca  22620
gcacgaagaa gcagcggaag agggaagtac agggggccac acctacgaac atctcacaga  22680
ggtggacgaa gatggctgcc tggaggacgg agtggggtgt gaggtgttga agctgaagcc  22740
caaactcctc cagcagcagc aagaagaagg gcgagaatcg gcaacgccaa cccgtagaag  22800
atgtaggagg tgaacagcac gaactccccg gcggtgagat cgccatgagg gacggcgccg  22860
gcgcggaact tccggcgagc cctggcgcgc tccatccaag caggccgcgc accaggttga  22920
gcgcctcctt agactgaaag cagtcaggat gaccaagcga ggccatggcg tgtgcggcgg  22980
cgcgagcgtg gaacagagga gcacgaaggc aaaggggtgc aggcgattgg gagagaatgc  23040
gaaaaggtaa ctgctgcacg cggggtgaat cctttttcaa ggaaacctga gtccttgttc  23100
agggaaaccc ttccgtgcgc ccttgaattg ccacaggaaa tctcgcccga tgcgcacata  23160
ggacccaggc agcccactct atgacacggt ggcccgggtc cacaagtcat acagattgtg  23220
tgctggattt cgagtgcgga aagagcgaat cgccatgcga actgccgcgc acgatagcgc  23280
acctcctcgg ggccgctgca gaagacaaaa ggttatgcag cggcaacgag gcgtcccacg  23340
cgtggcccga cgaaaccacc aggcatgggg ccatgggtca gtcagctgca gagacagata  23400
tggcagttga cgtgactgaa ggcggattga cagcgggcgt gtctgcagac gcgctaaaac  23460
ggcatgccaa tcaccgatca ggtcacgttg aagcaaagta caagctttgg ccccacatgc  23520
aggctcgcat cctcccctaa ggtgggtccg ggggccactt tcggcaccct gaaacaaggg  23580
```

```
taccccttac tactgtataa atacgcagta cccacgcgac tatctttagt cgcgtggtaa  23640
aagagctgta tgtgggacca aaccatgact cgccctagcc tcgggcgact actctaggcc  23700
agcaacagca cctgacccca ccacatgggc gggtccgggg ccgccatgtg tccagagaaa  23760
gtgatgtact ccaaggcatc aatagtgagt ccggaccccc ataggagagt gccgaaccca  23820
tgccagaccc ctgtatatac ggtccaggcc tccaagtttg gtcatgcgtt actctgtcag  23880
cattagttat ttacataatc tatttcttcc attatgctcc taggcccgca tgtcgaggct  23940
cagcatcctt gtatgtgcct cctgtgacac cccagtgtca cctagggttt ctcttaaaaa  24000
gccaaaccaa ggaccattat tttatgtgaa ccaaagtaag catgagcatc aaaataactt  24060
aagtaagaaa gaattcacca agtatatgct taaaagtgtc atgatcaaga caattgagtc  24120
tcttaaagga taagaatgtg caaccctaat taagaaccct aagtgaaccc catgaacaaa  24180
attcaagaaa ataagcaaaa gggaatgaaa agtttaaaat tttgagttga gccaattata  24240
taagttaaag tatatttgat aagcaacaag atagattgag aaagcttagc caaaataatt  24300
caagaaaacc cccaaatcaa gcttcttttg ttgggactca ttgggaattc tgaatttcag  24360
aattctgaaa ttcagacctt gagccaaaga tcagggatgt tcaccttgat ccctaactcg  24420
aatcctaatg gccccattga caaaattgtg tctaactaac ccctctgtct tgtgccagaa  24480
gatggcattg ggacgcgagc cctagacacg acaaaacttg ggatttgcct cgggtttggg  24540
cagggagaca gaccagattt cctggctcca tatctctgca accagtaggc aaaatcctat  24600
gacctccaca caagaatggt agcttgtagg gaggagaaga ggttttgtgc actgaccaag  24660
gcgagagcag gctcggatga gcgaccacac gcgccagagc ttgggcagaa cgcacgggca  24720
cacgtgttcg accctggtcg gcacgccaga gctcgcccaa cccgcgcgcg cgctcgcccc  24780
ggcgtccggt caagtccgcc gcgcgcccac gccctcggcc gtgcccgccc gcgcctataa  24840
agcctccccg ggcgcacctc tcttcgcccc gcactcaccc tcaccggcca gccactgttc  24900
cttagctccg gcgagctcat ttccgcccgc cattgccgcc agaactacgg ccgccgtggc  24960
cagcccactc cagccaccct ccagcccaac cagtgctcgg ctagctccgc cagtagcccg  25020
tgaagcttgc caagccctcg gacccgaccg gaacttcacc gggaggcccg aagaatcaac  25080
ctcaccggac ttcggtcttc cgccgccgcg cgtggaccaa gctatccagt gagtctcccg  25140
cccgattcct ttcgctcatg tcttctctgg catcccgtgg acctccatga cctatttgat  25200
tgaactatct cgccgcgacc aggccggtct cctcgccgcc gacgagcatc cccgcctgcg  25260
cgcgtggacc gaccgactcc ggccatctcc gacggtgttc cgcacaccgt tgtgatcccc  25320
gcgacctccc cttcaccctc ggccacttca ccggaacagt ctcgccgccg gtaagcccct  25380
ccgccctttt cttcgccgcg gctactgttt aaggtagaag aaggacctcg ggttaggttc  25440
tgtagaaccc gaggggtttt tcgtaatgtc agcgactcat gagaatagta acctaaggac  25500
tgaattgcga ggaaaactta gaaaaccgcc agggacccca gtgcaaagtg gatttccatt  25560
taatcaattt tgttatttct ttttaaaatg accagagaac ttagaaaatc cataacttga  25620
tgaaatctta atgaaaagct gtcaaaccaa ttttgctagc tctggaattt tatgacctat  25680
catttaaaaa tagtgaacca tatgctttct gttctaaatt ttagagttta aaattaaaaa  25740
cagaaacccc ctaaaccttg tttaattaag gaaaattagt ttttcttttg tgctgagctt  25800
aagaaaattt gtagatgctt ataccttaat tagacactgt ttaaaaatag taggagccct  25860
agcattagag attatgatgt agttattcat ttaaagccat tttgtccaaa acttagagaa  25920
aatcagaaag gccttagaga ttaatgaaca gtgattagta atatttttcc tagattactt  25980
```

```
atgcagcaga gaacctagga aaaatgcaga gaccattaat ttggaccagt ttctaattaa  26040
gatgctttaa ttagcattat gtagactgaa aatcaattat tagaattgca aaactataac  26100
caaagtggtt aacaaaaatc cagtgaactt ataaccacca gagccccact acaaaaatac  26160
agagcacccc agcctaactt tttaagtagg gaaaataaat acagaatgat aataaggcat  26220
tttcccacta aatcatgagc aaccccaaat aatgtgataa tgggcaacca aaattttgct  26280
aagtccatga tgagataaac caccagagaa aaatacaaac ccatgaaaaa gaagtgaacc  26340
catgcctttt gctagtaatt tgtgaggaag gccatttagc tcaaataatg caaaccaccc  26400
cttcccttag gcaaaaggaa gccaaactcc agaatgattg ctcttgcaca aaatactagc  26460
taagaaaaat aagaactctg ttgtttgatg tttttcaagt atagtggtag tagaaagcac  26520
ccctttggct agaaacctta agaaaatctt agggaaagaa ttaaagggta ttaatgacta  26580
gaaatttgta tcaagtcatg ttataacacc taaaagccag caaaaataag tttttgagaa  26640
ttacccacta ttaaataata gttgtagttc aaagtacccc ttctgcccta aaatttggta  26700
attttgtcca gagaaaacca ttcactttct gaaccccaaa ttttgagaca gagaaccata  26760
caccagtaac aagccactgt aatttttgca gaatttttgg aattttataa aagcaacttg  26820
tagttcaaac ctactccaaa acattaaaga gaataaaaga aaagagaaga agaaataaac  26880
ctcatcccaa taagactaac ccaatttacc aagtatacca ctaaagggtt ttacataagt  26940
aaagttaact ggttttaaat caaaagatca tacatcttta aagttataaa ttctaaagca  27000
catatcatat catgcatata tcttacgcat tgcattcatt agattgtaat cttgccgacg  27060
gagagtacgt gctcatccct gagcaaggac ctatccaaga ggaggaccag gagcaggctt  27120
cagaggctgc tattgaggat ctccccgcag ccccagcaat tgaaggcaag ccccggtttt  27180
atgcataacc atgttattat atgctacttt actacactta atgcttgtag gattgcaatg  27240
tgcacttaag tgtaggagtt gcttgaaacc tctagttgca tgaacttagg attccttttt  27300
gagatgaata ctagtatgct aggtcgagta gctgcttgct aatcaggatc tcggtagaag  27360
tcgagtgatt tttctagcac tcgcgcgagg tcaggaattg attgtattca tcttgataat  27420
ggggtatatg ttagtccgtg gacttgggtc cagggaggat gccatgtcca tgagacggga  27480
aaaatgaatt aaggattaat gtgtggatac ctgagtcaag cttttgaacg tactaagcac  27540
atgccgggaa aaatggtaac cggtaaacct agtacctgag tgaagccggg cgcggacttt  27600
atccctcatg cgacctgaga cagggtctcc catgctagct atggtgggta caagtgcggc  27660
cactgcatga cggcagtcgg ggtcagtgga gcattgtatg ccaaggcggt gaggcctgga  27720
cgcgaacggg gaatcgatgg ggacggttgt catgtgtggg gtcggagtac cctgacatgc  27780
cgtgtgttta ggtttacctt gcaaggttta aaaactcgat tcgaatcgtc tgcttctcgc  27840
agctaatgag actgcttgat tccttgtact gcatcgagta agaagtgaaa tgtggattat  27900
atgagataac ttgttgactg aactaattga ttgttaccat gtatgcttag aaggagcaaa  27960
tctagctaag ttaatgatgg tagaatttga aaagctaaaa gttgatttta gaaacagcta  28020
gtgcttttgg caaaccaaac ccctcagcca aacagctgca tagtctagag gtagaggagt  28080
agactcctca caccggttaa gtctagctga gtattagtat actcagcctt gcttgtggca  28140
ccatttttgc aggtaccatg caggatgtag ttgatggtgt gacttggcct accaccctgc  28200
caccgggttg gacggtcgag tgggatgttg ctccggcagg agaggagcat gaggagtagt  28260
gggctaggcc ttgcccattt cctcattacc gacgacatcg attatccgct gcactttaat  28320
```

```
ttatgaactt tattcgctac tcaaaaactc cgatttatgt aataactcag tacttaattt  28380
gaggtttcct gttttattgt atttcttctg tgactcacct tcgagtgaga ttgtgggatt  28440
tgatcctggt taagtggctt catcagacta gatctgaggg actgacgggt tattccgatt  28500
taagtgtgtt acggcccctg aggcgtgact taggcactta agctggaata attcgggcgg  28560
ttctgccaca gctggtatca gagcaaattc caccacagag aagggcaata aaccatgaat  28620
accaattttc aaaatctaaa acctgcctag aagctactac ggatcgtcag gactagaccg  28680
ctagacctag gacgaaaggc cttaggcata gagggagaaa taggtggcta actaattagg  28740
ccctgtgggc caatacttat attttaggat gccctaaaaa ggcaccctat tttccttttg  28800
agaggcaacg tttctttccg catgcatgca ttataaaaca taaagaggaa ttaaaattga  28860
gctaaccccc ttttcttcga aatcatccgg gctctctttt tctttttcct tccaccataa  28920
tctttatctt tgattccctt ccgcagatga attcacccac ccccgccagt ggaggagact  28980
ctcgtttcag ttctgacttc ctttctcgcg atggcttccc ttccattttg tgggaagtgc  29040
ttaattccgc cggttaccct acgccccctt tgtacacggt gcagttgtat gaggagcatc  29100
gggtacctcg ttgtcgggtc tggctaactt tggaggctca tccccttcag ccgggttggc  29160
gttctcttga ctctgagacg attggactca ggacggacga caccgttgag gcagcagcca  29220
tgaagactct gacgactttt tgtggctacc atcccctgga gatggtgatg caccccttgg  29280
gactcttccc cgctgagaag aaggatgatc ccatgtggtg taaccgcgtg agccatgtga  29340
aggatgtgtg ggcaatgtat cctgacttgg ttgggagggt cactgttcag tgcatgagtg  29400
cgctgtaccg ccttcaggcc cttcagagcg atgctatgac acttcttgcc aataccgctc  29460
aggcagccaa gctcaccctc gacagtcggg aagattttgt ggtcgaccta tccacagagt  29520
tggtggaaaa ggatctgcag gtggagaggc tgaaccagcg tattaccacc ctggagcagc  29580
aagtggagat ccgagataac actattgatg tcttggagaa ccagcttcac gacgtgcaga  29640
gggaactcga ggaagcaaat gaccacttgg acatgcacca cctggagatg gaggccaatg  29700
aagcaggaag cgagggagaa gaggctcccg aggagctagg accagcccct ggtgccaatg  29760
ggactacctc cgcgatacct ccttcacccg tatccagtgt cgcttccacc gctcagggtt  29820
aagcagtcgc tttgacattt ttaggcggat agaaacctat gcgagcttag tggtatcaca  29880
ttttggacta ggcttgtggg taccttcccc tgattaatgt aaccctgtaa acttttgata  29940
tctgtgggat ccttgtcacc atgttatctt cattcgaacc taatattatg attatggcat  30000
tttccttcca tatgagatga tatcttgtcg ttcggaaatg tgaattggga taacaatggc  30060
gacaatctct gttttcagat ggcagcgagg cagcgtcgcg ggcaaaatga gcaagctccc  30120
ccgccacctc ctccagctcc cacagtgcag gagctgatgg cccagcagaa tgagattctg  30180
cgacagctct tgcagcgcca gccccaccct cagcatcctg gtggaggcca gcatcagcga  30240
cctccggcta tggcaacata ccaggagttt ctgagcacgc agccgccctt gttcaccaag  30300
gcagaggatc cattggacgc cgacgtgtgg cttcgcgtcg tcgagtccaa gtttcccctc  30360
ctcacaggag actgccctga tgaggccaag gctcgcttcg ccgcacagca gcttcgcggc  30420
cctgctcgga cttggtggga tcacttccgt gctatgctcc ccggtgatcg tgaagtatct  30480
tgggaggaat tcaagactgc cttcagaggg caccacattc cagctggcat tcttgatcgg  30540
aagttgaacg aattcctggc cctcaatcaa ggaacccgca cggtactgca gtatgcgcaa  30600
gccttcaacg acttatgcca gtatgcaggg tatcatgctg attctgatga aaagaagagg  30660
gatcgcttcc gcaggggtct caataccaag ctgcgggaac gactcaacac tgtccgggcc  30720
```

```
gatagcttca atgagttggt caacatggcc atctctcagg aggattgcat tgttgctcac  30780
cgggcagaga agaagagaaa ggcaccaatg gcagcaccat ccgctcaggc tcagaggttc  30840
cggattgttt ctcacaatca gagcaggggt tttcagcagc aggcaggcag atgggtgatc  30900
aggccacctc agcagcagca gcagccggca cccaaccgct atccagctcc cgccccaaga  30960
aacaatcagc ctccgcagca gcagcagttc cgccagggca atgggaacaa gtgtttcact  31020
tgtggcaatg tgggccacta tgccaagaat tgtcccagga accagcagag gcagatgcca  31080
gcaccaaatc aagacaaggg aagaaagcag aaggtacaag tcaggcaagg gaagctcaac  31140
ttcactgctc tagaggaagt gccagaagga gctcccatca tgaccggtac cttttcagtt  31200
tataatcaac ctgctttaat tctgtttgat tctggtgcat ctcatagttt cattagccaa  31260
aagttcagtg ctaattgcaa acttccattc tctcactcaa aagggtcatt catgatagtc  31320
acacctgggg gtaaaattgc aactaatcaa ttaaaccaaa gtgtgcctat tcaactggga  31380
agccacatta tcaaaaccac tcttcttgtg ttgggattgg aaaatgtgga cattattcta  31440
ggagcaaatt ggatgacctt gcaccaagtt gtgctcgacg tagccagtcg taccgtggaa  31500
gttaattctc ccttctgcgg gaatttcact ttgattctgc ctagtcaggg ttcttctcag  31560
tcatgtgctt tctctatgac ggaattaccc ctgaagaaga tcccagtggt ctgtgagtat  31620
gcagatgtct ttcctgatga attgccaaga atgccactgg accgggatat tgagttcgcc  31680
atcgagttgc aaccgggaac ggccccaatt tccaagaggc cctaccgaat gccacccgct  31740
gagttggcag agttgaagaa gcagttgcaa gagttgctgg ataagggatt tattcgccca  31800
agcacttcgc cttggggctg tccagcactg tttgtgaaga agaaggatga aagcttgagg  31860
ttgtgtatag attaccgccc tcttaatgcg gtaactatca agaacaagta tcctttgcct  31920
cgtattgatg ttctctttga ccagttggtc ggggccaagg tgttttccaa gatagacctt  31980
cgctctggct accatcagat caaaatacga gcaagtgata ttccgaagac ggcattctca  32040
accagatatg ggctatatga attcttggtg atgtcattcg ggctgacgaa tgcaccagca  32100
tatttcatgt atctgatgaa ttctgttttc atgccagaat tggacaagtt cgtggtggtt  32160
ttcatcgatg atattctggt gtactcaagg aacgaagaag aacatgccgg gcatttgcat  32220
gtagtacttc aacgtctgcg agatcaccac ctttatgcca agttatccaa atgtgatttt  32280
tggctaaagg aaatcaaatt cttgggtcac actatctctc aggctggaat agctgttgat  32340
cctgataaag tgcaagaggt gatgaactgg aggccaccaa cgactgttcg ccagattcgg  32400
agttttctgg gattggctgg ttattaccga agatttattc cggacttctc tcgaattgcg  32460
aagcctatta ctgagttgct gaagaaagaa gtcaaatttg tgtggagtca gaagtgcgaa  32520
gatgccttcc atgcattaag gcagcatctg accacagcac cagtattggc gcaacccgac  32580
agcagcaagc cttttgatgt atattgtgat gcctctggca ccgggctagg ttgtgtcttg  32640
atgcaagaca accgagtcat tgcttatgcc tcaagagcac tcaggcctca tgagcaaaat  32700
tatcctactc atgaccttga gttagcagca gtggttcatg cattgaagat gtggaggcac  32760
tatctaatgg gaacccactg caacatcttc actgatcata agagccttaa gtacattttt  32820
actcaggctg atctcaacat gaggcagaga agatggctag agctgatcaa ggattatgac  32880
ctggaggtac attatcaccc agggaaagct aatgtggtag cagatgcctt gagtcggaag  32940
ttgcagtgca actgtattct gatggattct cgtgttaaca ccttgtgtga tgagttgagc  33000
aagatgcaaa ttgaagtgat tccttctggt tctttgtctc acattgctgt tgagccagcc  33060
```

```
ttgcaagacc agattatcat ggcccagctc agtgacaagg gagtgcaaat tatcaagaag  33120
aatctccatc agaaggttga gaagtataat tgtttccgcc aggatgagaa gggtgtgtta  33180
tggttcaaaa gcagattggt aattcctaag gaccaggatc tcaagaagaa aattttggat  33240
gaggctcatc tctccaaatt ctctatgcat ccgggaagca ccaagatgta ccatgatttg  33300
aagcataaca atccccaccc ttttcctata agtctcaccc ttcgcttcac cctgggagga  33360
ctctggcccg aatctcggga cgagattcct ttaagggggg aaggctgtga caccctagtg  33420
tcacctacgg tttctcttaa aaatgccaaa ccaagaacca ttattttatg tgaaccaaag  33480
taagcatgag gatcaaatta acttaggaat aaagaattcn nnnnnnnnnn nnnnnnnnnn  33540
nnnnnnnnnn nnnnnnnnnn nnnnnnnnnn nnnnnnnnnn nnnnnnnnnn nnnnnnnnnn  33600
nnnnnnnnnn nnnnnnnnng ggtgctaatc atgaaccagt ccagagcaac actatccgat  33660
ggccattgcg tccggtcgca cgagagacgc gtgcggaacg tcccgtagga gcggccaacc  33720
ccccattttg cagctagcag ccgtccagta gggacagccg ccgagctccc cgacatgtct  33780
ccttcgggac cgggcttcta tttcaagctg cgggacggtg cggtcaatcc atgtggacac  33840
catgcgagtt cgcgcttcac tatctgggct ggggacccac ctccatcaat ggtctgcatg  33900
acgcaggata ttccatcagc catggtgcag tggaatccgt tccagaggat ggcctctgca  33960
ccaaacgctc gccaaggtaa cagaagcaat ccaggcccat cgggcgtgat ctcccatcga  34020
tccgtatcga tcctttgaca tgaaaaggca atcacgggct cacgcttttc ggagtgtaat  34080
tcaggctccc gggtgcagct ttttgcgcgc ttgcggcagg gggcatctgg tggacatcaa  34140
atgatatggg cttgcttggt ccagggaacc ggcagcacct gctgtcccga gatcagttgt  34200
gatgctatgt catccgtcga tagtcggagc ttatccagct cggatcaggt gatacgcttc  34260
cctttcggag aggtttgagt ttcagacctg gtgctcagtt atgataaaaa gggtcggcag  34320
tgagagaaac cccgaaaact tgtcaatcga accaattacc ttatttactt ttcctgccct  34380
aggagtagat gtagcatagt tctagttgta gtcttccaca tatccacctc cacccctatt  34440
cgactctacg tcgtctagat ccgtcttggg tggcctgccg atcccaagac gaccctagga  34500
tctcacccct cccggggggc aagatctagt tgtccatcca agacttcttc ctcgatttga  34560
tctcttaatt cctaggcgac tccacgtcgt ctggggacgc cccgggtgac ctgtcgaccc  34620
ggagcacctt aagatctttc cccccagggg acgagatcta gattccagca aggagtagga  34680
agacgaccct gtcgccaggt cgcggaccgt ccggcccaga gctgcggacc gtccggtgtg  34740
acgcagggaa gacaccgctc ctgcgcccag gtcgcggacc gtccgaccca aggctgcgga  34800
ccgtccggcc caaggctgcg gaccgtccgc gcctgaccag agggcaccgc cacggttctt  34860
gttgagtgtt tggcgctcca aaaaggcgtc aacagtagcc gtcacatcat ctattgtgtg  34920
gctatgctta agtgtgcctt gatataattt agaataagtc gagtctctag aacgcggcaa  34980
tttttaaaag taaacagaag ctgaatttat tgattgctgt tttgggctgc acgcactgtt  35040
ttagttgtgc tgtttgtttg ataaaccaaa tcatgttttc tgtagaaaag tcatatagaa  35100
gagttgtaga tgacatgatt atcttgcttg tactaaaatt tgacagccat aaacctgatt  35160
gtttaggagt tgtgcttttc acaagcccag cacctgaatc tgtcaaattt ctgaacatat  35220
ttcagaaatt gcaatggttg cttaagttaa tgttgaaatt agttattggt ggtcacaaga  35280
aagttgtaga taactttatt atcgtacttg tgttaaaatt tgacaggcat aagtctaatt  35340
gtttaggagt tatgtttttt acaaattcag taactgaatc tgtccacttt ctgtacagat  35400
ttcagaagct gcattgtttg cttaagttaa tgttagaatc agcccttgta gattataaga  35460
```

aaagttgtag aggcttttct tatcttgctt gtgttaaaat ttcataacta taggcctgac 35520
ggtttaagag ttatgaattt tacaaactgg ttgctgtgtt ctgtccaccg tcagaacaga 35580
tttcgaaaac tgtaatattt gatttagtta aacctggaat cacttcttgg tgattatgaa 35640
agttgtgtag tacttttgct aagattttca aaaagtctta gatcactctt tttggtggtc 35700
tgaagattaa gttacatgtg tttgaagtgt gaagactgaa tctgtccagt tttggacagc 35760
acagccttca tagtatattt taaccttgat acatgctaaa ccagcctggg atgtttataa 35820
ataatttgta gaacatttaa ttagctttcc agaaagtcta ggatcaattt gtttggatgt 35880
ctgaatcttc agttatgaat ttttaaaatc acaagtctga atctgtccaa atctggacag 35940
agctgttgtg attgcacttt ttgaccttgc taagtgttta atcatgctgt gatgaaaata 36000
ccaaaattgt agagcacttt ctaaactttc cagaaagttt tagtttgcta tttttggatt 36060
aatatttgaa aagttattat taaaacaagt aactgctgtg ctgctgtcca aaaaatctgc 36120
acgtgctcaa atgaatattt agttcaccat tttggctaaa aacgcttagt tagcacttaa 36180
cggacataga cttgtgatgg ctaaacttag gttaacatgt gttccatgat taatgtgctt 36240
gcttgctata gttgattgtg atagaggagt ccatcgacat tgatgcatcg gtcctttatt 36300
aaacttgtgt ttgtgatgct tttgtgtgat caatagaaga actaatgaaa agccgtagca 36360
actaaataaa tgcttgtaca tatgatatcg tgttgcgttg gttaattgta ggtagtgatc 36420
attgtctttc cagtggtagt gtttacgtgt gcccaatgac acataaataa ctagtgtttg 36480
cgtatagttg ttgcagtgtc ttactaatta atgtttagtt cgccactgtg tcttggtata 36540
tcttatgtta cttttattat attcatacat atgcatcttg cacctcatat aggaccgaga 36600
gatgatgatc gagccagtga tgtggtgcca accacaagat gccgttgatg gacgacctaa 36660
agaatggact taaccagtgg atgctcgcca agcgagtacc tcccccagca aacactacct 36720
aagtgttaaa ttaaaggcaa gccccggttt tatgcataac tgttatatat atgctatttt 36780
actgcactta atgtttgtag gcttgtacca tgcacttaag tgtaggagtt gaatgaaacc 36840
ctagttgcat gaactcagga ttccctttga gatggatact agtatgctag gttgagtagc 36900
tgctttgcta attagggatc tcggtagaag tcgagtgatt tttctagcac tcgcgcgagg 36960
tcaggaattg gttgtatcca ctttgataac ataatggtga tggtctgtgg acacgggtcc 37020
atggggacgc gtggtctacg agatgaaatt ggaataagga ttaacgtgcg gatacctgtg 37080
tcaagcgttt gaacgtacta aacacatgcc gagaaatatg gtaaatcggt aagcctagta 37140
cctgagtgaa cctgcccgca gattgccctc ctcaggcgac ctgagacgtg gtctcccatt 37200
ccggttatgg tgggtacaag tgcggtcact gcacgacggc agtcggggtc agtgaggcat 37260
tgtacgccaa ggcggtgagc ccctttctgt tgccagggaa tcgatgggga cggttgatgt 37320
gtgtggggac ggagtgcccc tacatgtcgt gtgtttaggt ttaccttgca aggtttaaaa 37380
acttgattcg aatcgtctgc ttctcgcagc taatgagact tcttgatcca ttgtactgca 37440
ttgagtaata agtggaaatg aggtgattgg caaaagatgt tgtttgataa aaattcttga 37500
tatcatgtat gattagctag gtacacatct agtcaaaaag gatcatacta aaacttgaaa 37560
agctaaaact tgattttaga ctcagctagt gcttttggca aaccaaaccc ctcagccaaa 37620
cagctgcatg tctagaggta gagaagtaga ctcctcacac cgggtaagtc tagttgagta 37680
atgtatactc agccttgctt gtggcataat ttttgcagat attcattagg atgattggtt 37740
gatggtgtga cttggcctcc atccctacca ccgggataga tggtcgagtg ggttactgct 37800

```
tccgcaagag aggaccagga ggagtagagt ggccaggctt cgccatgtta ctcggttctt  37860
ctccgttagt tatttctgct gcattaaaat ttatggttat tatttctgaa actccgataa  37920
tgtaatcact aatgatactt attaaatttg tggtattatg ttttattgta tttctctgtg  37980
tctcaccttc gagtgagcta gtggtattcg atcctggata agtggcttta tcggactaga  38040
tccgagggac tgacggttta ttcctattta agtgtggtct agcctctaag gcgggacttg  38100
ggcacttaag tttgaataat tcgggcggtt ccgccacagc tggtatcgga gcgaatacca  38160
tcacagagaa gtcaataagt catgattacc aaccttttct aaaagtaaaa cttgctagaa  38220
accaatgttg gatagatgtc aggacgataa ggatagactt aggacgtgaa gccttaggaa  38280
atagatgggt agctaggtgg ctatttatat aggccataaa ggctactact actattaata  38340
aggatgctgt agaagcaacc gaaaaagtag ttaggtctga gaagacgact agaatgagca  38400
tgcatcatga ttgtcgcatt ataattgtct tttgtgcacc aacatgcttc tctcaccttt  38460
attcaaataa taaaaaaaat tgtgaataat gtgctgtatt gctaggaact gcaaaaaaaa  38520
tgtcttatct tgtgtgtcat gatagtcttt actaggttat gttatgtgct tctcttgtct  38580
tgctatctag gtagtattgt aattgttcaa ccctttttgc aaaacatttt gttgcttgtt  38640
ctgttcataa aaagactcct ccaaacaacc ttgagtttag caagtgaacc cgcttttaaa  38700
aaaatgcttg tgttggcgtt ttctagccct tgtgggtttt acccttgaag ttacacctgc  38760
acagcttgta gattcccata gcttgactcc tagatcgacc aaagcttcct tgtgcactgg  38820
ttacgtcaaa aaaaatttgt tgtttggtgt ctagttgcgc aaaccctatc aaggccatgt  38880
ttctttccat aaattccttg cccctaaaac ttcatagcat tcctgttgat catccagctg  38940
atcttgttgc ctacctctcc tttcgcatgg atctagtgat ctttttcctt gtgaatcatg  39000
ttgtgacctt atcatccgaa tctctgatct ttcatgattc tgccctatta tcttgttatc  39060
tactataacc cgttctcaag tatcgaatgt tgatctacct aagtctctca attctggtca  39120
ttctcatact cgttctctga ggatcatgac gatgtttatc aactttatct ctaaacagtg  39180
tatccatttg gttcaaggga tgttgttgtc atcttgtggt tctctcatgt ctctacaagt  39240
tcatcaacat gatctctgga gtgcttcctt ctcatatcaa atctcgtact aatcgctggc  39300
ctgctaatcc ccgtgatgat cataaaataa ctctatgagt tgaagaaaat tctcatgtga  39360
tgatcttttg ccaataatct ctgcttcaac tctgatcaca ttcttatttt ctgagccata  39420
ctctcatggg ctccaactat cagtgctatg tgaatttctt attggttgcg tttggtaatg  39480
atgtcatgac taacgactga tggtgccgcg acgaaaccga gagcctacta tggtgcacac  39540
atggttgagc tgctcggcac gcgctagtat cgcggttaat agtcgtgatc cattacgaga  39600
ctatactgat gtgctatttt tttgtggaca ctctcagaat gatcgctgca ttttgtctcg  39660
atatgtcgcg atattctaac caaatctgtc tccagtatct tgtcagatac cctctcatga  39720
atttgcatct atcttcagtc tgggagttac atgcttctcc acccataaat atcctcattc  39780
gaatctcggg acgagattct ttttaagggg ggaaggctgt gacaccccag gtgtcagttt  39840
cgtgttacgt cgcgagattt atcctaatct cggatgctca gtaaaaattt ctatttctcg  39900
ctcgcgtatg tccctgatta tccagattat tcattcacgt ttcaccgaat tcggagttac  39960
tcagtctcac agaaggccaa ttttggagcc tgttaaaact tttatcgtcg gcacaaatgc  40020
gaactcaaaa atcattctcg aattataaac ctcatctgaa gctcattaaa tcaaactctc  40080
gacgactgtt atttgatctg tgtccgaatc caatttctcg atgttcgatc gatgtccaac  40140
tattttaatc cgagtccata ctcacaaacg aaataatcaa tatgtcgtcc tctaatcaaa  40200
```

```
tcttactcga ctcagcttag catctctgta tccaatccga tttcaaaatc aacatcggca  40260
acgattttta tatatcacga ttcgctttct ccgactaaaa atccaaaacc gatcaaatct  40320
caggacgatt tattttcgat ttacgcgtag ggaattattt tcaagcgaaa tctaaacaga  40380
ctctcggccg agttaatcgc gcaaccttcc gttcgtccga actcttttcg ctctgtttct  40440
cagtagcgac gaattccgca ggaacatttt tagtccggaa aatatttagc gcgacccaat  40500
ttagtgtttt gggccaaatc cagtccagcc cattcggccc ataagaaacc ctaccctaat  40560
ttctcctcta taaatatggg cttccctccc ttgcattctg aaaattttcc atttccaccc  40620
cagccgccaa cacccttctc ttcctcctct accattttcc agccgtgggc tccttcaagc  40680
acgtagagct ggagctcctt ccccagcgcg caggggcttc catggccggg cgttccttcc  40740
ctccagcgcg ccgaagctct tcccgtggcg tcctctgcct ttcttcttcc ctgcttcaca  40800
gcagcaaggc caccagcagg ctccctgctc cccgcgcccc cagccatggc atccttcact  40860
cccctactgt ttttctccca gggcgcagca gcaaatccca tgcagcggct ccatggccga  40920
gcgccctgcc cggtgctcca gccggcctcc tctgcccctg ccattttcca caggagccga  40980
gctcctacct gcagcaggcg ccccctgctc tttcctatcc gcgaccaggg agcttcagct  41040
ggcgtgaaac ttcacttgcg cacggcggcc agcaccctct ccttgggctc caacagcttg  41100
gatgccgaac ccctttcttc cttcccctgg ccgagctcga gcttcccatg gcgccattcc  41160
tccctctctc tgttgtacat agcgccaagc agcaactcca ttttccctgc ccgcgcccaa  41220
ggtcggcgac cagcctcccc ttccctgttc ttgctgtggc cgagccacca cttccccagc  41280
cgtagccctc tccccctcca ttgtttcagc gcctgaaaca aacacctggc cgccatccac  41340
acttgtgctc gatgaaatgt gcagcagccc cgacggctcc gcgcgctgac ggcttgctgt  41400
tttgttgcgc agtgagcagc acgccgtgat gccgccgtgt gttcgctgtt tttgcgcagc  41460
cccaaacgtc gtcgtcgttc accccggtga gaccgcgacg ctccttgttc gattccgcat  41520
cgatgttatt ttcctatgat taattatgta tgtgtgttgc tttgttttat ttttgtggag  41580
gagagaaccc cgtgttttgc gaggagaaag caagtcgctt aacgctcgtc ggatgtttgg  41640
agcgatgcac gaatcggaat caccgtcatt cttgcaaaca tcgtttgggt ttgtttatgg  41700
tgagccgatg catgtcgctc tcgatcgact cgattaatca ttttgtatgg atgtgtgtaa  41760
aatgttcgat tatgcgcatt ggtaggatca tgtttgcgat tggagaacaa gaggttaatt  41820
gatgtgcgcg atttgtagtt gtctaattat gttttggtcg atgatgtgca tgtggttata  41880
tgtgtgtaaa agtataattt tataaatgga cgcgtgtagg gaagaaaatg aaatacaaaa  41940
gaactcgagt atttttattt tgataggaaa atatgcgatg cgttgtttga tgcgaaaact  42000
aagttacaaa atgtggattt tgttttggaa aatgcatcga tgtgtttatg tgaaaagtgt  42060
atttgtttta agcaatgtga tgggattcgt aattttagag gggatatatt tattgatgtg  42120
acgagtagtt tagagaatgc tagtttgcgt agaggatgta tcgttaagac atgagtgtcg  42180
gagtccattt atactagtgg tcgcgccaca tggattgaag tgtctcgagt gcacgccata  42240
atatggttgt atgcgagaca gggttatgcg tacgatgagt ttagtaaaaa ttccatcggt  42300
gtcagttgtg ttaagttgaa gtttatttgt gcgtataaag tagtaaggta tttaatgctt  42360
acgactctta atcgatggta gaaattgtct tgacttaaat agagaggtgg tgacatgcca  42420
gagtagtcat cgctttctct atatttatag gtcaagtcat gacgatgcgt attatgcgtt  42480
cgttaaaatt atgtttcgta tatagtgtat gattgtgctc acgatttcga gtagacactt  42540
```

```
caaataagtc aagtagcttt gtaatgcaag atgtgtgatg aagttagttt gttttaggat  42600
atgtgttgaa atgctccatt cctgtgatag acatgtaggg ttatttcaaa acgggtcgat  42660
gtgtgtgatg atgatattca tgatttaagt agatgtcctg aaattatgtg gcgaagctta  42720
ggttaagttg caagcgatgt ggaaatgttt tcgtaaagat atatgtggaa tgtgaacgag  42780
tcattcaatg tattcggtat gtcgtgtagt ggtggtatga aaaatgagtt aggaatcgat  42840
cggctaaatg ccaagttcgg ttagagttat tttgatagtt gggattgtgg ggtgaagtga  42900
tggcatgact acgtagctgt tggacaccaa aatgagcgga cggtccggcc catgggcccg  42960
gacggtccgc gtgtcccgag attagattaa ctcggatgtt tatccttatc tcgtgcgtgg  43020
ttatccatct aatcacgtgg gagtttgttg gctatctctt aggaaaaggt ccagacctcc  43080
tcccctataa atataaaggg gtacggccga ttgagaaccc ccgaacacat tccaatcgaa  43140
ccaattacct tatttacttt tcctgcccta ggagtagatg tagcatagtt ctagttgtag  43200
tcttccacat atccacctcc acccctattc gactctacgt cgtctagatc cgtcttgggt  43260
ggcctgccga tcccaagacg accctaggat ctcacccctc ccgggggca agatctagtt  43320
gtccatccaa gacttcttcc tcgatttgat ctcttaattc ctaggcgact ccacgtcgtc  43380
tggggacgcc ccgggtgacc tgtcgacccg gagcacctta agatctttcc ccccagggga  43440
cgagatctag attccagcaa ggagtaggaa gacgaccctg tcgccaggtc gcggaccgtc  43500
cggcccagag ctgcggaccg tccggtgtga cgcagggaag acaccactcc tgcgcccagg  43560
tcgcggaccg tccggcccaa ggctgcggat cgtccggccc aaggctgcag accgtccgcg  43620
cctgaccaga gggcaccgcc acggttcttg ttgagtgttt ggcgctccaa aaaggcgtca  43680
acatactttt tggcgactcc gctggggaag aagttgcaga tctacaaaat caggcttaca  43740
tggccgattc taaagatctc aacagtgctt ctccaaacag caacacaagg ctgactaatt  43800
tatcggccgc tgagcataaa aaattagaag atgacatgaa gaaaatagac gaggaggccc  43860
accgacaaaa ggatcaggtg ctcaaggtgg cggacaagtg gtacctctcg cacttcaagg  43920
tagactgcca ccagaagacc gtccaagaga gggagataaa cgccgagtat atgttagccg  43980
tgctgcaaca gctccccaca ataggtgatg ccaggtcagc cgatgatatt ccatctatta  44040
aaatttcttt tgataatcgg attaaaagta tcacggagga tatagagagg atgacacatg  44100
catttgttaa aactcacatg cctaattttt taaaacataa attaggcgat gagaacgatt  44160
actctagatt tcnnnnnnnn nnnnnnnnnn nnnnnnnnnn nnnnnnnnnn nnnnnnnnnn  44220
nnnnnnnnnn nnnnnnnnnn nnnnnnnnnn nnnnnnnnnn nnnnnnnnnn nngctgagca  44280
atattgccaa gagcggtagg accggtcgtc caaagagaat aaagtttatg actatgttca  44340
gaaataaaga aaggatcata taaacaagcg cgattaattc acgataggag tcctcatttg  44400
ttgcagagca tgggggcagt agacacgatg agggacgccg agtgataaga aaaaaggaga  44460
taagccgctc aaattcgcca ccccaatcgg tttgcatagc aatgattttt ctattgagca  44520
agcgctcaac aaggctttga aattctttga agaactgaaa cacctcagac ttatggcgaa  44580
gaagatagat ccaagtaaat ttactataat catcaatgaa gctgacataa taccttttat  44640
tacaaaaaga atcaatggcg ggtccccaga catcgaaaaa caccagatct aaaggagcag  44700
cagactgact ggtcgactta ggataaggca actgatgggc cttagcacga aggcaggcat  44760
cacaaacata ctccgaggaa tctaagcctg aacacactaa attattattt ctaatgacac  44820
gagcgacaat atcacgcgat ggatgaccta atctgcaatg ccaacgctca taggatggct  44880
ttattgcggc aaggtcgtgc ttctgggtag gtgtgcaaga gatgtcaatg ggtagaggcc  44940
```

```
accccctacat ggtccgcgca ccagcacttg cctcgtggcc tgatccttaa tcaagaaaaa  45000
gaacggatgg aactcaataa aggtgttatt atcaagattg aaacgatgaa tggaaacaag  45060
atttttatgg gtatgaggga cacgaaggac atgatttagg tgcagagggc ggaaggaagt  45120
gggcaaaaca gaataaccaa tgtgagtaat ctccatacct gcaccattag ccgcccgaat  45180
ctgatcattg ccattgtaac gatcatgctg ttagcttttc cagctcgtcg gtgatgtgat  45240
cagtcacacc gaagtcaagg taccagtttg gatcagcagc agtggaggat gatgccatgg  45300
ccgcaacccg atcatcagga gtgaattctt cataaaagcg gtaccaacag atattagctc  45360
tgtgaccgac tttaaggtag acctagcagc gtggacaaga ctggccaccg gattgatctg  45420
tcggtggacc ggaactgcgc ctgaagtagt tgttgttgct gtagttgccg cgcgaagacg  45480
acgaaggata gccatggcca tttccgcgcg agcgtccgcg accgtgattt tggagaacca  45540
tcatgccagg agccaccacg gccacgagta gccgtattgg ctgatccatg agcagcgtac  45600
ctgccgccgg actgcttcgc aagccgaagc tcatagctga gcatctgcga gtataacttg  45660
gcagaggaga ttggctcgac gcaagtgacg atggacgaca caagcgggtt gtagatttct  45720
tcatcaaggt cggtgaggac ataggcgacg aactcctcat cgcccagagg ttggccggac  45780
gccgacatct catcggcata actcttcatc ttggattaga atccggccat tgtggtcgtg  45840
cctttcttcg tggtggcgag cgcaatgcgc gtgttgacag aacgcgcacg tgtgcaagat  45900
ccgtacatag ccgcgaggga gctccagacg tcggccgagg tcgtggctgt cgtgacaccc  45960
atcaagacct cacgcatcag agaggagagg atatatccca gcagcgcttg atcgtgagtc  46020
acccagttga tgtactcggg attgggcgtc tccatatagg cgtcgttagt catcacagag  46080
acagtcttaa ccagcatctt ttctttgccg atgagcagac cgtagagctg tgcagattgg  46140
atgggcggta ggatttgggc actccatagg cggtagttgg ttttggtgag tttttcggtg  46200
accgggatcg agaaggagga ggggatggtg gtggaatttg agaatctact cgccatgatg  46260
gatgtgttgt agaggacctg gctatggtac catgtagatt ggaatggttg atgtggcaga  46320
accgcccgga ttattccagt ttaagtgccc aagtcacgcc ttaaaggccg caatgcactt  46380
aaatcggaat aagccatcag tccctcagat ctagtctaat aaagccactt atccaggatc  46440
aaataccaca agctcactcg aaggtgagtc acagaagaaa tacaataaaa caggaaaacc  46500
tcaaattaaa gtactggagt tattacataa atcagagttt ttcaagtagc tgagaaaagt  46560
tcacaaaata aactgcagcg gataatcgat gtcgtcaaaa gcgaggaata gggcaaggcc  46620
tggcccacta cttctcctgc tcctctcctg ccggagcagc atcccactcg accgtccaac  46680
ccggtgacag ggttgtaggc caagttacac cgtcaaccat atcctagagc gtacctgcaa  46740
aaattatgcc acaagcaagg ctaagtatac taatactcag ctagacttac ccggtgtgag  46800
gaatctactc ttctacctct agaccatgta gctgtttggt tgaggggttt ggtttgccaa  46860
aagcactagt tgtatctaag gtcaacttta tcttttccat ttctagtatc attattgtag  46920
ctaagtttgc tctttctaag catacatggt aacaatcatt taatacaatc aacaagttat  46980
ctcatgtaat cctcatttca cttcttactc aatgtagtac aaggggtcaa gcagtctcat  47040
tagctgcgag aagcagacga ttcaaatcga gtattaacct tgcaaggtaa acctaaacac  47100
acgacatgtc agggcactcc gtccccatcg attccccttt cgcggccagg gctcaccgcc  47160
ttggcataca atgctccact gacccgggct gccgccgtgc agtgaccgca cttgtaccca  47220
ccaaagctag cataggagac ccagtctcag gacgagtgag gagaaaagtc cgcgcccagc  47280
```

```
ttcaatcagg tactaggttt accggttacc atatttcccg acatgtgttt agtacgttca  47340
aacgcttgac tcaggtatcc acacattaat ccttaattca ttttcctgtc tcatggacaa  47400
ggcatccacc ctggatccaa gaccatagac catcatagat cccattatca agatgaatac  47460
aatcaattcc tgacctcgcg cgattgctag aaaaatcact cgacttctac cgagatccta  47520
attagtaaag cagctactcg acctagcata ctagtatcca tctcaaaaag gaatcctgag  47580
ttcatgcaac taagggtttc aagcaactcc tacacttaag tgcacattac aagcctacaa  47640
acactaagtg tagtaaagta gcatatataa attggttatg cataaaaccg gggcttgcct  47700
ccaaatgatg gggctgcggg gagatcctcg atggcagtct cgggagcttg ctcctggtct  47760
tcctcgtgga cagctccttg ctcagggatg agcacgtact ctccatcagc gaggttgcaa  47820
tctaatgaat gcaatgagta agatatatgc atggcatgat atttaattta gcaattaaaa  47880
tttgatggag gatgatcaat ttaatagggt agacctcatt ctcactactg gagatttttg  47940
gtggtacact caccaactta gggtcaagtt gattactgaa tggttaaccc atttttagtg  48000
ttctactgat tttcttcttt atatcttatg gatattttaa caagattctt agctgccatg  48060
ttggggtaat acttattaat ctttctaatt cctcccttct ttattccttt tatgctttta  48120
aggtgggttt gaactacaag atagcttaat aaatttccag aaattctgca aacattacag  48180
tagcttctta ctggtgtata attttctgtc tcaaaatttg gggcttaaaa agtgaggggt  48240
tctctctgta caaaattagc aagtgttagg gcaaagggga tgttttgaac tacaactctc  48300
ttttaacagt gggttattct ttaagactta tttttgctgg catttagatg ttataacatg  48360
attttgtaca aattttcagc cactaatatt tattagttat tttattatga ttttctaaag  48420
tttctagcca aaggggtgct ttctactacc actatacttg aaaaatatca aacaacagat  48480
ttccaatttt tcctatcttc ttctttgcgc aagagcaatc attctaaaat ttggtaacct  48540
ttttcttaag ggaagggtgg taggaatttc ttgaattaaa tggccttttt catgaagtag  48600
gggcaatggg tattactttg tagtttgaat aggttttgca ttttgctctg gtgatctatt  48660
ccattaataa tctagtaaaa atttattcgc ccattgttgc acacttttg gcttgcttat  48720
gatttaattg gaatatggct caatatcaag ttttatttgt tcaacccact taaaatgatg  48780
ggctaggtat ttatcatttt tgtagtggtg tcctagtggt tacaagtcta ctgaattttt  48840
cttaccaatt ttgaaattgt tctcatattt ctaataattg cccttctagc tttattagtg  48900
cctaataaaa catttcacct tgaatttgct ctggactagt gttcctttta ttttttctag  48960
gttcttcatt acttaagtgg gctaggaaaa atatttgcat ccactgttca ttattttcta  49020
gtacctttct tattttccta agttttggac aattatggct tttaatagat aaccctgttt  49080
aaatcttcaa tactagggtg ctcaatattt ttaaacagtg tctaagtggg gtttgaactt  49140
ctacaaattt tcttaagttc agcacagaag cataactaat tttcttcatt ttaataaggt  49200
ttggtcagtt tctttaatta attctaaact ccaaaattta aaacagaaag cacagggttc  49260
aatattttta tgtgatagtt cataatattt tgaatctagt aaaattggtt tgactaaatt  49320
tggttgaata tttctcaaga tacaaatttc ctaagtcctt tactgaattt aaaaagaata  49380
aacagaaatg gataaaggaa aaagggtttt gcactggggt ccctggcgaa aggttttaag  49440
tgtattacag acaggtcctt ggttcactat ttatctgagt ctatgactct gcagaaaacc  49500
cctagggttt tgcgaaatcg aacccgcgat ccttccccta atggaatagt gaccgcagtg  49560
gaagaaaagg gcggaggggc ttaccggcgg cgaggttgct ccggtgaggg gtcgggtgag  49620
gtccggggtc tctggcgatc acgtcgaggt gcggatcgtc ggcggtggtg gtcggagtag  49680
```

```
gttggtccac gtgcacaggc ggggagctcg tcggcggcga gggatccggc ctgctcacgg  49740
cgcgatagtc caattgaaca ggttagggag cttcaccaga ggtcaaggaa gacatgcgcg  49800
cgaggaattt gagaatgaat caccggattg ctcggtctac gcgcggctgc gggtgaccga  49860
agtccagcga ggtcgatcct gggtctctgg tgaaactctg ttgggtccga ggacttggaa  49920
agcttcacgg gccactggcg aagctaaccg agtgactggt gcagcttgga agtggctgga  49980
gggagctggc cgcggtggcc gaggctcggg cggtgatggc gggcgggggga gagctcgcgg  50040
agttggagtt cttgctcgag gcgtgaggcg gagtgaaggg cagaccattg tgcatccagg  50100
gtacttatag gcgccctcag gcatggctga gtgcaggcgc gggggacaga agccgaccgt  50160
gcatggcgcg cgatcagagg gcagccagtg cgcggccaag cgcttgagca cgcgatcgaa  50220
cacgtggaag tgtgattctg cccgagttca aacgcctgtt ggccgaccaa aacgtgcata  50280
tcttgccaag gatcctgtgt agcgtctctt caccgtgcca aggtcttcct gtcgtgtgtg  50340
agtcccgagt gaagatatgg cctaggtgag aagatatgat ggcctgaaga tagctctgtt  50400
agcactgtcc aaaccgagac aaaacttatg tcaagtcgtg tcaaacgatt cgggtttgat  50460
ctcaaacttc tccaaagtgt tcctagggta ttttggcgcc actttgatat ttggactttg  50520
tggattcgag ttttggaaaa cagggaacac atctgaactt tgggaaaggg tttgaaattc  50580
agttttctga atttctgaat ttccccatag ggcattggtt catgggctga tttgggattt  50640
tggaaaattc aaatggcaaa actttcttac tatattttgt tggttattta gtgcactaaa  50700
actttgttat ttggttctta ccaaaatttt gtattttccc aagtcttttc ccaaattccc  50760
tttatgtgct taaatggtcc acttaggatt aattagggtt tgagagttct tcttaccttg  50820
aggtgcatgg catgattaag gagaatttct taagatgaaa aagactcact taaaccttgt  50880
tcttaatttt tttatgttca ttcctctttt tggttcacat gtgataatgg ttggagtcaa  50940
ctctaggaaa aaccctacgt gacactgggg tgtcacagtt gaagcgttct accacactag  51000
gtggccaagg attgcatgtt tatataggca caaggctggg tgcaacaact tatacaataa  51060
ggtaaccgaa tcaatctatt gttggagttt ctatctatgc acagcctaga atatatcctt  51120
tctatctata ggagattgat tcggttggct aaagattaca tgcacaagaa acttctagaa  51180
tatcgtaact tcatctaaca gttacaactc atgaacacaa tataatattc tgctatagaa  51240
atcatgattg tgtaattgtt tgttgcaata tgttatattt gatttatggt tgatctgttt  51300
tatatcagct agggggttga gctagattat ggaaatgtca ccagcaggat cacaatcaac  51360
actgatcatg gtctctcaag ttacaacaag caatatgcaa gggactcttc aaaaaagtga  51420
tgccttaact accagcttca gaggctagcc atgcttcgag aataccaaca acaaaatgtt  51480
gatgaaaatc actgaaccaa cagtgacacc acaaagcagg aatgccagga ccacttctaa  51540
ggtatattct aactcacatt tgacagtaat ttgtgaaatc actcaaacaa cagaatacag  51600
ttcgcatgtt tgactaccaa tttgattttt tgtacactca tattttattc ttaaatctgt  51660
ggaagatgat atgaatctgc acatcatgag tgcagtttct gcaagttgct ttgcgaggtc  51720
aacagaaaca cagaaaactg atggtgatgc ccttatacct aaggtaaatt tttcttctaa  51780
ctgaagcctc ttttcgcctt ggaactcatt cctttagcta atactaagag atgatggaaa  51840
ttctctcatt ccaatgtcac cagcagtatg atgctaattt ctgtcaaatg ttcttgccat  51900
attaatctta gcatttcatt gaatttacat agtacttgaa aataaaataa catgagacac  51960
catgtctaaa atataatggt aatctatgtg cttgatcgcg ggttgctaca gatctttgat  52020
```

gctagtgtga acctggggtg gttctataac cgggacacag aagagtggta taaaaaaggt 52080
aacctttgta acgcaaaaat ctacttattt gtttccataa tacatatgag atcttatcct 52140
attgttgatt gcaatctact gataggactt acccaccctt cccctgccaa aaaagggcaa 52200
agaaactctt ccaagattgt gactttgaag atgttgatgg tgatgcctct gccaaagatg 52260
aggctgagct agggtactca gcctatctat ttctcaattt catcatattt ataattgtca 52320
atgcaattgg agatgataaa aatgctctat tttacataaa aacactgatc ttgatttgga 52380
ttgtttgcta aattgtctct ttatttgatg gtcttggcta tacttgtctc tggtagattt 52440
ttgcatcaca gggtgagcga tgcttagcca ccaagaaaga aaaaaatacc actacctctc 52500
tggtttcctt ttgtattgga tatttatgtc tcttgtcttt gtttttgctc caaagtctta 52560
tacattatcg ttgactgcat tttagtcctt ctcccaaaaa ttcacttgtt agtggcgagg 52620
atatcataat aattgttggg gacttgttct caaatgctat gagttaagaa caaggcaaca 52680
caaaatgtta aatgttaatg tccttcgtcc ttcgaagcat tatttccctt aggagataac 52740
gatcttcgga cgaaggttat gaaggacata ccttcataag tatgacatgt ataaacaaag 52800
gatgaagctt atgaaacata ggaagacaac ataaacaatt atataacatc ttaacataaa 52860
tatttattat taaataatca taagaacata agaataatat caaattacat ttataccttg 52920
agcttgatag aaggcaaaga taaaagtaag atgcgaaagc gtgaacagta cgagggtact 52980
gttcacctat ttataggcac agggcgcagc ctgtgtaaat ttacattcat gtcctctaca 53040
aatgattaca atcataacat agattatcat gggcccaatt cgtcatttca tctttaagtc 53100
ggtgcatctg gaaatacgct acgaagctct ctgattggta gcttcggcat cattcctgtt 53160
ctggccttcc gaaggtgttt tttctcacag gaccttcggc gacgaaacag acccccaaca 53220
gtagcccctt cacggtgcca gatcattttt tgtaacgagc tcgacccgtg aaaaattctt 53280
ttaggcttcg gaatgccgaa ggtccgaaaa acaccttccc tgagctcgtt gtcgagaaac 53340
gatttaagta ttcctagtgc gaggtggtcc caccatagga cgggtacgca cgatctggtg 53400
attctccttc tcgcgccatg cggtccaccg ttcagtgaat gcgagcgact gttcggcggg 53460
tgcaggtggc ttgatgattc accttcccac ctgtagcact atataaacag acgggtaggt 53520
gtgaagttac cacagcattc attactatcg tattgttgtg ctgctgaaaa atttgaccat 53580
agccgaagct tattcttcgt attctcaatt agagcatcgt cttgttcttt agcttcgtca 53640
aaagagggag cttcggcaaa atcaaaaagt aatcaacttt gtcaaaaccg cgagaaattc 53700
agcatcaaat ggccagggtg cgttcaactg ctagagtcac acgcgacggg gaggaggccg 53760
aagctgccga gaccgcccca atctccgaag taatgagaca atcaggcttg gttgtgctag 53820
agggtgtttc tgacgaaggt gcacgtgctg ccgaaaccga gcaggctgac attgaagaag 53880
gtgaggctga tgaagaggag atagattatt tcgtcatgcc atctaaaccc agccacttgg 53940
aatttggaaa gtctaccgtc tctgaggccg atatgcccat gatgacgaag ctaggctact 54000
tcggggaagc cgagaagaag ctaattcgtt ttggcggaga ataaatcact ccgaagctag 54060
aaaatgatga ggtggtagtt ttcagaagtt tctttaaagc aggactgagg tttcctctgc 54120
atgggatgat tgtggatgtt ttggaaaatt tcgaaattta ttttcatcag ctgactccta 54180
acgctatcgt taggcttagc gtctttatct gggctcttcg aagccaagga gtggagccgc 54240
ttgccgaagc cttctaccgg gtgcacgaac ttcactatca gacgaaggct agagaagatg 54300
gactgcacga gaacttcggc tgctataatt ttgcctaccg caaagacatg aagacaccgt 54360
tggttagcta ccgcaccaaa tggacaaccg gttggaaaac tgaatggttt tatgttaagg 54420

```
ttgatgagaa gaaggagaag ctagtttaga gcccactggg cctaaccttc gggttaacta  54480
ggccccagtg tcgcatgacg ctgggatcat catgcccaga tgttgtgggt gaatttagag  54540
ttgtgtccga gcatatcgga actagggatt tggttcagga atacttagcc aatagagtat  54600
tcccaacgtt aaaggaatgg agtatgccga agcttaaagg agagaagaaa aagaatgaac  54660
ttgttcgact gccctatcat tttaagttca agaaacactt caaagaaccc tgccaagaat  54720
ggttggatac gatcgaagtt atgtgcaatg aaatattggg caattatacg aagaaagaag  54780
atcaattgat gacggcagcc ttcggcaccc gaccgaaacg aaggctaaac cgagtaatga  54840
acactctgaa atttgaatac ccagactatg aacggttaag taaaggtgcc gaagggccaa  54900
aacaaaaaag agctgtcagt gttatgcaaa gacaagctgc cagaatgata aaagaagatg  54960
aaaatttagc aaaaaagaaa aaaaatccag ccctgagccg aaggtggccg tttcgaagaa  55020
aagaaaagct acagctccga agccaaaagc tgatttagaa gaagttccct caacaccttc  55080
tgccactgac gcagaagaaa ttttaaaggt aatgaccgaa tctctaccta ataagctaag  55140
cccgctggga ccggaactga tgaagctttt acagaagaag aagaaggaac cttcggttgc  55200
cgagaagccc gctgaaccaa aaaagcgaag gattattact atcattgagg ctattgaaga  55260
aacaccatcg tcggcctcag tgctaaaaac agcagcagcc aaagctgctc cagccgaagc  55320
ttctacttcc gaagttgcag cagccgaagc cacaaatttg gaaaacacgc ttactgacat  55380
tgatgaaata attttgaata tggctgagga agaaactgct gcagctgctg aggaaacccc  55440
ggctacagtg cctgaaaagg agaaggagct tgccgaagat gcttcggaag aaagaaatat  55500
caactttcaa aacataattg gacaagagtt gtctaaggct aaaaaagaag agctgaggga  55560
ctttgctata tcttgcgggt accagccagg ggcactgctc ttcggtggta tagacgaaga  55620
gagcttaggt tgcctttgag accggactgg ggagaaagtt gtcaggactt tatcgaaaag  55680
tgttggtttt ccgaaactcg aagccgatct cagcagatac cgacgacagc atatcgtcgg  55740
tagcctattt tattctaact ttaaggtaaa attcttccct taacttttta ttgttttgat  55800
atgaagatgt tttctgatga aggttatttt gtcagagcct actactaagc aaaaccttga  55860
ggatgcaaca agacctcgag gacaagaaaa acgaagttat aattgagggc ttagagaaca  55920
agattaaaga tcatgaagct gccctagaaa agaaagactt cataattcaa acaatggaag  55980
gttcactggc agaagctcaa gccgagatcg ccagactgaa tagtgaactt tccatgaagt  56040
caaaaagcat tgagcaagag aagaaagatt tcgaaacaaa actcgaagct gaagttgaaa  56100
aaagttcaaa tctgcagaaa tcactcaaag atcttcaaga agcatggtct tgtacttgtt  56160
tggtgacttg tgcccgcttg atttctgctg agagccgagg caagggctga gcgcttggtc  56220
acgtacccga gccccccctga caagggggtt gcccatgccg tagtggttga cacagtactg  56280
agtatggcaa aaagtcccta agtaatatgt cagctctgca gtatatggtg acgttgggcg  56340
cctttccgtt gtggatattg aggctagagt cgggctcggg cgaggcagaa gtccgcccga  56400
ggtcacgacc gagcccgctc cagtattcgc ggggagcagg taaacgaggc cgggctcagg  56460
cgaggcgaag tttgtcccga ggccgaggtc gccttcagcg aggcagagtt cacgtccgag  56520
agccatcctg cactcttgtc gtattgtacg tcccatcagg ggttgacaga tggcatgtgg  56580
gaatagtggt cgcatgcgtc atcgtagttg gtgaagcttg acaggaccgc ggtcttgttg  56640
ctcctgttca cctgcaactc tacgtggggt aggtatgcat attgaatgct cctgcccccct  56700
gcagactttg gttgagtctt gcattggggt tgtcttcctt acccgagatg tgctcgggcg  56760
```

```
aggcaaagac ttttgttctg ggagatggag cctcggccgg gacgagaatt ctccctagag  56820
cacaccatgt ccgagggcag gcttgagcga agcggaccta tggtgacccc tgagcggggc  56880
ctcgggcgaa gcgcggttta tgatcctttg atctcgggga atgtgtcttg aaggtggtct  56940
aagggttaag tgtgttttag ggcataatc tgggtacccc taattatgat acccgacaag  57000
tggtattgat tagaaatggc tcaacaaaag ataatggatg gttgaacaaa atgtgaatgg  57060
ctgacatcag ttttatagtg tatgtgtgta tatatgtgtg cacacataca atatctctcc  57120
tttatataac ataaacagac ataagttata gtggtagaag acgctcgctt gtatcgaaag  57180
agcatggttt gaatccccac gtcctatttt ttgtgtggtt attccacgcg cctggctggc  57240
tggttcgtga ctaggtcgga cccatgcaac tggctagccc aaatttcccc aattatttca  57300
taaccaacct ctcatttgtt ctcctttatc tttatgttat taggatcaat catttgtagt  57360
tatcaaggtg aatcacttgt acttttatca aggtcaatca ttatagttac taggatcagt  57420
cgtgtattta tcagggtcat tcattgtaat tattagggtc attttatttt ttaccagggc  57480
cagtcattgt attttatcag gatcagtcat tgtacttctt ctattagggt ctacatttta  57540
tcaaggtcag ttattgtagt tatcaggatc aatcattata ttttaatcag tgtcagtcaa  57600
tgtatttatt aaggtcaatc attgtattat taggatcagt cattgtattt atatcagagt  57660
cactcattat agttatcaag gtcggtcatt gtattttttt attagggtca gtcattgtat  57720
ttagcaggat atttttatca gggttagtta ttgtattatt aggttcaatc attgtatttt  57780
atcagggtca ctcattatag ctatcaagat aagtcattgt atttttttatt agagccagtc  57840
atcgtattta ttaggaccaa tcattgtatt tattagggtc ggacattgcg attaaataaa  57900
aaattgaaaa agatatagca tgagtgtcta gttttgttcg aaaatctcat aaacacgaat  57960
ataacaaaaa aagggatttt ggttttttat gcctatatat gcgggttgca tgactgcata  58020
cacgcatact cgctgagcgt ggtgccaaat agtatccact gcgtgccctg cgctctaacc  58080
ggatgctcta tccatcacac ctcaataacc cattgagcat ccctcccccc acacgcctgt  58140
gctccaatca gatgcttgtt tgactaatag caaggagatt ctccaatatc atgctaagaa  58200
tagctaggat ttccagaaga agatgtcatt cgtttgatga gaaataaaaa ggaatatcga  58260
gaattcgcgt ggctaaagct gaagcaacta ctttcgaagt aacagaaaga aaagcaacga  58320
ttggagtggg ggagtcagag tcaaaaagag aattcctcgc ttctttctct catgcaaaac  58380
cgtgcatgag actttcatct cgcacggctt ctaagtgata aaagaaagaa gtccaatcgt  58440
gataaaaata attacatcaa tttaatagaa aggaatgact taaaaacata ttatgagtct  58500
ctggatgaat aaactattgg atgacttaaa atatttgtaa gaaagtcttg taacaactgt  58560
tgacaatatg aaatatttta aataagtcat aaaatgacta aatgacatgt gatgactaga  58620
attgtaacag aatgacttaa tttaacataa tatgtactga atgacctaac gagtgaatga  58680
ctgagaaaaa aatagaatgt tttaaataat catcaaaatg tcttaaatga ttaagaaata  58740
cttgattatc ttataaaata actagtacaa cacatgtgcg ctgcgacgac atacaatcat  58800
atttgatacc aataaaaaaa taatatcaaa tatcaaagtg aacatatggt ccatatatca  58860
gatactaaac tgataaaaac aaatattacg cttttatctt agctaaaata tcaggaaagg  58920
tatgagttga aagaagcctg actacttttt taaagcttgc tcgatggctt gtcctccttt  58980
aggtagtgag gtggttctat gtgggagcgc tgcgctgcgt ttggcttccc tgtcgtgtta  59040
gacttgtgtg gtttctcacg gtccatctat agataaaatg tccactagta gggatttggg  59100
tggttttcac agcctatcta tagatgccca ctggtatgcg gattgatcta catgcttcgt  59160
```

```
gcatggcgta tgacgaccat cgaagctagt attttatagt agtggagatt ggaatgaatt  59220
aatgcaaaat gagaagtatg agaatgttga gtgacttaaa tggatcacga tagaaactgc  59280
attggggcct gaaacagcta ctaaacaagc gatcgcaata tcttttaaaa ataagttgcg  59340
gtccaaaaaa aagtgacaat ctatactctc taagcaggct cccaaccatg tcaattcact  59400
acaacaattt caatgaatta acatgagtga accatagttc tcacagggta tttcgtcgtt  59460
acaggtccat tcgattagaa gtgggtcatt atatggtggt ttgcactgta tctttccccc  59520
gttatcaatg agagccaaac gtgtacctta caacctttca gatgtcaatt ggaacttgca  59580
aaaaaaaata gaaagaattt tgacttgttg gggatttaaa ctagaaagca tctaggcccc  59640
tggttggttt tagtgattaa tgacaacgta attttatatg tgactaacat gtgttttgca  59700
gaggcaaatg gtaagttagg tcgcattaca ggtagatgta ctacaatggt gaaaacaatc  59760
ccggagataa aaacttgaag caacggctaa agcgacgaaa caaaaagtga aggtcttcgt  59820
attccgagtg tcaaggagtt gcggacactc gtgatatagt taggtctttt attttgtttt  59880
agccgtacta taaagagggg ttgtcgataa gtagtttgac caaaagagtt ctagtgtagt  59940
gttggtgcat attcacactc acatatagtg ctaggtgtaa ctctagaaca tactcacaag  60000
ttagaacaaa aaccaaattg aaaaaacagc acaaaacaga agctagggtt tctggctttg  60060
gggcaccgga ctgtccggtg caccctttgc cagtgggccc agcctggccc agggaagagg  60120
gttccctgcg cgcagaaacc cgagagcgcg ctgttcgtga gttgaatttt agaggcacac  60180
cggacagcgt atcggactgt ccggtatgcc atctgtccaa cggctagctg tcagaactag  60240
ccgtttgagt cgaccgttgg cgcaccggtg gcacaccgga ctgtccggtg cgcccatgcg  60300
cagcagattc ctggtaatgg ctagttggtg ggtgagggct atttataccc catccaccta  60360
ccatattgat ggtcttgctg cccacattta ctcctacaca ttggtagagc attgcaagca  60420
ccacaaagcc tagtgaggtg acttgagaat cttaatcccg catttggacc tcattaacgc  60480
tagcgagagc cacctagagc acacaccgca tgcattaggc ttctcttggt caagtgaaag  60540
tctatggctt attactcttg gtgatcggca tcacctagac ggcttggtgg cgttgggagc  60600
tcggtgatca ccgtggagat cttgttggtg acccgactca agtttgtaag cggtcgtgag  60660
ggatccaccg cgccggagtg gcaaaggatc atctcgttgt gagcacttgg ttcttgcgat  60720
gaccaaggga gagcgatacc cttacgcagg tgctccaacg aggactaggg gagagtgccg  60780
actctttgat acctctagaa aaattggagg agtcttctaa accttgcttt acattccgca  60840
cttaattcaa gtattttaca ttgtgtattt gtttagcaag tatttgaagt attatcttag  60900
cattgttgta tttctagtat tattctctta gtgctagttg tcggggtgaa gttgggctct  60960
tgcttagatt ttagttagtg ttgattttta gaaaagccca attcaacccc ccctcttggg  61020
catcgtgatc ctttcaattg gtataagagc cttgttgctc ttagattagc ttaaccgcta  61080
gagtaacgat gtccggtggg gatggacctt ctcccgtttt ttatggtgac gattttccat  61140
attggaaaat tcgtatggaa gcatatttag aggctataga cattggtgtc tacaaagccg  61200
ccacacaaag attccccgaa cctagagatc ccacaaatct tgtaggtgaa gagttgaact  61260
atgagaaatg gaatgctaag gccaaaaaca ccctttttag aggcctttgc aaagatgtgt  61320
ttaatagagt tagaaaccat aaaaattgtc atgatttgtg gatggacata tgtgctctac  61380
atgaaggaac tagaattgag cgtgaggaga gatatcacat tgctatgaga aaattaaatt  61440
cttttgaaat gcttgctaat gaaaatgcca atgctatgta ctcacgtctc aatattcttg  61500
```

```
tagaggaagt aaatggcttg gggcttacac aaatttcaca accggatgtt gtgaggaaga  61560
ttctcagtgt cctcccaatt gataaatatg gacacattgt cactgtgctg catcagatgg  61620
atctttcagt tgtcactcct acacaaattt tgggaaagat caatgcacat gagatgtaca  61680
tgcacatcaa tgacaaggat gagtcatctt acaagagaaa ggatttggct ctcaaagaaa  61740
atcaagaaag agaaggaaaa gctaaagtac aagttgagga ggaatcctca agtgacgatg  61800
atcttaatgc taacattgcc ttgatggtga ggaagaccac caagatatta aagaagctca  61860
acagagaagg catcaaattt gactcaagaa agaagaaatt cttttccagc aaaagaaagc  61920
ccatttctta aatggattgc tacaactgtg gagagcttgg tcatcttgct catcaatgta  61980
acaagtccaa gaagaacaag ttcaagggca agaaagaaga tgacagtgat gatgagaaaa  62040
atgaaaagag attcttcaag aggaaggatg gaaagcataa gaggttccac aaaaagaaaa  62100
atgtaaaggc atacattgtt ggtgattggc tcactgacat tgagtcgtca agtggatctt  62160
cttcaagtga agaagaaaat gatgaaaaag ttaccgccat cgctggggac ttctcttcac  62220
caccaccatc tccatcatcg acttctcacc tatgcctcat ggctagaggt gaacgaaaag  62280
tacaaaatga taatgatatt attgatgata gtgatagtga tagtgatgaa gaatttgctt  62340
caccttccta tgatgaacta gttgacttgc ttaatgaata cactcaactc attaggaagt  62400
caaaagctaa atgtgataag ttgaaagatg aaaatgaatt tttaaatgct aaatatgaca  62460
tagttatgaa agctagtaat gaaatgaaag aagaaaacaa aactatgtca tccactgtaa  62520
atgagcttac atcctcccta aaagatgcta aggataaatg tgacaagtta aatgaagcta  62580
atagggagtt gaaagataga ctagtaaaaa ataaggaaga ctatactaag attaaatttg  62640
atcatgataa tcttcttgtt gaaaatgaac ttttatcttg caatacacat gaggctatta  62700
accctgttgt taatattgat gtagcaacct catgtgatga tttgagtcaa ggtgatcaaa  62760
ctagtctaca tgatgaattg actgaaaaag ttgaagtctt gacattagac aaccaaaaat  62820
tgaagagata cttgactgat gcaactacta gaggaaaggt tgccattgag aacaatgact  62880
tcaacaatga gttggcagtg gataaagaaa ggcttaaaat gaggtcaaga aacttaagcg  62940
tgaaaatgaa catcttgcaa caagtgtgca aaagttcaac aagggccaat acctctaaaa  63000
tgaattgctc atgaacactg tcatgaaaaa caacaagagt ggtattggat ataactcctt  63060
tgtgcaaaag aaagctacaa ctcaatacaa gccaaatcag actcataagc atatcaaatg  63120
ctttgagtgt ggaaaagaag gtcatttttc ccacaactgc aaagccaaac caccaactcc  63180
cctgccaaag cactcaagac catttgcctt caatgctcat tatgttttaa gaagtagcaa  63240
atggaaaagt cgaagttaca ttcctaggtc caccaagcaa gagtagacct agacaaattt  63300
gggttgcaaa gtccttgatt gagaaagtca ctggtcctat gcaatatagg gccctcaaaa  63360
cttaggcttg atttgtctgt ggatgtaggt gaactacaag accggtggga gccattgggt  63420
tattgatagt ggatgcacat aacatatgat aggcaaccca cggatgttca cctcacttga  63480
tgataatgtt gatggacaag acaaaatcac atttggggac aattcaaagg gaaaagttca  63540
aggacttggc aaggtggcaa tttcaaatga tctatcaatt tcaaatgttc tcttggttgc  63600
acctttaaga ttcaacttat tatcagtggg tcaactctgt gttcttggac ttcaatgctt  63660
attcactcca acagaggtta ttgtatcaaa aatggatgat gaataaatgg tgctcaaagg  63720
atttagatac aacaatctct acttagtgga tttcacctct gaagatgcag acttaagaac  63780
ttgcctcttt accaaagcat ctcttggatg actatggcat agaaggcttg cacatgttgg  63840
aatgagcaca ctgaagaaag tattaaagaa ggacatggtt agaggactaa aggatgttat  63900
```

```
atttgaaaag gacaagcctt gtagtgctta tcaagctgga aagcaagttg ctaacacaca  63960
tcctacaaaa gctttcatgt caacatcaag gccactggaa ctacttcaca tggatctatt  64020
tggaccaaca acttatgcaa gtgctggtgg caacctctac tgtctggtga tagttgatga  64080
tttctcaaga tacacttggg tgtttttctc catgataaat ctgaagttgc atctatattc  64140
aagaagtttg ccaagaaagc tcaaaatgaa tttgattaca agatcaagaa gattagaagt  64200
gataatggaa aagaatttga caacaccaac attcatgaat actgtgatga gattgggatc  64260
aagcatgaag tatcagcaac atatacacct caacaaaatg gagttgttga aaggaaaaat  64320
aggaccttga tcacacttgc aaggacaatg attgatgagt ataacacacc ggagaggttt  64380
tgggccgaag ctatcaacac tgcatgttat gcatcaaaca ggctatttcc tcactggcta  64440
cttgcgaaga ctctctatga actgctaaat gggaaaaagc cagacgtctc attcttttgg  64500
gtgtttggat gcaaatgcta catttacaag aaacgccatc acctagggaa gtttcaaaga  64560
cgttgtgata ttggttttct tctgggttat tcattaaagt ccaaagcata tcgagtattc  64620
aatcatgcca ctggcgtggt agaataaaca tatgatgtgg agtttgatga gactaatggc  64680
tcccaaggag cacttgaaaa tcttgatgat gtaggtgatg agccacttaa ggaagccatg  64740
aagaacatgc caattggagc tatcaaacca aaagaagatg aagaagaggt gcaaaacatt  64800
aataggcctt cttcatcaag tgtaccacaa gatgatgaaa aagatgagag gcatgcaaat  64860
gaagatacat ttgtctctca tgaacaagca aggatacaag ccgaagatgt tgatgctcca  64920
ggatcttctt cctaagtggt tgataggaga aactcatcac tgcttcaagc acacccacaa  64980
gatcaaatca ttggaagtcc ttcacaaggg gttattactc gatcacataa acatgcttct  65040
tttattgaac atcactcctt tgtttcttgt gttgagccta ctgtatagat gaggcgctac  65100
aggatccgga ctgggtgaat gccatgcatg aacaactaaa caacttcacc cgtaaccaag  65160
tttggaccct ggagaagcct ccacaagatg caaggatcat tggaacaaag tggttattca  65220
gaaacaaaca agatgatcaa ggcgtgattg tgaggaacaa ggcaagactt gttgcaaagg  65280
gcttctctca agttgaaggt ttagattttg gagagacctt tgcaccggtt gctcgacttg  65340
aagccatctg tatcctactc gcatatgcat catgctatga taaaaagctt tatcaaatgg  65400
atgtaaaaag tgcattttta aatggcttca taaatgaact tgtatatgtt gagcaaccac  65460
ccgggtttga agaccctaga tatcctaacc atgcttatag gttgtccaag gcgctatatg  65520
ggttaaagca agctccaagg gcttggtatg agcgtcttcg cgacttcctc atcaaaaagg  65580
gcttcaagat caagaccgtc gacacaactc tattcacaaa gaaacataac ggtgatattt  65640
tcatttgtca agtatatgtt gatgacataa tctttggctc gataaatcgc tatcattgca  65700
aggaatttgg tgagttgatg tcgaaggagt tcgagatgtc aatgattggt gagctgatgt  65760
atttcctcgg ctttcaagtg aagcaaatga aagatggtaa cttcctctca caagagaagt  65820
ataccaaaga cttgttgaaa aggttcaaca tggagatcac ttgttgaaaa gatggtaact  65880
ctctaccgtt ctatgattgg tagtttattg tatcttattg catctaggcc cgatatcatg  65940
tttagtgtat gcatgtgtgc tagatttcaa tcaaatccta agaaagctca tatttgcgct  66000
cttaaaagaa ttcttaggta tctcaagcac accccaagtg ttggcctttg gtatcccaaa  66060
ggagctactt ttgatttaat tggctattcc gattcggatt atgccggttg caaaattgat  66120
agaaaaagta cttctagggg tgtaatttgc ttgggagatc actactatta tggacatcca  66180
aaaagaaaaa tagtgttgcc ttgtcaaccg ccgaagcgga atacattgcc gctggtgctt  66240
```

```
gttgcacaca gattttatat atgaaacaaa ctcttctaga ctatggtgta gttctagaaa  66300
aggtaccttt gttgtgtgac aatgagagtg ctgttaaaat tgctaataat cttgtacaac  66360
actctcgcac caagcacatt gatattcgtc atcacttcct tagagatcat attgctaaag  66420
gagacattat tttagaagaa gtgaggtcgg aagatcaatt agaggatatt ttcactaagc  66480
ctcttgataa aacccgcttt tgcatgttga gaaatgaatt aaacatactt gatctcagaa  66540
attttattta aagatctcaa aatagtgttg tcaagcctgc attgcatatt taaatttctt  66600
gtattgcatc tagggcttgt ctaacctagt taagataacc gccaacaaag cgagtgaaaa  66660
aagcttaact cgggctcaaa cttgacaagt cttagcttta agcttttagt acttaaattc  66720
ttatttacta tgccattgtt ggttcttgag atatgcatgt agtactacac ttaggggggg  66780
agtattcaaa actcaaatta ttcatgaaaa cccctagttc aaagctaaaa tgcaaatctc  66840
accatttgac tattttctct aaaaattgac tagcctatgg caaaatattt ttgaaaatta  66900
tgggaaaata tatgaggggg ccaataccta tcccaatagg tgttcttttg tatgattata  66960
agttgggatt tggtttggtt aaaatttaga tcgaaaaatt tgaaaatttt caaaatcacc  67020
tctgcctagg ctcaccggaa agtccggtgc actgtgcact gtnnnnnnnn nnnnnnnnnn  67080
nnnnnnnnnn nnnnnnnnnn nnnnnnnnnn nnnnnnnnnn nnnnnnnnnn nnnnnnnnnn  67140
nnnnnnnnnn nnnnnnnnnn nnagctactc gacctagcat actagtatcc atctcaaagg  67200
gaatcctgag ttcatgcaac tagggtttca ttcaactcct acacttaagt gcacggtaca  67260
agcctacaaa cattaagtgc agtaaaatag catatatata atggttatgc ataaaaccgg  67320
ggcttgcctt taatttaaca cttaggtagt gtttgctggg ggaggtactc gcttggtgag  67380
catccactgg ttaagtccat tcttcaggtc gtccatcaac ggcatcttgt ggttggcacc  67440
acatcactgg ctcgatcatc atctctcggt cctatatgag gtgcaagatg catatgtatg  67500
aatataataa aagtaacata agatatacca agacacagtg gcgaactaaa cattaattag  67560
taagacactg caacaactat acgcaaacac tagttattta tgtgtcattg ggcacacgta  67620
aacactacca ctggaaagac aatgatcact acctacaatt aaccaacgca acacgatatc  67680
atatgtacaa gcatttattt agttgctacg gcttttcatt aattcttata ttgatcacac  67740
aaaaacatca caaacacaag tttaataaaa ggaccgatgc atcaatgtcg atggactcct  67800
ctatcacaat caactacagc aagcaaacac attaattatg gaacacatgt taacctaagt  67860
ttagccatca caagtctatg tccgttaagt gcttactaaa gcgtttttag ccaaaatggt  67920
gaactaaata ttcatttgag cacgtgcaga tttttaggac agcagcacag cagctacttg  67980
ttttaatcat aacttttaaa atattaatcc aaaaatagca aactaaaact ttctggaaag  68040
tttagaaagt gctctacaat tttggtattt tcatcacagc atgattaaac acttagcaag  68100
gtcaaaaagt gcaatcacag cagctctgtc cagatttgga cagattcaga cttgtgattt  68160
taaaaattca taactgaaga ttcagacatc caaacaaatt gatcctagac tttctggaaa  68220
gctaattaaa tgttctacaa attatttata aacatcccag gctggtttag catgtatcaa  68280
ggttaaaata tactatgaag gctgtgctgt ccaaaactgg acagattcag tcttcacact  68340
tcaaacacat gtaacttaat cttcagacca ccaaaaagag tgatctaaga ctttttgaaa  68400
agcttagcaa aagtactaca caacttttat aatcaccaag aagtgattcc aggtttaact  68460
aaatcaaata ttacagtttt cgaaatctgt tctgacggtg gacagaacac agcaaccagt  68520
ttgtaaaatt cataactctt aaaccgtcag gcctatagtt atgaaatttt aacacaagca  68580
agacaagaaa agcctctaca actttcttat aattgacaag ggctgattct aacattaact  68640
```

```
taagcaaaca atgcagcttt tgaaatctgt acagaaagtg gacagattca gttactgaat  68700
ttgtaaaaaa cataactcct aaacaatcag acttatgcct gtcaaatttt aacacaagta  68760
cgataataaa gttatctaca actttttgt gaccaccaat aactaatttc aacattaact  68820
taagcaatca ttgcaatttc tgaaatatgt tcagaaattt gacagattca ggtgctgggc  68880
ttgtgaaaag cacaactcct aaacaatcag gtttatggct gtcaaatttt agtacaagca  68940
agataatcat gtcatctaca actcttctat atgacttttc tatagaaaac atgatttggt  69000
ttatcaaaca aacagcacaa ctaaaacagt gcgtgcagcc caaaacagca atcaataaat  69060
tcagcttcta tttactttta aaaattgccg cgttctagag actcgactta ttctaaatta  69120
tatcaaggca cgcttaagca tagccacgca atagatgacg tgacggctac gtagtcatgc  69180
catcacttca ccccacaatc ccaactatca aaataactgt cggagaccat aattaggggt  69240
accctcaaga ctcctaattc tcagctggta acccccacca gcataaagct gcaaaggcct  69300
gataggtgcg attaagtcag ggatcagtcc attcgagcga ctcgatcacg cctcgcccga  69360
gcctagcctc ggacaagggc agccgacccc agaggatttc cgtctcgccc gaggcccccc  69420
tctaacggcg gacacatctt cggctcgccc gaggccctgc cttcgctaag aagcaaccct  69480
gactaaatcg ccgcaccgac cgaccaagtc gcaggagcat ttaacgcaaa ggtggcctga  69540
cacctttatc ctgacgcgcg ccctccggca gagccgaagt gaccgccgtc acttcgccgc  69600
tccactgacc ggtctgacag aaggacagcg ccgcctgcgc cacttcgact gcagtgccac  69660
ttgacagagt gatattgaca ggaagccagg ccctgccaaa ggcgccatag gaagctccgc  69720
ccgacccagg gctcggactc gggctcagcc ccggaagacg gcgaactccg ctccgcccga  69780
cccagggctc ggactcgggc tcagccccgg aagacggcga actccgctcc gcccgaccca  69840
gggctcggac tcgggctaag acccggaaga cggcgaactc cgctctgccc gacccagggc  69900
tcggactcgg gctaagaccc ggaagacggc gaactccgct ccgcccgacc cagggctcgg  69960
actcgggcta agacccggaa gacgacgaac tccgcttcgc ccgaccccag ggctcgggct  70020
cgagctcagc cccagaagac gacgaattcc gcttcacccg agcccagggc tcggacaccg  70080
ccctggactt ttgccgacga ccttccgcct tggcccgacc cagtgggctt cggactcgac  70140
cctcggccat ggaagatcca ctccacctcg gcttcggagg agcctccacg tacccccaga  70200
ctagggcgca ggccagccac gtcaacagga agcgccatca ttaccctacc ccgagctgac  70260
tcggaccgta gagaacaaga ccggtgtccc atctggctgt ctccaccaga taggcaatga  70320
tggcgccccg catgccctgt gacgacggca gctctcagct ctcttacgga agcaggagga  70380
cgtcggcaag gacacaaccg ctccgacagc tgtccctccg ccaggctccg ccgctcctcc  70440
gacggccacg acatcacact agctgggttc caagatctct ccggctgcca cattggcatg  70500
tactcagggc actagctctc cctcgctaga cacgtagcac tctgctacac ccccattgta  70560
cacatggatc ctctccttgc gtctataaaa ggaaggacca gggccctctt agagagggtt  70620
ggccgcgcgg gacgaggacg ggacaggcgc tctcttgggg ccgctcgctt ccctcacccg  70680
cgtggacact tgtaaccccc tactgcaagc gcacccgacc tgggcgcggg acgaacacga  70740
aggccgcgtg attcccacct ctctcacgcc ggtctccggc cgcctcgctc ctttcccccc  70800
ttcacgcttg cccacgcgct cgacccatct gggctggggc acgcggcact cactcgtcgg  70860
cctgagggac cccccggtct cgaaacgcct acagttggcg cgccaggtag gggcctgctg  70920
cgtgttgacg aacagcttcc cgtcgagctc cagatgggca gtctccaaca acctctccaa  70980
```

```
cccgggacgg tgctccgttt cgggagtctt gagttcatgt ccctcgacgg cagctacgac  71040
atgatactcc ttccaccgcc gcgcgacaac gacgatggcg gccgacagcc cgcccgccgg  71100
cggcggaatc gacgacgtct tccccgcgtg gcggaagaac aacattcgag ctcgccccgt  71160
cctctccccc gccaacggag gaggaggcgg ggcaacaaag gccaagcagg aggccgcgcc  71220
tcgtcggctg tcgagcgagt cgacgtccct agcaccccaa cggggggcgc gttgggcgtc  71280
gacctcgcgt ttgagacaaa ggcgagcgcc gtctccccgc gacacgccaa tcccgagcaa  71340
gtggacgacg ccagcgcgct tgcgaaaagc ttgcaggaca tcgccctcgt acctgaggcg  71400
acgatgcggt cagtcctcga cgtgacttca tcgccgctcg acgaccaaaa ggtaccaacc  71460
gattcccatc ctacgtcatt tgtactcagc ctcaacccgt ctagcaatct tgctttggcg  71520
ggcgcccttg tagaggcgag tacaaaccct ctggggtttc gcttgcggtc gccttgggac  71580
cggctgacgg acgtctcgac ctacgggccc tctgggtccg aggaagatga cgaccccaac  71640
atctgttggg atttctctgg atttggcaac cctagtgcca gcggaacttc atgaccgcat  71700
gtgactactg cctctccgac tgttccgacg gtagccgcag cctcgacgac gaggactgcg  71760
gcccaagccg cgaatgtttc cacgtcgatc taggggggtcc ctccgaaggc aatcatctcg  71820
gcatgccgga ggacggtgct ccccctgggc cggtgcctcg cgctgacatc ccgcgggagc  71880
tagttgtggt ccctgttccg gcggggggtt acgacccaca gctcgagcaa gtccgcgggg  71940
cgcaggccag gatcgacgag ggagcaggag cgcttgagcc gatccgccgg gacgtcgggc  72000
aggcatgggc gggccaaccc ccggccggag aaatacgtca cctgccccag ggtctccagc  72060
accgcgtcgc cgatgtcgtc agggtcaggc caccacctgc atccagtggg gtcggtcaga  72120
acctggtcgc agcagcgatg ctcctccgcg cgatgccgga gccatccacc accgagggtc  72180
ggcgaatcta gggagagctc aaaaatctcc tggaaggcgc cacggtccga cgggccgaga  72240
gcactgcctc ccgaaggcaa ggataccccct cggaacctca tgccgcgact tcccgattca  72300
tgcgggaagc ctcggtctac accgggcgca cgcgcaacac cgcgcctgcg gccccgggcc  72360
acctcggcaa cgagcgccat cactgcgacc gtcgagccca cctcgacgag agggtgcgct  72420
gaggctatca ccccaggcgt gggggacgct acgacagcgg ggaggatcgg agtccctcgc  72480
ccgaaccacc cggtccgcag gccttcagcc gggccatccg gcgggcaccg ttcccgaccc  72540
ggttccgacc cccgactact atcacaaagt actcggggga aacgaggccg gatttgtggc  72600
tcgcggacta ccgcctggcc tgccaactgg gtggaacaga cgacgacaac ctcatcatcc  72660
gcaacctccc cctgttcctc tccgacaccg ctcgcgcctg gttggagcac ctgcctccgg  72720
ggcagatctc caactgggat gacctggtcc aagccttcgc cggaaatttc cagggcacgt  72780
atgtgcgccc tgggaattcc tgggacctcc gaagctgctg acagcagccg ggagagtctc  72840
ttcgggacta catccggcga ttctcgaagc agcgcaccga gctgcccaac atcaccgact  72900
cagatgtcat cggcgcgttc cttgccggca ccacctgccg cgacctggtg agcaagttgg  72960
gtcgcaagac ccccaccagg gcgagcgagc tgatggacat cgccaccaag ttcgcctctg  73020
gccaggaggc ggtcgaggct atcttccgaa aggacaagca gccccagggc cgcccgtcgg  73080
aagatgctcc cgaggcgtct actccgtgcg gcgccaagaa gaaaggcaag aagaagtcgt  73140
aagcgaaacg cgacgccgcc gacgcggacc ttgtcgccgc cgccgagtac aagaaccctc  73200
gaaagccccc cggaggtgcc aacctctttg acaagatgct caaggagccg tgcccctatc  73260
atcaggggcc cgtcaagcac acccttgagg agtgcgtcat gcttcggcgc cacttccaca  73320
gggccgggcc acccgcggag ggtggcaggg cccgcgacga cgacaagaag gaagatcacc  73380
```

```
aagtaggaga gttccacgag gtccgcgact gcttcatgat ctacggcggg catgtggcga  73440
atgcctcggc tcagcatcgc aagcaagagc gccgggaggt ctgctcggtg aaggtggcgg  73500
cgccagccta cctagactgg tccgacaagc ccatcacctt cgaccaagct gatcaccccg  73560
accacgtgcc gagcccgggg aaatacccac tcgtcgtcga ccctgtcatc ggtgacgtca  73620
ggctcaccaa ggtccttatg gacgggggca gcagcctcaa catcatcaac gccgagaccc  73680
tcgggctcct gcgcgtcgat ctgtcctccg tccgagcagg cgctgcgccc ttccacggga  73740
tcattcccgg gaagcgcgtc cagcccctcg gacgactcga cctccctgtc tgtttcggaa  73800
caccctccaa cttcggaagg gagactctga cgttcgaggt ggtcgggttc cgaggaacct  73860
accacgcggt gctggggagg ccatgctacg cgaagttcat ggccgtcccc aactacacct  73920
acctgaagct caagatgccg ggccccaacg gggtcatcac cgtcggcccc acgtacaaac  73980
acgcgttcga atgcgacgtg gagtgcgtgg agtacgccga ggccctcgcc gagtccgagg  74040
ccctcatcgc cgacctggag agcctctcca aagaggtgcc agacgtgaag cgtcatgccg  74100
gcaacttcga gccagtggag acggctaagg ccgtccccct cgaccccagt ggcgacgcct  74160
ccaagcagat ccggatcggt tccgggctcg agcccaaata ggaagcagtg ctcgtcgact  74220
ttctccgcgc gaacgccgac gtcttcgcgt ggagtccctc agacatgcct agcataccga  74280
gggatgtcgc cgagcactcg ctggatattc gggccggagc ccgaccggtc aagcagcctc  74340
tgcgccgatt cgacgaggag aagcgcagag cgataggcga ggagatccac aagctaatgg  74400
cagccgggtt catcaaagag gtattccatc ccgaatggct cgccaaccct gtgcttgtga  74460
gaaagaaagg ggggaaatgg cggatgtgtg tagactacac tggtctcaac aaagcatgtc  74520
cgaaggttcc ttaccctctg cctcgcatcg atcaaatcgt ggattccact gctgggtgcg  74580
aaaccctgtc tttcctcgat gcctactcag ggtatcatca aatcaggatg aaagagtccg  74640
accagctcgc gacttctttc atcacgccct tcggcatgta ctgctatgtc accatgccgt  74700
tcggtttgag gaatgcgggt gcgacgtacc agcggtgcat gaaccatgtg ttcggcgaac  74760
acatcggtcg cacggtcgag gcctacgtcg atgacatcat agtcaagaca aggaaagctt  74820
ccgacctcct ctccgacctt gaagtgacat tccggtgtct caaggcaaaa ggcgtcaagc  74880
tcaatcccga gaagtgtgtc ttcggggtgc cccggggcat gctcttgggg ttcatcgtct  74940
ccgagcgggg catcgaagcc aacctggaga agatcgcagc catcaccagc atggggccca  75000
tcaaggactt aaaaggtgta cagagggtca tgggatgtct cgcggccctg agccgcttca  75060
tctcacgcct cggcgaaaga ggcctgcctc tgtaccgcct cttaaggaag gccgagtgct  75120
tcacttggac ccctgaggcc gaggaagctc tcgtagacct gaaggcgctc ctcaccaagg  75180
tgcctatctt ggtgcccccca gctgatggag aaaaagccct cttggtctac gtcgccgcga  75240
ccactcaggt ggttagcgcc gcgattgtgg tcgagaggca agaagagggg catgcattgc  75300
ccattcagag gctagtttac ttcgtcagtg aggtactgtc cgaaaccaag atccgctacc  75360
cacaagttca gaagctgctg tatgcagtga tcctgacgag gcggaagttg cgacactact  75420
ttgagtctca cccggtaact gtggtgtcat ccttcccccct gggggagatc atccagtgcc  75480
gagaggcctc gggcaggatt gcgaagtggg cggtggaaat catgggcgag accatctcgt  75540
tcgcgcctcg gaaggccatc aagtcccagg tcttggcgga cttcgtagcc gaatgggtcg  75600
acacccagct accgacggct ccgatccaac cggagctctg gaccatgttt ttcgacgggt  75660
cattgatgaa gacaggagcc ggcgcgggcc tactcttcgt ctcacccctc gggaaacacc  75720
```

```
tacgctatgt gctacgcctc catttcccgg cgtcgaacaa tgtggctgag tacgaagctc  75780
tgaccaacgg attgcgaatc gccatcgagc taggggtccg acgcctcgac gctcgcggcg  75840
actcgcagct cgtcatcgac caagtcatga agaactccca ctatcgcgac tcgaagatgg  75900
aggcctattg cgatgaggtt cggcgcctgg aagacaagtt ctacgggctc gagcttaatc  75960
acatcgctcg gcgctacaac gagactgcag acgagctggc aaaaatagcc tcggggcgaa  76020
caacggttcc ccggacgtct tctcccggga tctgcattag ccctccgtca agatcgatga  76080
ccctcccgag cccgaggcgc cctcggacca gcccgaggta cgctcggcac ggcccgaggc  76140
accctcagct caacccgagg taccctcggt ctccgagggc gaggcatcgc gcatcgagga  76200
ggagcgaagt ggggccatgc ctgatcgaaa ttggcagacc ccgtacctgc aatatctccg  76260
ccaaggagag ctacccctcg accgagccga ggctcgacgg atagcgcgac gcgccaagtc  76320
gttcgtcttg ctgggcgatg agcaggagct ctaccaccgc aatccctcgg gcatcctcca  76380
gcgatgcatc tccatcgccg aaggtcagga actcctgcaa gagatacact cgggggcttg  76440
cggccatcac gcagcgcctc gagccctcgt tgggaatgct ttccggcaag gcttctactg  76500
gccaacggcg gtggctgacg ccactagaat tgtccgcacc tgcgaagggt gtcaattcta  76560
tgcaaagtag acccacctgc ccgctcaggc tctgcagaca atacccatca cctggccctt  76620
cgctgtgtgg ggtctggacc tcgtcggccc tttgcagaag gcgcccgggg gctacacgca  76680
cctgctggtc gccatcgaca aattctccaa gtgggtcgag gtccgacctc tgaacagcat  76740
caggtccgag caggcggtga cgttcttcac caacatcatc catcgcttcg ggtcctgaa  76800
ctccatcatc accgacaacg gcacccagtt caccggcaga aaattcttgg acttctgcga  76860
ggatcaccac atccgggtgg actgggccgc cgtagctcat cccatgtcga atgggcaagt  76920
agagtgtgcc agcggcatga ttctacaagg gctcaagcct cggatttaca acgacctcaa  76980
caagttcggc aagcgatgga tgaaggaact cccctcggtg gtctggagcc tgaggacgac  77040
gccgagccgg gccacgggtt ttcacgccgt tcttcctggt ctacggggct gaggccgtct  77100
tgcccactga cctagaatac ggctccccga ggacgagggc ctacgacgat caaagcaacc  77160
aagctagccg agaagactcg ctggaccagc tggaagaggc tcgggacaag gccttactac  77220
actcggcgcg gtatcagcag tccctgcggc gctaccacgc ccgaggggtc cgaccccgag  77280
acctccaggt gggcgacctg gtgcttcggc tgcggcaaga cgcccgaggg aggcacaagc  77340
tcacgccccc ctgggagggg ccattcgtca tcgccaaagt tctgaagccc ggaacgtaca  77400
agctggccaa cagtcaaggc gaggtctacg gcaacgcttg gaacatccaa cagctacgtc  77460
gcttctaccc ttaagatgtt ttcaggtcgt tcatatacct cgcacccacg caaagtttag  77520
tcatcaagga agggtcggcc tcgcctcggc aaagcccgac cctccctcgg gggctaaaag  77580
ggggggaacc ccctctgcgt cgaaattttc ctcgaaaaaa ggtctcttct gccagaatat  77640
ctttcgtgct ttttgactac ttcgaaaagt ggatcctgaa aacgacggag tacacgtaag  77700
cagtcaaggc ggaccgagcc gagggactcc tacgcctccg ggatacggat acctcactca  77760
tcaccttctg cgataagtaa ctcgcgttcg gataaagtga ttccgcggac cgaacaagtc  77820
ttcatgttcg gaagttcttc tgccgaagca atccttcgag ccttctcgac tgagtcggtg  77880
gcagggcctc atggacgagt gaaagtacgt gtaagcggca aggccgaccg agccgaggga  77940
cttccacgcc tccgggatac ggatacctca ctcatcacct tccgcgagaa gcaactccca  78000
ctcacacaaa catccctgtt accgacaaaa aagtcaagat actcgaaaca agaggaaagg  78060
agacgcagct ttacaacaca gcgagggcgt gtattctggc ctcggcggct gcagaaggca  78120
```

```
cacgctacaa gacaatctga ccctacaggc tcgggtcttg acgctggaag gggcagcaa  78180
caccctcggc atcgatgaca ccttcagcga ggcccgacct agcctcggac ggcgacgcgg  78240
tccgaggatc tccgctccga aggacgatgt catcaccacg cccgggcaat cgctgccagg  78300
gacttctccg ggaatccggc ccgagcaggc ggctcggccg gttacccctg gggcctcggc  78360
cgaccatctc ccaagggcgc cagcccgacc tgaggcctcg gctgatcagc cccgacgtcg  78420
gtcccgccaa cggacaaccc ggctaggctc cgaccaacca ggtttcattt tcgagccaac  78480
tccgcctctg ttcacactga tatcgctacc cctggcctcg gctcgtcgaa gagcggccga  78540
ggggtccctt taactaagct agaggagcct cggacagcaa ggccgaccga gccgagggac  78600
tcctacgcct ccgggatacg gatacctcac tcgtcacctt gacacggggc gactcatgct  78660
tggtgaagcg gttcagataa tcaacagacg agtcttagcg ctcaaaaatg aggaaaaaca  78720
cggctccgtg ccggaattac atacatgttc aggccccgaa agccgcaatg aacaaaaaca  78780
ccggcattcg aagtgccatt acaaacggaa ctccggttcc cccctccgca ggtacgaaca  78840
gccccactcg ataggggtgg gcctacggag caacagaaga ctgacgagcg gctcgccgcc  78900
gcccgctctg actacgacga catgcaagca actgcaccgc cacttgcgcc accaccgcgc  78960
ctcctcgatt gcggaaccaa taccgcgact cgaggcgacc cagcgtgcga cccagcagcg  79020
ccagcctgac gcggcggtca acacggccaa aagtgggccg gcagtaatga cggtggcagg  79080
cgcgtgggag cagcggtcac gtcgtcagcc aagctcacgt cccatccggg ggcagcaaga  79140
gaaccccctc tcacggcgtg aagacaacgc gcccgtgatc cgttcctcga acggctcgcg  79200
cacgcgcaac ggctgccccg ccaactactc gcctcgtcgc attaactccg cggctggaca  79260
ggcggcgctt ctggcaggag cagcgggcga cacttcgcct tcgccgaaat aaccgcgcca  79320
aaaaaggtac gccgcgtcgt tcggtttcgt atccttttcc ctttttcctc tttctctatc  79380
tcttgcgaca gggaccggga aagggggata ccccgaaagg gatccttccc cgtgaaggaa  79440
ccaggctccg agcctcctta ctgatcagag gttcgaaggc tggcccccg aagggttcaa  79500
cagccgcctc agatcgcgtg ggccctacac ccactactgg tcagaggttc gaaggccggc  79560
cccccgaagg gttccacggt cgcctcaggc tactcgggct ccgtgcccat tactgatcag  79620
gggttcgaag gctggccccc gaagggttca cagccgcctc agacgccgag cgagggatga  79680
ccaggggtac gttcgataca taaccaaggc tcgggctgcg ctcctgaggt accctaggac  79740
atttccgaga ccagcgggag cgatcttgta atggaatccc atcggaggga ggcatcgagc  79800
cctcggaccc cgtcgccagg ggaccgggtc cggcagatca cccgcaggta cttttgggcg  79860
tgcctctggg cccctagccg accccctaacg aacggggcac ggacgtccac tcggattacc  79920
tgcttgcagc tcaccggaga caccatgttc ggcgcccatc gagggtaaca tggcgccctc  79980
cccctagtcc tccttgcgga aaggcgacgc aggggcatat gtaaaaaagc cgagtctgtc  80040
cctgatcgcc ctcttgccct gtgcagaggc tcaggggctg ctctcgcaaa cccggctccg  80100
gccaaaccgt tgacagcgtc aacataccag cccgagaact tgggccccga ccgtacaccc  80160
gggctacggc cagctcgcat gagggaacaa ccagaccagc cgaagcatta cgcaaggcat  80220
taagacctcg aaggagtgaa accactcctc cgaggcctcg gggctacac ccggcgggtg  80280
cgctcgcgcg cacccaccgg aacaaaatgc aaccgagaaa ggctggtccc ttgcaaaaaa  80340
gtgcgacgaa agcctccaag cgagtgctaa cactcctttc gaggctcggg ggctactgtc  80400
ggggaccata attaggggta ccctcaagac tcctaattct cagctggtaa cccccatcag  80460
```

```
cataaagctg caaaggcctg atgggtgcga ttaagtcagg gatcagtcca ttcgagcgac  80520
tcgatcacgc ctcgcccgag cctagcctcg gacaagggca gccgaccccg gaggatttcc  80580
gtctcgcctg aggccccccct ctaacggcgg acacatcttc ggctcgcccg aggccctgcc  80640
ttcgctaaga agcaaccctg actaaatcgc cgcaccgacc gaccaagtcg caggagcatt  80700
taacgcaaac gtgacctgac acctttatcc tgacgcgcgc cctccggcag agccgaagtg  80760
accgccgtca cttcgccgct ccactgaccg gtctgacaga aggacagcgc cgcctgcgcc  80820
acttcgactg cagtgccact tgacagagag atactgacag gaagccaggc cctgccaaag  80880
gcgccatagg aagctccgcc cgacccaggg ctcggactcg ggctcagccc cggaagacgg  80940
cgaactccgc tccgcccgac ccagggctcg gactcgggct cagccccgga agacggcgaa  81000
ctccgctccg cccgacccag ggctcggact cgggctaaga cccggaagac ggcgaactcc  81060
gctccgtccg acccagggct cggactcggg ctaagacccg gaagacggcg aactccgctc  81120
caaccgaccc agggctcgga ctcgggctaa gacccggaag acgacgaact ccgcttcgcc  81180
cgaccccagg gctcgggctc gggctcagcc ccagaagacg acgaactccg cttcgcccga  81240
ccccagggct cggacaccgc cctggcctct gccgacgacc tccgcctcgc ccgacccagg  81300
ggctcggact cgtcctcggc catggaagac agactcgacc tcggcttcgg aggagcctcc  81360
acgtcgccca acctagggcg caggccagcc acgtcaacag gaagcgccat catcacccta  81420
ccccgagctg actcgggccg tagagaacaa gaccggtgtc ccatctggct gtctccacca  81480
gataggcaat gatggcgccc cgcatgccct gtgacgacgg cagctctcag ctctcttacg  81540
gaagcaggag gacgtcagca aggacacaac cgctccgaca gctgtccctc cgccaggctc  81600
cgccgctcct ccgacggcca cgacatcaca ctagctgggt tccaagatct cttcggctgc  81660
cacattggca tgtactcagg gcactagctc tccctcgcta gacacgtagc actctgctac  81720
acccccattg tacacctgga tcctctcctt gcgtctataa aaggaaggac cagggtcctc  81780
ttagagaggg ttggccgcgc gggacgagga cgggacaggc gctctcttgg ggccgctcgc  81840
ttccctcacc cgtgtggacg cttgtaaccc cctactgcaa gcgcacccga cctgggcgcg  81900
ggacgaacac gaaggccgcg ggattcccac ctctctcacg ccggtctccg gccgcctcgc  81960
tcctttcccc ccttcgcgct cgcccacgcg ctcgacccat ctgggctggc gcacgcggca  82020
ctcactcgtc gacctgaggg accccccggt ctcgaaacgc cgacaataac tctaaccgaa  82080
cttggcattt agccgatcga ttcctaaccc atttttcata ccaccactac atgacatacc  82140
gaatacattg aatgactcgt tcacattcca catatatctt tacgaaaaca tttccacatc  82200
gcttgcaact taacctaagc ttcgccacat aatttcagga catctactta aatcatgaat  82260
atcatcatca cacacatcga cccgttttga aataacccta catgtctatc acaggaatgg  82320
agcatttcaa cacatatcct aaaacaaact aacttcatca cacatcttgc attacaaagc  82380
tacttgactt atttgaagtg tctactcgaa atcgtgagca caatcataca ctatatacga  82440
aacataattt taacgaacgc ataatacgca tcgtcatgac ttgacctata aatatagaga  82500
aagcgatgac tactctggca tgtcaccacc tctctattta agtcaagaca atttctacca  82560
tcgattaaga gtcgtaagca ttaaatacct tactacttta tacgcacaaa taaacttcaa  82620
cttaacacaa ctgacaccga tggaattttt actaaactca tcgtacgcat aaccctgtct  82680
cgcatacaac catattatgg cgtgcactcg agacacttca atccatgtgg cgcgaccact  82740
agtataaatg gactctgaca ctcatgtctt aacgatacat cctctacgca aactagcatt  82800
ctctaaacta ctcgtcacat caataaatat atcccctcta aaattatgaa tcccatcaca  82860
```

```
ttgcttaaaa caaatacact tttcacataa acacatcgat gcatttccca aaacaaaatc  82920
cacattttgt aacttagttt tcgcatcaaa caacgcatcg catattttcc tatcaaaata  82980
aaaatactcg agttcttttc tatttcaatt tcttccctac acgcgtccat ttataaaatt  83040
atacagttac acacatataa ccacatgcac atcatcgacc aaaacataat tagacaacta  83100
caaatcgtgc acatcaatta acctcttgtt ctccaatcgc aaacgtgatc ctaccaatgc  83160
gcataatcga acattttaca cacatccata caaaatgatt aatcgagtcg atcgagagcg  83220
acatgcatcg gctcaccata aacaaaccca aatgatgttt gcaagaatga cggtgattcc  83280
gattcgtgca tcgctccaaa catccaacga gcgttaagcg acttgctttc tcctcgcaaa  83340
acacggggtt ctctcctcca caaaaataaa acaaagcaac acacatacat aattaatcat  83400
aggaaaataa catcgatgcg gaatcaaaca aggagcgtcg cggtctcacc ggggtgaacg  83460
acgacgacgt ttggggctgc gcaaaaacag cgaacacacg gcggcatcac ggcgtgctgc  83520
tcactacgca acaaaacagc aagccggcag cacgcggagc cgtcggggct gctgcacatt  83580
tcatcgagca caagtgtgga tggcggccag gtgtttgttt caggcgctga aacaatggag  83640
ggggagaggg ctacggctgg ggaagtggtg gctcggccac ggcaagaaca gggaagggga  83700
ggctggtcac cgaccttggg cgcggccagg gaaaatggag ttgctgcttg gcactatgta  83760
caacagagag agggaggaat ggctccatgg gaagctcgag ctcggccagg ggaaggaaga  83820
aaggggttcg gcatccaagc tgttggagcc caaggagagg gtgctggccg ccgtgcgcaa  83880
gtgaagtttc acgccagctg aagctccctg gtcgcggaca ggaaagagca gggggcgcct  83940
gctgcaggta ggagctcgac tcctatggaa aatggcaggg gcagaggagg ccggctggag  84000
caccgggcag ggtgctcggc catggagccg ctgcatggat ttgctgctgc gccctgggag  84060
aaaaacagta ggggagtgaa ggatgccatg gctgggggcg cggggagcag ggagcctgct  84120
ggtggccttg ctgccgtgaa gcggggaaga agaaaggcag aggacgctac gagaagagct  84180
tcgacgcgct ggagggaagg aacgcccggc catggaagcc cctgcgcgct ggggaaggag  84240
ctccagctct acgtgcttga aggagcccat ggctggaaaa tggtagagga ggaagagaag  84300
ggtgttggcg gctggggtgg aaatggaaaa ttttcagaat gcaaggtagg gaagcccata  84360
tttatagagg agaaattagg gtagggtttc ttatgggcca aacgggctgg actggatttg  84420
gcccaaaaca ctaaattggg tcgcgctaaa taatttccgg actaaaaatg ttcctgcgga  84480
attcgtcgct actgagaaac agagcgaaaa gagttcggac gaacggaagg ttgcgcgatt  84540
aactcagccg agagtctgtt tagattttgc ttgaaaataa ttccctacgc gtaaatcgaa  84600
aataaaccgt cctgagattt gatcggtttt ggatttttag tcggagaaag cgaatcgtga  84660
tatataaaaa tcgttgccga tgttgatttt gaaatcggat tggatacaga gatgctaagc  84720
tgagtcgagt aagatttgat cagaggacga catattgatt atttcgtttg tgagtatgga  84780
ctcggattaa aatagttgga catcgatcga acatcgagaa attggattcg gacacagatc  84840
aaataacagc cgtcgagagt ttgatttatt gagcttcaga tgaggtttat aattcgagaa  84900
tgatttttga gttcgcattt gtgccaagga taaaagtttt aacaggctcc aaaattggcc  84960
ttctatgaga ctgagtaact ccgaattcgg tgaaacatga atgaataatc tggataatca  85020
gggacatacg cgagcgagaa atagaaattt ttactgagca tccgagatta ggataaatct  85080
cgcgacgtaa cacgaaactg acacctgggg tgtcacaact ccagcactgc caccctgctg  85140
gcaggcggat ccgtcgaaga aaagcatcca gtggggctca gtgaagaccg aagcccttgg  85200
```

```
ctccgcaggt gtggtgtccg aatcgggatc tggaccccca ggagcgctcg gggaaggggt  85260
ccactccacg atgaagtcag ccaggacctg gctcttgaca gcgtggcggg gctggaactc  85320
cagttggaac tcagcaagct ccgtggccca cttggcgatg ttgcctgtgg cgtttgagtt  85380
gtggagaatg gcccttaacg ggaaggaggt caccaccaca actctgtgtg cctaaaaata  85440
gtggcgcaat ttcctggaca caacaagtat agcatagata agcttgtgcg tctcaaggta  85500
cctggctttt gcctcatgga ggacctcgct gacgtagtag accggcttct ggatggttcg  85560
gacccctgca ttcagtcccg agtcctcaaa ctcctggcct tctgtcaaca tcgtggtggt  85620
cagaccacca ccttctccta ggggaacttt atgactcccc tagggatgtt gtgtcgtact  85680
ttcgacgacc agcaccatgc tcaccgcctc tgtagccgct gcaatgtact agtataatgg  85740
ctctcctggc tctggagcta ccagtattga tagggacaca tggtgctgct tcaactcttg  85800
aaaggcttgt tctgtctctt tggtccaaga gaatgggtcg gacttccgca atagcttgaa  85860
gaagggtagt gccctctcaa ccagtcttga gatgaagcga ctaagggcgg ccagtgaccc  85920
cgtaagcttc tggacgtctt tgattcaggc cggaggcctc attgtctcta ttgctttgat  85980
cttctctggg tttgcttcaa tgccccggtg tgaaaccagg aatcctagca acttccctgc  86040
agagacacca aagacgcact tgtccgggtt cagcttcatg cgtgttgcct gcagcttgtc  86100
aaagactagg gttaagtctt ccactagggt cgaccctccc ttagtcttga ctacgatgtc  86160
atcgacgtat acctctaccc tgtccctaat caagtcacca aaagtattac tcatcgcccg  86220
tacaaatgtt ggcaaggcgt ttttcagact gtaaggcatt acaacataac agtaaagtcc  86280
atccacagtt acaaaagcgg tatgcttcct atcttgccta gacatctcga tctgatggaa  86340
actagagtaa gcatccagga aggataggag gttgcaccca gaggtagaat ccacgatttg  86400
atctattcgt ggaagtggat atgggtcctt gggacaggcc ttattgaggc tggtgtagtc  86460
gatgcacatc caaagcttcc cgttagcctt ggggacgatg actagattgg ccagccatac  86520
tgggtgatgg acctcttcga tgaaaccagc gtccagcagc ttccggacct ccttacggat  86580
gaaatcctgc cgctcgatgg actgtctttg aggcttctga ctcaccggtt tggcgtcagg  86640
gtggatcttc agatgttgct cgatcacctc cctagggatc ccaggcatct gcgatagttc  86700
ccatgcgaat acattggcat ttgcctggag gaaggcgatg agcgcgattt cctatttctc  86760
ctccagatcg cccgtgatgc gagtggtctg ggaggaatcc ccgttgagcc ggatggtctt  86820
gacagggacg ccgtctgccc cagatggttg caccttaggc accttagcag gcatcttggt  86880
acaggaagtc gaggggtccc tcccctcgtc atccgggcga gcagcttctg ccgctagggc  86940
atgcaacttc tcgatagctg caagcgcagc gggacggtcg ccccgcatgg tgaggacccc  87000
agcaggggat ggcatcttga ggaccaagta cctgtaatgg gcaatggaca tgaaccggta  87060
cagggccggc ctgccaatga tggcattgaa agggaggtta acctccgcaa catcgaacta  87120
gacattctta gtgtggaagt tatcctcagt cccgaatgta accaggagtg tgatgctccc  87180
aaggggatac accggtttag ggcccactcc agagaacgtg cgagagggtc ctagtcggga  87240
tcctgggatc tgcagctgct tgaacgcagc gtggctgatg acgttgagcc caacccccacc  87300
atcaatcagc acatgatgca acttcatgtt ggcgatgaca ggggcagtga tgagtggtag  87360
tataccagcc cctgccatgt tttcggggca gtcgggtgcc ccgaaggaga tagtggtgct  87420
ccgccaccgc tgatgtgggg ctgccttcgg gacccctggg gtcgccaaaa ggacctcgcg  87480
gcgcagggac ttcacgttcc tacgggaggt gagctcccag cttccaccat acattacgta  87540
cagcttcttg cggcggtcgt tgtcatcacc ggagtcggag tctccagtga ggatatcctt  87600
```

```
gaggacttgc tcgggggcct aattctcgag gtcccattct cccgtggcca ggtcaccttc  87660
gtcgaccttc tccttgccag gccggcgccg aggcggcgag ccatccctgg aggcatgctc  87720
gcgccgctca ctgatgcgct tcacgagctt caggatctct cgtcattctg aggcactgtg  87780
gcgactgttg gggtggacag ggcatgaccc aatgtcactt ccctgttgcc gtggatgctt  87840
gccgcgctcg tcccggtccc cagccgtagc tacagcaact ggagcaccag actacggcct  87900
atcgtgacac ggtgcttctt ctttttcttg ccaccaccct gggtggcagc acctgagcca  87960
cccatttggg tgactctggt ttgcagcgtc gagtgccatg cacggccctc agtagctctg  88020
gcacatttgt cggccagagt gaagagcgta gtgacggttt ccacgtcatg cgtcgccaat  88080
ttctccaaca tcttcttatc acgcaccccc ctgttggaaa gcagtgataa tggaggcatc  88140
ggagatgcga ggtatagtcc cctgtacctt ggtgaagcgg gagatgaaag cccggagagt  88200
ctcctcgggt tcctgcctca ctgcatggag atgagcctcc acgccatgct actgataagc  88260
actggcgaag ttcattgtga accgtgcaca gagctcttcc caggagtaga tcgaccccgg  88320
ggtgaggttc atgagccagg tctgtgccgg cacattcaag gctacatgga aatagcttac  88380
cattacagca gtgttcccac cagctgccgt aatggcggtg acatagacct acaggaattt  88440
cgacaggttc gatgtcccat cgtacttctc cggcaggtgt ggccggaaca tgggtggcca  88500
agtcgccgcg cggagatgat ctgctagtgc ggcgcagccc acgccgacca atgggacacc  88560
catctggatt cgggcgtccc ttgcagtgaa gtcttggtcg aggttgcgac cctcgaagtt  88620
ttgccggcgc tcacgcgccc tctccagaga gattcgagca tcctcgcctg cacgcctgtg  88680
gttgagttct gctcgcaggt cgttagtctg tgccccctca ctgagggtga atgcacagac  88740
gttgacgcct cgcgctgatg ccggaatgat cgaggcctgg acctggccga gctaggatgg  88800
gccatgccga ggagacggtc gacatcttca cgccactgcc tcatggcccc cggggaggcc  88860
gtggaacttg gtgggttacg cagcaactcc ctggctgcag acaatggccc accataggta  88920
gccctcgacg gagtcctaga ggtctgtgcg ggcgtgtgtt gctgcgcagc gtgcatagca  88980
gcagcaccag gcacagcgcg gttggagcct cgtggcatgg aagataatgc cccttcctcc  89040
atcaagaagt cctcgggaga caagccacgg tgctcgacga tctgaaccat cgtgtcgagc  89100
aagaaaacag gcaaaaacct aaagccaaag ccccctacct ggagcaccaa atgtcgaagg  89160
gaaaatcctc cggccgggtg gcggaatgca cccgccctaa tcctaagatg aggagggggc  89220
ctaagcggtt gcctgtttgg tgaattcggg atgaacacaa gaggacacga gggattatag  89280
tggttcaggc cgccggagcg taatacacta cctccactgt gtgtatgttg tattgagtgt  89340
gtacagcgtg tcccttgtaa cgttgtgtgc cttccctttt atagtttaag ggaggcacat  89400
acaaggatgc tgagccccga catgtgggcc caggagcata atggaagaaa tacattatgt  89460
gaataactaa tgctgacaga gtaacacatg agtaatcagc gggagtcatg atggctgcag  89520
tccatgcagc attgatagac agtaaccctt ttcttggaaa catacgagta atggtgagtc  89580
attgccctcg atatggtaac gtgtgagtaa ctgcatggcc cacgtatcgt ggactgagca  89640
tgccgcctgt cagtggaatg gacaggcgca catcttctcc gtaatgaatg cgaaggcacg  89700
cgtagcccag aggcatcatg ccaggttcca cccgttggtt tatgccgcgc gcagtatgcc  89760
acgtggcagc atcgggtctc cgcctgagca gggagaagga gtgtatgcgg ataggtccgg  89820
atcccaccag accaggtcta gacacgtgtc ggctccggac ccccacctgg gtcctaatca  89880
aggcccgggt atgttctgtc ctagaaccct gggaccccac tatgggtggc ccagacccat  89940
```

```
acggggggtt cggatcccat cctaggggtc cggtttgtac acgtggaggt cctggaccaa  90000
acttggaggc ctggaccgta tatacagggg tctggcactg gtccggcact ctcccatggg  90060
gtccggactc actgttgatg ccttggagta catcactttc tctggacaca tggcggcccc  90120
gaacccgccc atgtggtggg gtcaggtgct gttgctggcc cagagtagtc gcccgaggct  90180
agggcgagtc atggtctggt cccacataca gcttatttac cacgcgacta aagatagtcg  90240
tgtgggtact gcgtctttat acagtagtaa ggggtaccct agttttaggg tgccgacaca  90300
catcttcctc tagaacacca tgaagaaacg cgttctgcac atccagttgg cagaggctcc  90360
aaccctgaga gacagcaaga gacaaaataa ggcggacagt agcaaattta actactaggc  90420
taaaagtgtc atcatagtca atgtcgtagc gctgtttaaa acctttagcc accaatcgag  90480
ctttatgatg gtcaatagac tcatcagctt ttctcttgag tttataaacc cacttgcaat  90540
caatcaaatt tctgtcaggt gcgggaggaa ccaagtgcca tgttttattc cgcataaggg  90600
cagaaaattc taggtccatg gcagcttttc cagtttgggt caaacaatgc aacagacaag  90660
ctggagggtt cttcacaaat tgccaaattt ccatacctga tcgtgccatc tgtaaacttt  90720
ctgggcttca caataccact ctgtagccga gtgcgcctag caggaagcgg aataggacac  90780
gaggctgatg gcgagggcag atggctgtca gtgagagagg gaccagccgc gccagagtcg  90840
gcacgaggca atcccgaagt ggctgctgct attgatgcgg ccgtggtggt gggaagcacc  90900
gcgttgctgg gcgcacctgt agccgcgtcg gaggggtgtg gcgtggagcc tagcaacaga  90960
tcagcaccgg gattgaggcc accagccggg acagaatttg cagcagggat cattggtggc  91020
tgcaaaagct ggttaggcca caaaatcgga gcaagcatgc tggattcagc aggagaatta  91080
gtcacaagat catctgagtt ggcccgagaa ttattaggat cgggtagaag aagcacgtca  91140
gaggtatatc gagcaccgac tgtgggatgg agagcagcaa agggaaaagc gtctcatcaa  91200
aaacaacatc atgtgaaata taaacacggc ccgttgagat gtcaagacac ttgtaaccct  91260
tgtgaaggtt gctatagact agaaaagcac accaaatgga ccgaaactag agtttatggg  91320
tgttgtatgg ccgcaaattt ggctaacatg catagccaaa gacgcgtaga ttagagtaat  91380
ctggggtagc acctaagaga cggtggagcg atgtgtcata atcaagaagc ttagtaggag  91440
ttctattgat aagatgtgtt gaggtgagga acgcttggtc ccaaaacttg agcggtattg  91500
tccattagcg agtaaagaga ggcccatctc aacaatgtgc aacgaatcaa gctgatacat  91560
aagannnnnn nnnnnnnnnn nnnnnnnnnn nnnnnnnnnn nnnnnnnnnn nnnnnnnnnn  91620
nnnnnnnnnn nnnnnnnnnn nnnnnnnnnn nnnnnnnnnn nnnncaattc tagaagattt  91680
cgtcgatctt gatggtgtcg ttggccttga tgagcgggtc ggggtagcgg atggtgcggt  91740
cgtcgtaggt gtttaggcag gggatgcctt tctggccaaa ctgaacagac cttaccttgc  91800
agagcatgaa ctgcacacaa accaatagaa aagcagtgag aatttcacag gcgtactatg  91860
aaagggcatg ggaatttcca gcgatgtaaa tggatagata gacagagcaa catctattaa  91920
tagtcctaac gattgtagca catgacattt tcaatgcaag actttcatgc acacaacata  91980
tatggacagt atagcaagga taaggtacat agatctacag aaaaaaaaga acaacctgaa  92040
gcattagaca aatggggaag tacagaagat tgtaggtacc aaagctagaa aatattgttt  92100
tgtcggcgtt tcgaccccgg ggggtccctg gaccgacgag taaattgtcg ctgcgtgtcc  92160
cagcccagat gggtcgacgc gagacagaac acaaaggggg gaaaacagca aaggggaacc  92220
cgcggccttc gtgttgtcct gcgcccaggg cggatgcgct tgcagtaggg ggttacaagc  92280
gttcgtgtgg gagagagaga gagccttgtg cgtcagcccg ttctcccgcg cggccaaccc  92340
```

```
tctcgtacga gagccctgga ccttcctttt atagacgtaa ggagagggcc caggtgtaca  92400
atggggggtg tagcaatgtg ctaacatgtc tagcagagag gagacagagc cctaagtaca  92460
tgccgtcgtg gctgtcggag aggttttggc gccctgttca tgtgatgtcg tggccgtcgg  92520
aggagcgttt gagccctgtg gaagtacaac tatcggggct gtcggatcct tgctgacgtc  92580
tccttgcttc cgtaaggggc tgagagccgc cgtcgtcacg gagcacgcgg ggtgccatca  92640
ttacttgttt accggggcga gccagatggg acgccggtct tgttccccat agcctgagct  92700
agctaggggt agggtaatga tggctccccc tgcgacgtgt cggtccgagc ctgaggtcgg  92760
gcgaggcgga ggctcctccg aggtcgaggt tgagcccgag ccctaggatc gggcgaggca  92820
gagtccgtct tccgaggtcg aggctaagtc caagccctgg ggtcgggcga ggcggagtcc  92880
atcgtccgag gtcgaggctg agtccgagcc ctggggtcgg gcgagccgga gtccgtcttt  92940
cgaggtcgag gttgagtccg agccctgggg tcgggcgagg cggagtccgt cgtccgacgt  93000
ccaggttgag cccgagctct ggggtcgggc gaggcggagc ttcccatggc gcccgaggct  93060
ggacttagct gctgtcagcc tcactctgtc gagtggcata gcagtcggag cagggcaggc  93120
gatgctattt tcccgtcagg tcggtcagtg gagcggcgat gtgactgcag tcacttcggc  93180
cctgtcgact gaggagcacg cgtcaggata aggtgtcagt cgatccttgc attaaatgct  93240
cctgcgatac ggttggttgg cgtggcgatc tggccaaggt tccttctccg cgaagcttgg  93300
gcctcgggcg agccgaaggt gcgtccgttg cttgagggga ccctcgggca agacgtgaat  93360
cctcctgggt cggctgcctt tgcctgaggc taggctcggg cgaggcggga tcgtgtccct  93420
tgagtggaca gagccttgac ctgaattgcg cccatcaggc ctttgcagct ttgtgctgat  93480
gggggttacc agctgagatt aggagtcttg gggggtacccc taattatggt ccccgacagt  93540
agcccccgag cctcgaaggg agtgttggta ctcacttgga ggcttttgtc gcactttttt  93600
gcaaggggac cggcctttct cggttgcgtt tcgttccggt gggtgcgcgc gagtgcaccc  93660
gccgggtgta gcccctgagg cctcggagga gtggtttgac tccttcgagg tcttagcacg  93720
tttcgtgatg cttcggccgg tctggttgtt ccctcatgcg aactggccgt agcccgggtg  93780
catagtcagg ttccaagttc tcgggctggt ttggttgttc cctcatgcga gagcagcccc  93840
cgagcctccg cacagagcga gaggacggcc aaggactgac tcggcttttt tcatacgccc  93900
ctgcgtcgcc tttccgcaag gaggaggggg gggaaagcgc catgttgccc tcagagggcg  93960
tcgaacatgg tgtctccagt gagttgctaa cggttgatcc gagtggacgc ccgtgccccg  94020
ttcgataagg gtcggctagt ggcccagagg cgcgctccaa aagtacctac aggtgatttg  94080
ccggacccgg tcccgtttga tagggtccga gggctcgatg cctccctctg atgggattcc  94140
gttacagaat cgctcctgtt ggtctcggaa atgtcctagg gtacctcggg agcgtagccc  94200
gagcctcggc catgtatcgg acgtacccag agtcatccct cgctctgcgt gctctgaggc  94260
ggctggcgaa tccttcgggg gccagcctac aaacccctga tcagtagtgg gcgcagagct  94320
cgagtggctt gaggcggctg tcgaacccct ccgaggggct agccttcgaa cctctgacca  94380
gtagtgggca cggaacccga gtgctctgag gcggctgtcg aacccttccg aggggccagc  94440
cttcgaacct ctgatcagta ggagggcgcg gagcccgagt gctctaaggc gactgtcgaa  94500
cccttccgag gggccagcct tcgaacctct gattagtagg agggctcggg gcccgcttcc  94560
ttcgcggaga aggatccctt tcggagtatc ctctttcccg gtccctatag caagagagag  94620
aaagaggaag ggtaaaagga tacgaaatca aacgacgtgg cgcacctttt ttgacgcggt  94680
```

```
cattaaggcg gaggtgaagc gtcacctgct tcgcctgcca aaggtgccgc ctgtcctgcc  94740
gcagagttaa tgcgacggga tgagtggttc gcggggcagc cgttgtgcgt gcgctagccg  94800
ttcgaggaac ggaacacggg cgtgtcgtct tcacgccgtg ggagggggct ctctcgctgt  94860
cccaggaggg gacgtgagcc tacagacgac ttgaccgctg cttccgcccg cctgccgccg  94920
ccattactgc cggcccactt ttggccatat caaccatcgc gccttctccc gcggctgact  94980
gacccgtgat cgatgtgctc ggttggcact gttgggccat gcgcagggtt gcctcgagtc  95040
gcggcaccgg ttccgcagtc gagaaggcgc ggtactagca caagtggcgg tgcagtttct  95100
cgcgcgtagt aaccggcgcg ccggttacat gacgtgtggg cctgggcccc cgtgctggac  95160
gcgtcggagt cgaaagggtg cacccccttg gtgcggttgc atgccgcctg catggcggtc  95220
cgccctttca cccgccggtc tgggcgaaag tggaggagtg cttgtaaccg ctgggcagtt  95280
acgcactctg cgcgcgacgg tttggcttct tctgccctgg gccagcttgc atgacgcgtg  95340
ggacccagcc cccatgtcgt agggggagga ccttggagcg tgttggtgaa gactcagtcc  95400
gcgacggctg aggacgcaag tggggagagt cgcctttaaa aggagggcga ccccccttgga  95460
tggcaaccat gtcttcacac tcccttcatg catcgcgccc ttccaacttc cgagcccccg  95520
gatggggagc gcccgcgttg ctttcgtctt gtcgtcgttg gaggaacgca acttcgcgga  95580
agttggtacc tttcagccat cgctcggctt caaggatttt catcaggcgg cccggctgca  95640
tcccctcgct ggtggtcacc caagacggtg accaccagtt tgatggtggg gacgtgggcg  95700
agggccttgt cgcagcagcg tctgcactga ggtcatcgct gctgctgttt ggctgtccgg  95760
agcggaggtc gttgtcgctg ctgccagagc gggcctcggc gagctgtcta gggttttgtt  95820
gctgaaagtt ccctttgacc cgggaacagg atctggatgt cgcctagagg gggggtgaat  95880
aggcgaataa aacttttcac tttaaaactt aaattcttac tctactcgaa gacttagtat  95940
gcagtggagt gagaagactc ttcaagtagg ttgcagcgga atagaagatc ctgtctcaaa  96000
atgtcctgca cttcaaataa agcttatacc acagataagt attgaagtgc agatataaag  96060
gcgagtagaa agagagtcag gatacaatac agaacagagc acacagacgc aaggatttat  96120
cctgaggttc ggccaagcct gaaatgcttg cctagtcctc gttggagtta gccacacctg  96180
ggcttggagt ctatttcaac tccttcctcc gtttgctcag atctgtcagt atgacagata  96240
gagcctttca ctattgagtg gggttacaac agaaccgcgg ctgcttacag acttcttggc  96300
agcaccccgg tagagtaacg atatgctcaa gaccttgctc tagctcttag cagcactact  96360
cctctctcta aggcttatag ttgtgccttc tacacaaact atagagttac acacaagagg  96420
gagagtgaga attgattcca gtggagtcta cacttgttgg ctgcacttct attttgctgg  96480
aggcacctag gggtcccttt tatagacaca aggggcctag gagccgttgg aagcaatcca  96540
ggaaggcaaa tcttgccttc tgtcgggtgg cgcaccggac agtccggtgc acaccggaca  96600
ctgtccggtg cccgatttct ttccttctac gtcgaagccg accgttggca gtcttggagc  96660
cgttcgcgca ccggacatgt ccggtgcaca ccggacagtc cggtgcctcc atctagccgt  96720
tggctcggcc acgtgtcccg cgcagatcgc gcggccaacc gttggcccgg ccgaccgttg  96780
gctcaccgga tagtccggtg cacaccggac agtccggtga attatagccg tacgtcgccg  96840
gtgaattccc gagagtggcc agttcgccag agttcagcct ggcgcaccgg acactgtccg  96900
gtgcaccacc ggacagtctg gtgtgccaga ctgaactaag tcttggctgt acacagccaa  96960
gcctttcaca cctcttccct tttcttcttc tttctgtttc taacacttag acaagtatat  97020
tagtccccaa aaccaatgta ctaagtctag aaacatacct tctattaatc attacatcta  97080
```

```
tagcatttca caagcttgag ctttgatgtt ggactcataa attatcaagt cagcttgact  97140
tgatctagat tgacatcgct tggctccaac atcctgtaaa ggtcacatag aacatctcca  97200
aacataggaa caacccaaac taaagatcaa agtgaactta gctcttttgg gctgcttcca  97260
gttctggttt cgacacttgt tctccttcta gtgaccttga tctcctcctt agagcttgat  97320
cttgagcctt atgacttaca ccacataact atagctgtta cctcattggc tgtaagtcac  97380
gtccttatgt agtgatcctt gatgtgccgt agctgttctc aactcgatca cccttgactt  97440
tgcaagcctt cttcttcacc cttggctttg ggttcctcag cctccttgac cttctcccat  97500
gcatttggta cctcgaagct tttcttgcct ccgtccttgg cttgatcagt tgtcttcgag  97560
ctacgcaccc gagtctcact ttgtgcaatg tccatcttac ttgtgatgtc cattatgtat  97620
ccataatcca gttcttggac catcacattt gttcacttgt gttgaaccct gtaggcttta  97680
ccttaagcac atgttcaaca cttagtatac ttgttagtcc tttaattgag ttgtcatcca  97740
aacaccaaaa ctcacaagag agctttcaat ctcccccttt ttggtgattg gtggcaacac  97800
aattaaagct tacataagaa taagatttga agcacaaatt tgaattctaa gattatagaa  97860
tgctccccct aaataagtgc ttacttcaaa aacctaattt tgaccacaaa cgtcaatttg  97920
cacatactta ggaaaattga aacatttcta caccttagca ctttttagga tgcattatgt  97980
caagaatcaa accatgatgc tataacacac aaatgcacat aatcagagtt aaacaccatt  98040
caaattagtg gatatatcac aggaatatca acctaccact attcaccatt aagataccaa  98100
cttaaactaa gatatcaatt taaagcaatc ttaaagcacc attaaccaca tgactatcta  98160
tttcactata gaagccaaat aattcatcgc agcggaaaca ctggtctagt ccatatgatc  98220
aacacgtata atactgcaag aaacatatga atataaaaca ctagtctagt ccatatgatc  98280
aacacgtata atactgcaag aaacatatga atatcacact tggcaaagct caaactaaca  98340
catcacccat taggataagc tttcctctca ggttgagata agctttaatg cacaacttct  98400
ccccctttga catcaaacac caaaaaccat actcaagcaa gaacatatga tgatgtcaag  98460
ggacagcagg gtgttaaggg gaaaaacgac tatcaaaact ccccccttatt tattgaacat  98520
atgtcctatc aacatttagg taagatacat atatgcaaaa agattaatac ttccttttgt  98580
acctttacca tgatgtagtg tacttcccat cttgaaagta gttaatctct cgagagcttc  98640
tccacacttg tgcctgattc tctctcctaa ctttttcttg ttgctaagac accaaactta  98700
gaacaagtta tagtattggg cacaagaaga aacttctatt ctcatgatta tcaaaagatg  98760
tcaattgaag cgaactatta cggctaccaa ttgaaagata ccaattgcaa agttcattta  98820
ttatcatggc tccatgatat ttaagaataa gcatctatta tcaccagata ttatagagca  98880
tgagcaatct aaaaatatgc acttactcac aacttgagat accaattttc ttgacttaca  98940
gaggtaccca agtcctgatt gctccatttc ttgcttatct tctcttttcc acctagagac  99000
tatacaagat tgctcaagaa acagttagtc tcaaaagaca caagttatgt gtgctccccc  99060
tcaagttgtg catcaagtat ttgaatgact tgcactttgc acattctagc ttccttagaa  99120
ttagagggga tcacaacata ccttggtcaa ggcatactct accactttca tcacccaaag  99180
atgccaattt gaatatcaaa tgaaacgcca cataacacca attgaaggct aaatgaaagg  99240
ttgactaaat acaacaatgc acgcctcagt ggcacctaag ccaattgaat actcacagga  99300
agtctaacat ttacgcaact tgtacatgct tcatatttaa ctatcattgt atataccaat  99360
taaagataaa cacaatcgaa atatctaagc atgttataat taagaaggtt tcttaggtgc  99420
```

```
acaaaagaaa caacatttta aaggcataaa ttacctaagc caagatatta ccaattgaaa  99480
ggcaagaaca tagctatgat cacaatgaat ggaatttcaa gaatatttaa tgaaattgca  99540
tagctccatt ttccatacct ttgcctttat gagagccctt gttatcgcca atttagggct  99600
ccttttgctt acgcacctca tagctcaaaa gggcacgaca tggatttgaa attcacacag  99660
taccaaacta gggtaatcat gtgaacatgg actaaacaaa atgtcataat tgcacatagc  99720
atgacttaca aaagttacag gtttatccat atacatcaag agagttatcg ttgtggatat  99780
aacaaatgaa atagctaccc atgaatgatt caaaagatat atcctttata gcaccagtca  99840
tgattaagca accatcatta tgatcaattt aacacaggca atcataaagc ataactactc  99900
taaggacagg tagcacaaca agccaactta agagcaatac taaattgcaa ttatgtactt  99960
aaaatacacg ggtaccgtcc tttggagagc aggttgtaga ttctcatcaa gatcctttac 100020
ttgattcacc aataatgatt caggacctat acaccttatt tctcttgaga tgaacatggg 100080
attagtgttt cacaataatt caaccttggg tcaataaaca ctaaaacaat taacagctta 100140
agcatagagt tttagataac cgtcttaatc tttcccatgg tctccagtcc atctcgaggc 100200
acctgcatgg tctagttggc acagtttggt atccatctcg ggatgggtac ataatgatca 100260
tgtaaatgtg cctttggtac ccaaattgcc tttgtgctag ttctaggtga tctcgttata 100320
gatctagcac aagtgtatga tttgggtctc ctatgcgaat aagattgaca caaattcact 100380
tgtttaggaa tcttaccttt gtaacatacc ttggatagat gaccttgctc accacacttg 100440
tagcagaagc gtcgctcaac ttgacatgac gcttgttttg tgtcattttc cttggtgagg 100500
gtcactttgg aggatgcata tccttgattc ttcatgaccg gacatgaagt gatcatgtgg 100560
tccttattgt tgcatccaaa acaactcctt gttctttcat ccttgtcttt gtacggacaa 100620
gacgcgatga ggtggcctgt ctccttgcat ttgaagcacc tcctttttcc tcttcccttt 100680
ttgtgcttga atgacatgga gagatgatca gtgcaaacaa catgactaat tgaattttta 100740
ccttttttcct tgttcatgtt gatttcttca tttatagctt tgggaacatt cttcttattg 100800
agcttaacac ttgctgcagt ttttcctttc tcaagcttct tcaccacgcg cccgtggata 100860
tcttgagaga gttgagcaat gtgtcttctc cttagttgtc tttgcttctt gttcccacag 100920
aatttctttt gtgaccctaa aacttgttgc tcaatcaatg attggctttc ttttgagcaa 100980
caggggttag cacatggtga tatacacttc aaatgcgcac acgtgcgaga atgaggttca 101040
catgaattta agtttgcaat tataacctca tgagcaacat taagcatgat atggtcatca 101100
actaatttat tatgagaatt tgacaacata tcatactttt tacctagagc acgtttttct 101160
aagttcattg tttctacttg actcttaagc atagaatttt ccgttttaag ttgagcaata 101220
ttagataatg catcatgact atttctttgc tcaattaaaa catattcata cctttggacc 101280
aaatcatcat gagagcgcct tagcttctca tgttctttgg tcatcttctc caggctgttg 101340
ttggttttga tgagggactc ctctagcctg agaagcgtct cgccttgttc cttgttcctt 101400
ctcaacagct taaccaagag tgccttgtcc tctttgttga gatggatgta gaaacggtga 101460
atctcctctt cctccacatc atcggtctca ttttccctgt cattaatgtc agtggaagca 101520
atataggaaa atgtaccttg tgatgatgaa gattcatcct catatttctc cttatcatgg 101580
ctttcgtctc caccgtcatt gttagcaata aaacatttat cactagtgga gaacaaacct 101640
gtcgacgagg tggattcatc gtttggatgc catcgttctt gttcttctcc ctttgaatgg 101700
ttagtatcac aagtaatata gggagtagga gcatcacagt ttgccacaaa atattttct 101760
ttaatcctat tccataaatc atgagcatca acaaatagat cactatcact actcatgatg 101820
```

gcaaaatagg cacctctaga tagagaatca actaagatgt tgcaagcatg gtgatttaga 101880
gttagacatc ttagttcttc attggatggg tttttactaa tattggaggg aaaaatacta 101940
ctactaaaga cctgtctcaa atcaggatca acactcatga aagcactata aatagagaca 102000
gaccaagact tgtaattaga gccatcgtct aaaagaagtt ccacagttac ctcttgtgac 102060
gacatcgtca tctccggacg gctaagccca cactggagag gcctagctct gataccaatt 102120
gaaagttccc tttgacccgg gaacaggatc tggatgtcgc ctagaggggg gggggtgaat 102180
aggcgaataa aacttttcac tttaaaactt aaattcttac tctactcgaa gacttagtat 102240
gcagtggagt gagaagactc ttcaagtagg ttgcagccga atagaagatc ctgtctcaaa 102300
atgtcctgca cttcaaataa agcttatacc acagataagt attgaagtgc agatataaag 102360
gcgagtagaa agagagtcag gatacaatac agaacagagc acacagacgc aaggatttat 102420
cccgaggttc ggccaagcct gaaatgcttg cctagtcctc gttggagtta gccacacctg 102480
ggcttggagt ctatttcaac tccttcctcc gtttgctcag atctgtcagt atgacagata 102540
gagcctttca ctattgagtg gggttacaac agaaccgcgg ctgcttacag acttcttggc 102600
agcaccccgg tagagtaacg atatgctcaa gaccttgctc tagctcttag cagcactact 102660
cctctctcta aggcttatag ctgtgccttc tacacaaact atagagttac acacaagagg 102720
gagagtgaga attgattcca gtggagtcta cacttgttgg ctgcacttct attttgctgg 102780
aggcgcctag gggtcccttt tatagacaca aggggcctag aagccgttgg aagcaatcca 102840
ggaaggcaaa tcttgccttc tgtcgggtgg cgcaccggac agtccggtgc acaccggaca 102900
ctgtccggtg cacaccggac actgtccggt gcccgatttc tttccttcta cgtcgaagcc 102960
gaccgttggc agtcttggag ccgttggcgc accggacatg tccggtgcac accggacaat 103020
ccggtgcctc catctagccg ttggctcggc cacgtgtccc gcgcagatcg cgcggccaac 103080
cgttggcccg gccgaccgtt ggctcaccgg acagtccggt gcacaccgga cagtccggtg 103140
aattatagcc atacatcgcc ggtgaattcc cgagagcggc cagttcgcca gagttcagcc 103200
tggcgcaccg gacactgtcc ggtgcaccac cggacagtcc ggtgtgccag actgaactaa 103260
gtcttggctg tacacagcca agcctttcgc acctcttccc ttttcttctt ctttctgttt 103320
ctaacactta gacaagtata ttagtcccca aaaccaatgt actaagtcta gaaacatacc 103380
ttctattaat cattacatct atagcatttc acatgcttga gctttgatgt tggactcata 103440
aattatcaag tcagcttgac ttgatctaga ttgacatcgc ttggctccaa catcctgtaa 103500
aggtcacata gaacatctcc aaacatagga acaacccaaa ctaaagatca aagtgaactt 103560
agctcttttg ggctgcttcc agttctggtt tcgacacttg ttctccttct agtgaccttg 103620
atctcctcct tagagcttga tcttgagcct tatgacttac accacataac tatagctgtt 103680
acctcattgg ctgtaagtca cgtccttatg tagtgatcct tgatgtgccg tagctgttct 103740
caactcgatc acccttgact ttgcaagcct tcttcttcac ccttggcttt gggttcctca 103800
gcctccttga ccttctcccg tgcatttggt acctcgaagc ttttcttgcc tccgtccttg 103860
gcttgatcag ttgtctccga gctacgcacc cgagtctcac tttgtgcaat gtccatctta 103920
cttgtgatgt ccattatgta tccataatcc agttcttgga ccatcacatt tgttcacttg 103980
tgttgaaccc tgtaggcttt accttaagca cctgttcaac acttagtaca cttgttagtc 104040
ctttaattga gttgtcatcc aaacaccaaa actcacaaga gagctttcag ttgccccgca 104100
ggccctccaa tgtggggggt cgttcgtacc tgtgggggcg gaaccagagt tctgtttgta 104160
atggcacctt gagtgccggt gtctgttcat tgcggctgtc ggggcctgaa gatgtgtatt 104220
ttggctaaag ccgtattttt tcctcatttc gagcactagg actcgcctgt cggctagctg 104280
aaccgcttaa ccaagtgtga gttgcctcgt gcggaaggtg acgagtgagg tatccgtatc 104340
ccggaggcgt aggagtccct cggatcggtc ggccttgccg cccgaggctt ctcttgctta 104400
gttaaagaaa ccctcggccg ctctgcgatg agccggagct agaggcagcg gtgtcagcgg 104460
tgtcagcgtg gacagaggcg gagttggctc aaaaagaagc ttcatcggcc ggagcctggt 104520
cgggccgtcc actggtggga ccgacgccgg agtcgggttg ccgaggccat gagccgggct 104580
gatgtcctcg gggacagct ggctgaggct acagagcggt cggtcgagtc gtctactcgg 104640
gccgggttcc tggaggacac ctcggcgatg gcccaggcgc ggtgctgaca ggttccttcg 104700
agatggagat cctccgaccg tgtcgccgtc cgaggctggg tcggactccg ccgaaggtgg 104760
agtcgacgcc gagggtgctg ctgctccccc actgatgtct gatcctgcag gaacaattta 104820
tctgtagtgt gcgtatgttt tttgcggccg ccgaggccca aacataccgt cgtcgtgttg 104880
taaagcggcg tttcttttcc ccttgtttcg agtatcggga cttgttcgtc agtaacagaa 104940
ttgcttatcc gagcaagagt tacttttcac ggaaggtgat gagtgaggta tccgtatccc 105000
gaaggtgtag gagtccctcg gctcggtcgg ccttgccgct tacgtgtact cttactcgtc 105060
cgttggattc tgttatcgat atagtcgaga aggcacaaaa aatcgtttcg gcagaaaagc 105120
tttcgaacgt taagacttgt tcggccagcg ggatcgctta tccgagcgtg agttacttat 105180
cgcagaaggt gatgagtgag gtatccgtat cccggaggcg taggagtccc tcggctcggt 105240
cgtccttgcc tgcttacgtg tactccgtcg ttttcaggat cccactttcg aagtagtcga 105300
aaagcacgaa agatgttctg gcagaaagac ttttttcgag gaaaattttg acgtagaggg 105360
ggtgcccccc ttctagcccc cgagggaggg tcgggctttg ccgaggcaag gctgaccctt 105420
ccttgatggt tagactttgt tggcgtatgt aaacgaggtg tatgaacgac ttgaaaacat 105480
cttaagggta gaagcgacgt agctgtcgga tgttccaagc gttgatgtag acctcgcctt 105540
gactgttggc cagcttgtat gttccgggct tcttagggag gcgtgagctt gtgacaccct 105600
cgggcgtctt gacgtagccg aagcaccaag tcgcccacct ggaggtctcg ggaccgaacc 105660
ccttgggcgt ggtagcgtcg cagggactgc tgataccgcg ccgagtgtag taaggccatg 105720
tcccgagcct cttccagctg gtccagtgag tcttctcggt tggttcgatt gcttcggtcg 105780
tcgtacgccc tcgtccccat agactagaaa aaacagcgtg aagatggccc agtgagtctg 105840
tgggcaagat ggcctcggcc ccatagacta gaaaaaacgg cgtgaagccc gtggctcagc 105900
ttggtgtcgt tctcagactc cagaccaccg aggggagttc cttcatccat cgcctgctga 105960
acttgttgag gtcgttgtag atccgtggct tgagtccttg tagaatcatg tcgttggcac 106020
gctctagctg cccattcgtc atggggtgag ctacggcggc ctagtccacc cggatgtggt 106080
aatcctcgca gtaggaactt tctaccggtg aactgggtgc cgttgtcggt gatgatggag 106140
ttcgggaccc caaagcgatg gatgatgttg gtgaagaacg ccaccgcctg ttcggacctg 106200
atgctgttta ggggtctgac ctcgatccac ttggagaatt tgtcgatggc gaccagcagg 106260
tgcgtgtagc ccccgggtgc cttctgcaag gggctgacaa ggtccagacc ccacacagca 106320
aacggccagg tgatgggtat tgtttgcaga gcctgagcgg gcaggtgggt ctgctttgca 106380
tagaattgac acccttggca ggtgcgtaca atcctagtgg cgtcggccac cgcggttggc 106440
cagtagaaac cctgtcggaa ggcatttcca acgagggctc gaggtgctgc gtggtgaccg 106500
caagcccccg agtgtatttc ttgtaataac tcctgacctt cggcgatgga tatgcaacgt 106560
tgtaggacgc ctgaggggct gcggtggtag agctccttcc cgtcacccag caagacgaac 106620
gacttggcgc cccacgctag ttgccgagct tcggctctgt cgaggggtag ctctcctcgg 106680
tggagatatt gcaggtacag ggtctgccag tttcgattag gcgtgacccc ataccgctct 106740
tcctcgacgc gcagtgcctc accctcgggg gccgagggtg cctcgggcag ggccaaggct 106800
ttctcgggct cgggcgtgtc gctggtcttg actgagggtt gatgtaggtc tcgggagaag 106860
acgtccgggg gaaccgttgt ccgcgccgag gctatcttag ccagctcatc cgtagtctcg 106920
ttgtatcgtc gggcgatgtg gttgagctcg agcccataga acttgtcctc caggcgccga 106980
acctcatcgc agtaggcttc catcttcggg tcgcgacagt gggagttctt catgacttgt 107040
cgatgacaag ttgcgagtcg ccgcgagcgt cgaggcgtcg gacccctagc tcggtggcaa 107100
ttcgcaaccc gttaaccgag cctcgtactc ggccacgttg ttggacgccg ggaaatggag 107160
gtgcaacacg tagcggaggt gcttcccgag gggcgagatg aagagcaggc ccgcgcccgc 107220
tcctgttttc atcaacgacc cgtcgaaaaa catggtccag agttccagtt ggatcggagc 107280
tgctggaagc tgggtgtcga cccattcagc cacaaagtcc gccaagactt gggacttgat 107340
ggccttccga ggggcgaatg agattgtctc gcccataatc tccactgccc actttgcaat 107400
cctacccgag gcctctcggc actggatgat ctctcccagg gggaaggatg acaccacagt 107460
caccggatga gactcgaagt agtgtcgcaa ctttcgccgc gtcagaatta ccgcgtaaag 107520
tagcttctgg aatttgcggg tagcggattt tggtctcaga cagtacttca ctgatgaagt 107580
agaccggcct ctggacgggc aatgcgtgcc cctcttctcg tctctcgacc atgatcgcgg 107640
cgctgaccac ctgagtggta gcggcgacgt agaccaagag ggcttctccg gcaacagggg 107700
gcaccaagat gggcgcgctt gtgaggagca cctttaggtt cccgagggct tcctcggcct 107760
cgggggtcca agtgaagcgc tcggtcttcc tcaagaggcg gtacagaggt aggcctcttt 107820
cgccgaggcg tgagatgaaa cggctcagag ccgcaaggca tcccatgacc ctctgtactc 107880
ctttcaagtc cttgatgggg cccatgttgg tgatggccgc gattttctcc gggttggcct 107940
cgatgccccg ctcggagacg atgaacccca agagcatgcc tcgggggact ccgaagacac 108000
acttctcggg attgagtttt acgcctttcg ccttgagaca cttgaatgtc gtttcaaggt 108060
cggagaggag gtcggaggct ttcctcgtct tgactatgat gtcatcgacg taagcctcaa 108120
ccgttcgacc aatgtgctct ccgaacacgt ggttcatgca tctttggtat gtcgcacccg 108180
cattcctcaa accgaatggc atagtaacgt agcagtacat gccaaagggt gtgatgaaag 108240
aagtcgcgag ctggtcggac tctttcatcc tgatttggtg ataccctgag taggcatcga 108300
ggaaagacag ggtttcgcac ccagcagtgg aatccatgat ttgatcgatg cgaggcagag 108360
ggagggaact ttcggacatg ctttgtttag accagtgtag tctacacaca tccgccattt 108420
ccctccttta tttctcacaa gcacagggtt gacaagccat tcgggatgga atacctcttt 108480
aatgaaccct gcagccatca gcttgtggat ctcctcgcct atggctctgc gcttttcttc 108540
gtcgaatcga tgtagaggct gcttcacggg tcgggctcca gctcggatat ccagcgagtg 108600
ctcggcgaca tccctcggta tgctaggcat gtccgaggga ctccatgcaa aaacctcggc 108660
gttcgcgcgg agaaagtcga cgagcactgc ttcctatttg gggtcgagct cggagccgat 108720
ccggatctgc ttggaggcgt cgttgctggg gccgagaggg acggacttaa tcgtctcagc 108780
tggctcgaag ttgccggcgt ggcgcttcgc atctggcgcc tccttggaga ggctccccag 108840
gtcggcgatg agggcctcgg attcggcgag ggcctcggcg tactccacgc actccacgtc 108900

```
gcattcgtac gtgtgtcggt acgtggagcc gatggtgatg accccgttgg ggcccgacat 108960
cttgagcttg aggtaggtgt agttggggac ggccatgaac ttggcgtagc atggtctccc 109020
cagcactgcg tggtaggttc ctcggaaccc gaccacctcg aacgtgaggg tttcctttcg 109080
gaagttggag ggagtcccga agcagactga cagattgagt tgcccaaggg gttggacgcg 109140
tttcccgggg atgatcccgt gaaaaggcgt cgcaccggcc cggatcgagg acagatcgat 109200
ctgcaggagc ccgagggtcg cggcgtagat gatgttgagg ctgctgcctc cgtccatgag 109260
gaccttggta agcctgacgt tgccgatgac ggggtcgaca atgagagggt actttcctag 109320
gctcggcacg cggtcggggt ggtcgccctg gtcgaaggtg atgggcttgt cggaccagtc 109380
taggtagact ggcgctgcca cctttactga gcagacctcc cgacgctctt gcttgcggtg 109440
ccgagtcgag gcgttcgcca cttgcccacc atagatcatg aagcagtcgt ggacctcggg 109500
gaactcctct gccttgtgat cctccttctt gtcgttgttg tgggctctgc cacctttcgc 109560
cggtggcccg gccttgtgga agtagcgtcg aagcatgacg cattcctcaa gggtgtgctt 109620
gatgggaccc tgatgatagg ggcacgactc cttgaccatc ctatcgaaca ggttggcgcc 109680
tccgggaggc ttccgagggt ttctgtgctc ggcggcggcg acaatgtctg tgtcggcgac 109740
gtcgcgtttt gcttgtgact tcttcttgcc cttcttcctc gcgccgcgct gagcggacgc 109800
cttggggacg tcttccggct gacgcccctg aggctgcttg tccttccgga agatggcctc 109860
gaccgcctcc tgaccagagg cgaacttggt ggcgatgtcc atcagctcgc tcgccctagt 109920
gggagtcttg cgacccagct tgctcaccag gtcgcgacaa gtggtaccgg tgaggaacgc 109980
gccgatgaca tccgagttgg tgatgttggg cagctcggtg ccctgcttcg aaaatcgccg 110040
gatgtagtcc cagagggatt ctctcggctg ctggcggcac cttcggagat cccaggagtt 110100
cccagggcgc acgtatgtgc cctggaagtt gccgacgaaa gctttgacca ggtcgtccca 110160
gttggagatc tgcacaggag atagatgctc cagccaggct cgggcggcgt cggagaggaa 110220
caggggaagg atgcagatga tgaggttgtc atcgtccgtc ccactcagct ggcaggccag 110280
ccggtagtcc gcgagccaca gttccggctt cgactccccc gagtacttgg tgatggtagt 110340
cggggttcag aaccaggtcg ggaacggtgc ccgttgtatg gcccggctga aagcttgcgg 110400
actgggtggt tcgggcgagg ggctccgatc ctccacgctg tcgtagcgtc ccccacgcct 110460
ggggtggtag cctcgacgca ccttctcgtc gaggtgggct tgacggtcgc ggcggtgctc 110520
gttgccgagg cgtcttgggg ccgcaggcgc tgtgtcccgc gtgcgcccgg tgtggaccga 110580
ggcttcccgc atgaatcggg aagtcgcagc gcgatgctcc gggggtaccc ctgccttcgg 110640
gaggcagagc tctcggcccg tcggaccgcg acatcctcta ggagattttt gagctctcct 110700
tggatacgcc acccctcggt ggtggatggt ttcggcatcg ctcggagtag tatcgctgct 110760
gcagccaggt tctggccgac cccactggaa gccgggggca gcctcgccct ggcatcgtcg 110820
gtgatgcggt gctggacgtc ctgggccaga tgacgcgctt ctccagccgg tgctcggcct 110880
gcccactcct gcccgatatt ttgccgaagc tgcacaagtt gtcctgcttc ctcgtcgagc 110940
ctggcctgta cctcgcggat ttgctcaagc cgtgcgtctt gaccccccgc agggactggg 111000
accacagcta gctcccgaag gatgtcaacg cgaggcgcag gcctaggggg atcaccatcc 111060
tccggcatac caagatggtt gccttcgtca agacccccta gatcgacgtg gaagcattcg 111120
caccttgggc cacagtcctc gtcgccgagg ctgtggctgc tatcggagca atcggagagg 111180
cagtagtcac atgcggtcat gaagtcccgc atgacactgg ggttatcgag cccggagaaa 111240
tcccaaccag agtcaggctc gtcatcttcc tcggaacccg gggcccata ggtcgagacg 111300
```

gccgtcagtc ggtcccaggt tgaccgcata tgataccccg gagggtttgg acatgccttt 111360
atgaaagcgt ccaccgaagc gggatcgctt ggtgggtcac aactgaatct aaaaggcatg 111420
ggatgggaaa cggacggtac ctcttgatcg acgggtggtg acgaagtcgc gtcagggacg 111480
gactgcaccg ttgtctcagg tacgaggtta acgcccagga agtccttcgc gagcgtgctg 111540
gcgtcatccg tctgcttggg gttggcgtgt tgcggggaaa cgacgcttgt cttcgtctca 111600
gacgcgaggt caacgcccga cgtgtccccc gttggggcgt cggcgccgtc gactcgctcg 111660
acagccgacg aggtgccgcc tcctgattgg ccatgcctac cccgcctcct cctccgtcag 111720
cggggaaggt gacgggacag acccggatat cgctcttccg ccacgtgggg aagacgtcgt 111780
cgattccgcc gccgacgggc gggctgacgg ccgccattgt cgttgtcgcg cggcggagga 111840
aggagtgtca tgtcgtagct gccgtcgagg gacatgaact caagactcct gaaatggagc 111900
accgtcccgg gttggagtgg ttgctggaga ctacccatct ggaacttgac gggaagctgt 111960
tcgtcaccat gcagtaggcc cctacctggc gtgccaactg tcagcgtttc gaccccgggg 112020
ggtccctgga ccgacgagta aactgtcgct gcgtgtccca ttccagatgg gtcggcacga 112080
gacgaaacac aaagggggga aaacagcaaa ggggaacccg tggccttcgt gttgtcctgt 112140
gcccagggcg gatgcgcttg cagtaggggg ttacaagcgt tcgtgtggga gagagagaga 112200
gagagccttg tgcgtcagcc cgttctcccg cgcggccaac cctctcgtac gagagcccta 112260
gaccttcctt ttatagacgt aaggagaggg cccaggtgta caatgggggg tgtagcaatg 112320
tgctaacgtg tctagcagag aggagccaga gccctaagta catgctgtcg tggctgtcgg 112380
agaggttttg gcgccctgtt catgtgatgt cgtggccgtc ggaggagcgt ttgagccctg 112440
tggaagtaca gctgtcgggg ctgtcggatc cttgctgacg tctccttgct tccataaggg 112500
gctgagagcc gccgtcgtca cggagcacat ggggtgccat cattacttgt ttaccggggc 112560
gagccagatg ggacgtcggt cttgttcccc gtagcctgag ctagctaggg gtagggtaat 112620
gatggctccc cctgcgacgt ggtcggtccg agcccgaggt cgggcgaggc ggaggctcct 112680
ccgaggtcga ggttgagccc gagccctggg atcgggcgag gcggagtccg tcttccgagg 112740
tcgaggctga gtccgagccc tggggtcggg cgaggcggag tccgtcgtcc ggcgtcgagg 112800
ttgagcccga gctctggggt cgggcgaggc ggagcttctc atggcgcccg aggctggact 112860
tagctgctgt cagcctcact ctgtcgagtg gcacagcagt cggagcaggg caggcggcgc 112920
tattttcccg tcaggtcggt cagtggagcg gcgaagtgac tgcggtcact tcggccctat 112980
cgactgagga gcgcgcgtta ggataaggtg tcagtcgatc cttgcattaa atgctcctgc 113040
gatacggttg gttggcgtgg cgatctgtcc aaggttgctt ctccgcgaag cctgggcctc 113100
gggcgagccg aaggtgcgtc cgttgcttga ggggaccctc gggcgagacg tgaatcctcc 113160
tgggtcggct gcctttgccc gaggctgggc tcgggcgagg cgggatcgtg tcccttgagt 113220
ggacggagcc ttgacctgaa tcgcgcccat caggcctttg cagctttgtg ctgatggggg 113280
ttaccagctg agattaggag tcttgggggt accccctaatt atggtccccg acatgtttac 113340
ttacaaaagc tccaccaagc ttgtcgagca tccaatgctt gggcgcattg agcctcttca 113400
agtgcttctt caatccccta gcctggattg caaaataata atgatcaaca aaagcgcaac 113460
agattccagt atggcattca taggtgactc atccagattg cattagctgt taaaagtaac 113520
agcaactaca cactacttga aaacaaaaga cccttttcat acatgtctat ctctattact 113580
tatatatgag cagtgccatc gtcagcacct cctgtatgta tacctaggac gacatcagct 113640
ggcgaggggc acggggacgc acgggcgtct tggacgggct caccctaaaa acacactaga 113700
acgactctgt tatccaaccg cccagaagag ctccttcctc aatgcaaagc gtaagaagat 113760
cagttagagt tttaccttat tggcaaggat cccagtacca caccgctaca gtgagagcgg 113820
cagtagcact ttctgccttg aaaaaaaatt gaggcccagt cttaaaacaa ctcgcagaat 113880
aataaggcat ttgaacagca gaccaaacaa ctagcagaat aaaaaagaag ctacgcaaat 113940
ttgaaggcga aggtatgctt agctgaccat cacgaatccc agtttcagcc catggagcgg 114000
gatttgttgc tcatgtctgc ctttctgtcc ttttagatag ctaatgccaa tagttcatgc 114060
aaaactatta tcaactgttc cattgtacat gtataatact tggaaataaa cacagccagt 114120
agccaccaat acccattcct tatgccaaat ttgtgacatg agatggaaat agtacatcaa 114180
taaccaaacg aggggtgagc atagaaattt aacatccaac atcaaaactt gcaaaacttg 114240
gatgtttgag tccacctctc gagcctaacg gacgtgaaat cgccatgacc tggcagcctt 114300
tgcatcaaaa aataactcca gttctatagt aaatgtaacc atgtgtgcat acgtaccttg 114360
cagttctgtg cggcctagta cttggtcacc tgcacaaggt acttgtaaca cccctggtgt 114420
tactgcaact aaaacttgag catagcatca taaacattgg cattgcatat gtttgacaca 114480
cctagagtgc attcactagg taaaaatttc aaacaagttg tattgtttta gtgttttgca 114540
aatagaaccc tagataggga atttaaccct aaatagggat taaaggggta agatataacc 114600
caaattgaga aaacctaaaa gctctaggga aatagtcatc aaatattctc aagaataaag 114660
ttgaaccaca tttataccc tcggatacca aaaaccctaa ttggaaccct agaaaaccct 114720
aaatccaaac cctaggggct tatgtgcaaa attcgaccac ttttggacta aagtgcaaaa 114780
accaagttaa ataagtatct taagtcattt gggtcactca tatgtgaatt tacaagccaa 114840
accctaagtt ttggcctcat ttgcaaaaag gaccctattt gaggttttat actaagtctg 114900
aaaacagtgt tatgggctca acttttgagc cttgtaactt ttaaatcata gggtttttgc 114960
cctaggtcac cacattaaaa ttatagccca atcataggag aacaactttg cttaagagtg 115020
tgagcatagt tttaagaaaa tattggagat aattgagcct gaagttggac tgtcagactg 115080
cttgaaatct gaaattcaga ttaacagtgg gatgacatga acttagggct taattttaag 115140
caagattcag tgactttttg tgggagcaca ttgtagcaaa gttatagctg gattgtagct 115200
ctacaacttt gctgtaggtc actggatgag ttgttatttg aaattgagag aaaactgggc 115260
tccaaacttg actgtcaggc tgtctgaata taaatctcca tggtacagtg ctaccaggga 115320
gatcagacca ccagcgcggc agtctctcac cgccgatgac tgatcttcgc tgagattcac 115380
gccgccgccg ttgcgattca cgtcgccggt gaccagataa gatcgctcgg taaaggcatg 115440
cgctggacgg cactccggtg aacccccagt acttcccctc taccgtgcgg cttgagcaga 115500
taagcccgct ggggatcccc gtcgctcggc cttacgccac gtatccgggc acctctgtcg 115560
catcgccgtg actccccact gttgtctcat cattgccggt gagcccgcca cggcggtgga 115620
cacgaaatcg cgaagccgat gatcttcctt atctccggcc gcccacactg tccactcaaa 115680
ttaagcgcca ccgcccctgg gatctataaa ttgaccctgc agagagcttc acaacatcat 115740
cacccaccca gccaccacgt attgctagca attgttcgcc caagctcgcg aattttgaat 115800
tcgccccaaa tcaattctcc gccacccgaa acccaacctc actgcggcca gccttattct 115860
ggtcagttcg tctccttctc tccctcattt aagctttccc ttaagtctac gatgcttgcc 115920
gacccacaca atcgagctag gagccctttg gtcgccggga acgcgactgt cttgccgcga 115980
tgttcacggc caccgtggcc agagcaagcc attgggccat agatggaatt aggttagggg 116040
aaatgctcgg gctaggtcca atttgatgtc cgccgctcgg gaaccctagc cgttgccccg 116100
ttcggccggt gcaggcactc gccggagttc ggctgggcgt gaacgccgtc gaggacctcc 116160
ctctgcgaag agttagaact acaggggctt ctctgcaatc tgtcagcgac acagtgtaat 116220
agtgatagaa gccagttctg attagccaaa ccccgaggac ctctgtgcaa agtcgccagg 116280
gcgcgagcgc gcgcgcgcgt tttcccctag tactgggccg gctgggctag aatcagccca 116340
acactattca atctttttcc ttttcttttt ttgtagagct ttggaaattt gttaaaaatt 116400
gtagaaaaat cctaaaattg tgaaaccaat tttcctaggc ttcttatttt ccatagaatt 116460
taataaaaat agttgtatga attttaggtt aactaaggaa ttttaaggta tttaaagtag 116520
tttaaggtag tggttctgga tttttagaaa ataaatggaa tttccaaaaa tgtccaaact 116580
ttttacataa gttctataca ttatttagag gccttgggta gaatttgggt tgatttggac 116640
cttgtttgat acttagaacc taaaaccccc ctgccctttg aactccttta ctgactccgg 116700
aaaccctaag ttctcggagt tccgtgaagg aaagttgtat tcaagactta gataataaat 116760
ctttattatc ttcgcactct catgagcatt acatggcatt cattcttata tatataccta 116820
tatggttata tttagaaaat gaagaagaga ttgaagtgac caaagagaag acaccaccac 116880
ctacggattc tcaggccggc aattgtttct acttcgatat ctgcgggact gagcctgact 116940
cacctactaa cgaaggcaag ccccggtgca tttaccacct ccttgatgct tttaaaatct 117000
ttctcacttg attgctgcat taggtgatag gagttgaatg cttaaacaat tcctgcacta 117060
ccttccttga atttgattac cttccttgat cacccgtttt acaaaaggat tttgatgctt 117120
tgccttgctc tagaaaaaca aaaggatttg ttttacaaaa gatgtttggc aaaagtggga 117180
gggttatttt tgaaaataaa acttgatggt gaatctgtca aaggccttga tggattcaac 117240
atcggaaaag atgtacctct gccaggtacc aaactttggg tttgaaatga ttaagccgag 117300
accgggcggg tgacttgcac gagaaaggag tctcggtgta gtgtctccgt ctgagtcgat 117360
taaggaccgt ctcgatgtag gcctgctgac cggggaccct ttaactggtc acatgcctcg 117420
tcatgggtaa gccttgcctc gggcagacta aggccagaat aagataacac gaaatgggcg 117480
tggagcggtg gcgggagtag cgtgtaccct ccgtggcaag aggctggacg gtggtgtatc 117540
tgtgctctcg gtttgtgtga acctgatctg gtcttaaaaa ccccagtggc gggttgacat 117600
atgcaagggt taagtgctac atatgtcgtg tgattggaga tcctcagctg agtataatcg 117660
attcggatcg ccgtaccttc gcggttatga agacttggtc actgacttac acgtagcatt 117720
ccactaaaga tgatggtttt gttaagaaat tggctagtgc aggacaagtg atttgaacta 117780
gggtagaaag aactctagtt acaggtaatt ctacttaatt tgacaaataa aactggattt 117840
ttaaggatcc actttagtaa gcatttctgc aaaacagagt ctttgattat tgaaaagcct 117900
taccttgact cccttaacca gcataccctt gagagtcttt tctttagtcg ggtaagactt 117960
gctgagtaat tccatactca gggtttatcc ctccgttgtt tttaggtgag gaagcgacaa 118020
atttttattg cttctgctcc aaggtggttc ccaaggaaga aaaacaagag tgaagccgcg 118080
ggaggacttg gtcctccata taggactttt gtttaaaaac tatcgggagg agtttttgcc 118140
tcccttggta ttgtaataat attactctgc actcctagga taactctggt ctgtaataag 118200
taacttgatc ttacttttta aataaatgta agttatgtaa tcgcttctgc atttctatat 118260
cttcgatgtt ctgtaatgtc tgcaagacgg gtgaaacgtt cctggaaagg taagaaagaa 118320
gataccgaac ttgtgaagta atttaggaac atctataggg tgtctgatgt ctgttggaca 118380
aggacaactg taggtgggct taattacttg ggaggttccg tcacagctgg tatcggagcg 118440
tagcccttct ttgcagatat tatgaggcat cttcaaaaag attttctaaa agtcttacct 118500
agaaactctc ttcctttctt acctaagtat tctgaagagt ctatcttaaa gaccaggtag 118560
taagagtgca acatatagaa ggtgtgaatc aactaaggtt gattctgtaa ttatacatgc 118620
atcatgctaa gaaccatact aatcaaattt tccccttag aaaatgccgc cgcgcacaag 118680
gagaacaacg cgcaaacata ctggaccgat tggtgtgccg agtcaccagc tgaccccaag 118740
gcatgataat agtagtagcg gaagcaatga tcctataggg gatcttgaag ctgaagtaag 118800
tcgactccaa gcgaaactcc gccgcagaac gactatctgg gtcatagatg gcgaccgcat 118860
aaatgagttg agaagagata tctgccatct gcgagatcag ctcgcggacc gggatttggc 118920
acttgactgg gttgttcaat cccgttcgct tgcatgggac aaggagcaaa aagctcaagc 118980
tcgagtagcc gagctcaact tggctgttga tgaactgcag acatattgca ataccttaca 119040
tgaagagatt catgtattat attcgcaact gcatcccagt gagcctacga atcctggtga 119100
gtcggaagcc ggaccctcgc atgttgcggg acacgcgctt ggtggtgagt tagacctttt 119160 tcagcccccct ccttctatga ggctagtcga cgaatggtct cccacacccg acgacgaggc 119220
cgccaaaagc aacggaaagc aggaataatg gggtagtaga agtagaagta gtgtattgta 119280
taacaggttg ctctaatgta taatattttg tactattgca taataggttg tgctattgta 119340
taataggtaa tgtatcctgt tgtaaaaatt cgagtctgta cattactctt tttggtaatg 119400
taaaatggat ggtttttcct tggcatatca tattgttttc caaatgttgt tgccacagat 119460
gccttccaag actcgagcac aggacggagc tagtacctcc tgtgggaggg agtctacccc 119520
aaatccacct cctgttcctc ccacactggc cgaggcgatt gtggccttgg taaatgcaac 119580
cgcggataat acccgttttc ttagagagat ggcgggtcaa caattgcaac aacaaggtgg 119640
gcggggttat caacagggcc cccgtgaaac ctcttacttg gacttctcag agacgcgacc 119700
accgctgttt gtcaaagccg aagacccgtt agaagcagat gaatggcttc gtgtgattga 119760
gcaaaagttt ggactgctgc gatgttcaga aacccagaag cctttattcg cagcccagca 119820
actgcgcgga cctgccagca cttggtgggg taattttgtg gccgttcaac cggccaatca 119880
ttagataact tgggaagaat tcaaggtggc cttccgcgag cactatatac cagaaggtgt 119940
tcttcacatg aagcaagaag agtttatgaa gctgaaacaa ggaggggata ctgttaacca 120000
gtatctcaat aagttcaatc atttgtcaca atatgcaatc gatcaagtga acactgattt 120060
gaagaagaag aattgcttta tgagaggatt aaatgatcga ctgcaaagga agatggcaac 120120
ctgcatagat cttacttatg gaagagctgt cagtacagca ctggcagtag aagcgaagta 120180
tgcaggcgct ggtaaatcca agggttttgg aggtgacagg tctagtcagg gcccggtgaa 120240
caggcaacgg ttcgtcatcc ggccttctaa ccagaatcgt tctttcgctc gtccaccctc 120300
ctttcctttt aagcagccag tctttattcg tcccaataat gcccctacta catcaagtca 120360
gccgggtgcc ccaggcactc gattccctgc tttacccagc tcgtcgactg gatgtttcaa 120420
ttgtggcaaa tctgggcatt ttatcaagga ttgcccttat ccaaagcaga accagtcaaa 120480
taatcagcaa ggatctggga attcatctca agccaaggaa aataatatgg gcaaaaatac 120540
aaagaagacg ggacgcatat attatacgca agtggccact acaccggacg gtgagccggt 120600
aatgatgggt acgtttcttg tggccaatca tcccgcagtt attctctttg attctggtgc 120660
ttcgcataca ttcatcagca agaaatttgt ggagcaacat tgcatctcat gccatgaatc 120720
aaaagagggg tttaaaaatt cactcaccag ggggacaaat atttactaga gaagtggcct 120780
atcaagtgcc cgtaaccttg gccggatggg actttcctac taatatgatc attctgaaag 120840
gccaagatat atatgtcatt ttgggtatga attggttagc cagacataaa gcaactctca 120900
acactgatca gagaattatc aggttgagtc ataaccagga agaaattctt ttgcctatcc 120960
ccattccaac caaagctact ggcagagctt atgaagccat tataccggaa atcaaggata 121020
ttccggtggt atgcgagttt cccaatgtct ttcccgagga tttgcccgga ctgccacctg 121080
aacgggaggt agagtttgta attgagttga aacccggtac ggctccagta tctagaagat 121140
cgtaccgaat gcctcctaat gagttggcag aactgaagat ccaattacaa gatctacttg 121200
agaaaggatt tatccggcca agctcatcgc cgtggggttg tccagccata ttcgtcaaaa 121260
agaaggatca aactttacaa atgtgtgtgg attatcgacc cctgaatgag gtcaccatca 121320
aaaacaagta ccctcttcca aggattgaca ttttatttga tcaactgact ggagcaaggg 121380
tattttccaa gattgatctc agatcgggct atcaccagat ccgtattcgg cccgaagata 121440
taccaaagac cgccttcact acgcggtatg gattatttga atacctggta atgtctttcg 121500
gattgacaaa tgctcctgcc cacttcacgt atttgatgaa ctcggtattt atgcccgagt 121560
tggacaagtt tgtggtagtc ttcattgacg atattttgat atattccaag aatgaagagg 121620
agcacgccca acatttacgg atcgtgttaa cgcgcttgag agaacatcag ttatatgcca 121680
agtttagcaa atgcgtgttt tggctggacg aaattcagtt tctgggacat gtattgtctg 121740
ccagggggat tgcggtagat cccagcaaag tcaaggacat tttggagtgg aaacccccga 121800
ccactgttca tcaggtccga agtttccttg gactggctgg atattaccgc cgattcatac 121860
cagatttttc taagcttgtg aagccaatca caagtttatt gaagaatgat attaagttca 121920
attggtcttc aaagtgtgat gaagcttttg aacaattgaa gacattagta accactactc 121980
cggtattggc tcaaccggac atcaccaagc cctttgatgt atattgtgat gcatcaggca 122040
gtggactcgg ttgtgtgcta atgcaagaag gccgagtaat tgcatatgct tcaaggcagt 122100
tgcgccgaca tgaggaacat tatcctactc atgatctgga gttagctgtg gtggttcatg 122160
ccctaaagat ctggcgtcat tatttgctgg gtaatgtctg tcatatttat acagaccata 122220
aaagcttgaa atacatcttc acccagtcag aattgaatat gagacagagg cgatggctcg 122280
agctaatcaa ggattatgaa ttagaaatcc attatcaccc aggaaaagca aatgtagtgg 122340
cagatgcgct caattgcaag gcttcctgcc attgtttaac agtgaggact tctgacatta 122400
cattatgcca ggagatggag aaattaaacc tgggaatgat tcaacatggg acttcaaatc 122460
atttgaagct ggagtcaatc atcatacgaa gaataattga cgcacaaaaa gatgatgagg 122520
gtatgaagca catacgtgag aagataatgg ctggaacagc caaatgtttc aaagaagatg 122580
atcaaggtgt gatatggttc aataaccgca tagtggtgcc gaagaatgaa gaactccgcc 122640
agcaaatctt agatgaagca catcttagtc gctattctat tcatctggga agcactaaga 122700
tgtatcatga tctaaagcag cactactggt ggacgaagat gaaaattgaa attgcacgct 122760
atgtggctaa gtgtgacact tgcagacttg tcaaggccat acacatgaag atagctggtc 122820
cattacaacc tttgccgatc ccaacataga aatgggaaga tattagtatg gacttcattg 122880
tgggattacc caggactaca aaagggtatg attctatctg ggttataatt gatcggctta 122940
cgaaaattgc tcactttcta ccggtcaaga cagatcaccc ggttactgtc tatgcccatt 123000
tgtacattgc tcgtattctt agtctgcatg gtgttccgaa gacccatagt gtcggatcgt 123060
ggacctcaat ttgtagccaa gttttgggaa gcacttcaca aatccttggg tactaagttg 123120

```
ctccatagtt cggcctacca tcctcaaacc agtggacaga ctgagagagt aaaccaaata 123180
cttgaagata tgctgcgggc atgtgttctg gaatttccac aaaaatggga tgaatgtttg 123240
ccgttagcgg aattttcata taataatagc tatcaagaaa gcatcaagat ggcacccttt 123300
gaagctttat atggacgacg atgtcgtact ccgctaaatt ggtctgaacc tggtgaaagg 123360
tacttcttca ggcctgatat ggtgaaagag actgaagaaa gagttcaaag gataattcat 123420
aatttgaaga aagctcaagc tcgtcaaaag agttacgtag acaaacggcg aatgccctta 123480
tatttccttg aaggatacta tgtctactta aaggtttcac caatgaaggg agtatcgcgt 123540
ttcggagtta aaggaaagct tgcaccataa tatattggtc cttttcttat cctggaaaga 123600
tatgggccag tggcataccg acttcagtta cccgaaacct tgtttgctgt gcataatgtg 123660
tttcacgtgt cccaattgaa gaagtgtctt cgggttcctg atcgaaccgt tgaagtgaca 123720
gatgttgtcc ttgaaccgga cttgacatat tctgagcacc ctattcgagt cttggatcaa 123780
aaggacaggg ttacccggag aaaactctca agttttataa gatacagtgg aaccaacatt 123840
ccgaagatga ggctacatgg gaaactcaag actttttaga taagaatttc ccaggctttt 123900
tagcttcttg taaattgtaa agcctgtata gctgttgtaa taaaggagtg attccaaaac 123960
cacccctgcc ttgtaccaga aataaggaaa taaaagtatg tcgtgtttcc ttttccatta 124020
cttaccctag gacttttaat ctcgggacga gattctttta tggggggaag gatgtaacac 124080
ccctggtgtt actgcaacta aaacttgagc atagcatcat aaacattggc attgcatatg 124140
tttgacacac ctagagtgca ttcactaggt aaaaatttca aacaagttgt attgttttag 124200
tgttttgcaa atagaaccta gatagggaat ttaaccctaa atagggatta aaggggtaag 124260
atataaccca aattgagaaa acctaaaagc tctagggaaa tagtcatgaa atattcccaa 124320
gaataaagtt gaaccacatt tatacctctg ggataccaaa aaccctaatc ggaaccctag 124380
aaaaccctaa atccaaaccc taggggctta tgtgcaaaat tagtccactt ttggactaaa 124440
gtgcaaaaac caagttaaat aagtatctta agtcatttgg gtcactcata tgtgaattta 124500
caagccaaac cctaagtttt ggcctcattt gcaaaaagga ccctatttga gattttatac 124560
taagtctgaa aaatagtgtt atgggctcaa cttttgagcc ttgtaacttt taaatcatag 124620
ggttttttcc ctaggtcacc acattaaaat tatagcccaa tcataggaga acaacttttc 124680
ttaagagtgt gagcatagtt gttaagaaaa tactggagat aattgagcct aaagttggac 124740
tgtcagactg cttgaaatct gaaattcaga ttaacagtgg gatgacatga acttagggct 124800
taattttaag caagatccag tgactttttg tgggagcaca ttgtagcaaa gttatagctg 124860
gattgtagct ctacaacttt gctgcaggtc actggatgag ttgttatttg aaattgagag 124920
aaaattgggc tccaaacttg actgtcaggc tgtctaaata taactctcca tggtacagtg 124980
ctaccaggga gatcagacag ccagcgcggt agtctctcac cgccgacgac tgatcttcgc 125040
tgagattcac gtcgccgccg ttgtgattca cgtcgccggt gaccagataa gatcgctcgg 125100
taaaggcatg cgctggacgg cactccggtg aacccccagt acttcccctc tgccgtgcgg 125160
cttgagcaga taagcccgcc ggggatcacc gtcgctcggc cttacaccat gtatccgagc 125220
acctctgtcg catcgccgtg actccccact gttgtctcat cattgccggt gagcccgcca 125280
cggcggtgga cacgaaatcg cgaagccgat gatcttcctt atctccggcc gcccacactg 125340
tcggctcaaa ttaagcgcca ccgcccctgg gatctataaa ttgaccccgc agagagcttc 125400
acaacatcat cacccaccca gccaccacgt attgctagca attgttcgcc cgagctcacg 125460
aattttgaat tcgccccaaa tcaattctcc gccacccgaa accgaacctc acctcggcca 125520
```

gccttattcc ggtcagttcg tctccttctc tccctcgttt aagctttccc ttaagtctat 125580
gatgcttgcc gacccacaca atcgagctag gagccctttg gtcgccggga acgcgactgt 125640
cttgccgcga tgttcacggc caccgtggcc agagcaagcc attgggccat agatggaatt 125700
aggttagggg aaatgctcgg gctaggtcca atttgatgtc cgccgctcgg gaaccctagt 125760
cgttgccccg ttcggccggt gcaggcactc gccggagttc ggctgggcgt gaacgccgtc 125820
gaggacctcc ctctgcgaag agttagaact gcaggggctt ctctgcaatc tgtcagcgac 125880
acagtgtaat agtgatagaa gccagttcta attagccaaa ccccgaggac ctctgtgcaa 125940
agtcgccagg gcgagggcgc gcgcgcgcgt tttcccctgg tactgggccg gctgggctag 126000
aatcagccca acactattca atctttttcc ttttcttttt ctatagagct ttggaaattt 126060
tttaaaaatt gtagaaaaat cctaaaattg tgaaaccaat tttcctaggc ttcttatttt 126120
ccatagaatt taataaaaat agttatatga attttaggtt aactaaggaa ttttaaggta 126180
tttaaagtag tttaaggtag tggttttgga tttttagaaa ataaatggaa tttccaaaaa 126240
tgtccaaact ttttacataa gttctatgca ttatttagag gccttgggta gaatttgggt 126300
tgatttggac cttgtttgat acttagaacc taaaaccccc ctgccctttg aactccttta 126360
ctgactccgg aaaccctaag ttctcggagt tccgtgaagg aaagttgtat tcaagactta 126420
gataataaat ctttattatc ttcgcactct catgagcatt acatggcatt cattcttata 126480
tatatatata cctatatggt tatatttaga aaacgaagaa gagattgaag tgaccgaaga 126540
gaagacaccc ccaccttcgg attctcaggc cggcaattgt ttctacttcg atatctgcgg 126600
gaccgagcct aactcaccta ctaacgaagg caagccccgg tgcatttgcc acctccttga 126660
tgcttttaaa atctttctca cttgattgct gcattaggtg ataggagttg aatgcttaaa 126720
caattcctgc attaccttcc ttgaatttga ttaccatcct tgatcacccg ttttacaaaa 126780
ggattttgat gcttagcctt gctctagaaa aacaaaagga tttgttttac aaaagatgtt 126840
tggcaaaagt gggagggttg ttttcaaaaa taaaacttga tggtgaatct gtcaaaggcc 126900
ttgatggatt caacatcgga aaagatgtac ctctgccagg taccaaactt tgggtttgaa 126960
atgattaagc cgagaccggg cgggtgactt gcacgagaaa ggagtctcgg tgtagtgtct 127020
ccgtctgagt cgattaagga ccgtctcgat gtaggcctgc tgatcgggga ccctttaact 127080
ggtcacatgc ctcgtcatgg gtaagccttg cctcgggcag actaaggcca gaataagata 127140
acacaaaatg ggcgtggagc ggtggcggga gtagcgtgta ccctccgtgg caagaggctg 127200
gacggtggtg tatctgtgct ctcggtttgc gtgaacctga tctggtctta agaaccccgg 127260
tggcgggttg acatatgcaa gggttaagtg ctacatatgt cgtgtgattg gagatcctca 127320
gctgagtata atcgattcgg atcgccgtac cttcgcggtt atgaagactt ggtcactgac 127380
ttacacgtag cattccacta aagatgatgg ttttgttaag aaattggcta gtgcaggaca 127440
agtgattgaa ctagggtaga aagaactcta gttacaggta attctactta atttgacaaa 127500
taaaactgga tttttaagga tccactttag taagcatttc tgcaaaacag agtctttgat 127560
tattgaaaag ccttaccttg actcccttaa ccagcatacc cttgagagtc ttttctttag 127620
tcgggtaaga cttgctgagt aattccatac tcatggttta ttcctccgtt gtttttaggt 127680
gaggaagcga caaatttttg ttgcttctgc tccaaggtgg ttcccaagga agaaaaacaa 127740
gagtgaagcc gcgggaagac ttggtcctcc atatagaact tttgtttaaa aaccatcggg 127800
aggagttttt gcctcccttg gtattgtaat aatattactc tgcacttcta ggataactct 127860
ggtctgtaat aagtaacttg atcttacttt ttaaataaat gtaagttatg taatcgcttc 127920
tgcatttcta tatctccgat gttctgtaat gtctgcaaga tgggtgaaac gttcctggaa 127980
aggtaagaaa gaagataccg aacttgtgaa gtgatttagg aacatctata gggtgtctga 128040
tgtctgttgg acaaggacaa ctataggtgg gcctaattac ttgggaggtt ccgtcacagt 128100
actgatggta ctccggtggc gccatttaca tctcaagcaa tttttctcaa agttggattc 128160
ttgatccctg catatcgctg gtcgtgaccc gtgggcacgg cgctcggatc cggcagcagc 128220
agatcgaggc gaggccgcga gggaggagaa gagccatgat ggggggcatc agatcatcgc 128280
tcaacgacag cagtatgggc gtcctcttcc tgctggtgct cctgctggat gcgggcgtcg 128340
tcctcctagc cgtgctccta gcagtagagg ctccagtagc aggagaagag gcaggatgcg 128400
ggcgtcgtcc tcctggccgt gctcctactg ggcggcgtgt cgtgctcctg ctggtgctcg 128460
acgactggag cctgctgctt ggtggtgctc ggcggatgag caggggatcc gatcgggtag 128520
gggatgagga tgagatgact gatcggatca gatgggcagg ggatgaggat gagtggatga 128580
ccgaccggat gagttggttt gctcggaagc tgccggctgg gggatgggga ttagatcatt 128640
agtgtttgtc ggtttgggtg tttgccactt tgggtctttg gcggaatgat gccttagtgg 128700
gcaatgggct ggcgcttggc gcctgggcac aatggacaat ggtgggctgg cgatttgttc 128760
attggtgtcc atgtgtggat cgacagtaat ggactaatgg ttaatttcgg atatccaacg 128820
aattacccgc gggtgaggtt taatatccaa atccatgtct gctttatctc ggatcgggta 128880
cgggtctaac ccgcaggtca aaaaacatat ccatatcctg atccgtcggg tcgaatatcc 128940
gacggatatc actatccacg cattaaattg ccatccctag atgtgagact taaggcatgt 129000
ttgttcgcta cctaagttat cacactttgc ctaacttttt cgtctaaggt tagttattca 129060
attcggacga ctaaacttag gcaaagtgtg gcacatttag ccacaaacca aacatgcctt 129120
taaccctctg gtttagatcc cgtttcgttt gagctgaata tacttattaa atgtctaaag 129180
catagcctag agcctgtcat gtcatgaatc atgaaatgac aataaaacat aaacaaaagc 129240
atagcctggg agtttggagc accgcgctgg gggcactgaa gacgacggat cttgcctctc 129300
agcctcggcg atgggcgtcg gacgcaggag atggcattaa ccaccgctat attaataaaa 129360
cgtattgtat atatgtgcaa tacgtatata aagagaaata ttcgtggcat taaccaccgc 129420
ttatcaggtt gcttataccg tacaaagaga cgatattata actataaaca tactgttgat 129480
gagaaaataa aaaataatca tatttcaaac gtataatttt atttgaagaa gattcttatt 129540
taagcaagat tttttaccta tatgatatat agaaaccgta cgaacataca gtcagctaac 129600
tagttcattt taaattccaa aaaatgttta gttcaatcta atcagaattt actattgact 129660
atgtttttc acaatatgtc ctatcaaaaa tatcgtacga gacggtttta tgtttacaag 129720
tttctagtat actcactaac atctaagaca attttgtata gtctagatga ctctaataat 129780
atctttattt gagatggttt catatacaga agtgtctaat atactaacca aaataaaaga 129840
cacttcttgt aaacttaatg cctcaaaagg tatatttatt tgagacggtt ttcaacatca 129900
aactgtatta aatcaatata agacatttcc aaccatatat ctgcctcaaa aaccttcttc 129960
attaaagacg gatatccaac aaaccgtctt accgtactca gcaccatatg ataaaagacg 130020
cttctataaa atgcactgat atttgtctta agatgtatgt cttaaataag catatttcta 130080
gtagtggatg tccaagacat ccacagagtc attaacttag gtcataatca aaattttgaa 130140
cgaaacgcag tacgataagg ccttcacagg cagctaactg agggtttgcc actaatctag 130200
tctagaactc gtcgaagtcc tgaaactcct gaaagtcctc cacgttgcct tcatcttctc 130260
ctgagcacta gttgcaatgg ggacaacctg gggtttggtg tttttaagca atggtgagta 130320
cacctcaacg tactcaacaa atgtcctgtt tggctaaagt ggactagctg tatgtggggt 130380
taagcttaaa gcagttgctt ttagttggtt aggtatttat taccagtaga gagccatgtt 130440
ttagcaataa ccccaagtta taaacccaaa cattactccc tccaagagga aataccaaga 130500
attcataatc ataatcacca tcattaagca tcatcataaa agtatccaga gtaactctaa 130560
tcaaaggagc tcccaaggct gctcataact gtgagcatgg ctgatatact agcttctaac 130620
actctacaga ggttgcacac tttacccaca agtcgtgatc cctttttgcc tcaggtcgat 130680
caaaccctca aacactacca aggtgagtcg gcaaggtttc actacgtagc tgtaacaccc 130740
tgaattttgg ggtataaaaa tttccttgct ctatactcaa aatctaggtg ttaccctttc 130800
ctttattcac ttttcttttc cctttatcaa aacagtagag agttattttg gttctatatt 130860
ggtgtgagct ctagaagtgt catgattgtt gcattcatgc tgctacatag tgtttccaag 130920
tgatgatccg aggtgaggac gagctgacca gtcgggccca gcgctagggc acagatgact 130980
gacaagtggg gcccaggggc aagggcaccc acgtgaagcg atatccagcg atctagaccg 131040
ctagatcaag gctaaacggc taggattagg cgtcaggggg gttaacagca ctgcggccgg 131100
cgctgctcca tccgcagcgg tgaagtcgcc aaagacgaga caagcgcgga ccccaggggg 131160
tctggggtcg ctggagttgg ccagaccggt gagggggacc cgacgaactc gatggcaggg 131220
ttctggccat gagaacggga ctggaggtga gtgaatggcg gagggggcgc tctgggcggg 131280
acacttattg tgatatcctg gcccctggga tgggatgtcc tggcccaagg cttaatagaa 131340
ttaatagtgt aatcatacca acaaggtgca tcttcttttt cggaagccta tctcgaaaga 131400
acctccaagt taagcgtgct tggcttggag caatttggga tgggtgaccg accgggaagt 131460
tttctcgggt gcgcatgagt gaggacaaag tgcgcacaaa agactcgtgt tggtctgtgg 131520
ggacaatata tgatcctaga cagctgccag gagtaagtac cgccggtcca gggattagac 131580
ggggtgttac aagtggtatc agagccgaca ctcgcggttt cacgggcgtg tgtgggctag 131640
ggggttcggg tatatggcgc atggcacatg tgggcccgga gtggtcacat ggcatggcat 131700
atgacggcac tagacacaca gacgtggcca agaggggagg ttcctggatt ggggttgacc 131760
gacgaggacg tcggtcttct aagggggggtg gattgtgata tcctggcccc tgggatggga 131820
tgtcctggcc caaggcttaa tagaattaat agtgtaatca taccaacaag gtgcatcttc 131880
tttttcggaa gcctatctcg aaagaacctc caagttaagc gtgcttggct tggagcaatt 131940
tgggatgggt gaccgaccgg gaagttttct cgggtgcgca tgagtgagga caaagtgcgc 132000
acaaaagact cgtgttggtc tgtggggaca atatatgatc ctagacagct gccaggagta 132060
agtaccgccg gtccagggat tggacggggt gtgtaacacc ccaggtgttt attttccgct 132120
caacaacgag ttcggattta agcacgcaat atcagtggat aaaacgaatt ttaaatttta 132180
atcattgtcg cttatcgcta ttttaatatc gcatcggtgt cgtttgtcgc gagtgcgaca 132240
tcgtttttat ttttttatct gtccgggctc ttcctaaatt ttcgtaatgt tcggaaccta 132300
gctgttccga aaatcggtgc gtccgatgag tatttaaaat ccatcgctcg cgcgaacaca 132360
aattcggaag cccgaactca ctcgaatgat cttatttcga gcaaattaat ttgaacttga 132420
cgactaaaat gttcagggta aaataatctg aatcgcgcat tgtctgagaa agatcgtgcg 132480
cggggatatg atctaatttg ttctttagcc cgcaatgtag gataaccaaa tcaactgtgt 132540
tttggtgacg gataagtttt tatctgattt caattaaatg taacaccgat taaaacattg 132600

```
taactaaaat catttttaat tttagtcctc ttacatcttt ccaaattcta gtcccaatct 132660
ccagctgata attgtatttt tattcaaatt tttgagtaaa agaaaacgaa ggaagaaaat 132720
atctgcaacc gctcttctct ctgattttat ccaccgcttt tcccttccat atctgaagtc 132780
actagcctgg atattttctc cacgtagttc tcctcttcct cacgtctcct tctctcttat 132840
ccattggacg ctagctcgct ggaaaatctc acgcacgtct ctcctccagc cttacccagc 132900
gaccagcatt tcttccatcc atcagcatcc aaaggcagcc ggctgccggc tgtgctcgtc 132960
ggaccctccg agcacctctg tgcccgacga cctgaccaag ctcgtctcca gcttgcgtcc 133020
atcctgtgct cagtttccat ccactagcac cgtgtctctg gtcctgctcg tcgtggacat 133080
cgtcggctct agttccttgc tcgagctcgc cctttgcgca gaccgcgtct cccctcacct 133140
tgccgcggtc gggctggccg tcgtcgtcag cttgtgtcca tgccgacgaa tttgtcgaac 133200
tgctcactgc atctctttaa tctcgtcgcc tgatttttct gtaccgcgcc gcgcaacccc 133260
tagaaataaa aatcacgccg ccgagcgctc ctatccttat cccgccaccg cccttggtct 133320
cctacaaatc tccagcgcgc aggtttcttc tccacgcacg cccggcagca agccgcagcc 133380
gagcagctcc ttcccatctc ccctctgctc gctggctgaa tccccagccg ctcggctctg 133440
cttttctccc atggcgcggg gttccctgca ggctgctcgc ggtatccatc tcctctgctc 133500
ctgctcgtcc gtccctgagc tcctgtgccg cggcacctct gttcggccac gcctgatcgg 133560
atttcttgtg ccgtggcttc ccctccgagc tcgcccagct ctattgccgc gcccatggcc 133620
ggcgctccct gcttggttcc gtctgtcgcg ccgtcgtctt actgctcgcc tttgcgtcgc 133680
gcgcatagcg ttctgttgtt cttgcacgcg cgaagctctt tgctcgtcaa cgcttcagcc 133740
tggatttcgc tttgtcgccc agctcggctc tacatgacta catctcccat gactgtctac 133800
tctagctcgc cgtagttcct gcgcgcgtcg agttttctct actctagctc gccgtagttc 133860
ctgcgcgcgt cgagttttcg tgtggagctc tctgctcacg cgtagctcgc tctttctttg 133920
ttgccgcgcg cacgaatttt atctgctcgt cacagcgtgt cgagttctca caccatcatc 133980
gcttctgtcg caagctcgtt ggtcacagtt gtcttgaccg cgttaactcg cgactgtggt 134040
cgtgttcatc gaattcgcca actctttgtt gccgatttga ctgtcgtcgc ttcgcgtgtt 134100
gtcgagccgt cgtttttttcc tgtcttgtgc tcgcacggtt tcctgctcgc cagcgtgccc 134160
tctcggctcg ctcggcttta atttccaatc acgtcgtcga tctcgtcgtt tgccgtcgag 134220
ttgtcaaaca cgtcatctcc ggctcgatcc ccacctcacc agcttacccc agacttcaat 134280
cgaaggtcat cgtcgctcgt gcgtccccaa gaaaacccaa gaatcgggtg aagacgaagt 134340
tagcagcgcg atattcccta agcgctcgac aaattgcgtg gatcgaaaaa tcactgccga 134400
tctcatggat tcgtgtcaac tgttgaaacg gtaagctgat gaattgttta gaatagttcg 134460
atcgttgaat aagttaatgt gttagtgcga ggctcattag ggtgctcgat aaattgcgta 134520
agtcacgaaa ctctcgtcga cttcgcagtt cttgcgatta tcgagccagg ttcagttata 134580
gcgagttatt tcgctattcc ggtcacttag ctgaattagt ggaccgagta gaattttagt 134640
aggcatatgt gttgataaaa tattttaatc acttataaag atgtagtata atttataagg 134700
caagggatta gttcagaatt taattaatta actgataagt tgtgattagg ctaattatat 134760
ttcttgtgta tagtttgttg ttcgtgatgt ttgcgttagg ttcgagaagc gtaatcattg 134820
cgcgtagtcg catattaata actagtgttt ccgtacaaaa ttgtacaacg cctcgccact 134880
aggtgtttaa tacgctatcg tatagcacta tttagatttg tgctattctt gtttatatgc 134940
attcatgtgc atcgtgcatc tcaattaggt acgataattg atcgcgtgat gcggaagaca 135000
```

agccaagtcg accccaagcg cgggctaatc cgcaggatga tgctgatgga caaacctgaa 135060
aatggtcgcc aagtggacgt cgtctaacaa cactaaccta gtgttaccca ggcaagcccc 135120
ggtgcatttg ccacctccct tgatgttttt aaaatctttc tcacttgatt gctgcattag 135180
gtgacaggag ttgattgatt aaacaattcc tgcattacct tccttgatct tgattaccct 135240
ccttgaaaac ctgtttttac aaaaaggttt tactatgctt agtattgctt agaaaaacaa 135300
aaggatttgt tttagaaaag atgtttggca aagtgggagg gttgttttca aaaataaaac 135360
ttgatggtga atccatcatg gctatgatgg attcaacatc ggaaaagatg tacctctgct 135420
aggtaccaag tttttggtta aaagattaag ctaaggccgg gcgggtgact tgcacgggaa 135480
aggagtctcg gtgtagtgtc tccgtctgag tcgattaagg accttgtcga tgtaggcttg 135540
atgatcgagg accctttaac tggtcacatg cctcgtcatg ggtaagcctt gcctcgggca 135600
gactaaggcc agaataagat aacacgaaat gggcgtggag cagtggcgag agtagcgtgt 135660
accctccgtg gcaagaggct ggacggtggt gtaactgtgc tctcggtttg cgtgaacctg 135720
atctggtctt aagaaccccg gtggcgggtt gacatatgca agggttaagt gctacatatg 135780
tcgtgtgatt ggagatcctc agctgagtat aatcgattcg gatcgccgta ccttcgtggt 135840
tatgaagact tggtcactgc cctacacgta gcattccact aaagatgatg ggtttttgtt 135900
aagaaattgg ctagtgcagg accagtgatt gaactagggt agaaagaact ctagttacag 135960
gtaattctac ttaacttgac aaataaaact ggattttaag gatccacatt agtaagcatt 136020
tctgcaaaac agagtctttg attattgaaa agccttacct tgactcccat atacccagca 136080 taccettgag agtcttttct ttagtcgggt aagacttgct gagtaattcc atactcaggg 136140
ttttatccta acgaatcaag ctgatcatca acnnnnnnnn nnnnnnnnnn nnnnnnnnnn 136200
nnnnnnnnnn nnnnnnnnnn nnnnnnnnnn nnnnnnnnnn nnnnnnnnnn nnnnnnnnnn 136260
nnnnnnnnnn nnggtcagcc cagattgctt ctgcgagcgc accggctatt gggtcttcct 136320
gtgttctgct agccgctggt gcagactctg agatgcatct cacatatttg ctgggacttc 136380
tcactcttct gactaccagc ggcagatatg ttgaggagtg ggtccgtgtg ttcaatgcgt 136440
cagtatggat cgaccccgat caccagtgga tgaggttccg ctttgagcga gaggatgtta 136500
cacttcatgc tagctagatt cgccagctgt ttggattcaa tgagtcatcg acttgtcttc 136560
atagcttgtg ctatggtacc tctgatcctc ctcgtcgccc tcacgacgga gttgctccag 136620
ctacagctca catcgcggct ttgttccgac cgcccttctc agatgggtcg cgacgttctc 136680
cggcagattt cactacagta gccaagtact tatatcagct catgagacgg acgcttctgt 136740
cgtggatggg ttatagagag gctaccactc atattcagct ttggctcctc ggtgccctga 136800
tctttcattc agagtttgat gttgttgact tccttatttg tgagatcgag gacacggtat 136860
tggatggtct tcgtgctcgg cgacagctgc caaatgctca ttatctctgc cacatcttcg 136920
cacagctgat ccgaccacca tagttccagg gcacccttga ggcctcacgc ctcctatttg 136980
gctcctacca tccagcccct gaggatccag taccagtacc tgatccagtg acagacattc 137040
aggcagagga tacaagtttc catcagtttg agacttaggg cgcagcagtt cctgacgatg 137100
atgatgatga tgatgatgat gattttggga ttccgcctct gcctcctgtg cctccacgct 137160
cacatgacca tgaggcccgg agttctcgtg ctgcccctgc tgttcctcct gccattgacc 137220
ctgctctggc tgcgatcctc cagactctta ctcagcagca ggctcatctg gcagcggtgc 137280
aacagcagat gtccgagaga atgctatcga tgttttagac tattcaggac agacaggaca 137340
ctctgcagca gcagcttttg gcagacaagg ctgagaaccg ggccttcatg actcacatac 137400
ttcagcatac cggtgctcag attcctcctg ttcagtctgc accccctcta gatcttcagg 137460
ccgctgttgt gctagccctt caggcaggac cccctctacc ttcatttggt ccttcttcct 137520
ctccgctcct gccggtcacc ctggttttct cgtcgccggt catcagctcc atcagcgctc 137580
agccgccagt gccaccagct cctgctgtta ccactgctgt tgtggcggtg tctgtgacct 137640
cttcagcttc ggtagctcct gcagcacagc ctccatccga gtcagtacta gctccagctt 137700
ctacggtaga tcctggatcc gaggctgact ctgaccctca gctggcgttt gctcttctgc 137760
cacgatcgtg atcggatgcg ccccagccac ctccttcctc ttctggtctg taggttcagg 137820
tttccttttg gtgtttgacg ccaaaggggg agagatatga gagttgtgag agctaggggg 137880
agttagggag ttagtataga gtcattttga tgtaatatat gtgcttgata ctctctgtac 137940
tagatccact tttgtatgac gattttggct cacaaactct attatatgct ctcgatgctt 138000
atgttgactg tgtgtgtatt gtgttttcac cttatatgtt atcaccagtc tctagttctt 138060
gttcatcgat ttgatttcac ttttatatga acaagaaact tacaatgtgt atgcactcac 138120
tcttattatt atgttacaca ctctttctgt caaaaatttt tgagtataac taaccatctt 138180
ctctattgac agaaatttca aaacaaacta ctctcacaat cttgtaggtt gtcatcaatc 138240
accaaaaagg gggagattga aagcatctag gcccctggtt ggttttagtg attaatgaca 138300
atgtaatttt atatgtgact aacatgtgtt ttgcagaggc aaatggtaag ttaggtcgca 138360
ttacatgtag atgtactaca acggtgaaaa caatctcgga gataagaact tgaagcgacg 138420
gctaaagcga caaaacaaaa agtgaaggtc ttcgtattcc gagtgtcaag gagttgcgga 138480
cactcgtgat atagttaggt cttttatttt gttttagtcg tactataaag aggggttgtc 138540
gatgagtagt ttgaccaaga gagttctagt gtagtgttgg tgcatattca cactcacata 138600
tagtgctagg tgccactcta gaacatactc acaagttaga acgaaaaccg aattgaaaaa 138660
acagcacaaa acagaaacta gggtttctgg ctttggggca ccggactgtc cggtgtgcac 138720
cggactgtcc ggtgcaccct ctgccagtgg ggccagcctg gcccaaggaa gagggttccc 138780
tgcgcacaga aacctgagag cgcgttgttc gcgagttgaa ttttagtgga ctgtccggtg 138840
tgccatctgc ccaacggcta gctgtcagaa ctagccattg gagtcgaccg ttggcgcacc 138900
gttggcgcac cggactgtcc ggtgcgccca tgtgcagcag attcctggta atggctagtt 138960
ggtgggtgag ggctatttat acccccctcca cccactatat tgatggtctt gctacccaca 139020
tttactccta cacattggta gagcattgca agcaccacaa agcctagtga ggttatttga 139080
gaatcttaat cccgcatttg gaccttatta gcgctagcga gagccaccta gagcatacac 139140
cgcatgcatt aggcttctct tggtcaagtg aaagtctatg gcttgttact cttggtgatc 139200
gtcatcacct agacggcttg gtggcgttgg gagctcggtg atcaccgtgg agatcttgtt 139260
ggtgacccga ctcaagtttg taagcggtcg tgagggatcc actgcgctgg agtggcaaag 139320
gatcatctcg ttgtgagcac ttggttcttg cgaggaccaa gggggagtga tacccttgcg 139380
agggtgctcc aacgaggact agaggagagt gccgactctt cgatacctcg agaaaaattg 139440
gagtcttcta aaccttgctt tacattccgc acttaattaa aacattttac attgtgtatt 139500
tgtttagcaa gtatttgaaa tattgtctta acattgttgt atttctatta ttattctctt 139560
agtgatagtt atcggggtga agttggactc ttgcttagat tttaattagt gttgattttt 139620
agaaaagtcc aattcaccct cctcttgggc atcgtgatcc tttcaaaact cactcaattc 139680
cgtctaatcc acgtggattc aaaataaaac gaacagaccc taatacatgc gatccgacgc 139740
tacaccggaa ctatcagtgg tcagcttcta ggcttcagca ttatacgtac tatgaaaata 139800
tgaatgcact tcaggtcatc atcaacaacc aaaatggata tagcaaatat tcaggctcat 139860
tatacttgaa aacaatagaa ttacattaaa aaaggccgaa accgtgaggc tggattaaca 139920
agagaaacgg taatggtaca gtaattcatg aagtgaagga ttttacatca ccaccagctg 139980
gtgctgaacc ttcccgttgg atccagctaa ctgcccttgg caggagcatc tacaaccaat 140040
acccaaagtg ggttatctta cttatctaga gccctggtat cgcaagccca atatgcctca 140100
gggtcagggc aggaccaaga aatgtggtga agttcacatt cccaaggcaa ccctacgtct 140160
caatgccacc tcgaagtatc atctagtaaa agcaaagttc aacagaaatg ctgtgccagc 140220
aagttgtctt ggaaccgacg tggtaaaatg agcatcgttt gatcactttg tttttcttct 140280
cgatgcaatc tccgctgccc atgcttttcc caagtctgtc tgaaatttgc ctgcatggga 140340
attaggtgcg gggatatggt tttgttacac aatgactcta atgctaatag cctaggctaa 140400
gtttaccatc cccatattca aattccactc tgcgaatagt gcaatctaag tgcaaaacag 140460
tgttttgggt gggtgaactg ctggacacgg tctaatacaa tgtaaaaatg agatcaaaca 140520
taagcacgtg ataaaagaaa accataaaag gcataggcat gtatcagttc atggtaaaga 140580
aaaccattat aggtggtagt gtccagtttt caattagcaa taatcattca ggcactaata 140640
tgttctgaat tgctgatgaa tgtttatatt atctcaggaa aacattttta agtgtaagac 140700
caaaaaaatg gcaacatcct tctcagctta aatgaactgt tcaaatttat gtacaggatg 140760
ctcatgaaaa ttgagaagag caagatttat gtactggatt gtcatgaaaa ttgagaagag 140820
caagatttat gtactggata ctcatgaaaa ttgagaagag cataacagaa agagaaaaat 140880
cacacctgct gttgattgga agaattcttc aaggtcccgt ccttgctctg aaaattttaa 140940
aatacatagg cgtaagtgtg atactgttaa ccccatctat caacaaggag ttcaccaggt 141000
gttaagtgat agtacattga tcatatgtat cacttctcac acccagaagg ccgtggagca 141060
aattaaataa tggtgtaagc acagatgggc agatctaggg cggaggctgc cacatgagtg 141120
gggtcttgag atgggataaa tcgagacaag cctcccctgc aaatgcagag aggctgtttc 141180
gaactggcaa catagtgact tagtgagact gccctcacca ctacaccagg cctacccaat 141240
ataagcacaa atgatgcaaa gaaaaagatg tgctgtattt gaaatgtgaa atgtgagctg 141300
attttactat atacatttat ttggttatta caacaagaat atttgatgaa tgcatttaaa 141360
tagttgtggt ttgtacttta tagctactgt gcatgggaaa tgttagttca aatattcaag 141420
caccagtatg aactcaccct tttcatactc cagagcttga agtatcatct caacctggaa 141480
atataacagt gcaacaaagg attacagcat gcaaaggaaa aggaagaagt ggagccatat 141540
gggttagggc cataaatcat aatgattgcc tacattagtt aaatatcctg ccagttatat 141600
gcattgccta ttgaatgatc acaagaacta ccatctgata gcttcagaca gacgttgcaa 141660
tcatgccacc aacttgatgg attgaaatat gaaactgtac cttgtcaaaa tctttgacaa 141720
ccttcgcttc caaagacgca ttctcctcat actccatcca aagttcacga atttcttgtg 141780
ctgcaagaca acagcatgca gataaaggca agtatttatt atatatacca tgtcaaagat 141840
cacatgaact ctttagtctc gcctgtacag agaacatcct tttatcctgc atgaaaaact 141900
gtttccaaaa ggctgctaag atactttatt tagttctaaa aggttcactt cacatgtaag 141960
ggatgctgga tctctccaat attttttaac gattaatgat atgaataatg agaacacaac 142020
cagaatacta gaattctatg ttgtgaaact cttagggaaa aaatgttgga tgctatgata 142080
gccatttgag cataaataat ttacgatcca taatgcttca aggtagaaaa tcattagaga 142140
tggaataata ttatcaccat caattacaat atcatgttca aattccaaaa ctcatagtca 142200
tcaacatttg ctgaatataa actcttcggt tttggcttct acaaaaacat cccttatctt 142260
ttcaacctcc atttcaaaat gtagggcgta aggattcaaa aaagtcaatg aaactagtca 142320
aaatatttgt atatttattg cacaaagata aatctataga ttcatatttc acatgcattt 142380
tagtgagaca ttgcttttgt agtaattgat aatatattga gttcatatat tgcaagggaa 142440
attattggat aaagcatatc tttgaatgaa attctcaaac actaatacac cttataaaaa 142500
gaaaaagaga agtataaata acagtttctc tggaaataat ctgagtgatt ttaagttacc 142560
aagagtttcc ttgacaccta actaagggat gtgaatactc taagaattat ccaatactta 142620
tttaaactat gtatcaaaaa ataagaacaa aagctgcccg ctggatttct acaaaataat 142680
tgccaggtta tgatctgctt ccctgatgga agtgaaaagt atcggatgga aaaatgacca 142740
tctaagaaat aataataaca gatgaatagc ttttcaaggg taaaataaaa tatgtatatg 142800
acctgcaagt actatagtat tgtattcaca aaattcattg gcatccacat attgttcttt 142860
tttccttgaa actatggtac tatgcacaca taatgggatc attaagtcta gactattgag 142920
taatctagaa agatgatgcc agtgtgcaat agcaccacat tcatttcata tataactaaa 142980
tcatgaaaag acaatttgag gcataagatg cctaattaac tacagcataa aatgctaatg 143040
tatcacaatt gcaagtttca gtattcacct cttgaaccac caccaagcag ctcgcacata 143100
tggtccaatg cttctttctc cctgcggttc ttctcttcct tgggtacatt atcagaaggg 143160
gtgatgtcac caacaattgc tggagtacca aaagaaaaaa caattgaaat gagtcaactg 143220
aacccacatc ctcataggca gttagttcca gaaacaggca agctggctta ggaacagcag 143280
caagagtcca tatgagcgga gggcaaaatc atgtgttcat ttctaagctg agcatgcttc 143340
tgaatgaaaa taggaaaatg tgcacatagt ttaaagtttt acactttggc tagcagaggt 143400
caaagaacca actaattggc acaagtactt gaacacacat cctacattcc tactacaggt 143460
ctccagtcca gtggtctagt taccatctac caacatctca ggtagtaata ggctcgcata 143520
ttcacaaaat tgcatccctc atctcacaca aagccccaaa acttcagtga agccgtctag 143580
acggaagtct tttgagacca taccttctgc aatgtcgtgc acaatcgcca tcttgacaca 143640
cctgtaattg aagggataaa taaacagtgt atgaaaacgg aaccgtaaga aggctaaata 143700
ctgccgagct agacttgaga gcgaaactgt caggatcacc tgtcgcggtt gacgccgggt 143760
agatcggccg cgacgagcgc catgacgccc atccggtaca tgtggtcggc caccgactcg 143820
ggcgcctgca ccccgcgctt cacccacccc gccctcttgg tcgtctgcaa ttacatccac 143880
aatctcatcc atcgcgtcac atttccatcc atctcaacca agccggcccg tggaaatgcg 143940
aagcgactaa acaggggcgc tcagtcgctc accttgaggc ggtagcagag cgtgaggaag 144000
tcgatggcgt tggacgccga aggggccggg gcaccggcgt ccaccgatgc ggcgggggtc 144060
ggggaggaag aggaggacat ggcggcggcg aggcggtggg ggagcgcgcg gtgagccggg 144120
gcgaagggga cggggtgctg tgggggcttg gcggcggcga gggtggtggc gcagagggag 144180
gagagggaaa gggctcggct cccaccaccc atcgttatta gctgaggccg gagtaggcgg 144240
aggagcggtg ggcagcgcag ggcaggctcc gcggatggcg gggtggtcgc tcgcggaacc 144300
ggcgcatgcc cgcccgcgag cccgtggccc agcttgcgcg gcgggcggac cgtggatcac 144360
gtggggtact gaggttctcc taatttgggc cccagcgcac ggggatcgat cgcgctagag 144420
ggtcgatcct ttcctttttc attttcggct gccgggccca ttcggccaat ccggattccg 144480
gagtctgcaa tgttgcggat agcccatggt tggccaagaa tgcggcccgg cccgtgaggg 144540
gtccaccccc acgtggaaat aacaccagcc catcaattta tatgtctttg agtctgaatt 144600
ttaacccagc taaatctgtc gagaacttac agcaagggaa gagattaagc gctgtttgga 144660
tcaaaatatt agactcactt atccaataaa ataggtaaca cagaatttta gatgatatta 144720
tttacagagt tgcgtttaat ataggaataa aatagaggat acaatagggg atcagttgga 144780
gatggcctta tactatcaaa aaatcttatg tgggctaata tcaaacgaga agctctagtc 144840
gtctatataa caaggaaata gttttttgtg cttctgcctc gacaaaaaga gaataagccc 144900
tccattgctg aggagagggt tcaaggtctg aatttggaaa ttgcaccaca gcaagtcctc 144960
ccgccttgcc taattgtctt acatgatagg cttcgtttcc gttcgctgaa taaagaagca 145020
cggtatgtcg tttttgaccg ctctagacaa ttgtttagta gattttgttc aaactagatt 145080
gttttctcgc ggtcagatac atattgtaga gtgatttctt actgtcagat acatattgta 145140
gattgattta tgtatacact agcatgttaa atcctgatga tttgacctgc ttaatatatc 145200
caatctatta cttttactta aaaagccatc gatgtcctac taaccgcggg tcgtacgaat 145260
caccccgatg gcgaggctcg tgcgccagtc gcgtgcacta cacacccacc ccaccggtgg 145320
cccacacgtt gcgttcatga atagatcggt catgccggct tctagtcgta cactatgtcg 145380
gcgcccccaa ctctgcgcct tgatgtcaca ctgacccacg cacccatgcc ctgctgctgg 145440
tcacgccatc tcgagctgag atggttcacg ctgcgtcagc ccacggcgcc accccgcact 145500
gggtcgcgct tgctcggcca gctggggcgc agctcgtcgg catatgcttc agccacgcct 145560
cgtcagcacg ccctggaccg gctcccgtgg gtcatgcaat ttatctattt aaatttctat 145620
tattgataat tagcacgcct aattaaccta aagttaattt tgtgtgacgg actatggttg 145680
aagacaacag aattgattcg tggagcttgt cctcaatggc aagaactaac cgacctagac 145740
taacgactgc aagtttcacc tagaggcgat atagctagga aaggagatct tctggtaggg 145800
cccgaatgac acttgcctga aacttcatga gaaagcaaaa attacgatct tcgtcgggca 145860
ccacatccat ccaggcctga agatggagta tccagaggtg aaagaccata tgatattgtg 145920
gacagagcta tgtgagtgtt tcagtgtgga gaagcatgtg atgctcccgc gggcgcaaca 145980
tgaatgggcc actctcgact tcaatgcagt tgaggcttac aacactgtca tccatcgcat 146040
tgtcgctcag ctacatttct gtggccagat agccatagac ttagagatga tcgagaaaac 146100
tctccaaacc ttctacccct ccaatatggt gctccaacag cagtactgta gcaacaagta 146160
cacaaataat gtgacctcgt caacatgttg cttggtgcta aggctcagaa tgagcttctg 146220
atgcagaact actagaagca tccattcggc acgcggtcat gcataaagca cacgccaact 146280
tctagtctta aggaagaaa ggtccctcca gagaaagggg tcatgggcac tgtaataatc 146340
aggggatgag agggggaatt tttacgaagc caccacaaaa tggcagtaga gtagcaatgg 146400
ctatggcaaa ggcaaaggca aaggcaaaac ctcagaaggg ctatgcaagc tcctcaaagc 146460
atgccagtga aggttgtttc aaagaaacac ttgattggca tgtatcagga gtggaagaaa 146520
cgcatagctc ataggctcac cttatttatt catgcatcta tacacgctat gattatagag 146580
cctatgtaac accctgaatt tgggggtata aaatttcttc tctaatatct accaaattca 146640
ggtgttacca cttttctcat ctccgtagat ttcctatttt cttcctttct aatagagttt 146700
tggttatata tttgggagat gtattttttt tctttactat attcaaacct aggggagaca 146760
tgaattgttg catcatgctg agcttaaact ttgtttttgg ttgatgcaca tgtttgaaat 146820
attcaaattt gaatttgtgg tttcgttgga tttgaattca atagagaaaa taaaaataaa 146880
aggaactaga aattcagaat aaaaagaaaa tagaaaagca gcccagccta cgcacctgcc 146940
ctctctctcc atctgccagg tgggcccgac ctattggtgc cgctcaccct cgcgcgcacg 147000
cccccgctct ccctctgtgc agtgggccca gcccatcagc gctgaatcat ttcctcctca 147060
cacgtgctcg tgcctctact ctgtgggccc gccttgtcag tctcatcttc cccgcaaccg 147120
ctgctgaccc gcacacgcac tcacgccgag gaagccgacc acgttgccta cccacgcccc 147180
cagctccctt ttgagccccg cctacacccg ctctccctcc ccttcctaat ttcacccact 147240
ctcaacctct ctcgcgctta gccgccgccg ctcaagctcg ccggagaagc gcgccaccgc 147300
gtcgtctgcc cggagctcct agcatcgtgt caagcatccc cgagcacact cctaaggtaa 147360
ggaaccatcc ccgtgccctt cctgccccga ttcttttccc tctacggtga atttgtgttc 147420
gctggagctc tatcgcgctg gtttgccgcg cccgctcggt gtccgaccga ttcagccccg 147480
ccccgtgccc gtgccttggc cctaggcgtc cctcacccct caccgaagct tgtgctggcc 147540
tcggtgcacc ggattccgcc tcctcacggt cgggattgct caccggagta accccgacct 147600
gtggcagaac ctcccaagtt attaggccca catgcaccta tccttgtccc aaagacctca 147660
gaccccaaaa aacgtgcacc agataactta acaggatctg taagatctac caaaggacat 147720
cggataaacc acttacaacc agaaccgcga gaaaacgaat cccaaatcac acacaccaat 147780
attgttgcag cgaacatctt actaccaaat tttacaggtt acaaaaattt tacattagtt 147840
tatcggagtg attacaaaag tataagtttg aaatatatat gctagctcaa gggatcatcc 147900
tcaataagaa gtatagaagg gttacttaga ctcataagaa ggccgagccc accggcactt 147960
aacaccatca acaacagcac aaagttagaa cctgaaaaac aacaaggaat aaaaccctga 148020
gtatggaatt actcagcaag tcttacccga ctaaagaaaa gactctcaag ggtatgctgg 148080
ttatatggga gtcaaggtaa ggcttttcaa taatcaaaga ctctgttttg cagaaatgct 148140
tactaaagtg gatccttaaa atccagtttt atttgtcaag ttaagtagaa ttacctgtaa 148200
ctagagttct ttctacccta gttcaatcac ttgtcctgca ctagccaatt tcttaacaaa 148260
aacccatcat ctttagtgga atgctacgtg tagggcagtg accaagtctt cataaccacg 148320
aaggtacggc gatccgaatc gattatactt agctgaggat ctccaatcac acgacatatg 148380
tagcacttaa cccttgcata tgtcaacccg ccaccggggt tcttaagacc agatcaggtt 148440
cacgcaaacc gagagcacag ttacaccacc gtccagcctc ttgccacgga ggtacacgct 148500
actctcgcca ccgctccacg cccatttcgt gnnnnnnnnn nnnnnnnnnn nnnnnnnnnn 148560
nnnnnnnnnn nnnnnnnnnn nnnnnnnnnn nnnnnnnnnn nnnnnnnnnn nnnnnnnnnn 148620
nnnnnnnnnn nttcagggat taaacaatgt cattttgaga aagactggat ttgtagagca 148680
taccagtcgg aagcaagtgg cactcatcat ccacacacga acaaaaagac aacgaccgcc 148740
cagtgaagat cctcccccaa agcaacagtc aagcatccct gacagaactc ttaacgtaag 148800
taagtacctt caggcccttc ctgccccgat tcttttccct ctacggtgaa tttgtgttcg 148860
ctggagctct atcgcggtgg tttgccgcgc ccgctcggtg tccgaccgat tcagccccgc 148920
cccgtgcccg tgccttggcc ctaggcgtcc ctcacccctc accgaagctt gtgctggcct 148980
cggtgcaccg gattccgcct cctcacggtc gggattgctc accggagtaa ccccgacctg 149040
tggcagaacc tcccaagtta ttaggcccac atgcacctat ccttgtccca aagacctcag 149100
acggctgtgc atgtgcacca gataacttaa caggatgtgt ccgattgccc caaggacatc 149160
ggataaacca atttcaacca gaaccgcgag attaagtctt gaaactcaca cacggataca 149220
aagtggtagc ggaaatatta ttgacaaatt tgacaggtta cacaaatttt tcatacctct 149280
atcggaggga atacaaaatt ctaagtctga aatataaatg ctagctcaag ggatcatcct 149340
caataagaag tatagaaggg ttacttagac tcataagaag gccgagccca ccggcactta 149400
acaccatcaa caacagcaca aagttagaac ctgaaaaaca acaaggaata aaaccctgag 149460
tatggaatta ctcagcaagt cttacccgac taaagaaaag actctcaagg gtatgctggt 149520
tatatgggag tcaaggtaag gcttttcaat aatcaaagac tctgttttgc agaaatgctt 149580
actaaagtgg atccttaaaa tccagtttta tttgtcaagt taagtagaat tacctgtaac 149640
tagagttctt tctaccctag ttcaatcact tgtcctgcac tagccaattt cttaacaaaa 149700
acccatcatc tttagtggaa tgctacgtgt agggcagtga ccaagtcttc ataaccacga 149760
aggtacggcg atccgaatcg attatactta gctgaggatc tccaatcaca cgacatatgt 149820
agcacttaac ccttgcatat gtcaacccgc caccggggtt cttaagacca gatcaggttc 149880
acgcaaaccg agagcacagt tacaccaccg tccagcctct tgccacggag ggtacacgct 149940
actctcgcca ccgctccacg cccatttcgt gttatcttat tctggcctta gtctgcccga 150000
ggcaaggctt acccatgacg aggcatgtga ccagttaaag ggtcctcgat catcaagcct 150060
acatcgacaa ggtccttaat cgactcagac ggagacacta caccgagact cctttcccgt 150120
gcaagtcacc cgcccggtct tagcttaatc ttttaaccca aaaacttggt acctggcaga 150180
ggtacatctt ttccgatgtt gaatccatca tagccatgat ggattcacca tcaagtttta 150240
tttttgaaaa caaccctccc actttgccaa acatcttttc taaaacaaat ccttttgttt 150300
ttctaagcaa tactaagcat agtaaaacct ttttgtaaaa acgggttttc aaggagggta 150360
atcaagatca aggaaggtaa tgcaggaatt gtttaatcaa tcaactcctg tcacctaatg 150420
cagcaatcaa gtgagaaaga ttttaaaaac atcaagggag gtggcaaatg caccggggct 150480
tgcctgggta acactaggtt agtgttgtta gacgatgtcc acttggcgac cattttcagg 150540
tttgtccatc agcatcatcc tgcggattag cccgcgcttg gggtcgactt ggcttgtctt 150600
ccgcatcacg cgatcaatta tcgtacctaa ttgagatgca cgatgcacat gaatgcatat 150660
aaacaagaat agcacaaatc taaatagtgc tatacgatag cgtattaaac acctagtggc 150720
gaggcgttgt acaattttgt acagaaacac tagttattaa tatgcgacta cgcacaatga 150780
ttacgcttct cgaacctaac gcaaacatca cgaacaacaa actatacaca agaaatataa 150840
ttagcctaat cacaacttat cagttaatta attaaattct gaactaatcc cttgccttat 150900
aaattatact acatctttat aagtgattaa aatattttat caacacatat gcctactaaa 150960
attctactcg gtccactaat tcagctaagt gaccgaaata gcgaaataac tcgctataac 151020
tgaacctggc tcgataatcg caagaactgc gaagtcgacg agagtttcgt gacttacgca 151080
atttatcgag caccctaatg agcctcgcac taacacatta acttattcaa cgatcgaact 151140
attctaaaca attcattagc ttaccgaact attctaaaca attcatcagc ttaccgtttc 151200
aacagctgac acgaatccgt gagatcggca gtgatttttc gatccacgca atttgtcgag 151260
cgcttaggga atatcgcgct gctaacttcg tcttcacccg attcttgggt tttcttgggg 151320
acgcacgagc gacgatgacc ttcgattgaa gtctggggta agctggtgag gtggggatcg 151380
agccggagat gacgtgtttg acaactcgac ggcaaacgac gagatcgacg acgtgattgg 151440
aaattaaagc cgagcgagcc gagagggcac gctggcgagc aggaaaccgt gcgagcacaa 151500
gacaggaaaa acgacggctc gacaacacgc gaagcgacga cagtcaaatc ggcaacaaag 151560
cgttggcgaa ttcgatgaac acgaccacag tcgcgagtta acgcggtcaa gacaactgtg 151620
accaacgagc ttgcgacaga agtgatgatg gtgtgggaac tcgacacgct gtgacgagca 151680
gataaaattc gtgcgcgcgg caacaaagaa agagcgagct gcgcgtgagc agagagctcc 151740
acacgaaaac tcgacgcgcg caggaactac ggcgagctag agtagagaaa actcgacgcg 151800
cgcaggaact acggcgagct agagtagaca gtcatgggag atgtagtcat gtagagccga 151860
gctgggcgac aaagcgaaat ccaggctgaa gcgttgacga gcaaagagct tcgcgcgtgc 151920
aagaacaaca gaacgctatg cgcgcgacgc aaaggcgagc agtaagacga cggcgcgaca 151980
gacggaacca agcagggagc gccggccatg ggcgcggcaa tagagctggg cgagctcgga 152040
ggggaagcca cggcacaaga aatccgatca ggcgcggccg aacagaggtg ccgcggcaca 152100
ggagctcagg gacggacgag caggagcaga ggagatggat accgcgagca gcctgcaggg 152160
aaccccgcgc catgggagaa aagcagagcc gagcggctgg ggattcagcc agcgagcaga 152220
ggggagatgg gaaggagctg ctcggctgcg gcttgctgcc gggcgtgcgt ggagaagaaa 152280
cctgcgcgct ggagatttgt aggagaccaa gggcggtggc gggataagga taggagcgct 152340
cggcggcgtg atttttattt ctaggggttg cgcggcgcgg tacagaaaaa tcaggcgacg 152400
agattaaaga gatgcagtga gcagttcgac aaattcgtcg gcatggacac aagctgacga 152460
cgacggccag cccgaccgcg gcaaggtgag gggagacgcg gtctgcgcaa agggcgagct 152520
cgagcaagga actagagccg acgatgtcca cgacgagcag gaccagagac acggtgctag 152580
tggatggaaa ctgagcacag gatggatgca agctggagac gagcttggtc aggtcgtcgg 152640
gcacagaggt gctcggaggg tccgacgagc acagccggct gccggctgcc tttggatgct 152700
gatggatgga agaaatgctg gtcgctgggt aaggctggag gagagacgtg cgtgagattt 152760
tccagcgagc tagcgtccaa tggataagag agaaggagac gtgaggaaga ggagaactac 152820
gtggagaaaa tatccaggct agtgacttca gatatggaag gggaaagcgg tggataaaat 152880
cagagagaag agcggttgca gatattttct tccttcgttt tcttttactc gaaaatttga 152940
ataaaaatac aattatcagc tggagattgg gactagaatt tggaaagatg taagaggact 153000
aaaattaaaa atgattttag ttacaatgtt ttaatcggtg ttacatttaa ttgaaatcag 153060
ataaaaactt atccgtcacc aaaacacagt tgatttggtt atcctacatt gcgggctaaa 153120
gaacaaatta gatcatattg aaagggaatt aggcttacac ctagttccta aataattttg 153180
gtggttgaat tgcccaacac aaatcttttg gactaacttg tttgcccaag tgtatagtgt 153240
atacaggagt aaaaggttca cactcagcca ataaaaagac caagttttgg attcaacaaa 153300
agagcaaagg ggcaaccgaa ggcacccctg gtctggcgca ccggactgtc cggtgtgcca 153360
ccggacagtg aacagtacct gtccggtgca ccaggggact cagactcaaa ctcgccacct 153420
tcgggaattt ctaaggcgac tcggctataa ttcaccggac tgtccggtgt acaccggaca 153480
gtgtccggtg cgccaaggga ggtcggcctc aggaactcgc tagcctcggg ttcgcgcggc 153540
agccgctccg ctaaaattca ccggactgtc cggtgtgcac cggactgtcc ggtgtgccag 153600
cggagcaacg gctccctgcg gcgccaacgg ctccctgcgg tgcatttaat gcgcgcgcag 153660
cgcgcgcaga cgccaggcac gcccataccg gtgcaccgga catcaaattc cagatgtccg 153720
cagtccgcta cacactggta ttgtgaagcc cataaaattt accgatggct cgatcccgta 153780
tggaaatttg acaatttgtg aagaaccctc cagcttgtct gttgcattgt ttgacccaaa 153840
ctggaaaagc tgccatggac ctagaatttt ctgcccttat gcggaataaa acatggcact 153900
tggttcctcc cgcacctgac agaaatttga ttgattgcaa gtgggtttat aaactcaaga 153960
gaaaagctga tgagtctatt gaccatcata aagctcgatg ggtggctaaa tgttttaaac 154020
agcttnnnnn nnnnnnnnnn nnnnnnnnnn nnnnnnnnnn nnnnnnnnnn nnnnnnnnnn 154080
nnnnnnnnnn nnnnnnnnnn nnnnnnnnnn nnnnnnnnnn nnnnntgaaa ctagagattc 154140
gtcctcagct ggtttaggcg tgagcagaag gattgtcccc tcatataagg accggtttgt 154200
catcttcact acctgtactc tttaatagta caaccactcg agactgtgtg ggcagtcact 154260
caatctgaac tcgtacggtc caaccccagg gttatgaagg ctggggagca ccgggaggat 154320
aaggaggggg aaagttttgt ccggtttgga catggtggtg gcctgactcc ttcaggataa 154380
ccattaaggt taggacatgc ggggaaagaa agagagtcgg attcgggtct cattgatcat 154440
gggatcgcag agctggacta gtgggtaaag tgtacacctc tgcgcagagt ttgaaaacct 154500
attcgaatag tctgtgtcca caggaatgga cgagtctggt atggtatggc aattaatgtt 154560
ttgttttcca aaaaaaagag atgcttttga aaagtggttt ttaaaaggtc cggcggttga 154620
gccgtgagct atggtggacg ggaagtccag tagctgtttt tgaaaatgaa aaccagtggg 154680
aaactgctga gatacctgga tggtttagtc caggggattt tgttataata ctgaaaaact 154740
tcctgctcct tttggagagg atgcactttg caaaatacaa aatgtttttc aaaacaaccc 154800
tgcataaaat attgctgttt ctgcaaatat cctgagctct acatattcca tgcattatat 154860
ctgatttccc cattccgcgg gtgaaggtgg gctgctgagt acgtttgtac tcacccttgc 154920
ttatttgttg tttttcagaa aaaagagatc gggtaagagt tacgactgtt cccaaccttg 154980
cctgtggctg ttggaccgct gaattgcttc actgcgtata tcgggctgct tcagccccac 155040
tctgatgata tgtcccgagt tgtggaccaa ctcttaaagt tgatcgccac ctttataggt 155100
ttgtctcgtt taagcagatc tgaatcatct gatgtataaa tgtgtttact agcctcctgg 155160
gactagtaat tgtatcacat ttgagtccca gaggattggg gacgcttcaa gctgtggcag 155220
aacctcccaa gttattgggc ccacatgcac ctgtccttgt cccaaagacc tcagacggct 155280
gtgcatgtgc accagataac ttaacaggat ctgtccgatt gccccaagga catcggataa 155340
accacttaca accagaaccg caggattaag taacacaaat cacacacacc aatattgttg 155400
cagcggaaat cttactacca aattttacag gttacaaaaa ttttacatta gtttatcgga 155460
gtgattacaa aagtataagt ttgaaatata tatgctagct caagggatca tcctcaataa 155520
gaagtataga agggttactt agacttataa gaaggccgag cccaccggca cttaacacca 155580
tcaacaacag cacaaagtta gaacctgaaa aacaacaggg aataaaaccc tgagtatgga 155640
attactcagc aagtcttacc cgactaaaga aaagactctc aagggtatgc tggttatatg 155700
ggagtcaagg taaggctttt caataatcaa agactctgtt ttgcagaaat gcttactaaa 155760
gtggatcctt aaaatccagt tttatttgtc aagttaagta gaattacctg taactagagt 155820
tctttctacc ctagttcaat cactggtcct gcactagcca atttcttaac aaaaacccat 155880
catctttagt ggaatgctac gtgtagggca atgaccaagt cttcataacc gcgaaggtac 155940
ggcgatccga atcgattata ctcagctgag gatctccaat cacacgacat atgtagcact 156000
taacccttgc atatgtcaac ccgccaccgg ggttcttaag accagatcag gttcacgcaa 156060
accgagagca cagttacacc accgtccagc ctcttgccac ggagggtaca cgctactctc 156120
gccaccgctc cacgcccatt tcgtgttatc ttattctggc cttagtctgc ccgaggcaag 156180
gcttacccat gacgaggcat gtgaccagtt aaagggtcct cgatcatcaa gcctacatcg 156240
acaaggtcct taatcgactc agacggagac actacactga gactcctttc ccgtgcaagt 156300
cacccgcccg gtcttagctt aatcttttaa cccaaaaact tggtacctgg cagaggtaca 156360
tcttttccga tgttgaatcc atcatatcca tgatggattc accatcaagt tttatttttg 156420
aaaacaaccc tcccactttg ccaaacatct tttctaaaac aaatcctttt gtttttctaa 156480
gcaatactaa gcatagtaaa acctttttgt aaaaacgggt tttcaaggag ggtaatcaag 156540
atcaaggaag gtaatgcagg aattgtttaa tcaatcaact cctgtcacct aatgcagcaa 156600
tcaagtgaga aagattttaa aaacatcaag ggaggtggca aatgcaccgg ggcttgcctg 156660
ggtaacacta ggttagtgtt gttagacgac gtccacttgg cgaccatttt caggtttgtc 156720
catcagcatc atcctgcgga ttagcccgcg cttggggtcg acttggcttg tcttccgcat 156780
cacgcgatca attatcgtac ctaattgaga tgcacgatgc acatgaatgc atataaacaa 156840
gaatagcaca aatctaaata gtgctatacg atagcgtatt aaacacctag tggcgaggcg 156900
ttgtacaatt ttgtacggaa acactagtta ttaatatgcg actacgcgct atgattacgc 156960
ttctcgaacc taacgcaaac atcacgaaca acaaactata cacaagaaat ataattagcc 157020
taatcacaac ttatcagtta attaattaaa ttctgaacta atcccttgcc ttataaatta 157080
tactacatct ttataagtga ttaaaatatt ttatcaacac atatgcctac taaaattcta 157140
ctcggtccac taattcagct aagtgaccgg aatagcgaaa taactcgcta taactgaacc 157200
tggctcgata atcgcaagaa ctgcgaagtc gacgagagtt tcgtgactta cgcaatttat 157260
cgagcaccct aatgagcctc gcactaacac attaacttat tcaacgatcg aactattcta 157320
aacaattcat cagcttacta aactattcta aacaattcat cagcttaccg tttcaacagc 157380
tgacacgaat ccgtgagatc ggcagtgatt tttcgatcca cgcaatttgt cgagcgctta 157440
gggaatattg cgctgctaac ttcgtcttca cccgattctt gggttttctt ggggacgcac 157500
gagcgacgat gaccttcgat tgaagtctgg ggtaagctgg tgaggtgggg atcgagccgg 157560
agatgacgtg tttgacaact cgacggcaaa cgacgagatc gacgacgtga ttggaaatta 157620
aagccgagcg agccgagagg gcacgctggc gagcaggaaa ccgtgcgagc acaagacagg 157680
aaaaacgacg actcgacaac acgcgaagcg acgacagtca aatcggcaac aaagcgttgg 157740
cgaattcgat gaacacgacc acagtcgcga gttaacgcgg tcaagacaac tgtgaccaac 157800
gagcttgcga cagaagcgat gatggcgtgg gaactcgaca cgctgtgacg agcagataaa 157860
ttcgtgtgcg cggcacaaga tagagcgagt gctcgtgagc agagagctcc acacgaaact 157920
cgacgcgcgc tgactacgcg agctagagta gagaaactcg acgcgcgcag actacgtgag 157980
ctaagtagac agtcatggag atgtagtcat gtaaagcgag ctggcgacaa cgaatcagnn 158040
nnnnnnnnnn nnnnnnnnnn nnnnnnnnnn nnnnnnnnnn nnnnnnnnnn nnnnnnnnnn 158100
nnnnnnnnnn nnnnnnnnnn nnnnnnnnnn nnnnnnnnat ttattctaac catttcatca 158160
gctttataaa ctattctaaa caattcatca gcttaccgtt tcaacagctg acacgaatcc 158220
gtgagatcgg gcagtgattt ttcgatccac gcatttgtcg agcgcttagg gaatattgcg 158280
ctgctaactt cgtcttcacc cgattcttgg gttttcttgg ggaacgcacg agcgacgatg 158340
accttcgatt gaagtctggg gtaagctggt gaggtgggga tcgagccgga gatgacgtgt 158400
ttgacaactc gacggcaaac gacgagatcg acgacgtgat tggaaattaa agccgagcga 158460
gccgagaggg cacgctggcg agcaggaaac cgtgcgagca caagacagga aaaacgacga 158520
ctcgacaaca cgcgaagcga cgacagtcaa atcggcaaca aagcgttggc gaattcgatg 158580
aacacgacca cagtcgcgag ttaacgcggt caagacaact gtgaccaacg agcttgcgac 158640
agaagcgatg atggcgtggg aactcgacac gctgtgacga gcagataaaa ttcgtgtgcg 158700

```
cggcaacaaa gaaagagcga gttgcgcgtg agcagagagc tccacacgaa aactcgacgc 158760
gcgcaggaac tacggcgagc tagagtagag aaaactcgac gcgcgcagga acttcggtga 158820
gctagagtag acagtcatgg gagatgtagt catgtagagc cgagctgggc gacaaagcga 158880
aatccaggct gaagcgttga cgagcaaaga gcttcgcgcg tgcaagaaca acagaacgct 158940
atgcgcgcga cgcaaaggcg agcagtaaga cgacggcgcg acagacggaa ccaagcaggg 159000
agcgccggcc atgggagaaa agcagagccg agcggctggg gattcagcca gcgagcagag 159060
gggagatggg aaggagctgc tcggctgcgg cttgctgccg ggcgtgcgtg gagaagaaac 159120
ctgcgcgctg gagatttgta ggagaccaag ggcggtggcg ggataaggat aggagcgctc 159180
ggcggcgtga tttttatttc taggggttgc gcggcgcggt acagaaaaat caggcgacga 159240
gattaaagag atgcagtgag cagttcgaca aattcgtcgg catggacaca agctgacgac 159300
gacggccagc ccgaccgcgg caaggtgagg ggagacgcgg tctgcgcaaa gggcgagctc 159360
gagcaaggaa ctagagccga cgatgtccac gacgagcagg accagagaca cggtgctagt 159420
ggatggaaac tgagcacagg atggacgcaa gctggagacg agcttggtca ggtcgtcggg 159480
cacagaggtg ctcggagggt ccgacgagca cagccggctg ccggctgcct ttggatgctg 159540
atggatggaa gaaatgctgg tcgctgggta aggctggagg agagacgtgc gtgagatttt 159600
ccagcgagct agcgtccaat ggataagaga gaaggagacg tgaggaagag gagaactacg 159660
tggagaaaat atccaggcta gtgacttcag atatggaagg ggaaagcgat ggataaaatt 159720
agagagaaga gcggttgcag atattttctt ccttcgtttt cttttactcg aaaatttgaa 159780
taaaaataca attatcagct ggagattggg actagaattt ggaaagatgt aagaggacta 159840
aaattaaaaa tgattttagt tacaatgttt taatcggtgt tacatttaat tgaaatcaga 159900
taaaaactta tccgtcacca aaacacagtt gatttggtta tcctacattg cgggctaaag 159960
aacaaattag atcatatccc cgcgcacgat ctttctcaga caatgcgcga ttcggattat 160020
tttaccctga acattttagt cgtcaagttc aaattatttt gctcggaata agatcattcg 160080
agtgagttcg ggcttccgaa ttcgtgttcg cgcgagcgat ggattttaaa tactcatcgg 160140
acgcaccgat tttcggaaca gctaggttcc gaacattacg aaaatttagg aagagcccgg 160200
acagataaaa aaataaaaac gatgtcgcac tcgcgacaaa cgacaccgat gcgatattaa 160260
aatcgcgata agcgacgatg attaaaattt aaaatccgtt ttatccactg atattgcgtg 160320
cttaaatccg aactcgttgt tgagcggaaa ataaacacct ggggtgttac agccctcccc 160380
ccttaaaaga atctcgtccc gagattcaaa acgaaagact tctaagagta gagaagcatg 160440
taacccatgt ccatatcagc gataatcatg agacaattcc aaacaaagtc gagtgtctca 160500
aaatgtcgtt cctctagtgg acataacatg tgtcgcctta ggctaattta gaaatgtcca 160560
ccaatagaga cgatgtctgc cagaagtaca cataaggttc catgtgtgca gtttactttt 160620
tctgatgaca ctgtaatatc tgagtctgtt gagcgagtgg tagatatgca actttacaca 160680
aacagaatca gatgcaacct cttgggtaaa acacacagaa agagatttac caacaagtgg 160740
tcacggtaag ttcatagcac acgagacgag tgtggatgtc gaataacatc acagttaact 160800
cgtgttagcc agagaatcca agtccaagaa aaatgataaa gacttgaaaa aaattaccag 160860
cagagggatc tgtaaatgct gccttcgcaa ccaatccatt ttatcaagca ctaatcatgg 160920
atctacttga tcacacatgc tggaaaagca cacgtgagac gatcgaggca tgactagagc 160980
gatgtttagg tggttactgg ccgacttaat ctcgattctt gaaagtactt ccttaggatg 161040
```

gtttggacca tagcgagttt agataactcg atgaaacgat ctctaaactc gaccttcgtt 161100
cacaaagcag ttacaagtta gtaaaaccaa cttgttaaac tacttttgac attgagcaag 161160
tcctctcagt accattggta atccaagggt tgagagttca catttgctaa caggaaatca 161220
tgcacttggg tagaaatcca tttggtcacg ttgttcatcc gtttcttcta tacaagatga 161280
accgacttgg ttagggaata catggattaa ataagagagc gaatgaacaa attcttgcat 161340
ttcagcagca ggggaaacaa atctccattt tgggaactaa ttggttgtct tgcaacacta 161400
aaaagctcca aggcttcacc tttacacaaa ggatgtaaag ggaacttgta tgtgtgaagt 161460
caccatcaaa gtcaagagat aagagatcac acatgaaagt ggtatgccct tttgatccac 161520
agagatgata gatgttgctt gatcacttga caaacaacat agaaattgtt tcaagggagg 161580
actccacgga agatcacaca tcagtgtact tccacaatgg atcatgacca cagaccttga 161640
taccagcatc cgatgagtgg cacagtccta tgtgcgcatt cacaggaggc tctcagtttt 161700
cgttgcggca ccataagtca ttaatcatga ccaccactac cgaagctg 161748

<210> SEQ ID NO 104
<211> LENGTH: 634
<212> TYPE: DNA
<213> ORGANISM: Zea mays

<400> SEQUENCE: 104
caatccaggg ccaggccagg ccaggccaac caaaccctag gcactgcgcc acgcctagcg 60
cgcgtggtat ccatgggctg accgcgtccc ggtggggagc ccggatccgg agctagggtt 120
ccgtcctagg cggcaccacc atggagtggg acagcgagtc cgacggcgcc ggcagcgtcg 180
acgccggcta tgaggagcag gaggaggagg aggaggagcg gggaggcgag ggtggaggtg 240
gcgacgccgg gggcggcggt gggatgttca cgttcgcgat tgaaggcatg ctgcgctcct 300
ccgggccctg cgggctagtc gtcaccgacg cgctcgagcc cgattgcccc atcatctacg 360
tcaaccgcgg cttcgaggag gccacgggct accgcgccga ggaggtcctc ggcaggaact 420
gccgatttct gcagtgcaga gggccattcg ctcgaaggag gcaccccccta gttgatgctg 480 cactggtttc agagattcga agatgcatag acaatggcat tgagttccgt ggtgatttac 540
taaatttcag aaaagatgga tctccagtga tgaacagatt gcatctgacc cctatttatg 600
gagatgatga aaccataacc cattatatgg gcat 634

<210> SEQ ID NO 105
<211> LENGTH: 20
<212> TYPE: DNA
<213> ORGANISM: Artificial
<220> FEATURE:
<223> OTHER INFORMATION: Primer

<400> SEQUENCE: 105
accaccatgg agtgggacag 20

<210> SEQ ID NO 106
<211> LENGTH: 21
<212> TYPE: DNA
<213> ORGANISM: Artificial
<220> FEATURE:
<223> OTHER INFORMATION: Primer

<400> SEQUENCE: 106
ttcaatcgcg aacgtgaaca t 21

<210> SEQ ID NO 107
<211> LENGTH: 388
<212> TYPE: DNA
<213> ORGANISM: Zea mays
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t

<400> SEQUENCE: 107

```
ctgaacaaga tcgaccaaac agttcattca ccagctagaa aatgtgttca aataggagtg     60

gcagaaaaat aacacggttt accagattat actgtcacaa actgttaccg aacacttaaa    120

acaaagacta gatgttcccc aaaactgatg acaaagcaca gctcctcagt acttgatagg    180

ggcaagantc tccaactgag accccaactt ctcctcggnt gccttctcgg ccttgacacg    240

cagcttggcc aattgcttct tcctctcgta ggcaaccttg ggccttctcc ttgctctttc    300

tcctcaagtt ccctgatggt gtcatggtag ttccacccgg cctccttaga gagctcgccg    360

aggaggcagt acttgtgtcc aggctgta                                       388
```

<210> SEQ ID NO 108
<211> LENGTH: 21
<212> TYPE: DNA
<213> ORGANISM: Artificial
<220> FEATURE:
<223> OTHER INFORMATION: Primer

<400> SEQUENCE: 108

```
cgaccaaaca gttcattcac c                                               21
```

<210> SEQ ID NO 109
<211> LENGTH: 19
<212> TYPE: DNA
<213> ORGANISM: Artificial
<220> FEATURE:
<223> OTHER INFORMATION: Primer

<400> SEQUENCE: 109

```
ctcctcggcg agctctcta                                                  19
```

<210> SEQ ID NO 110
<211> LENGTH: 161748
<212> TYPE: DNA
<213> ORGANISM: Zea mays
<220> FEATURE:
<221> NAME/KEY: misc_feature
<222> LOCATION: (3611)..(3710)
<223> OTHER INFORMATION: n is a, c, g, or t
<220> FEATURE:
<221> NAME/KEY: misc_feature
<222> LOCATION: (7624)..(7723)
<223> OTHER INFORMATION: n is a, c, g, or t
<220> FEATURE:
<221> NAME/KEY: misc_feature
<222> LOCATION: (13118)..(13217)
<223> OTHER INFORMATION: n is a, c, g, or t
<220> FEATURE:
<221> NAME/KEY: misc_feature
<222> LOCATION: (25477)..(25576)
<223> OTHER INFORMATION: n is a, c, g, or t
<220> FEATURE:
<221> NAME/KEY: misc_feature
<222> LOCATION: (70085)..(70184)
<223> OTHER INFORMATION: n is a, c, g, or t
<220> FEATURE:

<221> NAME/KEY: misc_feature
<222> LOCATION: (94587)..(94686)
<223> OTHER INFORMATION: n is a, c, g, or t
<220> FEATURE:
<221> NAME/KEY: misc_feature
<222> LOCATION: (117477)..(117576)
<223> OTHER INFORMATION: n is a, c, g, or t
<220> FEATURE:
<221> NAME/KEY: misc_feature
<222> LOCATION: (128130)..(128229)
<223> OTHER INFORMATION: n is a, c, g, or t
<220> FEATURE:
<221> NAME/KEY: misc_feature
<222> LOCATION: (143525)..(143624)
<223> OTHER INFORMATION: n is a, c, g, or t
<220> FEATURE:
<221> NAME/KEY: misc_feature
<222> LOCATION: (151880)..(151979)
<223> OTHER INFORMATION: n is a, c, g, or t
<220> FEATURE:
<221> NAME/KEY: misc_feature
<222> LOCATION: (155542)..(155641)
<223> OTHER INFORMATION: n is a, c, g, or t
<220> FEATURE:
<221> NAME/KEY: misc_feature
<222> LOCATION: (159499)..(159598)
<223> OTHER INFORMATION: n is a, c, g, or t

<400> SEQUENCE: 110
cagcttcggt agtggtggtc atgattaatg acttatggtg ccgcaacgaa aactgagagc 60
ctcctgtgaa tgcgcacata ggactgtgcc actcatcgga tgctggtatc aaggtctgtg 120
gtcatgatcc attgtggaag tacactgatg tgtgatcttc cgtggagtcc tcccttgaaa 180
caatttctat gttgtttgtc aagtgatcaa gcaacatcta tcatctctgt ggatcaaaag 240
ggcataccac tttcatgtgt gatctcttat ctcttgactt tgatggtgac ttcacacata 300
caagttccct ttacatcctt tgtgtaaagg tgaagccttg gagcttttta gtgttgcaag 360
acaaccaatt agttcccaaa atggagattt gtttcccctg ctgctgaaat gcaagaattt 420
gttcattcgc tctcttattt aatccatgta ttccctaacc aagtcggttc atcttgtata 480
gaagaaacgg atgaacaacg tgaccaaatg gatttctacc caagtgcatg atttcctgtt 540
agcaaatgtg aactctcaac ccttggatta ccaatggtac tgagaggact tgctcaatgt 600
caaaagtagt ttaacaagtt ggttttacta acttgtaact gctttgtgaa cgaaggtcga 660
gtttagagat cgtttcatcg agttatctaa actcgctatg gtccaaacca tcctaaggaa 720
gtactttcaa gaatcgagat taagtcggcc agtaaccacc taaacatcgc tctagtcatg 780
cctcgatcgt ctcacgtgtg cttttccagc atgtgtgatc aagtagatcc atgattagtg 840
cttgataaaa tggattggtt gcgaaggcag catttacaga tccctctgct ggtaattttt 900
ttcaagtctt tatcattttt cttggacttg gattctctgg ctaacacgag ttaactgtga 960
tgttattcga catccacact cgtctcgtgt gctatgaact taccgtgacc acttgttggt 1020
aaatctcttt ctgtgtgttt tacccaagag gttgcatctg attctgtttg tgtaaagttg 1080
catatctacc actcgctcaa cagactcaga tattacagtg tcatcagaaa aagtaaactg 1140
cacacatgga accttatgtg tacttctggc agacatcgtc tctattggtg gacatttcta 1200
aattagccta aggcgacaca tgttatgtcc actagaggaa cgacattttg agacactcga 1260
ctttgtttgg aattgtctca tgattatcgc tgatatggac atgggttaca tgcttctcta 1320
ctcttagaag tctttcgttt tgaatctcgg gacgagattc ttttaagggg ggagggctgt 1380
aacaccccag gtgtttattt tccgctcaac aacgagttcg gatttaagca cgcaatatca 1440
gtggataaaa cggattttaa attttaatca tcgtcgctta tcgcgatttt aatatcgcat 1500

```
cggtgtcgtt tgtcgcgagt gcgacatcgt ttttattttt ttatctgtcc gggctcttcc   1560
taaattttcg taatgttcgg aacctagctg ttccgaaaat cggtgcgtcc gatgagtatt   1620
taaaatccat cgctcgcgcg aacacgaatt cggaagcccg aactcactcg aatgatctta   1680
ttccgagcaa aataatttga acttgacgac taaaatgttc agggtaaaat aatccgaatc   1740
gcgcattgtc tgagaaagat cgtgcgcggg gatatgatct aatttgttct ttagcccgca   1800
atgtaggata accaaatcaa ctgtgttttg gtgacggata agtttttatc tgatttcaat   1860
taaatgtaac accgattaaa acattgtaac taaaatcatt tttaatttta gtcctcttac   1920
atctttccaa attctagtcc caatctccag ctgataattg tatttttatt caaattttcg   1980
agtaaaagaa aacgaaggaa gaaaatatct gcaaccgctc ttctctctaa ttttatccat   2040
cgctttcccc ttccatatct gaagtcacta gcctggatat tttctccacg tagttctcct   2100
cttcctcacg tctccttctc tcttatccat tggacgctag ctcgctggaa aatctcacgc   2160
acgtctctcc tccagcctta cccagcgacc agcatttctt ccatccatca gcatccaaag   2220
gcagccggca gccggctgtg ctcgtcggac cctccgagca cctctgtgcc cgacgacctg   2280
accaagctcg tctccagctt gcgtccatcc tgtgctcagt ttccatccac tagcaccgtg   2340
tctctggtcc tgctcgtcgt ggacatcgtc ggctctagtt ccttgctcga gctcgccctt   2400
tgcgcagacc gcgtctcccc tcaccttgcc gcggtcgggc tggccgtcgt cgtcagcttg   2460
tgtccatgcc gacgaatttg tcgaactgct cactgcatct ctttaatctc gtcgcctgat   2520
ttttctgtac cgcgccgcgc aacccctaga aataaaaatc acgccgccga gcgctcctat   2580
ccttatcccg ccaccgccct tggtctccta caaatctcca gcgcgcaggt ttcttctcca   2640
cgcacgcccg gcagcaagcc gcagccgagc agctccttcc catctcccct ctgctcgctg   2700
gctgaatccc cagccgctcg gctctgcttt tctcccatgg ccggcgctcc ctgcttggtt   2760
ccgtctgtcg cgccgtcgtc ttactgctcg cctttgcgtc gcgcgcatag cgttctgttg   2820
ttcttgcacg cgcgaagctc tttgctcgtc aacgcttcag cctggatttc gctttgtcgc   2880
ccagctcggc tctacatgac tacatctccc atgactgtct actctagctc accgaagttc   2940
ctgcgcgcgt cgagttttct ctactctagc tcgccgtagt tcctgcgcgc gtcgagtttt   3000
cgtgtggagc tctctgctca cgcgcaactc gctctttctt tgttgccgcg cacacgaatt   3060
ttatctgctc gtcacagcgt gtcgagttcc cacgccatca tcgcttctgt cgcaagctcg   3120
ttggtcacag ttgtcttgac cgcgttaact cgcgactgtg gtcgtgttca tcgaattcgc   3180
caacgctttg ttgccgattt gactgtcgtc gcttcgcgtg ttgtcgagtc gtcgtttttc   3240
ctgtcttgtg ctcgcacggt ttcctgctcg ccagcgtgcc ctctcggctc gctcggcttt   3300
aatttccaat cacgtcgtcg atctcgtcgt ttgccgtcga gttgtcaaac acgtcatctc   3360
cggctcgatc cccacctcac cagcttaccc cagacttcaa tcgaaggtca tcgtcgctcg   3420
tgcgttcccc aagaaaaccc aagaatcggg tgaagacgaa gttagcagcg caatattccc   3480
taagcgctcg acaaatgcgt ggatcgaaaa atcactgccc gatctcacgg attcgtgtca   3540
gctgttgaaa cggtaagctg atgaattgtt tagaatagtt tataaagctg atgaaatggt   3600
tagaataaat nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn ctgattcgtt   3720
gtcgccagct cgctttacat gactacatct ccatgactgt ctacttagct cacgtagtct   3780
gcgcgcgtcg agtttctcta ctctagctcg cgtagtcagc gcgcgtcgag tttcgtgtgg   3840
```

```
agctctctgc tcacgagcac tcgctctatc ttgtgccgcg cacacgaatt tatctgctcg   3900
tcacagcgtg tcgagttccc acgccatcat cgcttctgtc gcaagctcgt tggtcacagt   3960
tgtcttgacc gcgttaactc gcgactgtgg tcgtgttcat cgaattcgcc aacgctttgt   4020
tgccgatttg actgtcgtcg cttcgcgtgt tgtcgagtcg tcgtttttcc tgtcttgtgc   4080
tcgcacggtt tcctgctcgc cagcgtgccc tctcggctcg ctcggcttta atttccaatc   4140
acgtcgtcga tctcgtcgtt tgccgtcgag ttgtcaaaca cgtcatctcc ggctcgatcc   4200
ccacctcacc agcttacccc agacttcaat cgaaggtcat cgtcgctcgt gcgtccccaa   4260
gaaaacccaa gaatcgggtg aagacgaagt tagcagcgca atattcccta agcgctcgac   4320
aaattgcgtg gatcgaaaaa tcactgccga tctcacggat tcgtgtcagc tgttgaaacg   4380
gtaagctgat gaattgttta gaatagttta gtaagctgat gaattgttta gaatagttcg   4440
atcgttgaat aagttaatgt gttagtgcga ggctcattag ggtgctcgat aaattgcgta   4500
agtcacgaaa ctctcgtcga cttcgcagtt cttgcgatta tcgagccagg ttcagttata   4560
gcgagttatt tcgctattcc ggtcacttag ctgaattagt ggaccgagta gaattttagt   4620
aggcatatgt gttgataaaa tattttaatc acttataaag atgtagtata atttataagg   4680
caagggatta gttcagaatt taattaatta actgataagt tgtgattagg ctaattatat   4740
ttcttgtgta tagtttgttg ttcgtgatgt ttgcgttagg ttcgagaagc gtaatcatag   4800
cgcgtagtcg catattaata actagtgttt ccgtacaaaa ttgtacaacg cctcgccact   4860
aggtgtttaa tacgctatcg tatagcacta tttagatttg tgctattctt gtttatatgc   4920
attcatgtgc atcgtgcatc tcaattaggt acgataattg atcgcgtgat gcggaagaca   4980
agccaagtcg accccaagcg cgggctaatc cgcaggatga tgctgatgga caaacctgaa   5040
aatggtcgcc aagtggacgt cgtctaacaa cactaaccta gtgttaccca ggcaagcccc   5100
ggtgcatttg ccacctccct tgatgttttt aaaatctttc tcacttgatt gctgcattag   5160
gtgacaggag ttgattgatt aaacaattcc tgcattacct tccttgatct tgattaccct   5220
ccttgaaaac ccgtttttac aaaaaggttt tactatgctt agtattgctt agaaaaacaa   5280
aaggatttgt tttagaaaag atgtttggca aagtgggagg gttgttttca aaaataaaac   5340
ttgatggtga atccatcatg gatatgatgg attcaacatc ggaaaagatg tacctctgcc   5400
aggtaccaag tttttgggtt aaaagattaa gctaagaccg ggcgggtgac ttgcacggga   5460
aaggagtctc agtgtagtgt ctccgtctga gtcgattaag gaccttgtcg atgtaggctt   5520
gatgatcgag gaccctttaa ctggtcacat gcctcgtcat gggtaagcct tgcctcgggc   5580
agactaaggc cagaataaga taacacgaaa tgggcgtgga gcggtggcga gagtagcgtg   5640
taccctccgt ggcaagaggc tggacggtgg tgtaactgtg ctctcggttt gcgtgaacct   5700
gatctggtct taagaacccc ggtggcgggt tgacatatgc aagggttaag tgctacatat   5760
gtcgtgtgat tggagatcct cagctgagta taatcgattc ggatcgccgt accttcgcgg   5820
ttatgaagac ttggtcattg ccctacacgt agcattccac taaagatgat gggtttttgt   5880
taagaaattg gctagtgcag gaccagtgat tgaactaggg tagaaagaac tctagttaca   5940
ggtaattcta cttaacttga caaataaaac tggattttaa ggatccactt tagtaagcat   6000
ttctgcaaaa cagagtcttt gattattgaa aagccttacc ttgactccca tataaccagc   6060
ataccttgta gagtcttttc tttagtcggg taagacttgc tgagtaattc catactcagg   6120
gttttattcc ctgttgtttt tcaggttcta actttgtgct gttgttgatg gtgttaagtg   6180
ccggtgggct cggccttctt ataagtctaa gtaacccttc tatacttctt attgaggatg   6240
```

```
atcccttgag ctagcatata tatttcaaac ttatactttt gtaatcactc cgataaacta   6300
atgtaaaatt tttgtaacct gtaaaatttg gtagtaagat ttccgctgca acaatattgg   6360
tgtgtgtgat ttgtgttact taatcctgcg gttctggttg taagtggttt atccgatgtc   6420
cttggggcaa tcggacagat cctgttaagt tatctggtgc acatgcacag ccgtctgagg   6480
tctttgggac aaggacaggt gcatgtgggc ccaataactt gggaggttct gccacagctt   6540
gaagcgtccc caatcctctg ggactcaaat gtgatacaat tactagtccc aggaggctag   6600
taaacacatt tatacatcag atgattcaga tctgcttaaa cgagacaaac ctataaaggt   6660
ggcgatcaac tttaagagtt ggtccacaac tcgggacata tcatcagagt ggggctgaag   6720
cagcccgata tacgcagtga agcaattcag cggtccaaca gccacaggca aggttgggaa   6780
cagtcgtaac tcttacccga tctctttttt ctgaaaaaca acaaataagc aagggtgagt   6840
acaaacgtac tcagcagccc accttcaccc gcggaatggg gaaatcagat ataatgcatg   6900
gaatatgtag agctcaggat atttgcagaa acagcaatat tttatgcagg gttgttttga   6960
aaaacatttt gtattttgca aagtgcatcc tctccaaaag gagcaggaag tttttcagta   7020
ttataacaaa atcccctgga ctaaaccatc caggtatctc agcagtttcc cactggtttt   7080
cattttcaaa aacagctact ggacttcccg tccaccatag ctcacggctc aaccgccgga   7140
ccttttaaaa accacttttc aaaagcatct cttttttttg gaaaacaaaa cattaattgc   7200
cataccatac cagactcgtc cattcctgtg gacacagact attcgaatag gttttcaaac   7260
tctgcgcaga ggtgtacact ttacccacta gtccagctct gcgatcccat gatcaatgag   7320
acccgaatcc gactctcttt ctttccccgc atgtcctaac cttaatggtt atcctgaagg   7380
agtcaggcca ccaccatgtc caaaccggac aaaactttcc ccctccttat cctcccggtg   7440
ctccccagcc ttcataaccc tggggttgga ccgtacgagt tcagattgag tgactgccca   7500
cacagtctcg agtggttgta ctattaaaga gtacaggtag tgaagatgac aaaccggtcc   7560
ttatatgagg ggacaatcct tctgctcacg cctaaaccag ctgaggacga atctctagtt   7620
tcannnnnnn nnnnnnnnnn nnnnnnnnnn nnnnnnnnnn nnnnnnnnnn nnnnnnnnnn   7680
nnnnnnnnnn nnnnnnnnnn nnnnnnnnnn nnnnnnnnnn nnnaagctgt ttaaaacatt   7740
tagccaccca tcgagcttta tgatggtcaa tagactcatc agcttttctc ttgagtttat   7800
aaacccactt gcaatcaatc aaatttctgt caggtgcggg aggaaccaag tgccatgttt   7860
tattccgcat aagggcagaa aattctaggt ccatggcagc ttttccagtt tgggtcaaac   7920
aatgcaacag acaagctgga gggttcttca caaattgtca aatttccata cgggatcgag   7980
ccatcggtaa attttatggg cttcacaata ccagtgtgta gcggactgcg gacatctgga   8040
atttgatgtc cggtgcaccg gtatgggcgt gcctggcgtc tgcgcgcgct gcgcgcgcat   8100
taaatgcacc gcagggagcc gttggcgccg cagggagccg ttgctccgct ggcacaccgg   8160
acagtccggt gcacaccgga cagtccggtg aattttagcg gagcggctgc cgcgcgaacc   8220
cgaggctagc gagttcctga ggccgacctc ccttggcgca ccggacactg tccggtgtac   8280
accggacagt ccggtgaatt atagccgagt cgccttagaa attcccgaag gtggcgagtt   8340
tgagtctgag tcccctggtg caccggacag gtactgttca ctgtccggtg gcacaccgga   8400
cagtccggtg cgccagacca ggggtgcctt cggttgcccc tttgctcttt tgttgaatcc   8460
aaaacttggt ctttttattg gctgagtgtg aaccttttac tcctgtatac actatacact   8520
tgggcaaaca agttagtcca aaagatttgt gttgggcaat tcaaccacca aaattattta   8580
```

```
ggaactaggt gtaagcctaa ttccctttca atatgatcta atttgttctt tagcccgcaa   8640
tgtaggataa ccaaatcaac tgtgttttgg tgacggataa gtttttatct gatttcaatt   8700
aaatgtaaca ccgattaaaa cattgtaact aaaatcattt ttaattttag tcctcttaca   8760
tctttccaaa ttctagtccc aatctccagc tgataattgt atttttattc aaattttcga   8820
gtaaaagaaa acgaaggaag aaaatatctg caaccgctct tctctctgat tttatccacc   8880
gctttcccct tccatatctg aagtcactag cctggatatt ttctccacgt agttctcctc   8940
ttcctcacgt ctccttctct cttatccatt ggacgctagc tcgctggaaa atctcacgca   9000
cgtctctcct ccagccttac ccagcgacca gcatttcttc catccatcag catccaaagg   9060
cagccggcag ccggctgtgc tcgtcggacc ctccgagcac ctctgtgccc gacgacctga   9120
ccaagctcgt ctccagcttg catccatcct gtgctcagtt tccatccact agcaccgtgt   9180
ctctggtcct gctcgtcgtg gacatcgtcg gctctagttc cttgctcgag ctcgcccttt   9240
gcgcagaccg cgtctcccct caccttgccg cggtcgggct ggccgtcgtc gtcagcttgt   9300
gtccatgccg acgaatttgt cgaactgctc actgcatctc tttaatctcg tcgcctgatt   9360
tttctgtacc gcgccgcgca accccctagaa ataaaaatca cgccgccgag cgctcctatc   9420
cttatcccgc caccgccctt ggtctcctac aaatctccag cgcgcaggtt tcttctccac   9480
gcacgcccgg cagcaagccg cagccgagca gctccttccc atctcccctc tgctcgctgg   9540
ctgaatcccc agccgctcgg ctctgctttt ctcccatggc gcggggttcc ctgcaggctg   9600
ctcgcggtat ccatctcctc tgctcctgct cgtccgtccc tgagctcctg tgccgcggca   9660
cctctgttcg gccgcgcctg atcggatttc ttgtgccgtg gcttcccctc cgagctcgcc   9720
cagctctatt gccgcgccca tggccggcgc tccctgcttg gttccgtctg tcgcgccgtc   9780
gtcttactgc tcgcctttgc gtcgcgcgca tagcgttctg ttgttcttgc acgcgcgaag   9840
ctctttgctc gtcaacgctt cagcctggat ttcgctttgt cgcccagctc ggctctacat   9900
gactacatct cccatgactg tctactctag ctcgccgtag ttcctgcgcg cgtcgagttt   9960
tctctactct agctcgccgt agttcctgcg cgcgtcgagt tttcgtgtgg agctctctgc  10020
tcacgcgcag ctcgctcttt ctttgttgcc gcgcgcacga attttatctg ctcgtcacag  10080
cgtgtcgagt tcccacacca tcatcacttc tgtcgcaagc tcgttggtca cagttgtctt  10140
gaccgcgtta actcgcgact gtggtcgtgt tcatcgaatt cgccaacgct ttgttgccga  10200
tttgactgtc gtcgcttcgc gtgttgtcga gccgtcgttt ttcctgtctt gtgctcgcac  10260
ggtttcctgc tcgccagcgt gccctctcgg ctcgctcggc tttaatttcc aatcacgtcg  10320
tcgatctcgt cgtttgccgt cgagttgtca aacacgtcat ctccggctcg atccccacct  10380
caccagctta ccccagactt caatcgaagg tcatcgtcgc tcgtgcgtcc ccaagaaaac  10440
ccaagaatcg ggtgaagacg aagttagcag cgcgatattc cctaagcgct cgacaaattg  10500
cgtggatcga aaaatcactg ccgatctcac ggattcgtgt cagctgttga aacggtaagc  10560
tgatgaattg tttagaatag ttcggtaagc taatgaattg tttagaatag ttcgatcgtt  10620
gaataagtta atgtgttagt gcgaggctca ttagggtgct cgataaattg cgtaagtcac  10680
gaaactctcg tcgacttcgc agttcttgcg attatcgagc caggttcagt tatagcgagt  10740
tatttcgcta tttcggtcac ttagctgaat tagtggaccg agtagaattt tagtaggcat  10800
atgtgttgat aaaatatttt aatcacttat aaagatgtag tataatttat aaggcaaggg  10860
attagttcag aatttaatta attaactgat aagttgtgat taggctaatt atatttcttg  10920
tgtatagttt gttgttcgtg atgtttgcgt taggttcgag aagcgtaatc attgtgcgta  10980
```

```
gtcgcatatt aataactagt gtttctgtac aaaattgtac aacgcctcgc cactaggtgt  11040
ttaatacgct atcgtatagc actatttaga tttgtgctat tcttgtttat atgcattcat  11100
gtgcatcgtg catctcaatt aggtacgata attgatcgcg tgatgcggaa gacaagccaa  11160
gtcgacccca agcgcgggct aatccgcagg atgatgctga tggacaaacc tgaaaatggt  11220
cgccaagtgg acatcgtcta acaacactaa cctagtgtta cccaggcaag ccccggtgca  11280
tttgccacct cccttgatgt ttttaaaatc tttctcactt gattgctgca ttaggtgaca  11340
ggagttgatt gattaaacaa ttcctgcatt accttccttg atcttgatta ccctccttga  11400
aaacccgttt ttacaaaaag gttttactat gcttagtatt gcttagaaaa acaaaaggat  11460
ttgttttaga aaagatgttt ggcaaagtgg gagggttgtt ttcaaaaata aaacttgatg  11520
gtgaatccat catggctatg atggattcaa catcggaaaa gatgtacctc tgccaggtac  11580
caagtttttg ggttaaaaga ttaagctaag accgggcggg tgacttgcac gggaaaggag  11640
tctcggtgta gtgtctccgt ctgagtcgat taaggacctt gtcgatgtag gcttgatgat  11700
cgaggaccct ttaactggtc acatgcctcg tcatgggtaa gccttgcctc gggcagacta  11760
aggccagaat aagataacac gaaatgggcg tggagcggtg gcgagagtag cgtgtaccct  11820
ccgtggcaag aggctggacg gtggtgtaac tgtgctctcg gtttgcgtga acctgatctg  11880
gtcttaagaa ccccggtggc gggttgacat atgcaagggt taagtgctac atatgtcgtg  11940
tgattggaga tcctcagcta agtataatcg attcggatcg ccgtaccttc gtggttatga  12000
agacttggtc actgccctac acgtagcatt ccactaaaga tgatgggttt ttgttaagaa  12060
attggctagt gcaggacaag tgattgaact agggtagaaa gaactctagt tacaggtaat  12120
tctacttaac ttgacaaata aaactggatt ttaaggatcc actttagtaa gcatttctgc  12180
aaaacagagt ctttgattat tgaaaagcct taccttgact cccatataac cagcataccc  12240
ttgagagtct tttctttagt cgggtaagac ttgctgagta attccatact cagggtttta  12300
ttccttgttg tttttcaggt tctaactttg tgctgttgtt gatggtgtta agtgccggtg  12360
ggctcggcct tcttatgagt ctaagtaacc cttctatact tcttattgag gatgatccct  12420
tgagctagca tttatatttc agacttagaa ttttgtattc cctccgatag aggtatgaaa  12480
aatttgtgta acctgtcaaa tttgtcaata atatttccgc taccactttg tatccgtgtg  12540
tgagtttcaa gacttaatct cgcggttctg gttgaaattg gtttatccga tgtccttggg  12600
gcaatcggac acatcctgtt aagttatctg gtgcacatgc acagccgtct gaggtctttg  12660
ggacaaggat aggtgcatgt gggcctaata acttgggagg ttctgccaca ggtcggggtt  12720
actccggtga gcaatcccga ccgtgaggag gcggaatccg gtgcaccgag gccagcacaa  12780
gcttcggtga ggggtgaggg acgcctaggg ccaaggcacg ggcacggggc ggggctgaat  12840
cggtcggaca ccgagcgggc gcggcaaacc accgcgatag agctccagcg aacacaaatt  12900
caccgtagag ggaaaagaat cggggcagga agggcctgaa ggtacttact tacgttaaga  12960
gttctgtcag ggatgcttga ctgttgcttt gggggaggat cttcactggg cggtcgttgt  13020
ctttttgttc gtgtgtggat gatgagtgcc acttgcttcc gactggtatg ctctacaaat  13080
ccagtctttc tcaaaatgac attgtttaat ccctgaannn nnnnnnnnnn nnnnnnnnnn  13140
nnnnnnnnnn nnnnnnnnnn nnnnnnnnnn nnnnnnnnnn nnnnnnnnnn nnnnnnnnnn  13200
nnnnnnnnnn nnnnnnncac gaaatgggcg tggagcggtg gcgagagtag cgtgtacctc  13260
cgtggcaaga ggctggacgg tggtgtaact gtgctctcgg tttgcgtgaa cctgatctgg  13320
```

```
tcttaagaac cccggtggcg ggttgacata tgcaagggtt aagtgctaca tatgtcgtgt  13380
gattggagat cctcagctaa gtataatcga ttcggatcgc cgtaccttcg tggttatgaa  13440
gacttggtca ctgccctaca cgtagcattc cactaaagat gatgggtttt tgttaagaaa  13500
ttggctagtg caggacaagt gattgaacta gggtagaaag aactctagtt acaggtaatt  13560
ctacttaact tgacaaataa aactggattt taaggatcca ctttagtaag catttctgca  13620
aaacagagtc tttgattatt gaaaagcctt accttgactc ccatataacc agcataccct  13680
tgagagtctt ttctttagtc gggtaagact tgctgagtaa ttccatactc agggttttat  13740
tccttgttgt ttttcaggtt ctaactttgt gctgttgttg atggtgttaa gtgccggtgg  13800
gctcggcctt cttatgagtc taagtaaccc ttctatactt cttattgagg atgatccctt  13860
gagctagcat atatatttca aacttatact tttgtaatca ctccgataaa ctaatgtaaa  13920
atttttgtaa cctgtaaaat ttggtagtaa gatgttcgct gcaacaatat tggtgtgtgt  13980
gatttgggat tcgttttctc gcggttctgg ttgtaagtgg tttatccgat gtcctttggt  14040
agatcttaca gatcctgtta agttatctgg tgcacgtttt ttggggtctg aggtctttgg  14100
gacaaggata ggtgcatgtg ggcctaataa cttgggaggt tctgccacag gtcggggtta  14160
ctccggtgag caatcccgac cgtgaggagg cggaatccgg tgcaccgagg ccagcacaag  14220
cttcggtgag gggtgaggga cgcctagggc caaggcacgg gcacggggcg gggctgaatc  14280
ggtcggacac cgagcgggcg cggcaaacca gcgcgataga gctccagcga acacaaattc  14340
accgtagagg gaaaagaatc ggggcaggaa gggcacgggg atggttcctt accttaggag  14400
tgtgctcggg gatgcttgac acgatgctag gagctccggg cagacgacgc ggtggcgcgc  14460
ttctccggcg agcttgagcg gcggcggcta agcgcgagag aggttgagag tgggtgaaat  14520
taggaagggg agggagagcg ggtgtaggcg gggctcaaaa gggagctggg ggcgtgggta  14580
ggcaacgtgg tcggcttcct cggcgtgagt gcgtgtgcgg gtcagcagcg gttgcgggga  14640
agatgagact gacaaggcgg gcccacagag tagaggcacg agcacgtgtg aggaggaaat  14700
gattcagcgc tgatgggctg ggcccactgc acagagggag agcgggggcg tgcgcgcgag  14760
ggtgagcggc accaataggt cgggcccacc tggcagatgg agagagaggg caggtgcgta  14820
ggctgggctg cttttctatt ttctttttat tctgaatttc tagttccttt tatttttatt  14880
ttctctattg aattcaaatc caacgaaacc acaaattcaa atttgaatat ttcaaacatg  14940
tgcatcaacc aaaaacaaag tttaagctca gcatgatgca acaattcatg tctcccctag  15000
gtttgaatat agtaaagaaa aaaaatacat ctcccaaata tataaccaaa actctattag  15060
aaaggaagaa aataggaaat ctacggagat gagaaaagtg gtaacacctg aatttggtag  15120
atattagaga agaaatttta taccccaaa ttcagggtgt tacataggct ctataatcat  15180
agcgtgtata gatgcatgaa taaataaggt gagcctatga gctatgcgtt tcttccactc  15240
ctgatacatg ccaatcaagt gtttctttga aacaaccttc actggcatgc tttgaggagc  15300
ttgcatagcc cttctgaggt tttgcctttg cctttgcctt tgccatagcc attgctactc  15360
tactgccatt ttgtggtggc ttcgtaaaaa ttccccctct catcccctga ttattacagt  15420
gcccatgacc cctttctctg gagggacctt tcttccttta agactagaag ttggcgtgtg  15480
ctttatgcat gaccgcgtgc cgaatggatg cttctagtag ttctgcatca gaagctcatt  15540
ctgagcctta gcaccaagca acatgttgac gaggtcacat tatttgtgta cttgttgcta  15600
cagtactgct gttggagcac catattggag gggtagaagg tttggagagt tttctcgatc  15660
atctctaagt ctatggctat ctggccacag aaatgtagct gagcgacaat gcgatggatg  15720
```

```
acagtgttgt aagcctcaac tgcattgaag tcgagagtgg cccattcatg ttgcgcccgc  15780
gggagcatca catgcttctc cacactgaaa cactcacata gctctgtcca caatatcata  15840
tggtctttca cctctggata ctccatcttc aggcctggat ggatgtggtg cccgacgaag  15900
atcgtaattt ttgctttctc atgaagtttc aggcaagtgt cattcgggcc ctaccagaag  15960
atctcctttc ctagctatat cgcctctagg tgaaacttgc agtcgttagt ctaggtcggt  16020
tagttcttgc cattgaggac aagctccacg aatcaattct gttgtcttca accatagtcc  16080
gtcacacaaa attaacttta ggttaattag gcgtgctaat tatcaataat agaaatttaa  16140
atagataaat tgcatgaccc acgggagccg gtccagggcg tgctgacgag gcgtggctga  16200
agcatatgcc gacgagctgc gccccagctg gccgagcaag cgcgacccag tgcggggtgg  16260
cgccgtgggc tgacgcagcg tgaaccatct cagctcgaga tggcgtgacc agcagcaggg  16320
catgggtgcg tgggtcagtg tgacatcaag gcgcagagtt gggggcgccg acatagtgta  16380
cgactagaag ccggcatgac cgatctattc atgaacgcaa cgtgtgggcc accggtgggg  16440
tgggtgtgta gtgcacgcga ctggcgcacg agcctcgcca tcggggtgat tcgtacgacc  16500
cgcggttagt aggacatcga tggcttttta agtaaaagta atagattgga tatattaagc  16560
aggtcaaatc atcaggattt aacatgctag tgtatacata aatcaatcta caatatgtat  16620
ctgacagtaa gaaatcactc tacaatatgt atctgaccgc gagaaaacaa tctagtttga  16680
acaaaatcta ctaaacaatt gtctagagcg gtcaaaaacg acataccgtg cttctttatt  16740
cagcgaacgg aaacgaagcc tatcatgtaa gacaattagg caaggcggga ggacttgctg  16800
tggtgcaatt tccaaattca gaccttgaac cctctcctca gcaatggagg gcttattctc  16860
tttttgtcga ggcagaagca caaaaaacta tttccttgtt atatagacga ctagagcttc  16920
tcgtttgata ttagcccaca taagattttt tgatagtata aggccatctc caactgatcc  16980
cctattgtat cctctatttt attcctatat taaacgcaac tctgtaaata atatcatcta  17040
aaattctgtg ttacctattt tattggataa gtgagtctaa tattttgatc caaacagcgc  17100
ttaatctctt cccttgctgt aagttctcga cagatttagc tgggttaaaa ttcagactca  17160
aagacatata aattgatggg ctggtgttat ttccacgtgg gggtggaccc ctcacgggcc  17220
gggccgcatt cttggccaac catgggctat ccgcaacatt gcagactccg gaatccggat  17280
tggccgaatg ggcccggcag ccgaaaatga aaaaggaaag gatcgaccct ctagcgcgat  17340
cgatccccgt gcgctggggc ccaaattagg agaacctcag taccccacgt gatccacggt  17400
ccgcccgccg cgcaagctgg gccacgggct cgcgggcggg catgcgccgg ttccgcgagc  17460
gaccaccccg ccatccgcgg agcctgccct gcgctgccca ccgctcctcc gcctactccg  17520
gcctcagcta ataacgatgg gtggtgggag ccgagccctt tccctctcct ccctctgcgc  17580
caccaccctc gccgccgcca agcccccaca gcaccccgtc cccttcgccc cggctcaccg  17640
cgcgctcccc caccgcctcg ccgccgccat gtcctcctct tcctccccga cccccgccgc  17700
atcggtggac gccggtgccc cggccccttc ggcgtccaac gccatcgact tcctcacgct  17760
ctgctaccgc ctcaaggtga gcgactgagc gcccctgttt agtcgcttcg catttccacg  17820
ggccggcttg gttgagatgg atggaaatgt gacgcgatgg atgagattgt ggatgtaatt  17880
gcagacgacc aagagggcgg ggtgggtgaa gcgcggggtg caggcgcccg agtcggtggc  17940
cgaccacatg taccggatgg gcgtcatggc gctcgtcgcg gccgatctac ccggcgtcaa  18000
ccgcgacagg tgatcctgac agtttcgctc tcaagtctag ctcggcagta tttagccttc  18060
```

```
ttacggttcc gttttcatac actgtttatt tatcccttca attacaggtg tgtcaagatg  18120
gcgattgtgc acgacattgc agaaggtatg gtctcaaaag acttccgtct agacggcttc  18180
actgaagttt tggggctttg tgtgagatga gggatgcaat tttgtgaata tgcgagccta  18240
ttactacctg agatgttggt agatggtaac tagaccactg gactggagac ctgtagtagg  18300
aatgtaggat gtgtgttcaa gtacttgtgc caattagttg gttctttgac ctctgctagc  18360
caaagtgtaa aactttaaac tatgtgcaca ttttcctatt ttcattcaga agcatgctca  18420
gcttagaaat gaacacatga ttttgccctc cgctcatatg gactcttgct gctgttccta  18480
agccagcttg cctgtttctg gaactaactg cctatgagga tgtgggttca gttgactcat  18540
ttcaattgtt ttttcttttg gtactccagc aattgttggt gacatcaccc cttctgataa  18600
tgtacccaag gaagagaaga accgcaggga gaaagaagca ttggaccata tgtgcgagct  18660
gcttggtggt ggttcaagag gtgaatactg aaacttgcaa ttgtgataca ttagcatttt  18720
atgctgtagt taattaggca tcttatgcct caaattgtct tttcatgatt tagttatata  18780
tgaaatgaat gtggtgctat tgcacactgg catcatcttt ctagattact caatagtcta  18840
gacttaatga tcccattatg tgtgcatagt accatagttt caaggaaaaa agaacaatat  18900
gtggatgcca atgaattttg tgaatacaat actatagtac ttgcaggtca tatacatatt  18960
ttattttacc cttgaaaagc tattcatctg ttattattat ttcttagatg gtcatttttc  19020
catccgatac ttttcacttc catcagggaa gcagatcata acctggcaat tattttgtag  19080
aaatccagcg ggcagctttt gttcttattt tttgatacat agtttaaata agtattggat  19140
aattcttaga gtattcacat cccttagtta ggtgtcaagg aaactcttgg taacttaaaa  19200
tcactcagat tatttccaga gaaactgtta tttatacttc tctttttctt tttataaggt  19260
gtattagtgt ttgagaattt cattcaaaga tatgctttat ccaataattt cccttgcaat  19320
atatgaactc aatatattat caattactac aaaagcaatg tctcactaaa atgcatgtga  19380
aatatgaatc tatagattta tctttgtgca ataaatatac aaatattttg actagtttca  19440
ttgacttttt tgaatcctta cgccctacat tttgaaatgg aggttgaaaa gataagggat  19500
gtttttgtag aagccaaaac cgaagagttt atattcagca aatgttgatg actatgagtt  19560
ttggaatttg aacatgatat tgtaattgat ggtgataata ttattccatc tctaatgatt  19620
ttctaccttg aagcattatg gatcgtaaat tatttatgct caaatggcta tcatagcatc  19680
caacattttt tccctaagag tttcacaaca tagaattcta gtattctggt tgtgttctca  19740
ttattcatat cattaatcgt taaaaaatat tggagagatc cagcatccct tacatgtgaa  19800
gtgaaccttt tagaactaaa taaagtatct tagcagcctt ttggaaacag tttttcatgc  19860
aggataaaag gatgttctct gtacaggcga gactaaagag ttcatgtgat ctttgacatg  19920
gtatatataa taaatacttg cctttatctg catgctgttg tcttgcagca caagaaattc  19980
gtgaactttg gatggagtat gaggagaatg cgtctttgga agcgaaggtt gtcaaagatt  20040
ttgacaaggt acagtttcat atttcaatcc atcaagttgg tggcatgatt gcaacgtctg  20100
tctgaagcta tcagatggta gttcttgtga tcattcaata ggcaatgcat ataactggca  20160
ggatatttaa ctaatgtagg caatcattat gatttatggc cctaacccat atggctccac  20220
ttcttccttt tcctttgcat gctgtaatcc tttgttgcac tgttatattt ccaggttgag  20280
atgatacttc aagctctgga gtatgaaaag ggtgagttca tactggtgct tgaatatttg  20340
aactaacatt tcccatgcac agtagctata aagtacaaac cacaactatt taaatgcatt  20400
catcaaatat tcttgttgta ataaccaaat aaatgtatat agtaaaatca gctcacattt  20460
```

```
cacatttcaa atacagcaca tctttttctt tgcatcattt gtgcttatat tgggtaggcc  20520
tggtgtagtg gtgagggcag tctcactaag tcactatgtt gccagttcga aacagcctct  20580
ctgcatttgc aggggaggct tgtctcgatt tatcccatct caagacccca ctcatgtggc  20640
agcctccgcc ctagatctgc ccatctgtgc ttacaccatt atttaatttg ctccacggcc  20700
ttctgggtgt gagaagtgat acatatgatc aatgtactat cacttaacac ctggtgaact  20760
ccttgttgat agatggggtt aacagtatca cacttacgcc tatgtatttt aaaattttca  20820
gagcaaggac gggaccttga agaattcttc caatcaacag caggtgtgat ttttctcttt  20880
ctgttatgct cttctcaatt ttcatgagta tccagtacat aaatcttgct cttctcaatt  20940
ttcatgacaa tccagtacat aaatcttgct cttctcaatt ttcatgagca tcctgtacat  21000
aaatttgaac agttcattta agctgagaag gatgttgcca tttttttggt cttacactta  21060
aaaatgtttt cctgagataa tataaacatt catcagcaat tcagaacata ttagtgcctg  21120
aatgattatt gctaattgaa aactggacac taccacctat aatggttttc tttaccatga  21180
actgatacat gcctatgcct tttatggttt tcttttatca cgtgcttatg tttgatctca  21240
tttttacatt gtattagacc gtgtccagca gttcacccac ccaaaacact gttttgcact  21300
tagattgcac tattcgcaga gtggaatttg aatatgggga tggtaaactt agcctaggct  21360
attagcatta gagtcattgt gtaacaaaac catatccccg cacctaattc ccatgcaggc  21420
aaatttcaga cagacttggg aaaagcatgg gcagcggaga ttgcatcgag aagaaaaaca  21480
aagtgatcaa acgatgctca ttttaccacg tcggttccaa gacaacttgc tggcacagca  21540
tttctgttga actttgcttt tactagatga tacttcgagg tggcattgag acgtagggtt  21600
gccttgggaa tgtgaacttc accacatttc ttggtcctgc cctgaccctg aggcatattg  21660
ggcttgcgat accagggctc tagataagta agataaccca ctttgggtat tggttgtaga  21720
tgctcctgcc aagggcagtt agctggatcc aacgggaagg ttcagcacca gctggtggtg  21780
atgtaaaatc cttcacttca tgaattactg taccattacc gtttctcttg ttaatccagc  21840
ctcacggttt cggccttttt taatgtaatt ctattgtttt caagtataat gagcctgaat  21900
atttgctata tccattttgg ttgttgatga tgacctgaag tgcattcata ttttcatagt  21960
acgtataatg ctgaagccta gaagctgacc actgatagtt ccggtgtagc gtcggatcgc  22020
atgtattagg gtctgttcgt tttattttga atccacgtgg attagacgga attgagtgag  22080
ttttgaaagg atcacgatgc ccaagaggag ggtgaattgg acttttctaa aaatcaacac  22140
taattaaaat ctaagcaaga gtccaacttc accccgataa ctatcactaa gagaataata  22200
atagaaatac aacaatgtta agacaatatt tcaaatactt gctaaacaaa tacacaatgt  22260
aaaatgtttt aattaagtgc ggaatgtaaa gcaaggttta gaagactcca atttttctcg  22320
aggtatcgaa gagtcggcac tctcctctag tcctcgttgg agcaccctcg caagggtatc  22380
actccccctt ggtcctcgca agaaccaagt gctcacaacg agatgatcct ttgccactcc  22440
agcgcagtgg atccctcacg accgcttaca aacttgagtc gggtcaccaa caagatctcc  22500
acggtgatca ccgagctccc aacgccacca agccgtctag gtgatgacga tcaccaagag  22560
taacaagcca tagactttca cttgaccaag agaagcctaa tgcatgcggt gtatgctcta  22620
ggtggctctc gctagcgcta ataaggtcca aatgcgggat taagattctc aaataacctc  22680
actaggcttt gtggtgcttg caatgctcta ccaatgtgta ggagtaaatg tgggtagcaa  22740
gaccatcaat atagtgggtg gagggggtat aaatagccct cacccaccaa ctagccatta  22800
```

```
ccaggaatct gctgcacatg ggcgcaccgg acagtccggt gcgccaacgg tgcgccaacg  22860
gtcgactcca atggctagtt ctgacagcta gccgttgggc agatggcaca ccggacagtc  22920
cactaaaatt caactcgcga acaacgcgct ctcaggtttc tgtgcgcagg gaaccctctt  22980
ccttgggcca ggctggcccc actggcagag ggtgcaccgg acagtccggt gcacaccgga  23040
cagtccggtg ccccaaagcc agaaacccta gtttctgttt tgtgctgttt tttcaattcg  23100
gttttcgttc taacttgtga gtatgttcta gagtggcacc tagcactata tgtgagtgtg  23160
aatatgcacc aacactacac tagaactctc ttggtcaaac tactcatcga caacccctct  23220
ttatagtacg actaaaacaa aataaaagac ctaactatat cacgagtgtc cgcaactcct  23280
tgacactcgg aatacgaaga ccttcacttt ttgttttgtc gctttagccg tcgcttcaag  23340
ttcttatctc cgagattgtt ttcaccgttg tagtacatct acatgtaatg cgacctaact  23400
taccatttgc ctctgcaaaa cacatgttag tcacatataa aattacattg tcattaatca  23460
ctaaaaccaa ccaggggcct agatgctttc aatctccccc tttttggtga ttgatgacaa  23520
cctacaagat tgtgagagta gtttgttttg aaatttctgt caatagagaa gatggttagt  23580
tatactcaaa aatttttgac agaaagagtg tgtaacataa taataagagt gagtgcatac  23640
acattgtaag tttcttgttc atataaaagt gaaatcaaat cgatgaacaa gaactagaga  23700
ctggtgataa catataaggt gaaaacacaa tacacacaca gtcaacataa gcatcgagag  23760
catataatag agtttgtgag ccaaaatcgt catacaaaag tggatctagt acagagagta  23820
tcaagcacat atattacatc aaaatgactc tatactaact ccctaactcc ccctagctct  23880
cacaactctc atatctctcc ccctttggcg tcaaacacca aaaggaaacc tgaacctaca  23940
gaccagaaga ggaaggaggt ggctggggcg catccgatca cgatcgtggc agaagagcaa  24000
acgccagctg agggtcagag tcagcctcgg atccaggatc taccgtagaa gctggagcta  24060
gtactgactc ggatggaggc tgtgctgcag gagctaccga agctgaagag gtcacagaca  24120
ccgccacaac agcagtggta acagcaggag ctggtggcac tggcggctga gcgctgatgg  24180
agctgatgac cggcgacgag aaaaccaggg tgaccggcag gagcggagag gaagaaggac  24240
caaatgaagg tagaggggt cctgcctgaa gggctagcac aacagcggcc tgaagatcta  24300
gagggggtgc agactgaaca ggaggaatct gagcaccggt atgctgaagt atgtgagtca  24360
tgaaggcccg gttctcagcc ttgtctgcca aaagctgctg ctgcagagtg tcctgtctgt  24420
cctgaatagt ctaaaacatc gatagcattc tctcggacat ctgctgttgc accgctgcca  24480
gatgagcctg ctgctgagta agagtctgga ggatcgcagc cagagcaggg tcaatggcag  24540
gaggaacagc aggggcagca cgagaactcc gggcctcatg gtcatgtgag cgtggaggca  24600
caggaggcag aggcggaatc ccaaaatcat catcatcatc atcatcatca tcgtcaggaa  24660
ctgctgcgcc ctaagtctca aactgatgga aacttgtatc ctctgcctga atgtctgtca  24720
ctggatcagg tactggtact ggatcctcag gggctggatg gtaggagcca aataggaggc  24780
gtgaggcctc aagggtgccc tggaactatg gtggtcggat cagctgtgcg aagatgtggc  24840
agagataatg agcatttggc agctgtcgcc gagcacgaag accatccaat accgtgtcct  24900
cgatctcaca aataaggaag tcaacaacat caaactctga atgaaagatc agggcaccga  24960
ggagccaaag ctgaatatga gtggtagcct ctctataacc catccacgac agaagcgtcc  25020
gtctcatgag ctgatataag tacttggcta ctgtagtgaa atctgccgga gaacgtcgcg  25080
acccatctga gaagggcggt cggaacaaag ccgcgatgtg agctgtagct ggagcaactc  25140
cgtcgtgagg gcgacgagga ggatcagagg taccatagca caagctatga agacaagtcg  25200
```

```
atgactcatt gaatccaaac agctggcgaa tctagctagc atgaagtgta acatcctctc  25260
gctcaaagcg gaacctcatc cactggtgat cggggtcgat ccatactgac gcattgaaca  25320
cacggaccca ctcctcaaca tatctgccgc tggtagtcag aagagtgaga agtcccagca  25380
aatatgtgag atgcatctca gagtctgcac cagcggctag cagaacacag gaagacccaa  25440
tagccggtgc gctcgcagaa gcaatctggg ctgaccnnnn nnnnnnnnnn nnnnnnnnnn  25500
nnnnnnnnnn nnnnnnnnnn nnnnnnnnnn nnnnnnnnnn nnnnnnnnnn nnnnnnnnnn  25560
nnnnnnnnnn nnnnnngttg atgatcagct tgattcgtta ggataaaacc ctgagtatgg  25620
aattactcag caagtcttac ccgactaaag aaaagactct caagggtatg ctgggtatat  25680
gggagtcaag gtaaggcttt tcaataatca aagactctgt tttgcagaaa tgcttactaa  25740
tgtggatcct taaaatccag ttttatttgt caagttaagt agaattacct gtaactagag  25800
ttctttctac cctagttcaa tcactggtcc tgcactagcc aatttcttaa caaaaaccca  25860
tcatctttag tggaatgcta cgtgtagggc agtgaccaag tcttcataac cacgaaggta  25920
cggcgatccg aatcgattat actcagctga ggatctccaa tcacacgaca tatgtagcac  25980
ttaacccttg catatgtcaa cccgccaccg gggttcttaa gaccagatca ggttcacgca  26040
aaccgagagc acagttacac caccgtccag cctcttgcca cggagggtac acgctactct  26100
cgccactgct ccacgcccat ttcgtgttat cttattctgg ccttagtctg cccgaggcaa  26160
ggcttaccca tgacgaggca tgtgaccagt taaagggtcc tcgatcatca agcctacatc  26220
gacaaggtcc ttaatcgact cagacggaga cactacaccg agactccttt cccgtgcaag  26280
tcacccgccc ggccttagct taatctttta accaaaaact tggtacctag cagaggtaca  26340
tcttttccga tgttgaatcc atcatagcca tgatggattc accatcaagt tttatttttg  26400
aaaacaaccc tcccactttg ccaaacatct tttctaaaac aaatcctttt gtttttctaa  26460
gcaatactaa gcatagtaaa accttttgt aaaaacaggt tttcaaggag ggtaatcaag  26520
atcaaggaag gtaatgcagg aattgtttaa tcaatcaact cctgtcacct aatgcagcaa  26580
tcaagtgaga aagattttaa aaacatcaag ggaggtggca aatgcaccgg ggcttgcctg  26640
ggtaacacta ggttagtgtt gttagacgac gtccacttgg cgaccatttt caggtttgtc  26700
catcagcatc atcctgcgga ttagcccgcg cttggggtcg acttggcttg tcttccgcat  26760
cacgcgatca attatcgtac ctaattgaga tgcacgatgc acatgaatgc atataaacaa  26820
gaatagcaca aatctaaata gtgctatacg atagcgtatt aaacacctag tggcgaggcg  26880
ttgtacaatt ttgtacggaa acactagtta ttaatatgcg actacgcgca atgattacgc  26940
ttctcgaacc taacgcaaac atcacgaaca acaaactata cacaagaaat ataattagcc  27000
taatcacaac ttatcagtta attaattaaa ttctgaacta atcccttgcc ttataaatta  27060
tactacatct ttataagtga ttaaaatatt ttatcaacac atatgcctac taaaattcta  27120
ctcggtccac taattcagct aagtgaccgg aatagcgaaa taactcgcta taactgaacc  27180
tggctcgata atcgcaagaa ctgcgaagtc gacgagagtt tcgtgactta cgcaatttat  27240
cgagcaccct aatgagcctc gcactaacac attaacttat tcaacgatcg aactattcta  27300
aacaattcat cagcttaccg tttcaacagt tgacacgaat ccatgagatc ggcagtgatt  27360
tttcgatcca cgcaatttgt cgagcgctta gggaatatcg cgctgctaac ttcgtcttca  27420
cccgattctt gggttttctt ggggacgcac gagcgacgat gaccttcgat tgaagtctgg  27480
ggtaagctgg tgaggtgggg atcgagccgg agatgacgtg tttgacaact cgacggcaaa  27540
```

```
cgacgagatc gacgacgtga ttggaaatta aagccgagcg agccgagagg gcacgctggc  27600
gagcaggaaa ccgtgcgagc acaagacagg aaaaaacgac ggctcgacaa cacgcgaagc  27660
gacgacagtc aaatcggcaa caaagagttg gcgaattcga tgaacacgac cacagtcgcg  27720
agttaacgcg gtcaagacaa ctgtgaccaa cgagcttgcg acagaagcga tgatggtgtg  27780
agaactcgac acgctgtgac gagcagataa aattcgtgcg cgcggcaaca aagaaagagc  27840
gagctacgcg tgagcagaga gctccacacg aaaactcgac gcgcgcagga actacggcga  27900
gctagagtag agaaaactcg acgcgcgcag gaactacggc gagctagagt agacagtcat  27960
gggagatgta gtcatgtaga gccgagctgg gcgacaaagc gaaatccagg ctgaagcgtt  28020
gacgagcaaa gagcttcgcg cgtgcaagaa caacagaacg ctatgcgcgc gacgcaaagg  28080
cgagcagtaa gacgacggcg cgacagacgg aaccaagcag ggagcgccgg ccatgggcgc  28140
ggcaatagag ctgggcgagc tcggagggga agccacggca caagaaatcc gatcaggcgt  28200
ggccgaacag aggtgccgcg gcacaggagc tcagggacgg acgagcagga gcagaggaga  28260
tggataccgc gagcagcctg cagggaaccc cgcgccatgg gagaaaagca gagccgagcg  28320
gctggggatt cagccagcga gcagagggga gatgggaagg agctgctcgg ctgcggcttg  28380
ctgccgggcg tgcgtggaga agaaacctgc gcgctggaga tttgtaggag accaagggcg  28440
gtggcgggat aaggatagga gcgctcggcg gcgtgatttt tatttctagg ggttgcgcgg  28500
cgcggtacag aaaaatcagg cgacgagatt aaagagatgc agtgagcagt tcgacaaatt  28560
cgtcggcatg gacacaagct gacgacgacg gccagcccga ccgcggcaag gtgaggggag  28620
acgcggtctg cgcaaagggc gagctcgagc aaggaactag agccgacgat gtccacgacg  28680
agcaggacca gagacacggt gctagtggat ggaaactgag cacaggatgg acgcaagctg  28740
gagacgagct tggtcaggtc gtcgggcaca gaggtgctcg gagggtccga cgagcacagc  28800
cggcagccgg ctgcctttgg atgctgatgg atggaagaaa tgctggtcgc tgggtaaggc  28860
tggaggagag acgtgcgtga gattttccag cgagctagcg tccaatggat aagagagaag  28920
gagacgtgag gaagaggaga actacgtgga gaaaatatcc aggctagtga cttcagatat  28980
ggaagggaaa agcggtggat aaaatcagag agaagagcgg ttgcagatat tttcttcctt  29040
cgttttcttt tactcaaaaa tttgaataaa aatacaatta tcagctggag attgggacta  29100
gaatttggaa agatgtaaga ggactaaaat taaaaatgat tttagttaca atgttttaat  29160
cggtgttaca tttaattgaa atcagataaa aacttatccg tcaccaaaac acagttgatt  29220
tggttatcct acattgcggg ctaaagaaca aattagatca tatccccgcg cacgatcttt  29280
ctcagacaat gcgcgattca gattatttta ccctgaacat tttagtcgtc aagttcaaat  29340
taatttgctc gaaataagat cattcgagtg agttcgggct tccgaatttg tgttcgcgcg  29400
agcgatggat tttaaatact catcggacgc accgattttc ggaacagcta ggttccgaac  29460
attacgaaaa tttaggaaga gcccggacag ataaaaaaat aaaaacgatg tcgcactcgc  29520
gacaaacgac accgatgcga tattaaaata gcgataagcg acaatgatta aaatttaaaa  29580
ttcgttttat ccactgatat tgcgtgctta aatccgaact cgttgttgag cggaaaataa  29640
acacctgggg tgttacacac cccgtccaat ccctggaccg gcggtactta ctcctggcag  29700
ctgtctagga tcatatattg tccccacaga ccaacacgag tcttttgtgc gcactttgtc  29760
ctcactcatg cgcacccgag aaaacttccc ggtcggtcac ccatcccaaa ttgctccaag  29820
ccaagcacgc ttaacttgga ggttctttcg agataggctt ccgaaaaaga agatgcacct  29880
tgttggtatg attacactat taattctatt aagccttggg ccaggacatc ccatcccagg  29940
```

```
ggccaggata tcacaatcca ccccccttag aagaccgacg tcctcgtcgg tcaaccccaa  30000
tccaggaacc tcccctcttg gccacgtctg tgtgtctagt gccgtcatat gccatgccat  30060
gtgaccactc cgggcccaca tgtgccatgc gccatatacc cgaaccccct agcccacaca  30120
cgcccgtgaa accgcgagtg tcggctctga taccacttgt aacaccccgt ctaatccctg  30180
gaccggcggt acttactcct ggcagctgtc taggatcata tattgtcccc acagaccaac  30240
acgagtcttt tgtgcgcact ttgtcctcac tcatgcgcac ccgagaaaac ttcccggtcg  30300
gtcacccatc ccaaattgct ccaagccaag cacgcttaac ttggaggttc tttcgagata  30360
ggcttccgaa aaagaagatg caccttgttg gtatgattac actattaatt ctattaagcc  30420
ttgggccagg acatcccatc ccaggggcca ggatatcaca ataagtgtcc cgcccagagc  30480
gccccctccg ccattcactc acctccagtc ccgttctcat ggccagaacc ctgccatcga  30540
gttcgtcggg tccccctcac cggtctggcc aactccagcg accccagacc ccctggggtc  30600
cgcgcttgtc tcgtctttgg cgacttcacc gctgcggatg gagcagcgcc ggccgcagtg  30660
ctgttaaccc ccctgacgcc taatcctagc cgtttagcct tgatctagcg gtctagatcg  30720
ctggatatcg cttcacgtgg gtgcccttgc ccctgggccc cacttgtcag tcatctgtgc  30780
cctagcgctg ggcccgactg gtcagctcgt cctcacctcg gatcatcact tggaaacact  30840
atgtagcagc atgaatgcaa caatcatgac acttctagag ctcacaccaa tatagaacca  30900
aaataactct ctactgtttt gataaaggga aaagaaaagt gaataaagga aagggtaaca  30960
cctagatttt gagtatagag caaggaaatt tttatacccc aaaattcagg gtgttacagc  31020
tacgtagtga aaccttgccg actcaccttg gtagtgtttg agggtttgat cgacctgagg  31080
caaaaaggga tcacgacttg tgggtaaagt gtgcaacctc tgtagagtgt tagaagctag  31140
tatatcagcc atgctcacag ttatgagcag ccttgggagc tcctttgatt agagttactc  31200
tggatacttt tatgatgatg cttaatgatg gtgattatga ttatgaattc ttggtatttc  31260
ctcttggagg gagtaatgtt tgggtttata acttggggtt attgctaaaa catggctctc  31320
tactggtaat aaatacctaa ccaactaaaa gcaactgctt taagcttaac cccacataca  31380
gctagtccac tttagccaaa caggacattt gttgagtacg ttgaggtgta ctcaccattg  31440
cttaaaaaca ccaaacccca ggttgtcccc attgcaacta gtgctcagga gaagatgaag  31500
gcaacgtgga ggactttcag gagtttcagg acttcgacga gttctagact agattagtgg  31560
caaaccctca gttagctgcc tgtgaaggcc ttatcgtact gcgtttcgtt caaaattttg  31620
attatgacct aagttaatga ctctgtggat gtcttggaca tccactacta gaaatatgct  31680
tatttaagac atacatctta agacaaatat cagtgcattt tatagaagcg tcttttatca  31740
tatggtgctg agtacggtaa gacggtttgt tggatatccg tctttaatga agaaggtttt  31800
tgaggcagat atatggttgg aaatgtctta tattgattta atacagtttg atgttgaaaa  31860
ccgtctcaaa taaatatacc ttttgaggca ttaagtttac aagaagtgtc ttttattttg  31920
gttagtatat tagacacttc tgtatatgaa accatctcaa ataaagatat tattagagtc  31980
atctagacta tacaaaattg tcttagatgt tagtgagtat actagaaact tgtaaacata  32040
aaaccgtctc gtacgatatt tttgatagga catattgtga aaaaacatag tcaatagtaa  32100
attctgatta gattgaacta aacatttttt ggaatttaaa atgaactagt tagctgactg  32160
tatgttcgta cggtttctat atatcatata ggtaaaaaat cttgcttaaa taagaatctt  32220
cttcaaataa aattatacgt ttgaaatatg attatttttt attttctcat caacagtatg  32280
```

```
tttatagtta taatatcgtc tctttgtacg gtataagcaa cctgataagc ggtggttaat  32340
gccacgaata tttctcttta tatacgtatt gcacatatat acaatacgtt ttattaatat  32400
agcggtggtt aatgccatct cctgcgtccg acgcccatcg ccgaggctga gaggcaagat  32460
ccgtcgtctt cagtgccccc agcgcggtgc tccaaactcc caggctatgc ttttgtttat  32520
gttttattgt catttcatga ttcatgacat gacaggctct aggctatgct ttagacattt  32580
aataagtata ttcagctcaa acgaaacggg atctaaacca gagggttaaa ggcatgtttg  32640
gtttgtggct aaatgtgcca cactttgcct aagtttagtc gtccgaattg aataactaac  32700
cttagacgaa aaagttaggc aaagtgtgat aacttaggta gcgaacaaac atgccttaag  32760
tctcacatct agggatggca atttaatgcg tggatagtga tatccgtcgg atattcgacc  32820
cgacggatca ggatatggat atgttttttg acctgcgggt tagacccgta cccgatccga  32880
gataaagcag acatggattt ggatattaaa cctcacccgc gggtaattcg ttggatatcc  32940
gaaattaacc attagtccat tactgtcgat ccacacatgg acaccaatga acaaatcgcc  33000
agcccaccat tgtccattgt gcccaggcgc caagcgccag cccattgccc actaaggcat  33060
cattccgcca aagacccaaa gtggcaaaca cccaaaccga caaacactaa tgatctaatc  33120
cccatccccc agccggcagc ttccgagcaa accaactcat ccggtcggtc atccactcat  33180
cctcatcccc tgcccatctg atccgatcag tcatctcatc ctcatcccct acccgatcgg  33240
atcccctgct catccgccga gcaccaccaa gcagcaggct ccagtcgtcg agcaccagca  33300
ggagcacgac acgccgccca gtaggagcac ggccaggagg acgacgcccg catcctgcct  33360
cttctcctgc tactggagcc tctactgcta ggagcacggc taggaggacg acgcccgcat  33420
ccagcaggag caccagcagg aagaggacgc ccatactgct gtcgttgagc gatgatctga  33480
tgccccccat catggctctt ctcctccctc gcggcctcgc ctcgatctgc tgctgccgga  33540
tccgagcgcc gtgcccacgg gtcacgacca gcgatatgca gggatcaaga atccaacttt  33600
gagaaaaatt gcttgagatg taaatggcgc caccggagta ccatcagtac tgtgacggaa  33660
cctcccaagt aattaggccc acctatagtt gtccttgtcc aacagacatc agacacccta  33720
tagatgttcc taaatcactt cacaagttcg gtatcttctt tcttaccttt ccaggaacgt  33780
ttcacccatc ttgcagacat tacagaacat cggagatata gaaatgcaga agcgattaca  33840
taacttacat ttatttaaaa agtaagatca agttacttat tacagaccag agttatccta  33900
gaagtgcaga gtaatattat tacaatacca agggaggcaa aaactcctcc cgatggtttt  33960
taaacaaaag ttctatatgg aggaccaagt cttcccgcgg cttcactctt gtttttcttc  34020
cttgggaacc accttggagc agaagcaaca aaaatttgtc gcttcctcac ctaaaaacaa  34080
cggaggaata aaccatgagt atggaattac tcagcaagtc ttacccgact aaagaaaaga  34140
ctctcaaggg tatgctggtt aagggagtca aggtaaggct tttcaataat caaagactct  34200
gttttgcaga aatgcttact aaagtggatc cttaaaaatc cagttttatt tgtcaaatta  34260
agtagaatta cctgtaacta gagttctttc taccctagtt caatcacttg tcctgcacta  34320
gccaatttct taacaaaacc atcatcttta gtggaatgct acgtgtaagt cagtgaccaa  34380
gtcttcataa ccgcgaaggt acggcgatcc gaatcgatta tactcagctg aggatctcca  34440
atcacacgac atatgtagca cttaaccctt gcatatgtca acccgccacc ggggttctta  34500
agaccagatc aggttcacgc aaaccgagag cacagataca ccaccgtcca gcctcttgcc  34560
acggagggta cacgctactc ccgccaccgc tccacgccca ttttgtgtta tcttattctg  34620
gccttagtct gcccgaggca aggcttaccc atgacgaggc atgtgaccag ttaaagggtc  34680
```

```
cccgatcagc aggcctacat cgagacggtc cttaatcgac tcagacggag acactacacc  34740
gagactcctt tctcgtgcaa gtcacccgcc cggtctcggc ttaatcattt caaacccaaa  34800
gtttggtacc tggcagaggt acatcttttc cgatgttgaa tccatcaagg cctttgacag  34860
attcaccatc aagttttatt tttgaaaaca accctcccac ttttgccaaa catcttttgt  34920
aaaacaaatc cttttgtttt tctagagcaa ggctaagcat caaaatcctt ttgtaaaacg  34980
ggtgatcaag gatggtaatc aaattcaagg aaggtaatgc aggaattgtt taagcattca  35040
actcctatca cctaatgcag caatcaagtg agaaagattt taaaagcatc aaggaggtgg  35100
caaatgcacc ggggcttgcc ttcgttagta ggtgagttag gctcggtccc gcagatatcg  35160
aagtagaaac aattgccggc ctgagaatcc gaaggtgggg gtgtcttctc ttcggtcact  35220
tcaatctctt cttcgttttc taaatataac catataggta tatatatata taagaatgaa  35280
tgccatgtaa tgctcatgag agtgcgaaga taataaagat ttattatcta agtcttgaat  35340
acaactttcc ttcacggaac tccgagaact tagggtttcc ggagtcagta aaggagttca  35400
aagggcaggg gggttttagg ttctaagtat caaacaaggt ccaaatcaac ccaaattcta  35460
cccaaggcct ctaaataatg catagaactt atgtaaaaag tttggacatt tttggaaatt  35520
ccatttattt tctaaaaatc caaaaccact accttaaact actttaaata ccttaaaatt  35580
ccttagttaa cctaaaattc atataactat ttttattaaa ttctatggaa aataagaagc  35640
ctaggaaaat tggtttcaca attttaggat ttttctacaa tttttaaaaa atttccaaag  35700
ctctatagaa aaagaaaagg aaaaagattg aatagtgttg ggctgattct agcccagccg  35760
gcccagtacc aggggaaaac gcgcgcgcgc gccctcgccc tggcgacttt gcacagaggt  35820
cctcggggtt tggctaatta gaactggctt ctatcactat tacactgtgt cgctgacaga  35880
ttgcagagaa gcccctgcag ttctaactct tcgcagaggg aggtcctcga cggcgttcac  35940
gcccagccga actccggcga gtgcctgcac cggccgaacg gggcaacgac tagggttccc  36000
gagcggcgga catcaaattg gacctagccc gagcatttcc cctaacctaa ttccatctat  36060
ggcccaatgg cttgctctgg ccacggtggc cgtgaacatc gcggcaagac agtcgcgttc  36120
ccggcgacca aagggctcct agctcgattg tgtgggtcgg caagcatcat agacttaagg  36180
gaaagcttaa acgagggaga gaaggagacg aactgaccgg aataaggctg gccgaggtga  36240
ggttcggttt cgggtggcgg agaattgatt tggggcgaat tcaaaattcg tgagctcggg  36300
cgaacaattg ctagcaatac gtggtggctg ggtgggtgat gatgttgtga agctctctgc  36360
ggggtcaatt tatagatccc aggggcggtg gcgcttaatt tgagccgaca gtgtgggcgg  36420
ccggagataa ggaagatcat cggcttcgcg atttcgtgtc caccgccgtg gcgggctcac  36480
cggcaatgat gagacaacag tggggagtca cggcgatgcg acagaggtgc tcggatacat  36540
ggtgtaaggc cgagcgacgg tgatccccgg cgggcttatc tgctcaagcc gcacggcaga  36600
ggggaagtac tgggggttca ccggagtgcc gtccagcgca tgcctttacc gagcgatctt  36660
atctggtcac cggcgacgtg aatcacaacg gcggcgacgt gaatctcagc gaagatcagt  36720
cgtcggcggt gagagactac cgcgctggct gtctgatctc cctggtagca ctgtaccatg  36780
gagagttata tttagacagc ctgacagtca agtttggagc ccaattttct ctcaatttca  36840
aataacaact catccagtga cctgcagcaa agttgtagag ctacaatcca gctataactt  36900
tgctacaatg tgctcccaca aaaagtcact ggatcttgct taaaattaag ccctaagttc  36960
atgtcatccc actgttaatc tgaatttcag atttcaagca gtctgacagt ccaactttag  37020
```

```
gctcaattat ctccagtatt ttcttaacaa ctatgctcac actcttaaga aaagttgttc  37080
tcctatgatt gggctataat tttaatgtgg tgacctaggg aaaaaaccct atgatttaaa  37140
agttacaagg ctcaaaagtt gagcccataa cactattttt cagacttagt ataaaatctc  37200
aaatagggtc ctttttgcaa atgaggccaa aacttagggt ttggcttgta aattcacata  37260
tgagtgaccc aaatgactta agatacttat ttaacttggt ttttgcactt tagtccaaaa  37320
gtggactaat tttgcacata agcccctagg gtttggattt agggttttct agggttccga  37380
ttagggtttt tggtatccca gaggtataaa tgtggttcaa ctttattctt gggaatattt  37440
catgactatt tccctagagc ttttaggttt tctcaatttg ggttatatct taccccttta  37500
atccctattt agggttaaat tccctatcta ggttctattt gcaaaacact aaaacaatac  37560
aacttgtttg aaatttttac ctagtgaatg cactctaggt gtgtcaaaca tatgcaatgc  37620
caatgtttat gatgctatgc tcaagtttta gttgcagtaa caccaggggt gttacatcct  37680
tccccccata aaagaatctc gtcccgagat taaaagtcct agggtaagta atggaaaagg  37740
aaacacgaca tacttttatt tccttatttc tggtacaagg caggggtggt tttggaatca  37800
ctcctttatt acaacagcta tacaggcttt acaatttaca agaagctaaa aagcctggga  37860
aattcttatc taaaaagtct tgagtttccc atgtagcctc atcttcggaa tgttggttcc  37920
actgtatctt ataaaacttg agagttttct ccgggtaacc ctgtcctttt gatccaagac  37980
tcgaataggg tgctcagaat atgtcaagtc cggttcaagg acaacatctg tcacttcaac  38040
ggttcgatca ggaacccgaa gacacttctt caattgggac acgtgaaaca cattatgcac  38100
agcaaacaag gtttcgggta actgaagtcg gtatgccact ggcccatatc tttccaggat  38160
aagaaaagga ccaatatatt atggtgcaag ctttccttta actccgaaac gcgatactcc  38220
cttcattggt gaaaccttta agtagacata gtatccttca aggaaatata agggcattcg  38280
ccgtttgtct acgtaactct tttgacgagc ttgagctttc ttcaaattat gaattatcct  38340
ttgaactctt tcttcagtct ctttcaccat atcaggcctg aagaagtacc tttcaccagg  38400
ttcagaccaa tttagcggag tacgacatcg tcgtccatat aaagcttcaa agggtgccat  38460
cttgatgctt tcttgatagc tattattata tgaaaattcc gctaacggca aacattcatc  38520
ccatttttgt ggaaattcca gaacacatgc ccgcagcata tcttcaagta tttggtttac  38580
tctctcagtc tgtccactgg tttgaggatg gtaggccgaa ctatggagca acttagtacc  38640
caaggatttg tgaagtgctt cccaaaactt ggctacaaat tgaggtccac gatccgacac  38700
tatgggtctt cggaacacca tgcagactaa gaatacgagc aatgtacaaa tgggcataga  38760
cagtaaccgg gtgatctgtc ttgaccggta gaaagtgagc aattttcgta agccgatcaa  38820
ttataaccca gatagaatca taccctttg tagtcctggg taatcccaca atgaagtcca  38880
tactaatatc ttcccatttc tatgttggga tcggcaaagg ttgtaatgga ccagctatct  38940
tcatgtgtat ggccttgaca agtctgcaag tgtcacactt agccacatag cgtgcaattt  39000
caattttcat cttcgtccac cagtagtgct gctttagatc atgatacatc ttagtgcttc  39060
ccagatgaat agaatagcga ctaagatgtg cttcatctaa gatttgctgg cggagttctt  39120
cattcttcgg caccactatg cggttattga accatatcac accttgatca tcttctttga  39180
aacatttggc tgttccagcc attatcttct cacgtatgtg cttcataccc tcatcatctt  39240
tttgtgcgtc aattattctt cgtatgatga ttgactccag cttcaaatga tttgaagtcc  39300
catgttgaat cattcccagg tttaatttct ccatctcctg gcataatgta atgtcagaag  39360
tcctcactgt taaacaatgg caggaagcct tgcaattgag cgcatctgcc actacatttg  39420
```

```
cttttcctgg gtgataatgg atttctaatt cataatcctt gattagctcg agccatcgcc  39480
tctgtctcat attcaattct gactgggtga agatgtattt caagctttta tggtctgtat  39540
aaatatgaca gacattaccc agcaaataat gacgccagat ctttagggca tgaaccacca  39600
cagctaactc cagatcatga gtaggataat gttcctcatg tcggcgcaac tgccttgaag  39660
catatgcaat tactcggcct tcttgcatta gcacacaacc gagtccactg cctgatgcat  39720
cacaatatac atcaaagggc ttggtgatgt ccggttgagc caataccgga gtagtggtta  39780
ctaatgtctt caattgttca aaagcttcat cacactttga agaccaattg aacttaatat  39840
cattcttcaa taaacttgtg attggcttca caagcttaga aaaatctggt atgaatcggc  39900
ggtaatatcc agccagtcca aggaaacttc ggacctgatg aacagtggtc gggggtttcc  39960
actccaaaat gtccttgact ttgctgggat ctaccgcaat ccccctggca gacaatacat  40020
gtcccagaaa ctgaatttcg tccagccaaa acacgcattt gctaaacttg gcatataact  40080
gatgttctct caagcgcgtt aacacgatcc gtaaatgttg ggcgtgctcc tcttcattct  40140
tggaatatat caaaatatcg tcaatgaaga ctaccacaaa cttgtccaac tcgggcataa  40200
ataccgagtt catcaaatac gtgaagtggg caggagcatt tgtcaatccg aaagacatta  40260
ccaggtattc aaataatcca taccgcgtag tgaaggcggt ctttggtata tcttcgggcc  40320
gaatacggat ctggtgatag cccgatctga gatcaatctt ggaaaatacc cttgctccag  40380
tcagttgatc aaataaaatg tcaatccttg gaagagggta cttgtttttg atggtgacct  40440
cattcagggg tcgataatcc acacacattt gtaaagtttg atccttcttt ttgacgaata  40500
tggctggaca accccacggc gatgagcttg gccggataaa tcctttctca agtagatctt  40560
gtaattggat cttcagttct gccaactcat taggaggcat tcggtacgat cttctagata  40620
ctggagccgt accgggtttc aactcaatta caaactctac ctcccgttca ggtggcagtc  40680
cgggcaaatc ctcgggaaag acattgggaa actcgcatac caccggaata tccttgattt  40740
ccggtataat ggcttcataa gctctgccag tagctttggt tggaatgggg ataggcaaaa  40800
gaatttcttc ctggttatga ctcaacctga taattctctg atcagtgttg agagttgctt  40860
tatgtctggc taaccaattc atacccaaaa tgacatatat atcttggcct ttcagaatga  40920
tcatattagt aggaaagtcc catccggcca aggttacggg cacttgatag gccacttctc  40980
tagtaaatat ttgtcccccct ggtgagtgaa tttttaaacc cctcttttga ttcatggcat  41040
gagatgcaat gttgctccac aaatttcttg ctgatgaatg tatgcgaagc accagaatca  41100
aagagaataa ctgcgggatg attggccaca agaaacgtac ccatcattac cggctcaccg  41160
tccggtgtag tggccacttg cgtataatat atgcgtcccg tcttctttgt atttttgccc  41220
atattatttt ccttggcttg agatgaattc ccagatcctt gctgattatt tgactggttc  41280
tgctttggat aagggcaatc cttgataaaa tgcccagatt tgccacaatt gaaacatcca  41340
gtcgacgagc tgggtaaagc agggaatcga gtgcctgggg cacccggctg acttgatgta  41400
gtaggggcat tattgggacg aataaagact ggctgcttaa aaggaaagga gggtggacga  41460
gcgaaagaac gattctggtt agaaggccgg atgacgaacc gttgcctgtt caccgggccc  41520
tgactagacc tgtcacctcc aaaacccttg gatttaccag cgcctgcata cttcgcttct  41580
actgccagtg ctgtactgac agctcttcca taagtaagat ctatgcaggt tgccatcttc  41640
ctttgcagtc gatcatttaa tcctctcata aagcaattct tcttcttcaa atcagtgttc  41700
acttgatcga ttgcatattg tgacaaatga ttgaacttat tgagatactg gttaacagta  41760
```

```
tcccctcctt gtttcagctt cataaactct tcttgcttca tgtgaagaac accttctggt  41820
atatagtgct cgcggaaggc caccttgaat tcttcccaag ttatctaatg attggccggt  41880
tgaacggcca caaaattacc ccaccaagtg ctggcaggtc cgcgcagttg ctgggctgcg  41940
aataaaggct tctgggtttc tgaacatcgc agcagtccaa acttttgctc aatcacacga  42000
agccattcat ctgcttctaa cgggtcttcg gctttgacaa acagcggtgg tcgcgtctct  42060
gagaagtcca agtaagaggt ttcacggggg ccctgttgat aaccccgccc accttgttgt  42120
tgcaattgtt gacccgccat ctctctaaga aaacgggtat tatccgcggt tgcatttacc  42180
aaggccacaa tcgcctcggc cagtgtggga ggaacaggag gtggatttgg ggtagactcc  42240
ctcccacagg aggtactagc tccgtcctgt gctcgagtct tggaaggcat ctgtggcaac  42300
aacatttgga aaacaatatg atatgccaag gaaaaaccat ccattttaca ttaccaaaaa  42360
gagtaatgta cagactcgaa tttttacaac aggatacatt acctattata caatagcaca  42420
acctattatg caatagtaca aaatattata cattagagca acctgttata caatacacta  42480
cttctacttc tactacccca ttattcctgc tttccgttgc ttttggcggc ctcgtcgtcg  42540
ggtgtgggag accattcgtc gactagcctc atagaaggag ggggctgaaa aaggtctaac  42600
tcaccaccaa gcgcgtgtcc cgcaacatgc gagggtccgg cttccgactc accaggattc  42660
gtaggctcac tgggatgcag ttgcgaatat aatacatgaa tctcttcatg taaggtattg  42720
caatatgtct gcagttcatc aacagccaag ttgagctcgg ctactcgagc ttgagctttt  42780
tgctccttgt cccatgcaag cgaacgggat tgaacaaccc agtcaagtgc caaatcccgg  42840
tccgcgagct gatctcgcag atggcagata tctcttctca actcatttat gcggtcgcca  42900
tctatgaccc agatagtcgt tctgcggcgg agtttcgctt ggagtcgact tacttcagct  42960
tcaagatccc ctataggatc attgcttccg ctactactat tatcatgcct tggggtcagc  43020
tggtgactcg gcacaccaat cggtccagta tgtttgcgcg ttgttctcct tgtgcgcggc  43080
ggcattttct aagggggaaa atttgattag tatggttctt agcatgatgc atgtataatt  43140
acagaatcaa ccttagttga ttcacacctt ctatatgttg cactcttact acctggtctt  43200
taagatagac tcttcagaat acttaggtaa gaaaggaaga gagtttctag gtaagacttt  43260
tagaaaatct ttttgaagat gcctcataat atctgcaaag aagggctacg ctccgatacc  43320
agctgtgacg gaacctccca agtaattaag cccacctaca gttgtccttg tccaacagac  43380
atcagacacc ctatagatgt tcctaaatta cttcacaagt tcggtatctt ctttcttacc  43440
tttccaggaa cgtttcaccc gtcttgcaga cattacagaa catcgaagat atagaaatgc  43500
agaagcgatt acataactta catttattta aaaagtaaga tcaagttact tattacagac  43560
cagagttatc ctaggagtgc agagtaatat tattacaata ccaagggagg caaaaactcc  43620
tcccgatagt ttttaaacaa aagtcctata tggaggacca agtcctcccg cggcttcact  43680
cttgtttttc ttccttggga accaccttgg agcagaagca ataaaaattt gtcgcttcct  43740
cacctaaaaa caacggaggg ataaaccctg agtatggaat tactcagcaa gtcttacccg  43800
actaaagaaa agactctcaa gggtatgctg gttaagggag tcaaggtaag gcttttcaat  43860
aatcaaagac tctgttttgc agaaatgctt actaaagtgg atccttaaaa atccagtttt  43920
atttgtcaaa ttaagtagaa ttacctgtaa ctagagttct ttctacccta gttcaaatca  43980
cttgtcctgc actagccaat ttcttaacaa aaccatcatc tttagtggaa tgctacgtgt  44040
aagtcagtga ccaagtcttc ataaccgcga aggtacggcg atccgaatcg attatactca  44100
gctgaggatc tccaatcaca cgacatatgt agcacttaac ccttgcatat gtcaacccgc  44160
```

cactggggtt tttaagacca gatcaggttc acacaaaccg agagcacaga tacaccaccg 44220
tccagcctct tgccacggag ggtacacgct actcccgcca ccgctccacg cccatttcgt 44280
gttatcttat tctggcctta gtctgcccga ggcaaggctt acccatgacg aggcatgtga 44340
ccagttaaag ggtccccggt cagcaggcct acatcgagac ggtccttaat cgactcagac 44400
ggagacacta caccgagact cctttctcgt gcaagtcacc cgcccggtct cggcttaatc 44460
atttcaaacc caaagtttgg tacctggcag aggtacatct tttccgatgt tgaatccatc 44520
aaggcctttg acagattcac catcaagttt tattttcaaa aataaccctc ccacttttgc 44580
caaacatctt ttgtaaaaca aatccttttg tttttctaga gcaaggcaaa gcatcaaaat 44640
ccttttgtaa aacgggtgat caaggaaggt aatcaaattc aaggaaggta gtgcaggaat 44700
tgtttaagca ttcaactcct atcacctaat gcagcaatca agtgagaaag attttaaaag 44760
catcaaggag gtggtaaatg caccggggct tgccttcgtt agtaggtgag tcaggctcag 44820
tcccgcagat atcgaagtag aaacaattgc cggcctgaga atccgtaggt ggtggtgtct 44880
tctctttggt cacttcaatc tcttcttcat tttctaaata taaccatata ggtatatata 44940
taagaatgaa tgccatgtaa tgctcatgag agtgcgaaga taataaagat ttattatcta 45000
agtcttgaat acaactttcc ttcacggaac tccgagaact tagggtttcc ggagtcagta 45060
aaggagttca aagggcaggg gggttttagg ttctaagtat caaacaaggt ccaaatcaac 45120
ccaaattcta cccaaggcct ctaaataatg tatagaactt atgtaaaaag tttggacatt 45180
tttggaaatt ccatttattt tctaaaaatc cagaaccact accttaaact actttaaata 45240
ccttaaaatt ccttagttaa cctaaaattc atacaactat ttttattaaa ttctatggaa 45300
aataagaagc ctaggaaaat tggtttcaca attttaggat ttttctacaa tttttaacaa 45360
atttccaaag ctctacaaaa aaagaaaagg aaaaagattg aatagtgttg ggctgattct 45420
agcccagccg gcccagtact aggggaaaac gcgcgcgcgc gctcgcgccc tggcgacttt 45480
gcacagaggt cctcggggtt tggctaatca gaactggctt ctatcactat tacactgtgt 45540
cgctgacaga ttgcagagaa gcccctgtag ttctaactct tcgcagaggg aggtcctcga 45600
cggcgttcac gcccagccga actccggcga gtgcctgcac cggccgaacg gggcaacggc 45660
tagggttccc gagcggcgga catcaaattg gacctagccc gagcatttcc cctaacctaa 45720
ttccatctat ggcccaatgg cttgctctgg ccacggtggc cgtgaacatc gcggcaagac 45780
agtcgcgttc ccggcgacca aagggctcct agctcgattg tgtgggtcgg caagcatcgt 45840
agacttaagg gaaagcttaa atgagggaga gaaggagacg aactgaccag aataaggctg 45900
gccgcagtga ggttgggttt cgggtggcgg agaattgatt tggggcgaat tcaaaattcg 45960
cgagcttggg cgaacaattg ctagcaatac gtggtggctg ggtgggtgat gatgttgtga 46020
agctctctgc agggtcaatt tatagatccc aggggcggtg gcgcttaatt tgagtggaca 46080
gtgtgggcgg ccggagataa ggaagatcat cggcttcgcg atttcgtgtc caccgccgtg 46140
gcgggctcac cggcaatgat gagacaacag tggggagtca cggcgatgcg acagaggtgc 46200
ccggatacgt ggcgtaaggc cgagcgacgg ggatccccag cgggcttatc tgctcaagcc 46260
gcacggtaga ggggaagtac tgggggttca ccggagtgcc gtccagcgca tgcctttacc 46320
gagcgatctt atctggtcac cggcgacgtg aatcgcaacg gcggcggcgt gaatctcagc 46380
gaagatcagt catcggcggt gagagactgc cgcgctggtg gtctgatctc cctggtagca 46440
ctgtaccatg gagatttata ttcagacagc ctgacagtca agtttggagc ccagtttttct 46500

```
ctcaatttca aataacaact catccagtga cctacagcaa agttgtagag ctacaatcca  46560
gctataactt tgctacaatg tgctcccaca aaaagtcact gaatcttgct taaaattaag  46620
ccctaagttc atgtcatccc actgttaatc tgaatttcag atttcaagca gtctgacagt  46680
ccaacttcag gctcaattat ctccaatatt ttcttaaaac tatgctcaca ctcttaagca  46740
aagttgttct cctatgattg ggctataatt ttaatgtggt gacctagggc aaaaacccta  46800
tgatttaaaa gttacaaggc tcaaaagttg agcccataac actgttttca gacttagtat  46860
aaaacctcaa atagggtcct ttttgcaaat gaggccaaaa cttagggttt ggcttgtaaa  46920
ttcacatatg agtgacccaa atgacttaag atacttattt aacttggttt ttgcacttta  46980
gtccaaaagt ggtcgaattt tgcacataag cccctagggt ttggatttag ggttttctag  47040
ggttccaatt agggtttttg gtatccgagg ggtataaatg tggttcaact ttattcttga  47100
gaatatttga tgactatttc cctagagctt ttaggttttc tcaatttggg ttatatctta  47160
ccccttttaat ccctatttag ggttaaattc cctatctagg gttctatttg caaaacacta  47220
aaacaataca acttgtttga aatttttacc tagtgaatgc actctaggtg tgtcaaacat  47280
atgcaatgcc aatgtttatg atgctatgct caagttttag ttgcagtaac accaggggtg  47340
ttacaagtac cttgtgcagg tgaccaagta ctaggccgca cagaactgca aggtacgtat  47400
gcacacatgg ttacatttac tatagaactg gagttatttt ttgatgcaaa ggctgccagg  47460
tcatggcgat ttcacgtccg ttaggctcga gaggtggact caaacatcca agttttgcaa  47520
gttttgatgt tggatgttaa atttctatgc tcacccctcg tttggttatt gatgtactat  47580
ttccatctca tgtcacaaat ttggcataag gaatgggtat tggtggctac tggctgtgtt  47640
tatttccaag tattatacat gtacaatgga acagttgata atagttttgc atgaactatt  47700
ggcattagct atctaaaagg acagaaaggc agacatgagc aacaaatccc gctccatggg  47760
ctgaaactgg gattcgtgat ggtcagctaa gcataccttc gccttcaaat ttgcgtagct  47820
tctttttat tctgctagtt gtttggtctg ctgttcaaat gccttattat tctgcgagtt  47880
gttttaagac tgggcctcaa ttttttttca aggcagaaag tgctactgcc gctctcactg  47940
tagcggtgtg gtactgggat ccttgccaat aaggtaaaac tctaactgat cttcttacgc  48000
tttgcattga ggaaggagct cttctgggcg gttggataac agagtcgttc tagtgtgttt  48060
ttagggtgag cccgtccaag acgcccgtgc gtccccgtgc ccctcgccag ctgatgtcgt  48120
cctaggtata catacaggag gtgctgacga tggcactgct catatataag taatagagat  48180
agacatgtat gaaaagggtc ttttgttttc aagtagtgtg tagttgctgt tacttttaac  48240
agctaatgca atctggatga gtcacctatg aatgccatac tggaatctgt tgcgcttttg  48300
ttgatcatta ttattttgca atccaggcta ggggattgaa gaagcacttg aagaggctca  48360
atgcgcccaa gcattggatg ctcgacaagc ttggtggagc ttttgtaagt aaacatgtcg  48420
gggaccataa ttaggggtac ccccaagact cctaatctca gctggtaacc cccatcagca  48480
caaagctgca aaggcctgat gggcgcgatt caggtcaagg ctccgtccac tcaagggaca  48540
cgatcccgcc tcgcccgagc ccagcctcgg gcaaaggcag ccgacccagg aggattcacg  48600
tctcgcccga gggtcccctc aagcaacgga cgcaccttcg gctcgcccga ggcccaggct  48660
tcgcggagaa gcaaccttgg acagatcgcc acgccaacca accgtatcgc aggagcattt  48720
aatgcaagga tcgactgaca ccttatccta acgcgcgctc ctcagtcgat agggccgaag  48780
tgaccgcagt cacttcgccg ctccactgac cgacctgacg ggaaaatagc gccgcctgcc  48840
ctgctccgac tgctgtgcca ctcgacagag tgaggctgac agcagctaag tccagcctcg  48900
```

```
ggcgccatga gaagctccgc ctcgcccgac cccagagctc gggctcaacc tcgacgccgg  48960
acgacggact ccgcctcgcc cgaccccagg gctcggactc agcctcgacc tcggaagacg  49020
gactccgcct cgcccgatcc cagggctcgg gctcaacctc gacctcggag gagcctccgc  49080
ctcgcccgac ctcgggctcg gaccgaccac gtcgcagggg gagccatcat taccctaccc  49140
ctagctagct caggctacgg ggaacaagac cgacgtccca tctggctcgc cccggtaaac  49200
aagtaatgat ggcaccccat gtgctccgtg acgacggcgg ctctcagccc cttatggaag  49260
caaggagacg tcagcaagga tccgacagcc ccgacagctg tacttccaca gggctcaaac  49320
gctcctccga cggccacgac atcacatgaa cagggcgcca aaacctctcc gacagccacg  49380
acagcatgta cttagggctc tggctcctct ctgctagaca cgttagcaca ttgctacacc  49440
ccccattgta cacctgggcc ctctccttac gtctataaaa ggaaggtcta gggctctcgt  49500
acgagagggt tggccgcgcg ggagaacggg ctgacgcaca aggctctctc tctctctctc  49560
ccacacgaac gcttgtaacc ccctactgca agcgcatccg ccctgggcac aggacaacac  49620
gaaggccacg ggttcccctt tgctgttttc ccccctttgt gtttcgtctc gtgccgaccc  49680
atctggaatg ggacacgcag cgacagttta ctcgtcggtc cagggacccc ccggggtcga  49740
aacgctgaca gttggcacgc caggtagggg cctactgcat ggtgacgaac agcttcccgt  49800
caagttccag atgggtagtc tccagcaacc actccaaccc gggacggtgc tccatttcag  49860
gagtcttgag ttcatgtccc tcgacggcag ctacgacatg acactccttc ctccgccgcg  49920
cgacaacgac aatggcggcc gtcagcccgc ccgtcggcgg cggaatcgac gacgtcttcc  49980
ccacgtggcg gaagagcgat atccgggtct gtcccgtcac cttccccgct gacggaggag  50040
gaggcggggt aggcatggcc aatcaggagg cggcacctcg tcggctgtcg agcgagtcga  50100
cggcgccgac gccccaacgg gggacacgtc gggcgttgac ctcgcgtctg agacgaagac  50160
aagcgtcgtt tccccgcaac acgccaaccc caagcagacg gatgacgcca gcacgctcgc  50220
gaaggacttc ctgggcgtta acctcgtacc tgagacaacg gtgcagtccg tccctgacgc  50280
gacttcgtca ccacccgtcg atcaagaggt accgtccgtt tcccatccca tgccttttag  50340
attcagttgt gacccaccaa gcgatcccgc ttcggtggac gctttcataa aggcatgtcc  50400
aaaccctccg gggtatcata tgcggtcaac ctgggaccga ctgacggccg tctcgaccta  50460
tgggccccccg ggttccgagg aagatgacga gcctgactct ggttgggatt tctccgggct  50520
cgataacccc agtgtcatgc gggacttcat gaccgcatgt gactactgcc tctccgattg  50580
ctccgatagc agccacagcc tcggcgacga ggactgtggc ccaaggtgcg aatgcttcca  50640
cgtcgatcta gggggtcttg acgaaggcaa ccatcttggt atgccggagg atggtgatcc  50700
ccctaggcct gcgcctcgcg ttgacatcct tcgggagcta gctgtggtcc cagtccctgc  50760
ggggggtcaa gacgcacggc ttgagcaaat ccgcgaggta caggccaggc tcgacgagga  50820
agcaggacaa cttgtgcagc ttcggcaaaa tatcgggcag gagtgggcag gccgagcacc  50880
ggctggagaa gcgcgtcatc tggcccagga cgtccagcac cgcatcaccg acgatgccag  50940
ggcgaggctg cccccggctt ccagtggggt cggccagaac ctggctgcag cagcgatact  51000
actccgagcg atgccgaaac catccaccac cgaggggtgg cgtatccaag gagagctcaa  51060
aaatctccta gaggatgtcg cggtccgacg ggccgagagc tctgcctccc gaaggcaggg  51120
gtacccccgg agcatcgcgc tgcgacttcc cgattcatgc gggaagcctc ggtccacacc  51180
gggcgcacgc gggacacagc gcctgcggcc ccaagacgcc tcggcaacga gcaccgccgc  51240
```

gaccgtcaag cccacctcga cgagaaggtg cgtcgaggct accaccccag gcgtggggga 51300
cgctacgaca gcgtggagga tcggagcccc tcgcccgaac cacccagtcc gcaagctttc 51360
agccgggcca tacaacgggc accgttcccg acctggttct gaaccccgac taccatcacc 51420
aagtactcgg gggagtcgaa gccggaactg tggctcgcgg actaccggct ggcctgccag 51480
ctgagtggga cggacgatga caacctcatc atctgcatcc ttcccctgtt cctctccgac 51540
gccgcccgag cctggctgga gcatctatct cctgtgcaga tctccaactg ggacgacctg 51600
gtcaaagctt tcgtcggcaa cttccagggc acatacgtgc gccctgggaa ctcctgggat 51660
ctccgaaggt gccgccagca gccgagagaa tccctctggg actacatccg gcgattttcg 51720
aagcagggca ccgagctgcc caacatcacc aactcggatg tcatcggcgc gttcctcacc 51780
ggtaccactt gtcgcgacct ggtgagcaag ctgggtcgca agactcccac tagggcgagc 51840
gagctgatgg acatcgccac caagttcgcc tctggtcagg aggcggtcga ggccatcttc 51900
cggaaggaca agcagcctca ggggcgtcag ccggaagacg tccccaaggc gtccgctcag 51960
cgcggcgcga ggaagaaggg caagaagaag tcacaagcaa aacgcgacgt cgccgacaca 52020
gacattgtcg ccgccgccga gcacagaaac cctcggaagc ctcccggagg cgccaacctg 52080
ttcgatagga tggtcaagga gtcgtgcccc tatcatcagg gtcccatcaa gcacaccctt 52140
gaggaatgcg tcatgcttcg acgctacttc cacaaggccg ggccaccggc gaaaggtggc 52200
agagcccaca acaacgacaa gaaggaggat cacaaggcag aggagttccc cgaggtccac 52260
gactgcttca tgatctatgg tgggcaagtg gcgaacgcct cgactcggca ccgcaagcaa 52320
gagcgtcggg aggtctgctc agtaaaggtg gcagcgccag tctacctaga ctggtccgac 52380
aagcccatca ccttcgacca gggcgaccac cccgaccgcg tgccgagcct aggaaagtac 52440
cctctcattg tcgaccccgt catcggcaac gtcaggctta ccaaggtcct catggacgga 52500
ggcagcagcc tcaacatcat ctacgccgcg accctcgggc tcctgcagat cgatctgtcc 52560
tcgatccggg ccggtgcgac gccttttcac gggatcatcc ccgggaaacg cgtccaaccc 52620
cttgggcaac tcaatctgtc agtctgcttc gggactccct ccaacttccg aaaggaaacc 52680
ctcacgttcg aggtggtcgg gttccgagga acctaccacg cagtgctggg gagaccatgc 52740
tacgccaagt tcatggccgt ccccaactac acctacctca agctcaagat gtcgggcccc 52800
aacggggtca tcaccatcgg ctccacgtac cgacacacgt acgaatgcga cgtggagtgc 52860
gtggagtacg ccgaggccct cgccgaatcc gaggccctca tcgccgacct ggggagcctc 52920
tccaaggagg cgccagatgc gaagcgccac gccggcaact tcgagccagc tgagacgatt 52980
aagtccgtcc ctctcggccc cagcaacgac gcctccaagc agatccggat cggctccgag 53040
ctcgacccca aataggaagc agtgctcgtc gactttctcc gcgcgaacgc cgaggttttt 53100
gcatggagtc cctcggacat gcctagcata ccgagggatg tcgccgagca ctcgctggat 53160
atccgagctg gagcccgacc cgtgaagcag cctctacatc gattcgacga agaaaagcgc 53220
agagccatag gcgaggagat ccacaagctg atggctgcag ggttcattaa agaggtattc 53280
catcccgaat ggcttgtcaa ccctgtgctt gtgagaaata aaggagggaa atggcggatg 53340
tgtgtagact acactggtct aaacaaagca tgtccgaaag ttccctccct ctgcctcgca 53400
tcgatcaaat catggattcc actgctgggt gcgaaaccct gtctttcctc gatgcctact 53460
cagggtatca ccaaatcagg atgaaagagt ccgaccagct cgcgacttct ttcatcacac 53520
cctttggcat gtactgctac gttactatgc cattcggttt gaggaatgcg ggtgcgacat 53580
accaaagatg catgaaccac gtgttcggag agcacattgg tcgaacggtt gaggcttacg 53640

```
tcgatgacat catagtcaag acgaggaaag cctccgacct cctctccgac cttgaaacga  53700
cattcaagtg tctcaaggcg aaaggcgtaa aactcaatcc cgagaagtgt gtcttcggag  53760
tcccccgagg catgctcttg ggttcatcg tctccgagcg gggcatcgag gccaacccgg  53820
agaaaatcgc ggccatcacc aacatgggcc ccatcaagga cttgaaagga gtacagaggg  53880
tcatgggatg ccttgcggct ctgagccgtt tcatctcacg cctcggcgaa agaggcctac  53940
ctctgtaccg cctcttgagg aagaccgagc gcttcacttg gaccccgag gccgaggaag  54000
ccctcgggaa cctaaaggtg ctcctcacaa gcgcgcccat cttggtgccc cctgttgccg  54060
gagaagccct cttggtctac gtcgccgcta ccactcaggt ggtcagcgcc gcgatcatgg  54120
tcgagagacg agaagagggg cacgcattgc ccgtccagag gccggtctac ttcatcagtg  54180
aagtactgtc tgagaccaaa atccgctacc cgcaaattcc agaagctact ttacgcggta  54240
attctgacgc ggcgaaagtt gcgacactac ttcgagtctc atccggtgac tgtggtgtca  54300
tccttccccc tgggagagat catccagtgc cgagaggcct cgggtaggat tgcaaagtgg  54360
gcagtggaga ttatgggcga gacaatctca ttcgcccctc ggaaggccat caagtcccaa  54420
gtcttggcgg actttgtggc tgaatgggtc gacacccagc ttccagcagc tccgatccaa  54480
ctggaactct ggaccatgtt tttcgacggg tcgttgatga aaacaggagc gggcgcgggc  54540
ctgctcttca tctcgcccct cgggaagcac ctccgctacg tgttgcacct ccatttcccg  54600
gcgtccaaca acgtggccga gtacgaggct cggttaacgg gttgcgaatt gccaccgagc  54660
taggggtccg acgcctcgac gctcgcggcg actcgcaact tgtcatcgac aagtcatgaa  54720
gaactcccac tgtcgcgacc cgaagatgga agcctactgc gatgaggttc ggcgcctgga  54780
ggacaagttc tatgggctcg agctcaacca catcgcccga cgatacaacg agactacgga  54840
tgagctggct aagatagcct cggcgcggac aacggttccc ccggacgtct tctcccgaga  54900
cctacatcaa ccctcagtca agaccagcga cacgcccgag cccgagaaag ccttggccct  54960
gcccgaggca ccctcggccc ccgagggtga ggcactgcgc gtcgaggaag agcggtatgg  55020
ggtcacgcct aatcgaaact ggcagaccct gtacctgcaa tatctccacc gaggagagct  55080
acccctcgac agagccgaag ctcggcaact agcgtggggc gccaagtcgt tcgtcttgct  55140
gggtgacggg aaggagctct accaccgcag cccctcaggc gtcctacaac gttgcatatc  55200
catcgccgaa ggtcaggagt tattacaaga aatacactcg ggggcttgcg gtcaccacgc  55260
agcacctcga gccctcgttg gaaatgcctt ccgacagggt ttctactggc caaccgcggt  55320
ggccgacgcc actaggattg tacgcacctg ccaagggtgt caattctatg caaagcagac  55380
ccacctgccc gctcaggctc tgcaaacaat acccatcacc tggccgtttg ctgtgtgggg  55440
tctggacctt gtcagcccct tgcagaaggc acccgggggc tacacgcacc tgctggtcgc  55500
catcgacaaa ttctccaagt ggatcgaggt cagaccccta aacagcatca ggtccgaaca  55560
ggcggtggcg ttcttcacca acatcatcca tcgctttggg gtcccgaact ccatcatcac  55620
cgacaacggc acccagttca ccggtagaaa gttcctactg cgaggattac cacatccggg  55680
tggactaggc cgccgtagct caccccatga cgaatgggca gctagagcgt gccaacgaca  55740
tgattctaca aggactcaag ccacggatct acaacgacct caacaagttc agcaggcgat  55800
ggatgaagga actcccctcg gtggtctgga gtctgagaac gacaccaagc tgagccacgg  55860
gcttcacgcc gttttttcta gtctatgggg ccgaggccat cttgcccaca gactcactgg  55920
gccatcttca cgctgttttt tctagtctat ggggacgagg gcgtacgacg accgaagcaa  55980
```

```
tcgaaccaac cgagaagact cactggacca gctggaagag gctcgggaca tggccttact  56040
acactcggcg cggtatcagc agtccctgcg acgctaccac gcccaagggg ttcggtcccg  56100
agacctccag gtgggcgact tggtgcttcg gctacgtcaa gacgcccgag ggtgtcacaa  56160
gctcacgcct ccctaagaag cccggaacat acaagctggc caacagtcaa ggcgaggtct  56220
acatcaacgc ttggaacatc cgacagctac gtcgcttcta cccttaagat gttttcaagt  56280
cgttcataca cctcgtttac atacgccaac aaagtctaac catcaaggaa gggtcagcct  56340
tgcctcggca aagcccgacc ctccctcggg ggctagaagg ggggcacccc ctctacgtca  56400
aaatttcct cgaaaaaagt ctttctgcca gaacatcttt cgtgcttttc gactacttcg  56460
aaagtgggat cctgaaaacg acggagtaca cgtaagcagg caaggacgac cgagccgagg  56520
gactcctacg cctccgggat acggatacct cactcatcac cttctgcgat aagtaactca  56580
cgctcggata agcgatcccg ctggccgaac aagtcttaac gttcgaaagc ttttctgccg  56640
aaacgatttt ttgtgccttc tcgactatat cgataacaga atccaacgga cgagtaagag  56700
tacacgtaag cggcaaggcc gaccgagccg agggactcct acaccttcgg gatacggata  56760
cctcactcat caccttccgt gaaaagtaac tcttgctcgg ataagcaatt ctgttactga  56820
cgaacaagtc ccgatactcg aaacaagggg aaaagaaacg ccgctttaca acacgacgac  56880
ggtatgtttg ggcctcggcg gccgcaaaaa acatacgcac actacagata aattgttcct  56940
gcaggatcag acatcagtgg gggagcagca gcaccctcgg cgtcgactcc accttcggcg  57000
gagtccgacc cagcctcgga cggcgacacg gtcggaggat ctccatctcg aaggaacctg  57060
tcagcaccgc gcctgggcca tcgccgaggt gtcctccagg aacccggccc gagtagacga  57120
ctcgaccgac cgctctgtag cctcagccag ctgtccccg aggacatcag cccggctcat  57180
ggcctcggca acccgactcc ggcgtcggtc ccaccagtgg acggcccgac caggctccgg  57240
ccgatgaagc ttctttttga gccaactccg cctctgtcca cgctgacacc gctgacaccg  57300
ctgcctctag ctccggctca tcgcagagcg gccgagggtt tctttaacta agcaagagaa  57360
gcctcgggcg gcaaggccga ccgatccgag ggactcctac gcctccggga tacggatacc  57420
tcactcgtca ccttccgcac gaggcaactc acacttggtt aagcggttca gctagccgac  57480
aggcgagtcc tagtgctcga aatgaggaaa aaatacggct ttagccaaaa tacacatctt  57540
caggccccga cagccgcaat gaacagacac cggcactcaa ggtgccatta caaacagaac  57600
tctggttccg cccccacagg tacgaacgac cccccacatt ggagggcctg cggggcaact  57660
gaaagctctc ttgtgagttt tggtgtttgg atgacaactc aattaaagga ctaacaagtg  57720
tactaagtgt tgaacaggtg cttaaggtaa agcctacagg gttcaacaca agtgaacaaa  57780
tgtgatggtc caagaactgg attatggata cataatggac atcacaagta agatggacat  57840
tgcacaaagt gagactcggg tgcgtagctc ggagacaact gatcaagcca aggacggagg  57900
caagaaaagc ttcgaggtac caaatgcacg ggagaaggtc aaggaggctg aggaacccaa  57960
agccaagggt gaagaagaag gcttgcaaag tcaagggtga tcgagttgag aacagctacg  58020
gcacatcaag gatcactaca taaggacgtg acttacagcc aatgaggtaa cagctatagt  58080
tatgtggtgt aagtcataag gctcaagatc aagctctaag gaggagatca aggtcactag  58140
aaggagaaca agtgtcgaaa ccagaactgg aagcagccca aaagagctaa gttcactttg  58200
atctttagtt tgggttgttc ctatgtttgg agatgttcta tgtgaccttt acaggatgtt  58260
ggagccaagc gatgtcaatc tagatcaagt caagctgact tgataattta tgagtccaac  58320
atcaaagctc aagcatgtga aatgctatag atgtaatgat taatagaagg tatgtttcta  58380
```

```
gacttagtac attggttttg gggactaata tacttgtcta agtgttagaa acagaaagaa  58440
gaagaaaagg gaagaggtgc gaaaggcttg gctgtgtaca gccaagactt agttcagtct  58500
ggcacaccgg actgtccggt ggtgcaccgg acagtgtccg gtgcgccagg ctgaactctg  58560
gcgaactggc cgctctcggg aattcaccgg cgatgtatgg ctataattca ccggactgtc  58620
cggtgtgcac cggactgtcc ggtgagccaa cggtcggccg ggccaacggt tggccgcgcg  58680
atctgcgcgg gacacgtggc cgagccaacg gctagatgga ggcaccggat tgtccggtgt  58740
gcaccggaca tgtccggtgc gccaacggct ccaagactgc caacggtcgg cttcgacgta  58800
gaaggaaaga aatcgggcac cggacagtgt ccggtgtgca ccggacagtg tccggtgtgc  58860
accggactgt ccggtgcgcc acccgacaga aggcaagatt tgccttcctg gattgcttcc  58920
aacggcttct aggccccttg tgtctataaa agggacccct aggcgcctcc agcaaaatag  58980
aagtgcagcc aacaagtgta gactccactg gaatcaattc tcactctccc tcttgtgtgt  59040
aactctatag tttgtgtaga aggcacagct ataagcctta gagagaggag tagtgctgct  59100
aagagctaga gcaaggtctt gagcatatcg ttactctacc ggggtgctgc caagaagtct  59160
gtaagcagcc gcggttctgt tgtaacccca ctcaatagtg aaaggctcta tctgtcatac  59220
tgacagatct gagcaaacgg aggaaggagt tgaaatagac tccaagccca ggtgtggcta  59280
actccaacga ggactaggca agcatttcag gcttggccga acctcgggat aaatccttgc  59340
gtctgtgtgc tctgttctgt attgtatcct gactctcttt ctactcgcct ttatatctgc  59400
acttcaatac ttatctgtgg tataagcttt atttgaagtg caggacattt tgagacagga  59460
tcttctattc ggctgcaacc tacttgaaga gtcttctcac tccactgcat actaagtctt  59520
cgagtagagt aagaatttaa gttttaaagt gaaaagtttt attcgcctat tcaccccccc  59580
ccctctaggc gacatccaga tcctgttccc gggtcaaagg gaactttcaa ttggtatcag  59640
agctaggcct ctccagtgtg ggcttagccg tccggagatg acgatgtcgt cacaagaggt  59700
aactgtggaa cttcttttag acgatggctc taattacaag tcttggtctg tctctattta  59760
tagtgctttc atgagtgttg atcctgattt gagacaggtc tttagtagta gtatttttcc  59820
ctccaatatt agtaaaaacc catccaatga agaactaaga tgtctaactc taaatcacca  59880
tgcttgcaac atcttagttg attctctatc tagaggtgcc tattttgcca tcatgagtag  59940
tgatagtgat ctatttgttg atgctcatga tttatggaat aggattaaag aaaaatattt  60000
tgtggcaaac tgtgatgctc ctactcccta tattacttgt gatactaacc attcaaaggg  60060
agaagaacaa gaacgatggc atccaaacga tgaatccacc tcgtcgacag gtttgttctc  60120
cactagtgat aaatgtttta ttgctaacaa tgacggtgga gacgaaagcc atgataagga  60180
gaaatatgag gatgaatctt catcatcaca aggtacattt tcctatattg cttccactga  60240
cattaatgac agggaaaatg agaccgatga tgtggaggaa gaggagattc accgtttcta  60300
catccatctc aacaaagagg acaaggcact cttggttaag ctgttgagaa ggaacaagga  60360
acaaggcgag acgcttctca ggctagagga gtccctcatc aaaaccaaca acagcctgga  60420
gaagatgacc aaagaacatg agaagctaag gcgctctcat gatgatttgg tccaaaggta  60480
tgaatatgtt ttaattgagc aaagaaatag tcatgatgca ttatctaata ttgctcaact  60540
taaaacggaa aattctatgc ttaagagtca agtagaaaca atgaacttag aaaaacgtgc  60600
tctaggtaaa aagtatgata tgttgtcaaa ttctcataat aaattagttg atgaccatat  60660
catgcttaat gttgctcatg aggttataat tgcaaactta aattcatgtg aacctcattc  60720
```

tcgcacgtgt gcgcatttga agtgtatatc accatgtgct aacccctgtt gctcaaaaga 60780
aagccaatca ttgattgagc aacaagtttt agggtcacaa aagaaattct gtgggaacaa 60840
gaagcaaaga caactaagga gaagacacat tgctcaactc tctcaagata tccacgggcg 60900
cgtggtgaag aagcttgaga aaggaaaaac tgcagcaagt gttaagctca ataagaagaa 60960
tgttcccaaa gctataaatg aagaaatcaa catgaacaag gaaaaaggta aaaattcaat 61020
tagtcatgtt gtttgcactg atcatctctc catgtcattc aagcacaaaa agggaagagg 61080
aaaaaggagg tgcttcaaat gcaaggagac aggccacctc atcgcgtctt gtccgtacaa 61140
agacaaggat gaaagaacaa ggagttgttt tggatgcaac aataaggacc acatgatcac 61200
ttcatgtccg gtcatgaaga atcaaggata tgcatcctcc aaagtgaccc tcaccaagga 61260
aaatgacaca aaacaagcgt catgtcaagt tgagcgacgc ttctgctaca agtgtggtga 61320
gcaaggtcat ctatccaagg tatgttacaa aggtaagatt cctaaacaag tgaatttgtg 61380
tcaatcttat tcgcatagga gacccaaatc atacacttgt gctagatcta taacgagatc 61440
acctagaact agcacaaagg caatttgggt accaaaggca catttacatg atcattatgt 61500
acccatcccg agatggatac caaactgtgc caactagacc atgcaggtgc ctcgagatgg 61560
actggagacc atgggaaaga ttaagacggt tatctaaaac tctatgctta agctgttaat 61620
tgttttagtg tttattgacc caaggttgaa ttattgtgaa acactaatcc catgttcatc 61680
tcaagagaaa taaggtgtat aggtcctgaa tcattattgg tgaatcaagt aaaggatctt 61740
gatgagaatc tacaacctgc tctccaaagg acggtacccg tgtattttaa gtacataatt 61800
gcaatttagt attgctctta agttggcttg ttgtgctacc tgtccttaga gtagttatgc 61860
tttatgattg cctgtgttaa attgatcata atgatggttg cttaatcatg actggtgcta 61920
taaaggatat atcttttgaa tcattcatgg gtagctattt catttgttat atccacaacg 61980
ataactctct tgatgtatat ggataaacct gtaacttttg taagtcatgc tatgtgcaat 62040
tatgacattt tgtttagtcc atgttcacat gattacccta gtttggtact gtgtgaattt 62100
caaatccatg tcgtgccctt ttgagctatg aggtgcgtaa gcaaaaggag ccctaaattg 62160
gcgataacaa gggctctcat aaaggcaaag gtatggaaaa tggagctatg caatttcatt 62220
aaatattctt gaaattccat tcattgtgat catagctatg ttcttgcctt tcaattggta 62280
atatcttggc ttaggtaatt tatgccttta aaatgttgtt tcttttgtgc acctaagaaa 62340
ccttcttaat tataacatgc ttagatattt cgattgtgtt tatctttaat tggtatatac 62400
aatgatagtt aaatatgaag catgtacaag ttgcgtaaat gttagacttc ctgtgagtat 62460
tcaattggct taggtgccac tgaggcgtgc attgttgtat ttagtcaacc tttcatttag 62520
ccttcaattg gtgttatgtg gcgtttcatt tgatattcaa attggcatct ttgggtgatg 62580
aaagtggtag agtatgcctt gaccaaggta tgttgtgatc ccctctaatt ctaaggaagc 62640
tagaatgtgc aaagtgcaag tcattcaaat acttgatgca caacttgagg gggagcacac 62700
ataacttgtg tcttttgaga ctaactgttt cttgagcaat cttgtatagt ctctaggtgg 62760
aaaagagaag ataagcaaga aatggagcaa tcaggacttg ggtacctctg taagtcaaga 62820
aaattggtat ctcaagttgt gagtaagtgc atatttttag attgctcatg ctctataata 62880
tctggtgata atagatgctt attcttaaat atcatggagc catgataata aatgaacttt 62940
gcaattggta tctttcaatt ggtagccgta atagttcgct tcaattgaca tcttttgata 63000
atcatgagaa tagaagtttc ttcttgtgcc caatactata acttgttcta agtttggtgt 63060
cttagcaaca agaaaaagtt aggagagaga atcaggcaca agtgtggaga agctctcgag 63120

```
agattaacta ctttcaagat gggaagtaca ctacatcatg gtaaaggtac aaaaggaagt  63180
attaatcttt ttgcatatat gtatcttacc taaatgttga taggacatat gttcaataaa  63240
taagggggag ttttgatagt cgtttttccc cttaacaccc tgctgtccct tgacatcatc  63300
atatgttctt gcttgagtat ggtttttggt gtttgatgtc aaagggggag aagttgtgca  63360
ttaaagctta tctcaacctg agaggaaagc ttatcctaat gggtgatgtg ttagtttgag  63420
ctttgccaag tgtgatattc atatgtttct tgcagtatta tacgtgttga tcatatggac  63480
tagactagtg ttttatattc atatgtttct tgcagtatta tacgtgttga tcatatggac  63540
tagaccagtg tttccgctgc gatgaattat ttggcttcta tagtgaaata gatagtcatg  63600
tggttaatgg tgctttaaga ttgctttaaa ttgatatctt agtttaagtt ggtatcttaa  63660
tggtgaatag tggtaggttg atattcctgt gatatatcca ctaatttgaa tggtgtttaa  63720
ctctgattat gtgcatttgt gtgttatagc atcatggttt gattcttgac ataatgcatc  63780
ctaaaaagtg ctaaggtgta gaaatgtttc aattttccta agtatgtgca aattgacgtt  63840
tgtggtcaaa attaggtttt tgaagtaagc acttatttag ggggagcatt ctataatctt  63900
agaattcaaa tttgtgcttc aaatcttatt cttatgtaag ctttaattgt gttgccacca  63960
atcaccaaaa agggggagat tgaaagctct cttgtgagtt ttggtgtttg gatgacaact  64020
caattaaagg actaacaagt atactaagtg ttgaacatgt gcttaaggta aagcctacag  64080
ggttcaacac aagtgaacaa atgtgatggt ccaagaactg gattatggat acataatgga  64140
catcacaagt aagatggaca ttgcacaaag tgagactcgg gtgcgtagct cgaagacaac  64200
tgatcaagcc aaggacggag gcaagaaaag cttcgaggta ccaaatgcat gggagaaggt  64260
caaggaggct gaggaaccca aagccaaggg tgaagaagaa ggcttgcaaa gtcaagggtg  64320
atcgagttga gaacagctac ggcacatcaa ggatcactac ataaggacgt gacttacagc  64380
caatgaggta acagctatag ttatgtggtg taagtcataa ggctcaagat caagctctaa  64440
ggaggagatc aaggtcacta gaaggagaac aagtgtcgaa accagaactg gaagcagccc  64500
aaaagagcta agttcacttt gatctttagt ttgggttgtt cctatgtttg gagatgttct  64560
atgtgacctt tacaggatgt tggagccaag cgatgtcaat ctagatcaag tcaagctgac  64620
ttgataattt atgagtccaa catcaaagct caagcttgtg aaatgctata gatgtaatga  64680
ttaatagaag gtatgtttct agacttagta cattggtttt ggggactaat atacttgtct  64740
aagtgttaga aacagaaaga agaagaaaag ggaagaggtg tgaaaggctt ggctgtgtac  64800
agccaagact tagttcagtc tggcacacca gactgtccgg tggtgcaccg gacagtgtcc  64860
ggtgcgccag gctgaactct ggcgaactgg ccactctcgg gaattcaccg gcgacgtacg  64920
gctataattc accggactgt ccggtgtgca ccggactatc cggtgagcca acggtcggcc  64980
gggccaacgg ttggccgcgc gatctgcgcg ggacacgtgg ccgagccaac ggctagatgg  65040
aggcaccgga ctgtccggtg tgcaccggac atgtccggtg cgcgaacggc tccaagactg  65100
ccaacggtcg gcttcgacgt agaaggaaag aaatcgggca ccggacagtg tccggtgtgc  65160
accggactgt ccggtgcgcc acccgacaga aggcaagatt tgccttcctg gattgcttcc  65220
aacggctcct aggccccttg tgtctataaa agggacccct aggtgcctcc agcaaaatag  65280
aagtgcagcc aacaagtgta gactccactg gaatcaattc tcactctccc tcttgtgtgt  65340
aactctatag tttgtgtaga aggcacaact ataagcctta gagagaggag tagtgctgct  65400
aagagctaga gcaaggtctt gagcatatcg ttactctacc ggggtgctgc caagaagtct  65460
```

```
gtaagcagcc gcggttctgt tgtaacccca ctcaatagtg aaaggctcta tctgtcatac  65520
tgacagatct gagcaaacgg aggaaggagt tgaaatagac tccaagccca ggtgtggcta  65580
actccaacga ggactaggca agcatttcag gcttggccga acctcaggat aaatccttgc  65640
gtctgtgtgc tctgttctgt attgtatcct gactctcttt ctactcgcct ttatatctgc  65700
acttcaatac ttatctgtgg tataagcttt atttgaagtg caggacattt tgagacagga  65760
tcttctattc cgctgcaacc tacttgaaga gtcttctcac tccactgcat actaagtctt  65820
cgagtagagt aagaatttaa gttttaaagt gaaaagtttt attcgcctat tcaccccccc  65880
tctaggcgac atccagatcc tgttcccggg tcaaagggaa ctttcagcaa caaaacccta  65940
gacagctcgc cgaggcccgc tctggcagca gcgacaacga cctccgctcc ggacagccaa  66000
acagcagcag cgatgacctc agtgcagacg ctgctgcgac aaggccctcg cccacgtccc  66060
caccatcaaa ctggtggtca ccgtcttggg tgaccaccag cgaggggatg cagccgggcc  66120
gcctgatgaa aatccttgaa gccgagcgat ggctgaaagg taccaacttc cgcgaagttg  66180
cgttcctcca acgacgacaa gacgaaagca acgcgggcgc tccccatccg ggggctcgga  66240
agttggaagg gcgcgatgca tgaagggagt gtgaagacat ggttgccatc caagggggtc  66300
gccctccttt taaaggcgac tctccccact tgcgtcctca gccgtcgcgg actgagtctt  66360
caccaacacg ctccaaggtc ctccccctac gacatggggg ctgggtccca cgcgtcatgc  66420
aagctggccc agggcagaag aagccaaacc gtcgcgcgca gagtgcgtaa ctgcccagcg  66480
gttacaagca ctcctccact ttcgcccaga ccggcgggtg aaagggcgga ccgccatgca  66540
ggcggcatgc aaccgcacca agggggtgca ccctttcgac tccgacgcgt ccagcacggg  66600
ggcccaggcc cacacgtcat gtaaccggcg cgccggttac tacgcgcgag aaactgcacc  66660
gccacttgtg ctagtaccgc gccttctcga ctgcggaacc ggtgccgcga ctcgaggcaa  66720
ccctgcgcat ggcccaacag tgccaaccga gcacatcgat cacgggtcag tcagccgcgg  66780
gagaaggcgc gatggttgat atggccaaaa gtgggccggc agtaatggcg gcggcaggcg  66840
ggcggaagca gcggtcaagt cgtctgtagg ctcacgtccc ctcctgggac agcgagagag  66900
ccccctccca cggcgtgaag acgacacgcc cgtgttccgt tcctcgaacg gctagcgcac  66960
gcacaacggc tgccccgcga accactcatc ccgtcgcatt aactctgcgg caggacaggc  67020
ggcacctttg gcaggcgaag caggtgacgc ttcacctccg ccttaatgac cgcgtcaaaa  67080
aaggtgcgcc acgtcgtttg atttcgtatc cttttaccct tcctctttct ctctcttgct  67140
atagggaccg ggaaagagga tactccgaaa gggatccttc tccgcgaagg aagcgggccc  67200
cgagccctcc tactaatcag aggttcgaag gctggcccct cggaagggtt cgacagtcgc  67260
cttagagcac tcgggctccg cgccctccta ctgatcagag gttcgaaggc tggcccctcg  67320
gaagggttcg acagccgcct cagagcactc gggttccgtg cccactactg gtcagaggtt  67380
cgaaggctag cccctcggag gggttcgaca gccgcctcaa gccactcgag ctctgcgccc  67440
actactgatc aggggtttgt aggctggccc ccgaaggatt cgccagccgc ctcagagcac  67500
gcagagcgag ggatgactct gggtacgtcc gatacatggc cgaggctcgg gctacgctcc  67560
cgaggtaccc taggacattt ccgagaccaa caggagcgat tctgtaacgg aatcccatca  67620
gagggaggca tcgagccctc ggaccctatc aaacgggacc gggtccggca aatcacctgt  67680
aggtactttt ggagcgcgcc tctgggccac tagccgaccc ttatcgaacg gggcacgggc  67740
gtccactcgg atcaaccgtt agcaactcac tggagacacc atgttcgacg ccctctgagg  67800
gcaacatggc gctttccccc ccctcctcct tgcggaaagg cgacgcaggg gcgtatgaaa  67860
```

```
aaagccgagt cagtccttgg ccgtcctctc gctctgtgcg gaggctcggg ggctgctctc  67920
gcatgaggga acaaccaaac cagcccgaga acttggaacc tgactatgca cccgggctac  67980
ggccagttcg catgagggaa caaccagacc ggccgaagca tcacgaaacg tgctaagacc  68040
tcgaaggagt caaaccactc ctccgaggcc tcaggggcta cacccggcgg gtgcactcgc  68100
gcgcacccac cggaacgaaa cgcaaccgag aaaggccggt ccccttgcaa aaaagtgcga  68160
caaaagcctc caagtgagta ccaacactcc cttcgaggct cgggggctac tgtcggggac  68220
cataattagg ggtaccccca agactcctaa tctcagctgg taaccccat cagcacaaag  68280
ctgcaaaggc ctgatgggcg caattcaggt caaggctctg tccactcaag ggacacgatc  68340
ccgcctcgcc cgagcctagc ctcaggcaaa ggcagccgac ccaggaggat tcacgtcttg  68400
cccgagggtc ccctcaagca acggacgcac cttcggctcg cccgaggccc aagcttcgcg  68460
gagaaggaac cttggccaga tcgccacgcc aaccaaccgt atcgcaggag catttaatgc  68520
aaggatcgac tgacacctta tcctgacgcg tgctcctcag tcgacagggc cgaagtgact  68580
gcagtcacat cgccgctcca ctgaccgacc tgacgggaaa atagcatcgc ctgccctgct  68640
ccgactgcta tgccactcga cagagtgagg ctgacagcag ctaagtccag cctcgggcgc  68700
catgggaagc tccgcctcgc ccgaccccag agctcgggct caacctggac gtcggacgac  68760
ggactccgcc tcgcccgacc ccagggctcg gactcaacct cgacctcgaa agacggactc  68820
cggctcgccc gaccccaggg ctcggactca gcctcgacct cggacgatgg actccgcctc  68880
gcccgacccc agggcttgga cttagcctcg acctcggaag acggactctg cctcgcccga  68940
tcctagggct cgggctcaac ctcgacctcg gaggagcctc cgcctcgccc gacctcaggc  69000
tcggaccgac acgtcgcagg gggagccatc attaccctac ccctagctag ctcaggctat  69060
ggggaacaag accggcgtcc catctggctc gccccggtaa acaagtaatg atggcacccc  69120
gcgtgctccg tgacgacggc ggctctcagc cccttacgga agcaaggaga cgtcagcaag  69180
gatccgacag ccccgatagt tgtacttcca cagggctcaa acgctcctcc gacggccacg  69240
acatcacatg aacagggcgc caaaacctct ccgacagcca cgacggcatg tacttagggc  69300
tctgtctcct ctctgctaga catgttagca cattgctaca ccccccattg tacacctggg  69360
ccctctcctt acgtctataa aaggaaggtc cagggctctc gtacgagagg gttggccgcg  69420
cgggagaacg ggctgacgca caaggctctc tctctctccc acacgaacgc ttgtaacccc  69480
ctactgcaag cgcatccgcc ctgggcgcag gacaacacga aggccgcggg ttcccctttg  69540
ctgttttccc ccctttgtgt tctgtctcgc gtcgacccat ctgggctggg acacgcagcg  69600
acaatttact cgtcggtcca gggacccccc ggggtcgaaa cgccgacaaa acaatatttt  69660
ctagctttgg tacctacaat cttctgtact tccccatttg tctaatgctt caggttgttc  69720
tttttttct gtagatctat gtaccttatc cttgctatac tgtccatata tgttgtgtgc  69780
atgaaagtct tgcattgaaa atgtcatgtg ctacaatcgt taggactatt aatagatgtt  69840
gctctgtcta tctatccatt tacatcgctg gaaattccca tgccctttca tagtacgcct  69900
gtgaaattct cactgctttt ctattggttt gtgtgcagtt catgctctgc aaggtaaggt  69960
ctgttcagtt tggccagaaa ggcatcccct gcctaaacac ctacgacgac cgcaccatcc  70020
gctaccccga cccgctcatc aaggccaacg acaccatcaa gatcgacgaa atcttctaga  70080
attgnnnnnn nnnnnnnnnn nnnnnnnnnn nnnnnnnnnn nnnnnnnnnn nnnnnnnnnn  70140
nnnnnnnnnn nnnnnnnnnn nnnnnnnnnn nnnnnnnnnn nnnntcttat gtatcagctt  70200
```

```
gattcgttgc acattgttga gatgggcctc tctttactcg ctaatggaca ataccgctca  70260
agttttggga ccaagcgttc ctcacctcaa cacatcttat caatagaact cctactaagc  70320
ttcttgatta tgacacatcg ctccaccgtc tcttaggtgc taccccagat tactctaatc  70380
tacgcgtctt tggctatgca tgttagccaa atttgcggcc atacaacacc cataaactct  70440
agtttcggtc catttggtgt gcttttctag tctatagcaa ccttcacaag ggttacaagt  70500
gtcttgacat ctcaacgggc cgtgtttata tttcacatga tgttgttttt gatgagacgc  70560
ttttcccttt gctgctctcc atcccacagt cggtgctcga tatacctctg acgtgcttct  70620
tctacccgat cctaataatt ctcgggccaa ctcagatgat cttgtgacta attctcctgc  70680
tgaatccagc atgcttgctc cgattttgtg gcctaaccag cttttgcagc caccaatgat  70740
ccctgctgca aattctgtcc cggctggtgg cctcaatccc ggtgctgatc tgttgctagg  70800
ctccacgcca cacccctccg acgcggctac aggtgcgccc agcaacgcgg tgcttcccac  70860
caccacggcc gcatcaatag cagcagccac ttcgggattg cctcgtgccg actctggcgc  70920
ggctggtccc tctctcactg acagccatct gccctcgcca tcagcctcgt gtcctattcc  70980
gcttcctgct aggcgcactc ggctacagag tggtattgtg aagcccagaa agtttacaga  71040
tggcacgatc aggtatggaa atttggcaat ttgtgaagaa ccctccagct tgtctgttgc  71100
attgtttgac ccaaactgga aaagctgcca tggacctaga attttctgcc cttatgcgga  71160
ataaaacatg gcacttggtt cctcccgcac ctgacagaaa tttgattgat tgcaagtggg  71220
tttataaact caagagaaaa gctgatgagt ctattgacca tcataaagct cgattggtgg  71280
ctaaaggttt taaacagcgc tacgacattg actatgatga cacttttagc ctagtagtta  71340
aatttgctac tgtccgcctt attttgtctc ttgctgtctc tcagggttgg agcctctgcc  71400
aactggatgt gcagaacgcg tttcttcatg gtgttctaga ggaagatgtg tgtcggcacc  71460
ctaaaactag ggtacccctt actactgtat aaagacgcag tacccacacg actatcttta  71520
gtcgcgtggt aaataagctg tatgtgggac cagaccatga ctcgccctag cctcgggcga  71580
ctactctggg ccagcaacag cacctgaccc caccacatgg gcgggttcgg ggccgccatg  71640
tgtccagaga aagtgatgta ctccaaggca tcaacagtga gtccggaccc catgggagag  71700
tgccggacca gtgccagacc cctgtatata cggtccaggc ctccaagttt ggtccaggac  71760
ctccacgtgt acaaaccgga cccctaggat gggatccgaa ccccccgtat gggtctgggc  71820
cacccatagt ggggtcccag ggttctagga cagaacatac ccgggccttg attaggaccc  71880
aggtgggggt ccggagccga cacgtgtcta gacctggtct ggtgggatcc ggacctatcc  71940
gcatacactc cttctccctg ctcaggcgga gacccgatgc tgccacgtgg catactgcgc  72000
gcggcataaa ccaacgggtg gaacctggca tgatgcctct gggctacgcg tgccttcgca  72060
ttcattacgg agaagatgtg cgcctgtcca ttccactgac aggcggcatg ctcagtccac  72120
gatacgtggg ccatgcagtt actcacacgt taccatatcg agggcaatga ctcaccatta  72180
ctcgtatgtt tccaagaaaa gggttactgt ctatcaatgc tgcatggact gcagccatca  72240
tgactcccgc tgattactca tgtgttactc tgtcagcatt agttattcac ataatgtatt  72300
tcttccatta tgctcctggg cccacatgtc ggggctcagc atccttgtat gtgcctccct  72360
taaactataa aagggaaggc acacaacgtt acaagggaca cgctgtacac actcaataca  72420
acatacacac agtggaggta gtgtattacg ctccggcggc ctgaaccact ataatccctc  72480
gtgtcctctt gtgttcatcc cgaattcacc aaacaggcaa ccgcttaggc cccctcctca  72540
tcttaggatt agggcgggtg cattccgcca cccggccgga ggattttccc ttcgacattt  72600
```

ggtgctccag gtagggggct ttggctttag gtttttgcct gttttcttgc tcgacacgat 72660
ggttcagatc gtcgagcacc gtggcttgtc tcccgaggac ttcttgatgg aggaaggggc 72720
attatcttcc atgccacgag gctccaaccg cgctgtgcct ggtgctgctg ctatgcacgc 72780
tgcgcagcaa cacacgcccg cacagacctc taggactccg tcgagggcta cctatggtgg 72840
gccattgtct gcagccaggg agttgctgcg taacccacca agttccacgg cctccccggg 72900
ggccatgagg cagtggcgtg aagatgtcga ccgtctcctc ggcatggccc atcctagctc 72960
ggccaggtcc aggcctcgat cattccggca tcagcgcgag gcgtcaacgt ctgtgcattc 73020
accctcagtg agggggcaca gactaacgac ctgcgagcag aactcaacca caggcgtgca 73080
ggcgaggatg ctcgaatctc tctggagagg gcgcgtgagc gccggcaaaa cttcgagggt 73140
cgcaacctcg accaagactt cactgcaagg gacgcccgaa tccagatggg tgtcccattg 73200
gtcggcgtgg gctgcgccgc actagcagat catctccgcg cggcgacttg gccacccatg 73260
ttccggccac acctgccgga gaagtacgat gggacatcga acctgtcgaa attcctgtag 73320
gtctatgtca ccgccattac ggcagctggt gggaacactg ctgtaatggt aagctatttc 73380
catgtagcct tgaatgtgcc ggcacagacc tggctcatga acctcacccc ggggtcgatc 73440
tactcctggg aagagctctg tgcacggttc acaatgaact tcgccagtgc ttatcagtag 73500
catggcgtgg aggctcatct ccatgcagtg aggcaggaac ccgaggagac tctccgggct 73560
ttcatctccc gcttcaccaa ggtacagggg actatacctc gcatctccga tgcctccatt 73620
atcactgctt tccaacaggg gggtgcgtga taagaagatg ttggagaaat tggcgacgca 73680
tgacgtggaa accgtcacta cgctcttcac tctggccgac aaatgtgcca gagctactga 73740
gggccgtgca tggcactcga cgctgcaaac cagagtcacc caaatgggtg gctcaggtgc 73800
tgccacccag ggtggtggca agaaaaagaa gaagcaccgt gtcacgatag gccgtagtct 73860
ggtgctccag ttgctgtagc tacggctggg gaccgggacg agcgcggcaa gcatccacgg 73920
caacagggaa gtgacattgg gtcatgccct gtccacccca acagtcgcca cagtgcctca 73980
gaatgacgag agatcctgaa gctcgtgaag cgcatcagtg agcggcgcga gcatgcctcc 74040
agggatggct cgccgcctcg gcgccggcct ggcaaggaga aggtcgacga aggtgacctg 74100
gccacgggag aatgggacct cgagaattag gcccccgagc aagtcctcaa ggatatcctc 74160
actggagact ccgactccgg tgatgacaac gaccgccgca agaagctgta cgtaatgtat 74220
ggtggaagct gggagctcac ctcccgtagg aacgtgaagt ccctgcgccg cgaggtcctt 74280
ttggcgaccc caggggtccc gaaggcagcc ccacatcagc ggtggcggag caccactatc 74340
tccttcgggg cacccgactg ccccgaaaac atggcagggg ctggtatact accactcatc 74400
actgcccctg tcatcgccaa catgaagttg catcatgtgc tgattgatgg tggggttggg 74460
ctcaacgtca tcagccacgc tgcgttcaag cagctgcaga tcccaggatc ccgactagga 74520
ccctctcgca cgttctctgg agtgggccct aaaccggtgt atccccttgg gagcatcaca 74580
ctcctggtta cattcgggac tgaggataac ttccacacta agaatgtcta gttcgatgtt 74640
gcggaggtta acctcccttt caatgccatc attggcaggc cggccctgta ccggttcatg 74700
tccattgccc attacaggta cttggtcctc aagatgccat cccctgctgg ggtcctcacc 74760
atgcggggcg accgtcccgc tgcgcttgca gctatcgaga agttgcatgc cctagcggca 74820
gaagctgctc gcccggatga cgaggggagg gacccctcga cttcctgtac caagatgcct 74880
gctaaggtgc ctaaggtgca accatctggg gcagacggcg tccctgtcaa gaccatccgg 74940

```
ctcaacgggg attcctccca gaccactcgc atcacgggcg atctggagga gaaataggaa  75000
atcgcgctca tcgccttcct ccaggcaaat gccaatgtat tcgcatggga actatcgcag  75060
atgcctggga tccctaggga ggtgatcgag caacatctga agatccaccc tgacgccaaa  75120
ccggtgagtc agaagcctca aagacagtcc atcgagcggc aggatttcat ccgtaaggag  75180
gtccggaagc tgctggacgc tggtttcatc gaagaggtcc atcacccagt atggctggcc  75240
aatctagtca tcgtccccaa ggctaacggg aagctttgga tgtgcatcga ctacaccagc  75300
ctcaataagg cctgtcccaa ggacccatat ccacttccac gaatagatca aatcgtggat  75360
tctacctctg ggtgcaacct cctatccttc ctggatgctt actctagttt ccatcagatc  75420
gagatgtcta ggcaagatag gaagcatacc gcttttgtaa ctgtggatgg actttactgt  75480
tatgttgtaa tgccttacag tctgaaaaac gccttgccaa catttgtacg ggcgatgagt  75540
aatacttttg gtgacttgat tagggacagg gtagaggtat acgtcgatga catcgtagtc  75600
aagactaagg gagggtcgac cctagtggaa gacttaaccc tagtctttga caagctgcag  75660
gcaacacgca tgaagctgaa cccggacaag tgcgtctttg gtgtctctgc agggaagttg  75720
ctaggattcc tggtttcaca ccggggcatt gaagcaaacc cagagaagat caaagcaata  75780
gagacaatga ggcctccggc ctgaatcaaa gacgtccaga agcttacggg gtcactggcc  75840
gcccttagtc gcttcatctc aagactggtt gagagggcac taccctttctt caagctattg  75900
cggaagtccg acccattctc ttggaccaaa gagacagaac aagcctttca agagttgaag  75960
cagcaccatg tgtccctatc aatactggta gctccagagc caggagagcc attatactag  76020
tacattgcag cggctacaga ggcggtgagc atggtgctgg tcgtcgaaag tacgacacaa  76080
catccctagg ggagtcataa agttccccta ggagaaggtg gtggtctgac caccacgatg  76140
ttgacagaag gccaggagtt tgaggactcg ggactgaatg caggggtccg aaccatccag  76200
aagccggtct actacgtcag cgaggtcctc catgaggcaa aagccaggta ccttgagacg  76260
cacaagctta tctatgctat acttgttgtg tccaggaaat tgcgccacta tttttaggca  76320
cacagagttg tggtggtgac ctccttcccg ttaagggcca ttctccacaa ctcaaacgcc  76380
acaggcaaca tcgccaagtg ggccacggag cttgctgagt tccaactgga gttccagccc  76440
cgccacgctg tcaagagcca ggtcctggct gacttcatcg tggagtggac cccttccccg  76500
agcgctcctg gggtccaga tcccgattcg gacaccacac ctgcggagcc aagggcttcg  76560
gtcttcactg agccccactg gatgcttttc ttcgacggat ccgcctgcca gcagggtggc  76620
agtgctggag ttgtgacacc ccaggtgtca gtttcgtgtt acgtcgcgag atttatccta  76680
atctcggatg ctcagtaaaa atttctattt ctcgctcgcg tatgtccctg attatccaga  76740
ttattcattc atgtttcacc gaattcggag ttactcagtc tcatagaagg ccaattttgg  76800
agcctgttaa aacttttatc cttggcacaa atgcgaactc aaaaatcatt ctcgaattat  76860
aaacctcatc tgaagctcaa taaatcaaac tctcgacggc tgttatttga tctgtgtccg  76920
aatccaattt ctcgatgttc gatcgatgtc caactatttt aatccgagtc catactcaca  76980
aacgaaataa tcaatatgtc gtcctctgat caaatcttac tcgactcagc ttagcatctc  77040
tgtatccaat ccgatttcaa aatcaacatc ggcaacgatt tttatatatc acgattcgct  77100
ttctccgact aaaaatccaa aaccgatcaa atctcaggac ggtttatttt cgatttacgc  77160
gtagggaatt attttcaagc aaaatctaaa cagactctcg gctgagttaa tcgcgcaacc  77220
ttccgttcgt ccgaactctt ttcgctctgt ttctcagtag cgacgaattc cgcaggaaca  77280
tttttagtcc ggaaattatt tagcgcgacc caatttagtg ttttgggcca aatccagtcc  77340
```

```
agcccgtttg gcccataaga aaccctaccc taatttctcc tctataaata tgggcttccc  77400
taccttgcat tctgaaaatt ttccatttcc accccagccg ccaacaccct tctcttcctc  77460
ctctaccatt ttccagccat gggctccttc aagcacgtag agctggagct ccttccccag  77520
cgcgcagggg cttccatggc cgggcgttcc ttccctccag cgcgtcgaag ctcttctcgt  77580
agcgtcctct gcctttcttc ttccccgctt cacggcagca aggccaccag caggctccct  77640
gctccccgcg cccccagcca tggcatcctt cactccccta ctgtttttct cccagggcgc  77700
agcagcaaat ccatgcagcg gctccatggc cgagcaccct gcccggtgct ccagccggcc  77760
tcctctgccc ctgccatttt ccataggagt cgagctccta cctgcagcag gcgccccctg  77820
ctctttcctg tccgcgacca gggagcttca gctggcgtga aacttcactt gcgcacggcg  77880
gccagcaccc tctccttggg ctccaacagc ttggatgccg aacccctttc ttccttcccc  77940
tggccgagct cgagcttccc atggagccat tcctccctct ctctgttgta catagtgcca  78000
agcagcaact ccattttccc tggccgcgcc caaggtcggt gaccagcctc cccttccctg  78060
ttcttgccgt ggccgagcca ccacttcccc agccgtagcc ctctccccct ccattgtttc  78120
agcgcctgaa acaaacacct ggccgccatc cacacttgtg ctcgatgaaa tgtgcagcag  78180
ccccgacggc tccgcgtgct gccggcttgc tgttttgttg cgtagtgagc agcacgccgt  78240
gatgccgccg tgtgttcgct gtttttgcgc agccccaaac gtcgtcgtcg ttcaccccgg  78300
tgagaccgcg acgctccttg tttgattccg catcgatgtt attttcctat gattaattat  78360
gtatgtgtgt tgctttgttt tatttttgtg gaggagagaa ccccgtgttt tgcgaggaga  78420
aagcaagtcg cttaacgctc gttggatgtt tggagcgatg cacgaatcgg aatcaccgtc  78480
attcttgcaa acatcatttg ggtttgttta tggtgagccg atgcatgtcg ctctcgatcg  78540
actcgattaa tcattttgta tggatgtgtg taaaatgttc gattatgcgc attggtagga  78600
tcacgtttgc gattggagaa caagaggtta attgatgtgc acgatttgta gttgtctaat  78660
tatgttttgg tcgatgatgt gcatgtggtt atatgtgtgt aactgtataa ttttataaat  78720
ggacgcgtgt agggaagaaa ttgaaataga aaagaactcg agtattttta ttttgatagg  78780
aaaatatgcg atgcgttgtt tgatgcgaaa actaagttac aaaatgtgga ttttgttttg  78840
ggaaatgcat cgatgtgttt atgtgaaaag tgtatttgtt ttaagcaatg tgatgggatt  78900
cataatttta gaggggatat atttattgat gtgacgagta gtttagagaa tgctagtttg  78960
cgtagaggat gtatcgttaa gacatgagtg tcagagtcca tttatactag tggtcgcgcc  79020
acatggattg aagtgtctcg agtgcacgcc ataatatggt tgtatgcgag acagggttat  79080
gcgtacgatg agtttagtaa aaattccatc ggtgtcagtt gtgttaagtt gaagtttatt  79140
tgtgcgtata aagtagtaag gtatttaatg cttacgactc ttaatcgatg gtagaaattg  79200
tcttgactta aatagagagg tggtgacatg ccagagtagt catcgctttc tctatattta  79260
taggtcaagt catgacgatg cgtattatgc gttcgttaaa attatgtttc gtatatagtg  79320
tatgattgtg ctcacgattt cgagtagaca cttcaaataa gtcaagtagc tttgtaatgc  79380
aagatgtgtg atgaagttag tttgttttag gatatgtgtt gaaatgctcc attcctgtga  79440
tagacatgta gggttatttc aaaacgggtc gatgtgtgtg atgatgatat tcatgattta  79500
agtagatgtc ctgaaattat gtggcgaagc ttaggttaag ttgcaagcga tgtggaaatg  79560
ttttcgtaaa gatatatgtg gaatgtgaac gagtcattca atgtattcgg tatgtcatgt  79620
agtggtggta tgaaaaatgg gttaggaatc gatcggctaa atgccaagtt cggttagagt  79680
```

```
tattgtcggc gtttcgagac cggggggtcc ctcaggtcga cgagtgagtg ccgcgtgcgc  79740
cagcccagat gggtcgagcg cgtgggcgag cgcgaagggg ggaaaggagc gaggcggccg  79800
gagaccggcg tgagagaggt gggaatcccg cggccttcgt gttcgtcccg cgcccaggtc  79860
gggtgcgctt gcagtagggg gttacaagcg tccacacggg tgagggaagc gagcggcccc  79920
aagagagcgc ctgtcccgtc ctcgtcccgc gcggccaacc ctctctaaga ggaccctggt  79980
ccttcctttt atagacgcaa ggagaggatc caggtgtaca atgggggtgt agcagagtgc  80040
tacgtgtcta gcgagggaga gctagtgccc tgagtacatg ccaatgtggc agccgaagag  80100
atcttggaac ccagctagtg tgatgtcgtg gccgtcggag gagcggcgga gcctggcgga  80160
gggacagctg tcggagcggt tgtgtccttg ctgacgtcct cctgcttccg taagagagct  80220
gagagctgcc gtcgtcacag ggcatgcggg gcgccatcat tgcctatctg gtggagacag  80280
ccagatggga caccggtctt gttctctacg gcccgagtca gctcggggta gggtgatgat  80340
ggcgcttcct gttgacgtgg ctggcctgcg ccctaggttg ggcgacgtgg aggctcctcc  80400
gaagccgagg tcgagtctgt cttccatggc cgaggacgag tccgagcccc tgggtcgggc  80460
gaggcggagg tcgtcggcag aggccagggc ggtgtccgag ccctggggtc gggcgaagcg  80520
gagttcgtcg tcttctgggg ctgagcccga gcccgagccc tggggtcggg cgaagcggag  80580
ttcgtcgtct tccgggtctt agcccgagtc cgagccctgg gtcggttgga gcggagttcg  80640
ccgtcttccg ggtcttagcc cgagtccgag ccctgggtcg gacggagcgg agttcgccgt  80700
cttccgggtc ttagcccgag tccgagccct gggtcgggcg gagcggagtt cgccgtcttc  80760
cggggctgag cccgagtccg agccctgggt cgggcggagc ggagttcgcc gtcttccggg  80820
gctgagcccg agtccgagcc ctgggtcggg cggagcttcc tatggcgcct ttggcagggc  80880
ctggcttcct gtcagtatct ctctgtcaag tggcactgca gtcgaagtgg cgcaggcggc  80940
gctgtccttc tgtcagaccg gtcagtggag cggcgaagtg acggcggtca cttcggctct  81000
gccggagggc gcgcgtcagg ataaaggtgt caggtcacgt ttgcgttaaa tgctcctgcg  81060
acttggtcgg tcggtgcggc gatttagtca gggttgcttc ttagcgaagg cagggcctcg  81120
ggcgagccga agatgtgtcc gccgttagag gggggcctca ggcgagacgg aaatcctccg  81180
gggtcggctg cccttgtccg aggctaggct cgggcgaggc gtgatcgagt cgctcgaatg  81240
gactgatccc tgacttaatc gcacccatca ggcctttgca gctttatgct gatgggggtt  81300
accagctgag aattaggagt cttgagggta cccctaatta tggtccccga cagtagcccc  81360
cgagcctcga aaggagtgtt agcactcgct tggaggcttt cgtcgcactt ttttgcaagg  81420
gaccagcctt tctcggttgc attttgttcc ggtgggtgcg cgcgagcgca cccgccgggt  81480
gtagcccccg aggcctcgga ggagtggttt cactccttcg aggtcttaat gccttgcgta  81540
atgcttcggc tggtctggtt gttccctcat gcgagctggc cgtagcccgg gtgtacggtc  81600
ggggcccaag ttctcgggct ggtatgttga cgctgtcaac ggtttggccg gagccgggtt  81660
tgcgagagca gcccctgagc ctctgcacag ggcaagaggg cgatcaggga cagactcggc  81720
ttttttacat atgcccctgc gtcgcctttc cgcaaggagg actaggggga gggcgccatg  81780
ttaccctcga tgggcgccga acatggtgtc tccggtgagc tgcaagcagg taatccgagt  81840
ggacgtccgt gccccgttcg ttaggggtcg gctaggggcc cagaggcacg cccaaaagta  81900
cctgcgggtg atctgccgga cccggtcccc tggcgacggg gtccgagggc tcgatgcctc  81960
cctccgatgg gattccatta caagatcgct cccgctggtc tcggaaatgt cctagggtac  82020
ctcaggagcg cagcccgagc cttggttatg tatcgaacgt acccctggtc atccctcgct  82080
```

```
cggcgtctga ggcggctgtg aacccttcgg gggccagcct tcgaacccct gatcagtaat  82140
gggcacggag cccgagtagc ctgaggcgac cgtggaaccc ttcgggggc cggccttcga  82200
acctctgacc agtagtgggt gtagggccca cgcgatctga ggcggctgtt gaacccttcg  82260
gggggccagc cttcgaacct ctgatcagta aggaggctcg gagcctggtt ccttcacggg  82320
gaaggatccc tttcggggta tccccctttc ccggtccctg tcgcaagaga tagagaaaga  82380
ggaaaaaggg aaaaggatac gaaaccgaac gacgcggcgt accttttttg gcgcggttat  82440
ttcggcgaag gcgaagtgtc gcccgctgct cctgccagaa gcgccgcctg tccagccgcg  82500
gagttaatgc gacgaggcga gtagttggcg gggcagccgt tgcgcgtgcg cgagccgttc  82560
gaggaacgga tcacgggcgc gttgtcttca cgccgtgaga gggggttctc ttgctgcccc  82620
cggatgggac gtgagcttgg ctgacgacgt gaccgctgct cccacgcgcc tgccaccgtc  82680
attactgccg gcccactttt ggccgtgttg accgccgcgt caggctggcg ctgctgggtc  82740
gcacgctggg tcgcctcgag tcgcggtatt ggttccgcaa tcgaggaggc gcggtggtgg  82800
cgcaagtggc ggtgcagttg cttgcatgtc gtcgtagtca gagcgggcgg cggcgagccg  82860
ctcgtcagtc ttctgttgct ccgtaggccc accctatcg agtggggctg ttcgtacctg  82920
cggagggggg aaccggagtt ccgtttgtaa tggcacttcg aatgccggtg tttttgttca  82980
ttgcggcttt cggggcctga acatgtatgt aattccggca cggagccgtg tttttcctca  83040
tttttgagcg ctaagactcg tctgttgatt atctgaaccg cttcaccaag catgagtcgc  83100
cccgtgtcaa ggtgacgagt gaggtatccg tatcccggag gcgtaggagt ccctcggctc  83160
ggtcggcctt gctgtccgag gctcctctag cttagttaaa gggacccctc ggccgctctt  83220
cgacgagccg aggccagggg tagcgatatc agtgtgaaca gaggcggagt tggctcgaaa  83280
atgaaacctg gttggtcgga gcctagccgg gttgtccgtt ggcgggaccg acgtcggggc  83340
tgatcagccg aggcctcagg tcgggctggc gcccttggga gatggtcggc cgaggcccca  83400
ggggtaaccg gccgagccgc ctgctcgggc cggattcccg gagaagtccc tggcagcgat  83460
tgcccgggcg tggtgatgac atcgtccttc ggagcggaga tcctcggacc gcgtcgccgt  83520
ccgaggctag gtcgggcctc gctgaaggtg tcatcgatgc cgagggtgtt gctgcccccct  83580
tccagcgtca agacccgagc ctgtagggtc agattgtctt gtagcgtgtg ccttctgcag  83640
ccgccgaggc cagaatacac gccctcgctg tgttgtaaag ctgcgtctcc tttcctcttg  83700
tttcgagtat cttgactttt ttgtcggtaa cagggatgtt tgtgtgagtg ggagttgctt  83760
ctcgcggaag gtgatgagtg aggtatccgt atcccggagg cgtggaagtc cctcggctcg  83820
gtcggccttg ccgcttacac gtactttcac tcgtccatga ggccctgcca ccgactcagt  83880
cgagaaggct cgaaggattg cttcggcaga agaacttccg aacatgaaga cttgttcggt  83940
ccgcggaatc actttatccg aacgcgagtt acttatcgca gaaggtgatg agtgaggtat  84000
ccgtatcccg gaggcgtagg agtccctcgg ctcggtccgc cttgactgct tacgtgtact  84060
ccgtcgtttt caggatccac ttttcgaagt agtcaaaaag cacgaaagat attctggcag  84120
aagagacctt ttttcgagga aaatttcgac gcagaggggg ttccccccct tttagccccc  84180
gagggagggt cgggctttgc cgaggcgagg ccgacccttc cttgatgact aaactttgcg  84240
tgggtgcgag gtatatgaac gacctgaaaa catcttaagg gtagaagcga cgtagctgtt  84300
ggatgttcca agcgttgccg tagacctcgc cttgactgtt ggccagcttg tacgttccgg  84360
gcttcagaac tttggcgatg acgaatggcc cctcccaggg gggcgtgagc ttgtgcctcc  84420
```

```
ctcgggcgtc ttgccgcagc cgaagcacca ggtcgcccac ctggaggtct cggggtcgga  84480
cccctcgggc gtggtagcgc cgcagggact gctgataccg cgccgagtgt agtaaggcct  84540
tgtcccgagc ctcttccagc tggtccagcg agtcttctcg gctagcttgg ttgctttgat  84600
cgtcgtaggc cctcgtcctc ggggagccgt attctaggtc agtgggcaag acggcctcag  84660
ccccgtagac caggaagaac ggcgtgaaaa cccgtggccc ggctcggcgt cgtcctcagg  84720
ctccagacca ccgaggggag ttccttcatc catcgcttgc cgaacttgtt gaggtcgttg  84780
taaatccgag gcttgagccc ttgtagaatc atgccgctgg cacactctac ttgcccattc  84840
gacatgggat gagctacggc ggcccagtcc acccggatgt ggtgatcctc gcagaagtcc  84900
aagaattttc tgccggtgaa ctgggtgccg ttgtcggtga tgatggagtt caggaccccg  84960
aagcgatgga tgatgttggt gaagaacgtc accgcctgct cggacctgat gctgttcaga  85020
ggtcggacct cgacccactt ggagaatttg tcgatggcga ccagcaggtg cgtgtagccc  85080
ccgggcgcct tctgcaaagg gccgacgagg tccagacccc acacagcgaa gggccaggtg  85140
atgggtattg tctgcagagc ctgagcgggc aggtgggtct actttgcata gaattgacac  85200
ccttcgcagg tgcggacaat tctagtggcg tcagccaccg ccgttggcca gtagaagcct  85260
tgccggaaag cattcccaac gagggctcga ggcgctgcgt gatggccgca agccccccgag  85320
tgtatctctt gcaggagttc ctgaccttcg gcgatggaga tgcatcgctg gaggatgccc  85380
gagggattgc ggtggtagag ctcctgctca tcgcccagca agacgaacga cttggcgcgt  85440
cgcgctatcc gtcgagcctc ggctcggtcg aggggtagct ctccttggcg gagatattgc  85500
aggtacgggg tctgccaatt tcgatcaggc atggccccac ttcgctcctc ctcgatgcgc  85560
gatgcctcgc cctcggagac cgagggtacc tcgggttgag ctgagggtgc ctcgggccgt  85620
gccgagcgta cctcgggctg gtccgagggc gcctcgggct cgggagggtc atcgatcttg  85680
acggagggct aatgcagatc ccgggagaag acgtccgggg aaccgttgtt cgccccgagg  85740
ctatttttgc cagctcgtct gcagtctcgt tgtagcgccg agcgatgtga ttaagctcga  85800
gcccgtagaa cttgtcttcc aggcgccgaa cctcatcgca ataggcctcc atcttcgagt  85860
cgcgatagtg ggagttcttc atgacttggt cgatgacgag ctgcgagtcg ccgcgagcgt  85920
cgaggcgtcg gacccctagc tcgatggcga ttcgcaatcc gttggtcaga gcttcgtact  85980
cagccacatt gttcgacgcc gggaaatgga ggcgtagcac atagcgtagg tgtttcccga  86040
ggggtgagac gaagagtagg cccgcgccgg ctcctgtctt catcaatgac ccgtcgaaaa  86100
acatggtcca gagctccggt tggatcggag ccgtcggtag ctgggtgtcg acccattcgg  86160
ctacgaagtc cgccaagacc tgggacttga tggccttccg aggcgcgaac gagatggtct  86220
cgcccatgat ttccaccgcc cacttcgcaa tcctgcccga ggcctctcgg cactggatga  86280
tctcccccag ggggaaggat gacaccacag ttaccgggtg agactcaaag tagtgtcgca  86340
acttccgcct cgtcaggatc actgcataca gcagcttctg aacttgtggg tagcggatct  86400
tggtttcgga cagtacctca ctgacgaagt aaactagcct ctgaatgggc aatgcatgcc  86460
cctcttcttg cctctcgacc acaatcgcgg cgctaaccac ctgagtggtc gcggcgacgt  86520
agaccaagag ggctttttct ccatcagctg gggcaccaa gataggcacc ttggtgagga  86580
gcgccttcag gtctacgaga gcttcctcgg cctcaggggt ccaagtgaag cactcggcct  86640
tccttaagag gcggtacaga ggcaggcctc tttcgccgag gcgtgagatg aagcggctca  86700
gggccgcgag acatcccatg accctctgta cacctttttaa gtccttgatg ggccccatgc  86760
tggtgatggc tgcgatcttc tccaggttgg cttcgatgcc ccgctcggag acgatgaacc  86820
```

```
ccaagagcat gccccggggc accccgaaga cacacttctc gggattgagc ttgacgcctt  86880
ttgccttgag acaccggaat gtcacttcaa ggtcggagag gaggtcggaa gctttccttg  86940
tcttgactat gatgtcatcg acgtaggcct cgaccgtgcg accgatgtgt tcgccgaaca  87000
catggttcat gcaccgctgg tacgtcgcac ccgcattcct caaaccgaac ggcatggtga  87060
catagcagta catgccgaag ggcgtgatga aagaagtcgc gagctggtcg gactctttca  87120
tcctgatttg atgataccct gagtaggcat cgaggaaaga cagggtttcg cacccagcag  87180
tggaatccac gatttgatcg atgcgaggca gagggtaagg aaccttcgga catgctttgt  87240
tgagaccagt gtagtctaca cacatccgcc atttcccccc tttctttctc acaagcacag  87300
ggttggcgag ccattcggga tggaatacct ctttgatgaa cccggctgcc attagcttgt  87360
ggatctcctc gcctatcgct ctgcgcttct cctcgtcgaa tcggcgcaga ggctgcttga  87420
ccggtcgggc tccggcccga atatccagcg agtgctcggc gacatccctc ggtatgctag  87480
gcatgtctga gggactccac gcgaagacgt cggcgttcgc gcggagaaag tcgacgagca  87540
ctgcttccta tttgggctcg agcccggaac cgatccggat ctgcttggag gcgtcgccac  87600
tggggtcgag gggacggcc ttagccgtct ccactggctc gaagttgccg gcatgacgct  87660
tcacgtctgg cacctctttg gagaggctct ccaggtcggc gatgagggcc tcggactcgg  87720
cgagggcctc ggcgtactcc acgcactcca cgtcgcattc gaacgcgtgt ttgtacgtgg  87780
ggccgacggt gatgaccccg ttggggcccg gcatcttgag cttcaggtag gtgtagttgg  87840
ggacggccat gaacttcgcg tagcatggcc tccccagcac cgcgtggtag gttcctcgga  87900
acccgaccac ctcgaacgtc agagtctccc ttccgaagtt ggagggtgtt ccgaaacaga  87960
cagggaggtc gagtcgtccg aggggctgga cgcgcttccc gggaatgatc ccgtggaagg  88020
gcgcagcgcc tgctcggacg gaggacagat cgacgcgcag gagcccgagg gtctcggcgt  88080
tgatgatgtt gaggctgctg cccccgtcca taaggacctt ggtgagcctg acgtcaccga  88140
tgacagggtc gacgacgagt gggtatttcc ccgggctcgg cacgtggtcg gggtgatcag  88200
cttggtcgaa ggtgatgggc ttgtcggacc agtctaggta ggctggcgcc gccaccttca  88260
ccgagcagac ctcccggcgc tcttgcttgc gatgctgagc cgaggcattc gccacatgcc  88320
cgccgtagat catgaagcag tcgcggacct cgtggaactc tcctacttgg tgatcttcct  88380
tcttgtcgtc gtcgcgggcc ctgccaccct ccgcgggtgg cccggccctg tggaagtggc  88440
gccgaagcat gacgcactcc tcaagggtgt gcttgacggg cccctgatga taggggcacg  88500
gctccttgag catcttgtca aagaggttgg cacctccggg gggctttcga gggttcttgt  88560
actcggcggc ggcgacaagg tccgcgtcgg cggcgtcgcg tttcgcttac gacttcttct  88620
tgcctttctt cttggcgccg cacggagtag acgcctcggg agcatcttcc gacgggcggc  88680
cctggggctg cttgtccttt cggaagatag cctcgaccgc ctcctggcca gaggcgaact  88740
tggtggcgat gtccatcagc tcgctcgccc tggtgggggt cttgcgaccc aacttgctca  88800
ccaggtcgcg gcaggtggtg ccggcaagga acgcgccgat gacatctgag tcggtgatgt  88860
tgggcagctc ggtgcgctgc ttcgagaatc gccggatgta gtcccgaaga gactctcccg  88920
gctgctgtca gcagcttcgg aggtcccagg aattcccagg gcgcacatac gtgccctgga  88980
aatttccggc gaaggcttgg accaggtcat cccagttgga gatctgcccc ggaggcaggt  89040
gctccaacca ggcgcgagcg gtgtcggaga ggaacagggg gaggttgcgg atgatgaggt  89100
tgtcgtcgtc tgttccaccc agttggcagg ccaggcggta gtccgcgagc cacaaatccg  89160
```

```
gcctcgtttc ccccgagtac tttgtgatag tagtcggggg tcggaaccgg gtcgggaacg  89220
gtgcccgccg gatggcccgg ctgaaggcct gcggaccggg tggttcgggc gagggactcc  89280
gatcctcccc gctgtcgtag cgtcccccac gcctggggtg atagcctcag cgcaccctct  89340
cgtcgaggtg ggctcgacgg tcgcagtgat ggcgctcgtt gccgaggtgg cccggggccg  89400
caggcgcggt gttgcgcgtg cgcccggtgt agaccgaggc ttcccgcatg aatcgggaag  89460
tcgcggcatg aggttccgag gggtatcctt gccttcggga ggcagtgctc tcggcccgtc  89520
ggaccgtggc gccttccagg agatttttga gctctcccta gattcgccga ccctcggtgg  89580
tggatggctc cggcatcgcg cggaggagca tcgctgctgc gaccaggttc tgaccgaccc  89640
cactggatgc aggtggtggc ctgaccctga cgacatcggc gacgcggtgc tggagaccct  89700
ggggcaggtg acgtatttct ccggccgggg gttggcccgc ccatgcctgc ccgacgtccc  89760
ggcggatcgg ctcaagcgct cctgctccct cgtcgatcct ggcctgcgcc ccgcggactt  89820
gctcgagctg tgggtcgtaa ccccccgccg gaacagggac cacaactagc tcccgcggga  89880
tgtcagcgcg aggcaccggc ccagggggag caccgtcctc cggcatgccg agatgattgc  89940
cttcggaggg accccctaga tcgacgtgga aacattcgcg gcttgggccg cagtcctcgt  90000
cgtcgaggct gcggctaccg tcggaacagt cggagaggca gtagtcacat gcggtcatga  90060
agttccgctg gcactagggt tgccaaatcc agagaaatcc caacagatgt tggggtcgtc  90120
atcttcctcg gacccagagg gcccgtaggt cgagacgtcc gtcagccggt cccaaggcga  90180
ccgcaagcga aaccccagag ggtttgtact cgcctctaca agggcgcccg ccaaagcaag  90240
attgctagac gggttgaggc tgagtacaaa tgacgtagga tgggaatcgg ttggtacctt  90300
ttggtcgtcg agcggcgatg aagtcacgtc gaggactgac cgcatcgtcg cctcaggtac  90360
gagggcgatg tcctgcaagc ttttcgcaag cgcgctggcg tcgtccactt gctcgggatt  90420
ggcgtgtcgc ggggagacgg cgctcgcctt tgtctcaaac gcgaggtcga cgcccaacgc  90480
gccccccgtt ggggtgctag ggacgtcgac tcgctcgaca gccgacgagg cgcggcctcc  90540
tgcttggcct ttgttgcccc gcctcctcct ccgttggcgg gggagaggac ggggcgagct  90600
cgaatgttgt tcttccgcca cgcggggaag acgtcgtcga ttccgccgcc ggcgggcggg  90660
ctgtcggccg ccatcgtcgt tgtcgcgcgg cggtggaagg agtatcatgt cgtagctgcc  90720
gtcgagggac atgaactcaa gactcccgaa acggagcacc gtcccgggtt ggagaggttg  90780
ttggagactg cccatctgga gctcgacggg aagctgttcg tcaacacgca gcaggcccct  90840
acctggcgcg ccaactgtag gcgtttcgag accggggggt ccctcaggcc gacgagtgag  90900
tgccgcgtgc cccagcccag atgggtcgag cgcgtgggca agcgtgaagg ggggaaagga  90960
gcgaggcggc cggagaccgg cgtgagagag gtgggaatca cgcggccttc gtgttcgtcc  91020
cgcgcccagg tcgggtgcgc ttgcagtagg gggttacaag tgtccacgcg ggtgagggaa  91080
gcgagcggcc ccaagagagc gcctgtcccg tcctcgtccc gcgcggccaa ccctctctaa  91140
gagggccctg gtccttcctt ttatagacgc aaggagagga tccatgtgta caatgggggt  91200
gtagcagagt gctacgtgtc tagcgaggga gagctagtgc cctgagtaca tgccaatgtg  91260
gcagccggag agatcttgga acccagctag tgtgatgtcg tggccgtcgg aggagcggcg  91320
gagcctggcg gagggacagc tgtcggagcg gttgtgtcct tgccgacgtc ctcctgcttc  91380
cgtaagagag ctgagagctg ccgtcgtcac agggcatgcg gggcgccatc attgcctatc  91440
tggtggagac agccagatgg gacaccggtc ttgttctcta cggtccgagt cagctcgggg  91500
tagggtaatg atggcgcttc ctgttgacgt ggctggcctg cgccctagtc tgggggtacg  91560
```

```
tggaggctcc tccgaagccg aggtggagtg gatcttccat ggccgagggt cgagtccgaa  91620
gcccactggg tcgggccaag gcggaaggtc gtcggcaaaa gtccagggcg gtgtccgagc  91680
cctgggctcg ggtgaagcgg aattcgtcgt cttctggggc tgagctcgag cccgagccct  91740
ggggtcgggc gaagcggagt tcgtcgtctt ccgggtctta gcccgagtcc gagccctggg  91800
tcgggcggag cggagttcgc cgtcttccgg gtcttagccc gagtccgagc cctgggtcgg  91860
gcagagcgga gttcgccgtc ttccgggtct tagcccgagt ccgagccctg ggtcgggcgg  91920
agcggagttc gccgtcttcc ggggctgagc ccgagtccga gccctgggtc gggcggagcg  91980
gagttcgccg tcttccgggg ctgagcccga gtccgagccc tgggtcgggc ggagcttcct  92040
atggcgcctt tggcagggcc tggcttcctg tcaatatcac tctgtcaagt ggcactgcag  92100
tcgaagtggc gcaggcggcg ctgtccttct gtcagaccgg tcagtggagc ggcgaagtga  92160
cggcggtcac ttcggctctg ccggagggcg cgcgtcagga taaaggtgtc aggccacctt  92220
tgcgttaaat gctcctgcga cttggtcggt cggtgcggcg atttagtcag ggttgcttct  92280
tagcgaaggc agggcctcgg gcgagccgaa gatgtgtccg ccgttagagg ggggcctcgg  92340
gcgagacgga aatcctctgg ggtcggctgc ccttgtccga ggctaggctc gggcgaggcg  92400
tgatcgagtc gctcgaatgg actgatccct gacttaatcg cacctatcag gcctttgcag  92460
ctttatgctg gtgggggtta ccagctgaga attaggagtc ttgagggtac ccctaattat  92520
ggtctccgac agttattttg atagttggga ttgtggggtg aagtgatggc atgactacgt  92580
agccgtcacg tcatctattg cgtggctatg cttaagcgtg ccttgatata atttagaata  92640
agtcgagtct ctagaacgcg gcaattttta aaagtaaata gaagctgaat ttattgattg  92700
ctgttttggg ctgcacgcac tgttttagtt gtgctgtttg tttgataaac caaatcatgt  92760
tttctataga aaagtcatat agaagagttg tagatgacat gattatcttg cttgtactaa  92820
aatttgacag ccataaacct gattgtttag gagttgtgct tttcacaagc ccagcacctg  92880
aatctgtcaa atttctgaac atatttcaga aattgcaatg attgcttaag ttaatgttga  92940
aattagttat tggtggtcac aaaaaagttg tagataactt tattatcgta cttgtgttaa  93000
aatttgacag gcataagtct gattgtttag gagttatgtt ttttacaaat tcagtaactg  93060
aatctgtcca ctttctgtac agatttcaaa agctgcattg tttgcttaag ttaatgttag  93120
aatcagccct tgtcaattat aagaaagttg tagaggcttt tcttgtcttg cttgtgttaa  93180
aatttcataa ctataggcct gacggtttaa gagttatgaa ttttacaaac tggttgctgt  93240
gttctgtcca ccgtcagaac agatttcgaa aactgtaata tttgatttag ttaaacctgg  93300
aatcacttct tggtgattat aaaagttgtg tagtactttt gctaagcttt tcaaaaagtc  93360
ttagatcact ctttttggtg gtctgaagat taagttacat gtgtttgaag tgtgaagact  93420
gaatctgtcc agttttggac agcacagcct tcatagtata ttttaacctt gatacatgct  93480
aaaccagcct gggatgttta taaataattt gtagaacatt taattagctt tccagaaagt  93540
ctaggatcaa tttgtttgga tgtctgaatc ttcagttatg aatttttaaa atcacaagtc  93600
tgaatctgtc caaatctgga cagagctgct gtgattgcac tttttgacct tgctaagtgt  93660
ttaatcatgc tgtgatgaaa ataccaaaat tgtagagcac tttctaaact ttccagaaag  93720
ttttagtttg ctatttttgg attaatattt taaaagttat gattaaaaca agtagctgct  93780
gtgctgctgt cctaaaaatc tgcacgtgct caaatgaata tttagttcac cattttggct  93840
aaaaacgctt tagtaagcac ttaacggaca tagacttgtg atggctaaac ttaggttaac  93900
```

```
atgtgttcca taattaatgt gtttgcttgc tgtagttgat tgtgatagag gagtccatcg  93960
acattgatgc atcggtcctt ttattaaact tgtgtttgtg atgtttttgt gtgatcaata  94020
taagaattaa tgaaaagccg tagcaactaa ataaatgctt gtacatatga tatcgtgttg  94080
cgttggttaa ttgtaggtag tgatcattgt ctttccagtg gtagtgttta cgtgtgccca  94140
atgacacata aataactagt gtttgcgtat agttgttgca gtgtcttact aattaatgtt  94200
tagttcgcca ctgtgtcttg gtatatctta tgttactttt attatattca tacatatgca  94260
tcttgcacct catataggac cgagagatga tgatcgagcc agtgatgtgg tgccaaccac  94320
aagatgccgt tgatggacga cctgaagaat ggacttaacc agtggatgct caccaagcga  94380
gtacctcccc cagcaaacac tacctaagtg ttaaattaaa ggcaagcccc ggttttatgc  94440
ataaccatta tatatatgct attttactgc acttaatgtt tgtaggcttg taccgtgcac  94500
ttaagtgtag gagttgaatg aaaccctagt tgcatgaact caggattccc tttgagatgg  94560
atactagtat gctaggtcga gtagctnnnn nnnnnnnnnn nnnnnnnnnn nnnnnnnnnn  94620
nnnnnnnnnn nnnnnnnnnn nnnnnnnnnn nnnnnnnnnn nnnnnnnnnn nnnnnnnnnn  94680
nnnnnnacag tgcacagtgc accggacttt ccggtgagcc taggcagagg tgattttgaa  94740
aattttcaaa tttttcgatc taaattttaa ccaaaccaaa tcccaactta taatcataca  94800
aaagaacacc tattgggata ggtattggcc ccctcatata ttttcccata attttcaaaa  94860
atattttgcc ataggctagt caatttttag agaaaatagt caaatggtga gatttgcatt  94920
ttagctttga actaggggtt ttcatgaata atttgagttt tgaatactcc ccccctaagt  94980
gtagtactac atgcatatct caagaaccaa caatggcata gtaaataaga atttaagtac  95040
taaaagctta aagctaagac ttgtcaagtt tgagcccgag ttaagctttt ttcactcgct  95100
ttgttggcgg ttatcttaac taggttagac aagccctaga tgcaatacaa gaaatttaaa  95160
tatgcaatgc aggcttgaca acactatttt gagatcttta aataaaattt ctgagatcaa  95220
gtatgtttaa ttcatttctc aacatgcaaa agcgggtttt atcaagaggc ttagtgaaaa  95280
tatcctctaa ttgatcttcc gacctcactt cttctaaaat aatgtctcct ttagcaatat  95340
gatctctaag gaagtgatga cgaatatcaa tgtgcttggt gcgagagtgt tgtacaagat  95400
tattagcaat tttaacagca ctctcattgt cacacaacaa aggtaccttt tctagaacta  95460
caccatagtc tagaagagtt tgtttcatat ataaaatctg tgtgcaacaa gcaccagcgg  95520
caatgtattc cgcttcggcg gttgacaagg caacactatt tttctttttg gatgtccata  95580
atagtagtga tctcccaagc aaattacacc cctagaagta ctttttctat caattttgca  95640
accggcataa tccgaatcgg aatagccaat taaatcaaaa gtagctcctt tgggatacca  95700
aaggccaaca cttggggtgt gcttgagata cctaagaatt cttttaagag cgcaaatatg  95760
agctttctta ggatttgatt gaaatctagc acacatgcat acactaaaca tgatatcggg  95820
cctagatgca ataagataca ataaactacc aatcatagaa cggtagagag ttaccatctt  95880
ttcaacaagt gatctccatg ttgaaccttt tcaacaagtc tttggtatac ttctcttgtg  95940
agaggaagtt accatctttc atttgcttca cttgaaagcc gaggaaatac atcagctcac  96000
caatcattga catctcgaac tccttcgaca tcaactcacc aaattccttg caatgatagc  96060
gatttatcga gccaaagatt atgtcatcaa catatacttg acaaatgaaa atatcaccgt  96120
tatgtttctt tgtgaataga gttgtgtcga cggtcttgat cttgaagccc tttttgatga  96180
ggaagtcgcg aagacgctca taccaagccc ttggagcttg ctttaaccca tatagcgcct  96240
tggacaacct ataagcatgg ttaggatatc tagggtcttc aaacccgggt ggttgctcaa  96300
```

```
catatacaag ttcatttatg aagccattta aaaatgcact ttttacatcc atttgataaa  96360
gctttttatc atagcatgat gcatatgcga gtaggataca gatggcttca agtcgagcaa  96420
ccggtgcaaa ggtctctcca aaatctaaac cttcaacttg agagaagccc tttgcaacaa  96480
gtcttgcctt gttcctcaca atcacgcctt gatcatcttg tttgtttctg aataaccact  96540
ttgttccaat gatccttgca tcttgtggag gcttctccag ggtccaaact tggttacggg  96600
tgaagttgtt tagttgttca tgcatggcat tcacccagtc cggatcctgt agcgcctcat  96660
ctatacagta ggctcaacac aagaaacaaa ggagtgatgt tcaataaaag aagcatgttt  96720
atgtgatcga gtaataaccc cttgtgaagg acttccaatg atttgatctt gtgggtgtgc  96780
ttgaagcagt gatgagtttc tcctatcaac cacttaggaa gaagatcctg gagcatcaac  96840
atcttcggct tgtatccttg cttgttcatg agagacaaat gtatcttcat ttgcatgcct  96900
ctcatctttt tcatcatctt gtggtacact tgatgaagaa ggcctattaa tgttttgcac  96960
ctcttcttca tcttcttttg gtttgatagc tccaattggc atgttcttca tggcttcctt  97020
aagtggctca tcacctacat catcaagatt ttcaagtgct ccttgggagc cattagtctc  97080
atcaaactcc acatcatatg tttattctac cacgccagtg gcatgattga atactcgata  97140
tgctttggac tttaatgaat aacccagaag aaaaccaata tcacaacgtc tttgaaactt  97200
ccctaggtga tggcgtttct tgtaaatgta gcatttgcat ccaaacaccc aaaagaatga  97260
gacgtctggc tttttcccat ttagcagttc atagagagtc ttcgcaagta gccagtgagg  97320
aaatagcctg tttgatgcat aacatgcagt gttgatagct tcggcccaaa acctctccgg  97380
tgtgttatac tcatcaatca ttgtccttgc aagtgtgatc aaggtcctat ttttcctttc  97440
aacaactcca ttttgttgag gtgtatatgt tgctgatact tcatgcttga tcccaatctc  97500
atcacagtat tcatgaatgt tggtgttgtc aaattctttt ccattatcac ttctaatctt  97560
cttgatcttg taatcaaatt cattttgagc tttcttggca aacttcttga atatagatgc  97620
aacttcagat ttatcatgga gaaaaacacc caagtgtatc ttgagaaatc atcaactatc  97680
accagacagt agaggttgcc accagcactt gcataagttg ttggtccaaa tagatccatg  97740
tgaagtagtt ccagtggcct tgatgttgac atgaaagctt ttgtaggatg tgtgttagca  97800
acttgctttc cagcttgata agcactacaa ggcttgtcct tttcaaatat aacatccttt  97860
agtcctctaa ccatgtcctt ctttaatact ttcttcagtg tgctcattcc aacatgtgca  97920
agccttctat gccatagtca tccaagagat gctttggtaa agaggcaagt tcttaagtct  97980
gcatcttcag aggtgaaatc cactaagtag agattgttgt atctaaatcc tttgagcacc  98040
atttattcat catccatttt tgatacaata acctctgttg gagtgaataa gcattgaagt  98100
ccaagaacac agagttgacc cactgataat aagttgaatc ttaaaggtgc aaccaagaga  98160
acatttgaaa ttgatagatc atttgaaatt gccaccttgc caagtccttg aacttttccc  98220
tttgaattgt ccccaaatgt gattttgtct tgtccatcaa cattatcatc aagtgaggtg  98280
aacatccgtg ggttgcctat catatgttat gtgcatccac tatcaataac ccaatggctc  98340
ccaccggtct tgtagttcac ctacatccac agacaaatca agcctaagtt ttgagggccc  98400
tatattgcat aggaccagtg actttctcaa tcaaggactt tgcaacccaa atttgtctag  98460
gtctactctt gcttggtgga cctaggaatg taacttcgac ttttccattt gctacttctt  98520
aaaacataat gagcattgaa ggcaaatggt cttgagtgct ttggcagggg agttggtggt  98580
ttggctttgc agttgtggga aaaatgacct tcttttccac actcaaagca tttgatatgc  98640
```

-continued

```
ttatgagtct gatttggctt gtattgagtt gtagctttct tttgcacaaa ggagttatat  98700
ccaataccac tcttgttgtt tttcatgaca gtgttcatga gcaattcatt ttagaggtat  98760
tggcccttgt tgaacttttg cacacttgtt gcaagatgtt cattttcacg cttaagtttc  98820
ttgacctcat tttaagcctt tctttatcca ctgccaactc attgttgaag tcattgttct  98880
caatggcaac ctttcctcta gtagttgcat cagtcaagta tctcttcaat ttttggttgt  98940
ctaatgtcaa gacttcaact ttttcagtca attcatcatg tagactagtt tgatcacctt  99000
gactcaaatc atcacatgag gttgctacat caatattaac aacagggtta atagcctcat  99060
gtgtattgca agataaaagt tcattttcaa caagaagatt atcatgatca aatttaatct  99120
tagtatagtc ttccttattt tttactagtc tatctttcaa ctccctatta gcttcattta  99180
acttgtcaca tttatcctta gcatctttta gggaggatgt aagctcattt acagtggatg  99240
acatagtttt gttttcttct ttcatttcat tactagcttt cataactatg tcatatttag  99300
catttaaaaa ttcattttca tctttcaact tatcacattt agcttttgac ttcctaatga  99360
gttgagtgta ttcattaagc aagtcaacta gttcatcata ggaaggtgaa gcaaattctt  99420
catcactatc actatcacta tcatcaataa tatcattatc attttgtact tttcgttcac  99480
ctctagccat gaggcatagg tgagaagtcg atgatggaga tggtggtggt gaagagaagt  99540
ccccagcgat ggcggtaact ttttcatcat tttcttcttc acttgaagaa gatccacttg  99600
acgactcaat gtcagtgagc caatcaccaa caatgtatgc ctttacattt ttctttttgt  99660
ggaacctctt atgctttcca tccttcctct tgaagaatct cttttcattt ttctcatcat  99720
cactgtcatc ttctttcttg cccttgaact tgttcttctt ggacttgtta cattgatgag  99780
caagatgacc aagctctcca cagttgtagc aatccattta agaaatgggc tttcttttgc  99840
tggaaaagaa tttcttcttt cttgagtcaa atttgatgcc ttctctgttg agcttcttta  99900
atatcttggt ggtcttcctc accatcaagg caatgttagc attaagatca tcgtcacttg  99960
aggattcctc ctcaacttgt actttagctt ttccttctct ttcttgattt tctttgagag 100020
ccaaatcctt tctcttgtaa gatgactcat ccttgtcatt gatgtgcatg tacatctcat 100080
gtgcattgat ctttcccaaa atttgtgtag gagtgacaac tgaaagatcc atctgatgca 100140
gcacagtgac aatgtgtcca tatttatcaa ttgggaggac actgagaatc ttcctcacaa 100200
catccggttg tgaaatttgt gtaagcccca agccatttac ttcctctaca agaatattga 100260
gacgtgagta catagcattg gcattttcat tagcaagcat ttcaaaagaa tttaattttc 100320
tcatagcaat gtgatatctc tcctcacgct caattctagt tccttcatgt agagcacata 100380
tgtccatcca caaatcatga caatttttat ggtttctaac tctattaaac acatctttgc 100440
aaaggcctct aaaaagggtg tttttggcct tagcattcca tttctcatag ttcaactctt 100500
cacctacaag atttgtggga tctctaggtt cggggaatct ttgtgtggcg gctttgtaga 100560
caccaatgtc tatagcctct aaatatgctt ccatacgaat tttccaatat ggaaaatcgt 100620
caccataaaa aacgggagaa ggtccatccc caccggacat cgttactcta gcggttaagc 100680
taatctaaga gcaacaaggc tcttatacca attgaaagga tcacgatgcc caagaggggg 100740
ggttgaattg ggcttttcta aaaatcaaca ctaactaaaa tctaagcaag agcccaactt 100800
caccccgaca actagcacta agagaataat actagaaata caacaatgct aagataatac 100860
ttcaaatact tgctaaacaa atacacaatg taaaatactt gaattaagtg cggaatgtaa 100920
agcaaggttt agaagactcc tccaattttt ctagaggtat caaagagtcg gcactctccc 100980
ctagtcctcg ttggagcacc tgcgtaaggg tatcgctctc ccttggtcat cgcaagaacc 101040
```

aagtgctcac aacgagatga tcctttgcca ctccggcgcg gtggatccct cacgaccgct 101100
tacaaacttg agtcgggtca ccaacaagat ctccacggtg atcaccgagc tcccaacgcc 101160
accaagccgt ctaggtgatg ccgatcacca agagtaataa gccatagact ttcacttgac 101220
caagagaagc ctaatgcatg cggtgtgtgc tctaggtggc tctcgctagc gttaatgagg 101280
tccaaatgcg ggattaagat tctcaagtca cctcactagg ctttgtggtg cttgcaatgc 101340
tctaccaatg tgtaggagta aatgtgggca gcaagaccat caatatggta ggtggatggg 101400
gtataaatag ccctcaccca ccaactagcc attaccagga atctgctgcg catgggcgca 101460
ccggacagtc cggtgtgcca ccggtgcgcc aacggtcgac tcaaacggct agttctgaca 101520
gctagccgtt ggacagatgg cataccggac agtccgatac gctgtccggt gtgcctctaa 101580
aattcaactc acgaacagcg cgctctcggg tttctgcgcg cagggaaccc tcttccctgg 101640
gccaggctgg gcccactggc aaagggtgca ccggacagtc cggtgcccca aagccagaaa 101700
ccctagcttc tgttttgtgc tgtttttca atttggtttt tgttctaact tgtgagtatg 101760
ttctagagtt acacctagca ctatatgtga gtgtgaatat gcaccaacac tacactagaa 101820
ctcttttggt caaactactt atcgacaacc cctctttata gtacggctaa aacaaaataa 101880
aagacctaac tatatcacga gtgtccgcaa ctccttgaca ctcggaatac gaagaccttc 101940
actttttgtt tcgtcgcttt agccgttgct tcaagttttt atctccggga ttgttttcac 102000
cattgtagta catctacctg taatgcgacc taacttacca tttgcctctg caaaacacat 102060
gttagtcaca tataaaatta cgttgtcatt aatcactaaa accaaccagg ggcctagatg 102120
ctttctagtt taaatcccca acaagtcaaa attctttcta ttttttttg caagttccaa 102180 ttgacatctg aaaggttgta aggtacacgt ttggctctca ttgataacgg gggaaagata 102240
cagtgcaaac caccatataa tgacccactt ctaatcgaat ggacctgtaa cgacgaaata 102300
ccctgtgaga actatggttc actcatgtta attcattgaa attgttgtag tgaattgaca 102360
tggttgggag cctgcttaga gagtatagat tgtcactttt ttttggaccg caacttattt 102420
ttaaaagata ttgcgatcgc ttgtttagta gctgtttcag gccccaatgc agtttctatc 102480
gtgatccatt taagtcactc aacattctca tacttctcat tttgcattaa ttcattccaa 102540
tctccactac tataaaatac tagcttcgat ggtcgtcata cgccatgcac gaagcatgta 102600
gatcaatccg cataccagtg ggcatctata gataggctgt gaaaaccacc caaatcccta 102660
ctagtggaca ttttatctat agatggaccg tgagaaacca cacaagtcta acacgacagg 102720
gaagccaaac gcagcgcagc gctcccacat agaaccacct cactacctaa aggaggacaa 102780
gccatcgagc aagctttaaa aaagtagtca ggcttctttc aactcatacc tttcctgata 102840
ttttagctaa gataaaagcg taatatttgt ttttatcagt ttagtatctg atatatggac 102900
catatgttca ctttgatatt tgatattatt tttttattgg tatcaaatat gattgtatgt 102960
cgtcgcagcg cacatgtgtt gtactagtta ttttataaga taatcaagta tttcttaatc 103020
atttaagaca ttttgatgat tatttaaaac attctatttt tttctcagtc attcactcgt 103080
taggtcattc agtacatatt atgttaaatt aagtcattct gttacaattc tagtcatcac 103140
atgtcattta gtcattttat gacttattta aaatatttca tattgtcaac agttgttaca 103200
agactttctt acaaatattt taagtcatcc aatagtttat tcatccagag actcataata 103260
tgtttttaag tcattccttt ctattaaatt gatgtaatta tttttatcac gattggactt 103320
ctttctttta tcacttagaa gccgtgcgag atgaaagtct catgcacggt tttgcatgag 103380
agaaagaagc gaggaattct ctttttgact ctgactcccc cactccaatc gttgcttttc 103440
tttctgttac ttcgaaagta gttgcttcag ctttagccac gcgaattctc gatattcctt 103500
tttatttctc atcaaacgaa tgacatcttc ttctggaaat cctagctatt cttagcatga 103560
tattggagaa tctccttgct attagtcaaa caagcatctg attggagcac aggcgtgtgg 103620
ggggagggat gctcaatggg ttattgaggt gtgatggata gagcatccgg ttagagcgca 103680
gggcacgcag tggatactat ttggcaccac gctcagcgag tatgcgtgta tgcagtcatg 103740
caacccgcat atataggcat aaaaaaccaa aatccctttt tttgttatat tcgtgtttat 103800
gagattttcg aacaaaacta gacactcatg ctatatcttt ttcaattttt tatttaatcg 103860
caatgtccga ccctaataaa tacaatgatt ggtcctaata aatacgatga ctggctctaa 103920
taaaaaatac aatgacttat cttgatagct ataatgagtg accctgataa aatacaatga 103980
ttgaacctaa taatacaata actaaccctg ataaaaatat cctgctaaat acaatgactg 104040
accctaataa aaaaatacaa tgaccgacct tgataactat aatgagtgac tctgatataa 104100
atacaatgac tgatcctaat aatacaatga ttgaccttaa taaatacatt gactgacact 104160
gattaaaata taatgattga tcctgataac tacaataact gaccttgata aaatgtagac 104220
cctaatagaa gaagtacaat gactgatcct gataaaatac aatgactggc cctggtaaaa 104280
aataaaatga ccctaataat tacaatgaat gaccctgata aatacacgac tgatcctagt 104340
aactataatg attgaccttg ataaaagtac aagtgattca ccttgataac tacaaatgat 104400
tgatcctaat aacataaaga taaaggagaa caaatgagag gttggttatg aaataattgg 104460
ggaaatttgg gctagccagt tgcatgggtc cgacctagtc acgaaccagc cagccaggcg 104520
cgtggaataa ccacacaaaa aataggacgt ggggattcaa accatgctct ttcgatacaa 104580
gcgagcgtct tctaccacta taacttatgt ctgtttatgt tatataaagg agagatattg 104640
tatgtgtgca cacatatata cacacataca ctataaaact gatgtcagcc attcacattt 104700
tgttcaacca tccattatct tttgttgagc catttctaat caataccact tgtcgggtat 104760
cataattagg ggtacccaga ttatgcccct aaaacacact taaccctta<br>g accaccttca 104820 agacacattc cccgagatca aaggatcata aaccgcgctt cgcccgaggc cccgctcagg 104880
ggtcaccata ggtccgcttc gctcaagcct gccctcggac atggtgtgct ctagggagaa 104940
ttctcgtccc ggccgaggct ccatctccca gaacaaaagt ctttgcctcg cccgagcaca 105000
tctcgggtaa ggaagacaac cccaatgcaa gactcaacca aagtctgcag ggggcaggag 105060
cattcaatat gcatacctac cccacgtaga gttgcaggtg aacaggagca acaagaccgc 105120
ggtcctgtca agcttcacca actacgatga cgcatgcgac cactattccc acatgccatc 105180
tgtcaacccc tgatgggacg tacaatacga caagagtgca ggatggctct cggacgtgaa 105240
ctctgcctcg ctgaaggcga cctcggcctc gggacaaact tcgcctcgcc tgagcccggc 105300
ctcgtttacc tgctccccgc gaatactgga gcgggctcgg tcgtgacctc gggcggactt 105360
ctgcctcgcc cgagcccgac tctagcctca atatccacaa cggaaaggcg cccaacgtca 105420
ccatatactg cagagctgac atattactta gggacttttt gccatactca gtactgtgtc 105480
aaccactacg gcatgggcaa ccccccttgtc agggggggctc gggtacgtga ccaagcgctc 105540
agcccttgcc tcggctctca gcagaaatca agcgggcaca agtcaccaaa caagtacaag 105600
accatgcttc ttgaagatct ttgagtgatt tctgcagatt tgaacttttt tcaacttcag 105660
cttcgagttt tgtttcgaaa tctttcttct cttgctcaat gctttttgac ttcatggaaa 105720
gttcactatt cagtctggcg atctcggctt gagcttctgc cagtgaacct tccattgttt 105780

```
gaattatgaa gtctttcttt tctagggcag cttcatgatc tttaatcttg ttctctaagc 105840
cctcaattat aacttcgttt ttcttgtcct cgaggtcttg ttgcatcctc aaggttttgc 105900
ttagtagtag gctctgacaa aataaccttc atcagaaaac atcttcatat caaaacaata 105960
aaaagttaag ggaagaattt taccttaaag ttagaataaa ataggctacc gacgatatgc 106020
tgtcgtcggt atctgctgag atcggcttcg agtttcggaa aaccaacact tttcgataaa 106080
gtcctgacaa ctttctcccc agtccggtct caaaggcaac ctaagctctc ttcgtctata 106140
ccaccgaaga gcagtgcccc tggctggtac ccgcaagata tagcaaagtc cctcagctct 106200
tctttttag ccttagacaa ctcttgtcca attatgtttt gaaagttgat atttctttct 106260
tccgaagcat cttcggcaag ctccttctcc ttttcaggca ctgtagccgg ggtttcctca 106320
gcagctgcag cagtttcttc ctcagccata ttcaaaatta tttcatcaat gtcagtaagc 106380
gtgttttcca aatttgtggc ttcggctgct gcaacttcgg aagtagaagc ttcggctgga 106440
gcagctttgg ctgctgctgt ttttagcact gaggccgacg atggtgtttc ttcaatagcc 106500
tcaatgatag taataatcct tcgctttttt ggttcagcgg gcttctcggc aaccgaaggt 106560
tccttcttct tcttctgtaa aagcttcatc agttccggtc ccagcgggct tagcttatta 106620
ggtagagatt cggtcattac ctttaaaatt tcttctgcgt cagtggcaga aggtgttgag 106680
ggaacttctt ctaaatcagc ttttggcttc ggagctgtag cttttctttt cttcgaaacg 106740
gccaccttcg gctcagggct ggattttttt tcttttttgc taaattttca tcttctttta 106800
tcattctggc agcttgtctt tgcataacac tgacagctct tttttgtttt ggcccttcgg 106860
cacctttact taaccgttca tagtctgggt attcaaattt cagagtgttc attactcggt 106920
ttagccttcg tttcggtcgg gtgccgaagg ctgccgtcat caattgatct tctttcttcg 106980
tataattgcc caatatttca ttgcacataa cttcgatcgt atccaaccat tcttggcagg 107040
gttctttgaa gtgtttcttg aacttaaaat gatagggcag tcgaacaagt tcattctttt 107100
tcttctctcc tttaagcttc ggcatactcc attcctttaa cgttgggaat actctattgg 107160
ctaagtattc ctgaaccaaa tccctagttc cgatatgctc ggacacaact ctaaattcac 107220
ccacaacatc tgggcatgat gatcccagcg tcatgcgaca ctggggccta gttaacccga 107280
aggttaggcc cagtgggctc taaactagct tctccttctt ctcatcaacc ttaacataaa 107340
accattcagt tttccaaccg gttgtccatt tggtgcggta gctaaccaac ggtgtcttca 107400
tgtctttgcg gtaggcaaaa ttatagcagc cgaagttctc gtgcagtcca tcttctctag 107460
ccttcgtctg atagtgaagt tcgtgcaccc ggtagaaggc ttcggcaagc ggctccactc 107520
cttggcttcg aagagcccag ataaagacgc taagcctaac gatagcgtta ggagtcagct 107580
gatgaaaata aatttcgaaa ttttccaaaa catccacaat catcccatgc agaggaaacc 107640
tcagtcctgc tttaaagaaa cttctgaaaa ctaccacctc atcattttct agcttcggag 107700
tgatttattc tccgccaaaa cgaattagct tcttctcggc ttccccgaag tagcctagct 107760
tcgtcatcat gggcatatcg gcctcagaga cggtagactt tccaaattcc aagtggctgg 107820
gtttagatgg catgacgaaa taatctatct cctcttcatc agcctcacct tcttcaatgt 107880
cagcctgctc ggtttcggca gcacgtgcac cttcgtcaga aacaccctct agcacaacca 107940
agcctgattg tctcattact tcggagattg gggcggtctc ggcagcttcg gcctcctccc 108000
cgtcgcgtgt gactctagca gttgaacgca ccctggccat ttgatgctga atttctcgcg 108060
gttttgacaa agttgattac tttttgattt tgccgaagct ccctcttttg acgaagctaa 108120
```

agaacaagac gatgctctaa ttgagaatac gaagaataag cttcggctat ggtcaaattt 108180
ttcagcagca caacaatacg atagtaatga atgctgtggt aacttcacac ctacccgtct 108240
gtttatatag tgctacaggt gggaaggtga atcatcaagc cacctgcacc cgccgaacag 108300
tcgctcgcat tcactgaacg gtggaccgca tggcgcgaga aggagaatca ccagatcgtg 108360
cgtacccgtc ctatggtggg accacctcgc actaggaata cttaaatcgt ttctcgacaa 108420
cgagctcagg gaaggtgttt ttcggacctt cggcattccg aagcctaaaa gaatttttca 108480
cgggtcgagc tcgttacaaa aaatgatctg gcaccgtgaa ggggctactg ttgggggtct 108540
gtttcgtcgc cgaaggtcct gtgagaaaaa acaccttcgg aaggccagaa caggaatgat 108600
gccgaagcta ccaatcagag agcttcgtag cgtatttcca gatgcaccga cttaaagatg 108660
aaatgacgaa ttgggcccat gataatctat gttatgattg taatcatttg tagaggacat 108720
gaatgtaaat ttacacaggc tgcgccctgt gcctataaat aggtgaacag taccctcgta 108780
ctgttcacgc tttcgcatct tacttttatc tttgccttct atcaagctca aggtataaat 108840
gtaatttgat attattctta tgttcttatg attatttaat aataaatatt tatgttaaga 108900
tgttatataa ttgtttatgt tgtcttccta tgtttcataa gcttcatcct ttgtttatac 108960
atgtcatact tatgaaggta tgtccttcat aaccttcgtc cgaagatcgt tatctcctaa 109020
gggaaataat gcttcgaagg acgaaggaca ttaacattta acattttgtg ttgccttgtt 109080
cttaactcat agcatttgag aacaagtccc caacaattat tatgatatcc tcgccactaa 109140
caagtgaatt tttgggagaa ggactaaaat gcagtcaacg ataatgtata agactttgga 109200
gcaaaaacaa agacaagaga cataaatatc caatacaaaa ggaaaccaga gaggtagtgg 109260
tattttttc tttcttggtg gctaagcatc gctcaccctg tgatgcaaaa atctaccaga 109320
gacaagtata gccaagacca tcaaataaag agacaattta gcaaacaatc caaatcaaga 109380
tcagtgtttt tatgtaaaat agagcatttt tatcatctcc aattgcattg acaattataa 109440
atatgatgaa attgagaaat agataggctg agtaccctag ctcagcctca tctttggcag 109500
aggcatcacc atcaacatct tcaaagtcac aatcttggaa gagtttcttt gcccttttt 109560
ggcaggggaa gggtgggtaa gtcctatcag tagattgcaa tcaacaatag gataagatct 109620
catatgtatt atggaaacaa ataagtagat ttttgcgtta caaaggttac cttttttata 109680
ccactcttct gtgtcccggt tatagaacca ccccaggttc acactagcat caaagatctg 109740
tagcaacccg cgatcaagca catagattac cattatattt tagacatggt gtctcatgtt 109800
attttatttt caagtactat gtaaattcaa tgaaatgcta agattaatat ggcaagaaca 109860
tttgacagaa attagcatca tactgctggt gacattggaa tgagagaatt tccatcatct 109920
cttagtatta gctaaaggaa tgagttccaa ggcgaaaaga ggcttcagtt agaagaaaaa 109980
tttaccttag gtataagggc atcaccatca gttttctgtg tttctgttga cctcgcaaag 110040
caacttgcag aaactgcact catgatgtgc agattcatat catcttccac agatttaaga 110100
ataaaatatg agtgtacaaa aaatcaaatt ggtagtcaaa catgcgaact gtattctgtt 110160
gtttgagtga tttcacaaat tactgtcaaa tgtgagttag aatatacctt agaagtggtc 110220
ctggcattcc tgctttgtgg tgtcactgtt ggttcagtga ttttcatcaa cattttgttg 110280
ttggtattct cgaagcatgg ctagcctctg aagctggtag ttaaggcatc actttttga 110340
agagtccctt gcatattgct tgttgtaact tgagagacca tgatcagtgt tgattgtgat 110400
cctgctggtg acatttccat aatctagctc aaccccctag ctgatataaa acagatcaac 110460
cataaatcaa atataacata ttgcaacaaa caattacaca atcatgattt ctatagcaga 110520
atattatatt gtgttcatga gttgtaactg ttagatgaag ttacgatatt ctagaagttt 110580
cttgtgcatg taatctttag ccaaccgaat caatctccta tagatagaaa ggatatattc 110640
taggctgtgc atagatagaa actccaacaa tagattgatt cggttacctt attgtataag 110700
ttgttgcacc cagccttgtg cctatataaa catgcaatcc ttggccacct agtgtggtag 110760
aacgcttcaa ctgtgacacc ccagtgtcac gtagggtttt tcctagagtt gactccaacc 110820
attatcacat gtgaaccaaa aagaggaatg aacataaaaa aattaagaac aaggtttaag 110880
tgagtctttt tcatcttaag aaattctcct taatcatgcc atgcacctca aggtaagaag 110940
aactctcaaa ccctaattaa tcctaagtgg accatttaag cacataaagg gaatttggga 111000
aaagacttgg gaaaatacaa aattttggta agaaccaaat aacaaagttt tagtgcacta 111060
aataaccaac aaaatatagt aagaaagttt tgccatttga attttccaaa atcccaaatc 111120
agcccatgaa ccaatgccct atggggaaat tcagaaattc agaaaactga atttcaaacc 111180
ctttcccaaa gttcagatgt gttccctgtt ttccaaaact cgaatccaca aagtccaaat 111240
atcaaagtgg cgccaaaata ccctaggaac actttggaga agtttgagat caaacccgaa 111300
tcgtttgaca cgacttgaca taagttttgt ctcggtttgg acagtgctaa cagagctatc 111360
ttcaggccat catatcttct cacctaggcc atatcttcac tcgggactca cacacgacag 111420
gaagaccttg gcacggtgaa gagacgctac acaggatcct tggcaagata tgcacgtttt 111480
ggtcggccaa caggcgtttg aactcgggca gaatcacact tccacgtgtt cgatcgcgtg 111540
ctcaagcgct tggccgcgca ctggctgccc tctgatcgcg cgccatgcac ggtcggcttc 111600
tgtcccccgc gcctgcactc agccatgcct gagggcgcct ataagtaccc tggatgcaca 111660
atggtctgcc cttcactccg cctcacgcct cgagcaagaa ctccaactcc gcgagctctc 111720
ccccgcccgc catcaccgcc cgagcctcgg ccaccgcggc cagctccctc cagccacttc 111780
caagctgcac cagtcactcg gttagcttcg ccagtggccc gtgaagcttt ccaagtcctc 111840
ggacccaaca gagtttcacc agagacccag gatcgacctc gctggacttc ggtcacccgc 111900
agccgcgcgt agaccgagca atccggtgat tcattctcaa attcctcgcg cgcatgtctt 111960
ccttgacctc tggtgaagct ccctaacctg ttcaattgga ctatcgcgcc gtgagcaggc 112020
cggatccctc gccgccgacg agctccccgc ctgtgcacgt ggaccaacct actccgacca 112080
ccaccgccga cgatccgcac ctcgacgtga tcgccagaga ccccggacct cacccgaccc 112140
ctcaccggag caacctcgcc gccggtaagc ccctccgccc ttttcttcca ctgcggtcac 112200
tattccatta ggggaaggat cgcgggttcg atttcgcaaa accctagggg ttttctgcag 112260
agtcatagac tcagataaat agtgaaccaa ggacctgtct gtaatacact taaaaccttt 112320
cgccagggac cccagtgcaa aaccctttt cctttatcca tttctgttta ttctttttaa 112380
attcagtaaa ggacttagga aatttgtatc ttgagaaata ttcaaccaaa tttagtcaaa 112440
ccaattttac tagattcaaa atattatgaa ctatcacata aaaatattga accctgtgct 112500
ttctgtttta aattttggag tttagaatta attaaagaaa ctgaccaaac cttattaaaa 112560
tgaagaaaat tagttatgct tctgtgctga acttaagaaa atttgtagaa gttcaaaccc 112620
cacttagaca ctgtttaaaa atattgagca ccctagtatt gaagatttaa acagggttat 112680
ctattaaaag ccataattgt ccaaaactta ggaaaataag aaaggtacta gaaaataatg 112740
aacagtggat gcaaatattt ttcctagccc acttaagtaa tgaagaacct agaaaaaata 112800
aaaggaacac tagtccagag caaattcaag gtgaaatgtt ttattaggca ctaataaagc 112860

```
tagaagggca attattagaa atatgagaac aatttcaaaa ttggtaagaa aaattcagta 112920
gacttgtaac cactaggaca ccactacaaa aatgataaat acctagccca tcattttaag 112980
tgggttgaac aaataaaact tgatattgag ccatattcca attaaatcat aagcaagcca 113040
aaaagtgtgc aacaatgggc gaataaattt ttactagatt attaatggaa tagatcacca 113100
gagcaaaatg caaaacctat tcaaactaca aagtaatacc cattgcccct acttcatgaa 113160
aaaggccatt taattcaaga aattcctacc acccttccct taagaaaaag gttaccaaat 113220
tttagaatga ttgctcttgc gcaaagaaga agataggaaa aattggaaat ctgttgtttg 113280
atatttttca agtatagtgg tagtagaaag caccccttg gctagaaact ttagaaaatc 113340
ataataaaat aactaataaa tattagtggc tgaaaatttg tacaaaatca tgttataaca 113400
tctaaatgcc agcaaaaata agtcttaaag aataacccac tgttaaaaga gagttgtagt 113460
tcaaaacatc ccctttgccc taacacttgc taattttgta cagagagaac ccctcacttt 113520
ttaagcccca aattttgaga cagaaaatta tacaccagta agaagctact gtaatgtttg 113580
cagaatttct ggaaatttat taagctatct tgtagttcaa acccacctta aaagcataaa 113640
aggaataaag aagggaggaa ttagaaagat taataagtat taccccaaca tggcagctaa 113700
gaatcttgtt aaaatatcca taagatataa agaagaaaat cagtagaaca ctaaaaatgg 113760
gttaaccatt cagtaatcaa cttgacccta agttggtgag tgtaccacca aaaatctcca 113820
gtagtgagaa tgaggtctac cctattaaat tgatcatcct ccatcaaatt ttaattgcta 113880
aattaaatat catgccatgc atatatctta ctcattgcat tcattagatt gcaacctcgc 113940
tgatggagag tacgtgctca tccctgagca aggagctgtc cacgaggaag accaggagca 114000
agctcccgag actgccatcg aggatctccc cgcagcccca tcatttggag gcaagccccg 114060
gttttatgca taaccaattt atatatgcta ctttactaca cttagtgttt gtaggcttgt 114120
aatgtgcact taagtgtagg agttgcttga aacccttagt tgcatgaact caggattcct 114180
ttttgagatg gatactagta tgctaggtcg agtagctgct ttactaatta ggatctcggt 114240
agaagtcgag tgatttttct agcaatcgcg cgaggtcagg aattgattgt attcatcttg 114300
ataatgggat ctatgatggt ctatggtctt ggatccaggg tggatgcctt gtccatgaga 114360
caggaaaatg aattaaggat taatgtgtgg atacctgagt caagcgtttg aacgtactaa 114420
acacatgtcg ggaaatatgg taaccggtaa acctagtacc tgattgaagc tgggcgcgga 114480
cttttctcct cactcgtcct gagactgggt ctcctatgct agctttggtg ggtacaagtg 114540
cggtcactgc acggcggcag cccgggtcag tggagcattg tatgccaagg cggtgagccc 114600
tggccgcgaa aggggaatcg atggggacgg agtgccctga catgtcgtgt gtttaggttt 114660
accttgcaag gttaatactc gatttgaatc gtctgcttct cgcagctaat gagactgctt 114720
gaccccttgt actacattga gtaagaagtg aaatgaggat tacatgagat aacttgttga 114780
ttgtattaaa tgattgttac catgtatgct tagaaagagc aaacttagct acaataatga 114840
tactagaaat ggaaaagata aagttgacct tagatacaac tagtgctttt ggcaaaccaa 114900
acccctcaac caaacagcta catggtctag aggtagaaga gtagattcct cacaccgggt 114960
aagtctagct gagtattagt atacttagcc ttgcttgtgg cataattttt gcaggtacgc 115020
tctaggatat ggttgacggt gtaacttggc ctacaaccct gtcaccgggt tggacggtcg 115080
agtgggatgc tgctccggca ggagaggagc aggagaagta gtgggccagg ccttgcccta 115140
ttcctcgctt ttgacgacat cgattatccg ctgcagttta ttttgtgaac ttttctcagc 115200
tacttgaaaa actctgattt atgtaataac tccagtactt taatttgagg ttttcctgtt 115260
```

ttattgtatt tcttctgtga ctcaccttcg agtgagcttg tggtatttga tcctggataa 115320
gtggctttat tagactagat ctgagggact gatggcttat tccgatttaa gtgcattgcg 115380
gcctttaagg cgtgacttgg gcacttaaac tggaataatc cgggcggttc tgccacatca 115440
accattccaa tctacatggt accatagcca ggtcctctac aacacatcca tcatggcgag 115500
tagattctca aattccacca ccatcccctc ctccttctcg atcccggtca ccgaaaaact 115560
caccaaaacc aactaccgcc tatggagtgc ccaaatccta ccgcccatcc aatctgcaca 115620
gctctacggt ctgctcatcg gcaaagaaaa gatgctggtt aagactgtct ctgtgatgac 115680
taacgacgcc tatatggaga cgcccaatcc cgagtacatc aactgggtga ctcacgatca 115740
agcgctgctg ggatatatcc tctcctctct gatgcgtgag gtcttgatgg gtgtcacgac 115800
agccacgacc tcggccgacg tctggagctc cctcgcggct atgtacggat cttgcacacg 115860
tgcgcgttct gtcaacacgc gcattgcgct cgccaccacg aagaaaggca cgaccacaat 115920
ggccggattc taatccaaga tgaagagtta tgccgatgag atgtcggcgt ccggccaacc 115980
tctgggcgat gaggagttcg tcgcctatgt cctcaccgac cttgatgaag aaatctacaa 116040
cccgcttgtg tcgtccatcg tcacttgcgt cgagccaatc tcctctgcca agttatactc 116100
gcagatgctc agctatgagc ttcggcttgc gaagcagtcc ggcggcaggt acgctgctca 116160
tggatcagcc aatacggcta ctcgtggccg tggtggctcc tggcatgatg gttctccaaa 116220
atcacggtcg cggacgctcg cgcggaaatg gccatggcta tccttcgtcg tcttcgcgcg 116280
gcaactacag caacaacaac tacttcaggc gcagttccgg tccaccgaca gatcaatccg 116340
gtggccagtc ttgtccacgc tgctaggtct accttaaagt cggtcacaga gctaatatct 116400
gttggtaccg cttttatgaa gaattcactc ctgatgatcg ggttgcggcc atggcatcat 116460
cctccactgc tgctgatcca aactggtacc ttgacttcgg tgtgactgat cacatcaccg 116520
acgagctgga aaagctaaca gcatgatcgt tacaatggca atgatcagat tcgggcggct 116580
aatggtgcag gtatggagat tactcacatt ggttattctg ttttgcccac ttccttccgc 116640
cctctgcacc taaatcatgt ccttcgtgtc cctcataccc ataaaaatct tgtttccatt 116700
catcgtttca atcttgataa taacaccttt attgagttcc atccgttctt tttcttgatt 116760
aaggatcagg ccacgaggca agtgctggtg cgcggaccat gtaggggtgg cctctaccca 116820
ttgacatctc ttgcacacct acccagaagc acgaccttgc cgcaataaag ccatcctatg 116880
agcgttggca ttgcagatta ggtcatccat cgcgtgatat tgtcgctcgt gtcattagaa 116940
ataataattt agtgtgttca ggcttagatt cctcggagta tgtttgtgat gcctgccttc 117000
gtgctaaggc ccatcagttg ccttatccta agtcgaccag tcagtctgct gctcctttag 117060
atctggtgtt tttcgatgtc tggggacccg ccattgattc tttttgtaat aaaaggtatt 117120
atgtcagctt cattgatgat tatagtaaat ttacttggat ctatcttctt cgccataagt 117180
ctgaggtgtt tcagttcttc aaagaatttc aaagccttgt tgagcgcttg ctcaatagaa 117240
aaatcattgc tatgcaaacc gattggggtg gcgaatttga gcggcttatc tcctttttc 117300
ttatcactcg gcgtccctca tcgtgtctac tgcccccatg ctctgcaaca aatgaggact 117360
cctatcgtga attaatcgcg cttgtttata tgatcctttc tttatttctg aacatagtca 117420
taaactttat tctctttgga cgaccggtcc taccgctctt ggcaatattg ctcagcnnnn 117480
nnnnnnnnnn nnnnnnnnnn nnnnnnnnnn nnnnnnnnnn nnnnnnnnnn nnnnnnnnnn 117540
nnnnnnnnnn nnnnnnnnnn nnnnnnnnnn nnnnnngaaa tctagagtaa tcgttctcat 117600

```
cgcctaattt atgttttaaa aaattaggca tgtgagtttt aacaaatgca tgtgtcatcc 117660
tctctatatc ctccgtgata cttttaatcc gattatcaaa agaaatttta atagatggaa 117720
tatcatcggc tgacctggca tcacctattg tggggagctg ttgcagcacg gctaacatat 117780
actcggcgtt tatctccctc tcttggacgg tcttctggtg gcagtctacc ttgaagtgcg 117840
agaggtacca cttgtccgcc accttgagca cctgatcctt ttgtcggtgg gcctcctcgt 117900
ctattttctt catgtcatct tctaattttt tatgctcagc ggccgataaa ttagtcagcc 117960
ttgtgttgct gtttggagaa gcactgttga gatctttaga atcggccatg taagcctgat 118020
tttgtagatc tgcaacttct tccccagcgg agtcgccaaa aagtatgttg acgccttttt 118080
ggagcgccaa acactcaaca agaaccgtgg cggtgccctc tggtcaggcg cggacggtct 118140
gcagccttgg gccggacgat ccgcagcctt gggccggacg gtccgcgacc tgggcgcagg 118200
agtggtgtct tccctgcgtc acaccggacg gtccgcagct ctgggccgga cggtccgcga 118260
cctggcgaca gggtcgtctt cctactcctt gctggaatct agatctcgtc ccctgggggg 118320
aaagatctta aggtgctccg ggtcgacagg tcacccgggg cgtccccaga cgacgtggag 118380
tcgcctagga attaagagat caaatcgagg aagaagtctt ggatggacaa ctagatcttg 118440
ccccccggga ggggtgagat cctagggtcg tcttgggatc ggcaggccac ccaagacgga 118500
tctagacgac gtagagtcga ataggggtgg aggtggatat gtggaagact acaactagaa 118560
ctatgctaca tctactccta gggcaggaaa agtaaataag gtaattggtt cgattggaat 118620
gtgttcgggg gttctcaatc ggccgtaccc ctttatattt ataggggagg aggtctggac 118680
cttttcctaa gagatagcca acaaactccc acgtgattag atggataacc acgcacgaga 118740
taaggataaa catccgagtt aatctaatct cgggacacgc ggaccgtccg ggcccatggg 118800
ccggaccgtc cgctcatttt ggtgtccaac agctacgtag tcatgccatc acttcacccc 118860
acaatcccaa ctatcaaaat aactctaacc gaacttggca tttagccgat cgattcctaa 118920
ctcatttttc ataccaccac tacacgacat accgaataca ttgaatgact cgttcacatt 118980
ccacatatat ctttacgaaa acatttccac atcgcttgca acttaaccta agcttcgcca 119040
cataatttca ggacatctac ttaaatcatg aatatcatca tcacacacat cgacccgttt 119100
tgaaataacc ctacatgtct atcacaggaa tggagcattt caacacatat cctaaaacaa 119160
actaacttca tcacacatct tgcattacaa agctacttga cttatttgaa gtgtctactc 119220
gaaatcgtga gcacaatcat acactatata cgaaacataa ttttaacgaa cgcataatac 119280
gcatcgtcat gacttgacct ataaatatag agaaagcgat gactactctg gcatgtcacc 119340
acctctctat ttaagtcaag acaatttcta ccatcgatta agagtcgtaa gcattaaata 119400
ccttactact ttatacgcac aaataaactt caacttaaca caactgacac cgatggaatt 119460
tttactaaac tcatcgtacg cataaccctg tctcgcatac aaccatatta tggcgtgcac 119520
tcgagacact tcaatccatg tggcgcgacc actagtataa atggactccg acactcatgt 119580
cttaacgata catcctctac gcaaactagc attctctaaa ctactcgtca catcaataaa 119640
tatatcccct ctaaaattac gaatcccatc acattgctta aaacaaatac acttttcaca 119700
taaacacatc gatgcatttt ccaaaacaaa atccacattt tgtaacttag ttttcgcatc 119760
aaacaacgca tcgcatattt tcctatcaaa ataaaaatac tcgagttctt ttgtatttca 119820
ttttcttccc tacacgcgtc catttataaa attatacttt tacacacata taaccacatg 119880
cacatcatcg accaaaacat aattagacaa ctacaaatcg cgcacatcaa ttaacctctt 119940
gttctccaat cgcaaacatg atcctaccaa tgcgcataat cgaacatttt acacacatcc 120000
```

```
atacaaaatg attaatcgag tcgatcgaga gcgacatgca tcggctcacc ataaacaaac 120060
ccaaacgatg tttgcaagaa tgacggtgat tccgattcgt gcatcgctcc aaacatccga 120120
cgagcgttaa gcgacttgct ttctcctcgc aaaacacggg gttctctcct ccacaaaaat 120180
aaaacaaagc aacacacata cataattaat cataggaaaa taacatcgat gcggaatcga 120240
acaaggagcg tcgcggtctc accggggtga acgacgacga cgtttggggc tgcgcaaaaa 120300
cagcgaacac acggcggcat cacggcgtgc tgctcactgc gcaacaaaac agcaagccgt 120360
cagcgcgcgg agccgtcggg gctgctgcac atttcatcga gcacaagtgt ggatggcggc 120420
caggtgtttg tttcaggcgc tgaaacaatg gagggggaga gggctacggc tggggaagtg 120480
gtggctcggc cacagcaaga acagggaagg ggaggctggt cgccgacctt gggcgcgggc 120540
agggaaaatg gagttgctgc ttggcgctat gtacaacaga gagagggagg aatggcgcca 120600
tgggaagctc gagctcggcc aggggaagga agaaaggggt tcggcatcca agctgttgga 120660
gcccaaggag agggtgctgg ccgccgtgcg caagtgaagt ttcacgccag ctgaagctcc 120720
ctggtcgcgg ataggaaaga gcagggggcg cctgctgcag gtaggagctc ggctcctgtg 120780
gaaaatggca ggggcagagg aggccggctg gagcaccggg cagggcgctc ggccatggag 120840
ccgctgcatg ggatttgctg ctgcgccctg ggagaaaaac agtaggggag tgaaggatgc 120900
catggctggg ggcgcgggga gcagggagcc tgctggtggc cttgctgctg tgaagcaggg 120960
aagaagaaag gcagaggacg ccacgggaag agcttcggcg cgctggaggg aaggaacgcc 121020
cggccatgga agcccctgcg cgctggggaa ggagctccag ctctacgtgc ttgaaggagc 121080
ccacggctgg aaaatggtag aggaggaaga gaagggtgtt ggcggctggg gtggaaatgg 121140
aaaattttca gaatgcaagg gagggaagcc catatttata gaggagaaat tagggtaggg 121200
tttcttatgg gccgaatggg ctggactgga tttggcccaa aacactaaat tgggtcgcgc 121260
taaatatttt ccggactaaa aatgttcctg cggaattcgt cgctactgag aaacagagcg 121320
aaaagagttc ggacgaacgg aaggttgcgc gattaactcg gccgagagtc tgtttagatt 121380
tcgcttgaaa ataattccct acgcgtaaat cgaaaataaa tcgtcctgag atttgatcgg 121440
ttttggattt ttagtcggag aaagcgaatc gtgatatata aaaatcgttg ccgatgttga 121500
ttttgaaatc ggattggata cagagatgct aagctgagtc gagtaagatt tgattagagg 121560
acgacatatt gattatttcg tttgtgagta tggactcgga ttaaaatagt tggacatcga 121620
tcgaacatcg agaaattgga ttcggacaca gatcaaataa cagtcgtcga gagtttgatt 121680
taatgagctt cagatgaggt ttataattcg agaatgattt ttgagttcgc atttgtgccg 121740
acgataaaag ttttaacagg ctccaaaatt ggccttctgt gagactgagt aactccgaat 121800
tcggtgaaac gtgaatgaat aatctggata atcagggaca tacgcgagcg agaaatagaa 121860
atttttactg agcatccgag attaggataa atctcgcgac gtaacacgaa actgacacct 121920
ggggtgtcac agccttcccc ccttaaaaag aatctcgtcc cgagattcga atgaggatat 121980
ttatgggtgg agaagcatgt aactcccaga ctgaagatag atgcaaattc atgagagggt 122040
atctgacaag atactggaga cagatttggt tagaatatcg cgacatatcg agacaaaatg 122100
cagcgatcat tctgagagtg tccacaaaaa aatagcacat cagtatagtc tcgtaatgga 122160
tcacgactat taaccgcgat actagcgcgt gccgagcagc tcaaccatgt gtgcaccata 122220
gtaggctctc ggtttcgtcg cggcaccatc agtcgttagt catgacatca ttaccaaacg 122280
caaccaataa gaaattcaca tagcactgat agttggagcc catgagagta tggctcagaa 122340
```

```
aataagaatg tgatcagagt tgaagcagag attattggca aaagatcatc acatgagaat 122400

tttcttcaac tcatagagtt attttatgat catcacgggg attagcaggc cagcgattag 122460

tacgagattt gatatgagaa ggaagcactc cagagatcat gttgatgaac ttgtagagac 122520

atgagagaac cacaagatga caacaacatc ccttgaacca aatggataca ctgtttagag 122580

ataaagttga taaacatcgt catgatcctc agagaacgag tatgagaatg accagaattg 122640

agagacttag gtagatcaac attcgatact tgagaacggg ttatagtaga taacaagata 122700

atagggcaga atcatgaaag atcagagatt cggatgataa ggtcacaaca tgattcacaa 122760

ggaaaaagat cactagatcc atgcgaaagg agaggtaggc aacaagatca gctggatgat 122820

caacaggaat gctatgaagt tttaggggca aggaatttat ggaaagaaac atggccttga 122880

tagggtttgc gcaactagac accaaacaac aaattttttt tgacgtaacc agtgcacaag 122940

gaagctttgg tcgatctagg agtcaagcta tgggaatcta caagctgtgc aggtgtaact 123000

tcaagggtaa aacccacaag ggctagaaaa cgccaacaca agcatttttt taaaagcggg 123060

ttcacttgct aaactcaagg ttgtttggag gagtcttttt atgaacagaa caagcaacaa 123120

aatgttttgc aaaaagggtt gaacaattac aatactacct agatagcaag acaagagaag 123180

cacataacat aacctagtaa agactatcat gacacacaag ataagacatt ttttttgcag 123240

ttcctagcaa tacagcacat tattcacaat ttttttttatt atttgaataa aggtgagaga 123300

agcatgttgg tgcacaaaag acaattataa tgcgacaatc atgatgcatg ctcattctag 123360

tcgtcttctc agacctaact actttttcgg ttgcttctac agcatcctta ttaatagtag 123420

tagtagcctt tatggcctat ataaatagcc acctagctac ccatctattt cctaaggctt 123480

cacgtcctaa gtctatcctt atcgtcctga catctatcca acattggttt ctagcaagtt 123540

ttacttttag aaaaggttgg taatcatgac ttattgactt ctctgtgatg gtattcgctc 123600

cgataccagc tgtggcggaa ccgcccgaat tattcaaact taagtgccca agtcccgcct 123660

tagaggctag accacactta aataggaata aaccgtcagt ccctcggatc tagtccgata 123720

aagccactta tccaggatcg aataccacta gctcactcga aggtgagaca cagagaaata 123780

caataaaaca taataccaca aatttaataa gtatcattag tgattacatt atcggagttt 123840

cagaaataat aaccataaat tttaatgcag cagaaataac taacggagaa gaaccgagta 123900

acatggcgaa gcctggccac tctactcctc ctggtcctct cttgcggaag cagtaaccca 123960

ctcgaccatc tatcccggtg gtagggatgg aggccaagtc acaccatcaa ccaatcatcc 124020

taatgaatat ctgcaaaaat tatgccacaa gcaaggctga gtatacatta ctcaactaga 124080

cttacccggt gtgaggagtc tacttctcta cctctagaca tgcagctgtt tggctgaggg 124140

gtttggtttg ccaaaagcac tagctgagtc taaaatcaag ttttagcttt tcaagtttta 124200

gtatgatcct ttttgactag atgtgtacct agctaatcat acatgatatc aagaattttt 124260

atcaaacaac atcttttgcc aatcacctca tttccactta ttactcaatg cagtacaatg 124320

gatcaagaag tctcattagc tgcgagaagc agacgattcg aatcaagttt ttaaaccttg 124380

caaggtaaac ctaaacacac gacatgtagg ggcactccgt ccccacacac atcaaccgtc 124440

cccatcgatt ccctggcaac agaaaggggc tcaccgcctt ggcgtacaat gcctcactga 124500

ccccgactgc cgtcgtgcag tgaccgcact tgtacccacc ataaccggaa tgggagacca 124560

cgtctcaggt cgcctgagga gggcaatctg cgggcaggtt cactcaggta ctaggcttac 124620

cgatttacca tatttctcgg catgtgttta gtacgttcaa acgcttgaca caggtatccg 124680

cacgttaatc cttattccaa tttcatctcg tagaccacgc gtccccatgg acccgtgtcc 124740
```

```
acagaccatc accattatgt tatcaaagtg gatacaacca attcctgacc tcgcgcgagt 124800
gctagaaaaa tcactcgact tctaccgaga tccctaatta gcaaagcagc tactcaacct 124860
agcatactag tatccatctc aaagggaatc ctgagttcat gcaactaggg tttcattcaa 124920
ctcctacact taagtgcatg gtacaagcct acaaacatta agtgcagtaa aatagcatat 124980
atataacagt tatgcataaa accggggctt gcctttaatt taacacttag gtagtgtttg 125040
ctgggggagg tactcgcttg gcgagcatcc actggttaag tccattcttt aggtcgtcca 125100
tcaacggcat cttgtggttg gcaccacatc actggctcga tcatcatctc tcggtcctat 125160
atgaggtgca agatgcatat gtatgaatat aataaaagta acataagata taccaagaca 125220
cagtggcgaa ctaaacatta attagtaaga cactgcaaca actatacgca aacactagtt 125280
atttatgtgt cattgggcac acgtaaacac taccactgga aagacaatga tcactaccta 125340
caattaacca acgcaacacg atatcatatg tacaagcatt tatttagttg ctacggcttt 125400
tcattagttc ttctattgat cacacaaaag catcacaaac acaagtttaa taaaggaccg 125460
atgcatcaat gtcgatggac tcctctatca caatcaacta tagcaagcaa gcacattaat 125520
catggaacac atgttaacct aagtttagcc atcacaagtc tatgtccgtt aagtgctaac 125580
taagcgtttt tagccaaaat ggtgaactaa atattcattt gagcacgtgc agatttttg 125640
gacagcagca cagcagttac ttgttttaat aataactttt caaatattaa tccaaaaata 125700
gcaaactaaa actttctgga aagtttagaa agtgctctac aattttggta ttttcatcac 125760
agcatgatta aacacttagc aaggtcaaaa agtgcaatca caacagctct gtccagattt 125820
ggacagattc agacttgtga ttttaaaaat tcataactga agattcagac atccaaacaa 125880
attgatccta gactttctgg aaagctaatt aaatgttcta caaattattt ataaacatcc 125940
caggctggtt tagcatgtat caaggttaaa atatactatg aaggctgtgc tgtccaaaac 126000
tggacagatt cagtcttcac acttcaaaca catgtaactt aatcttcaga ccaccaaaaa 126060
gagtgatcta agactttttg aaaatcttag caaaagtact acacaacttt cataatcacc 126120
aagaagtgat tccaggttta actaaatcaa atattacagt tttcgaaatc tgttctgacg 126180
gtggacagaa cacagcaacc agtttgtaaa attcataact cttaaaccgt caggcctata 126240
gttatgaaat tttaacacaa gcaagataag aaaagcctct acaacttttc ttataatcta 126300
caagggctga ttctaacatt aacttaagca aacaatgcag cttctgaaat ctgtacagaa 126360
agtggacaga ttcagttact gaatttgtaa aaaacataac tcctaaacaa ttagacttat 126420
gcctgtcaaa ttttaacaca agtacgataa taaagttatc tacaactttc ttgtgaccac 126480
caataactaa tttcaacatt aacttaagca accattgcaa tttctgaaat atgttcagaa 126540
atttgacaga ttcaggtgct gggcttgtga aaagcacaac tcctaaacaa tcaggtttat 126600
ggctgtcaaa ttttagtaca agcaagataa tcatgtcatc tacaactctt ctatatgact 126660
tttctacaga aaacatgatt tggtttatca aacaaacagc acaactaaaa cagtgcgtgc 126720
agcccaaaac agcaatcaat aaattcagct tctgtttact tttaaaaatt gccgcgttct 126780
agagactcga cttattctaa attatatcaa ggcacactta agcatagcca cacaatagat 126840
gatgtgacgg ctactgttga cgccttttg gagcgccaaa cactcaacaa gaaccgtggc 126900
ggtgccctct ggtcaggcgc ggacggtccg cagccttggg ccggacggtc cgcagccttg 126960
ggtcggacgg tccgcgacct gggcgcagga gcggtgtctt ccctgcgtca caccggacgg 127020
tccgcagctc tgggccggac ggtccgcgac ctggcgacag ggtcgtcttc ctactccttg 127080
```

```
ctggaatcta gatctcgtcc cctgggggga aagatcttaa ggtgctccgg gtcgacaggt 127140
cacccggggc gtccccagac gacgtggagt cgcctaggaa ttaagagatc aaatcgagga 127200
agaagtcttg gatggacaac tagatcttgc cccccgggag gggtgagatc ctagggtcgt 127260
cttgggatcg gcaggccacc caagacggat ctagacgacg tagagtcgaa taggggtgga 127320
ggtggatatg tggaagacta caactagaac tatgctacat ctactcctag ggcaggaaaa 127380
gtaaataagg taattggttc gattgacaag ttttcggggt ttctctcact gccgaccctt 127440
tttatcataa ctgagcacca ggtctgaaac tcaaacctct ccgaaaggga agcgtatcac 127500
ctgatccgag ctggataagc tccgactatc gacggatgac atagcatcac aactgatctc 127560
gggacagcag gtgctgccgg ttccctggac caagcaagcc catatcattt gatgtccacc 127620
agatgccccc tgccgcaagc gcgcaaaaag ctgcacccgg gagcctgaat tacactccga 127680
aaagcgtgag cccgtgattg ccttttcatg tcaaaggatc gatacggatc gatgggagat 127740
cacgcccgat gggcctggat tgcttctgtt accttggcga gcgtttggtg cagaggccat 127800
cctctggaac ggattccact gcaccatggc tgatggaata tcctgcgtca tgcagaccat 127860
tgatggaggt gggtccccag cccagatagt gaagcgcgaa ctcgcatggt gtccacatgg 127920
attgaccgca ccgtcccgca gcttgaaata gaagcccggt cccgaaggag acatgtcggg 127980
gagctcggcg gctgtcccta ctggacggct gctagctgca aaatgggggg ttggccgctc 128040
ctacgggacg ttccgcacgc gtctctcgtg cgaccggacg caatggccat cggatagtgt 128100
tgctctggac tggttcatga ttagcacccn nnnnnnnnnn nnnnnnnnnn nnnnnnnnnn 128160
nnnnnnnnnn nnnnnnnnnn nnnnnnnnnn nnnnnnnnnn nnnnnnnnnn nnnnnnnnnn 128220
nnnnnnnnng aattctttat tcctaagtta atttgatcct catgcttact ttggttcaca 128280
taaaataatg gttcttggtt tggcattttt aagagaaacc gtaggtgaca ctagggtgtc 128340
acagccttcc ccccttaaag gaatctcgtc ccgagattcg ggccagagtc ctcccagggt 128400
gaagcgaagg gtgagactta taggaaaagg gtggggattg ttatgcttca aatcatggta 128460
catcttggtg cttcccggat gcatagagaa tttggagaga tgagcctcat ccaaaatttt 128520
cttcttgaga tcctggtcct taggaattac caatctgctt ttgaaccata acacaccctt 128580
ctcatcctgg cggaaacaat tatacttctc aaccttctga tggagattct tcttgataat 128640
ttgcactccc ttgtcactga gctgggccat gataatctgg tcttgcaagg ctggctcaac 128700
agcaatgtga gacaaagaac cagaaggaat cacttcaatt tgcatcttgc tcaactcatc 128760
acacaaggtg ttaacacgag aatccatcag aatacagttg cactgcaact tccgactcaa 128820
ggcatctgct accacattag ctttccctgg gtgataatgt acctccaggt cataatcctt 128880
gatcagctct agccatcttc tctgcctcat gttgagatca gcctgagtaa aaatgtactt 128940
aaggctctta tgatcagtga agatgttgca gtgggttccc attagatagt gcctccacat 129000
cttcaatgca tgaaccactg ctgctaactc aaggtcatga gtaggataat tttgctcatg 129060
aggcctgagt gctcttgagg cataagcaat gactcggttg tcttgcatca agacacaacc 129120
tagcccggtg ccagaggcat cacaatatac atcaaaaggc ttgctgctgt cgggttgcgc 129180
caatactggt gctgtggtca gatgctgcct taatgcatgg aaggcatctt cgcacttctg 129240
actccacaca aatttgactt ctttcttcag caactcagta ataggcttcg caattcgaga 129300
gaagtccgga ataaatcttc ggtaataacc agccaatccc agaaaactcc gaatctggcg 129360
aacagtcgtt ggtggcctcc agttcatcac ctcttgcact ttatcaggat caacagctat 129420
tccagcctga gagatagtgt gacccaagaa tttgatttcc tttagccaaa aatcacattt 129480
```

ggataacttg gcataaaggt ggtgatctcg cagacgttga agtactacat gcaaatgccc 129540
ggcatgttct tcttcgttcc ttgagtacac cagaatatca tcgatgaaaa ccaccacgaa 129600
cttgtccaat tctggcatga aaacagaatt catcagatac atgaaatatg ctggtgcatt 129660
cgtcagcccg aatgacatca ccaagaattc atatagccca tatctggttg agaatgccgt 129720
cttcggaata tcacttgctc gtattttgat ctgatggtag ccagagcgaa ggtctatctt 129780
ggaaaacacc ttggccccga ccaactggtc aaagagaaca tcaatacgag gcaaaggata 129840
cttgttcttg atagttaccg cattaagagg gcggtaatct atacacaacc tcaagctttc 129900
atccttcttc ttcacaaaca gtgctggaca gccccaaggc gaagtgcttg ggcgaataaa 129960
tcccttatcc agcaactctt gcaactgctt cttcaactct gccaactcag cgggtggcat 130020
tcggtagggc ctcttggaaa ttggggccgt tcccggttgc aactcgatgg cgaactcaat 130080
atcccggtcc agtggcattc ttggcaattc atcaggaaag acatctgcat actcacagac 130140
cactgggatc ttcttcaggg gtaattccgt catagagaaa gcacatgact gagaagaacc 130200
ctgactaggc agaatcaaag tgaaattccc gcagaaggga gaattaactt ccacggtacg 130260
actggctacg tcgagcacaa cttggtgcaa ggtcatccaa tttgctccta gaataatgtc 130320
cacattttcc aatcccaaca caagaagagt ggttttgata atgtggcttc ccagttgaat 130380
aggcacactt tggtttaatt gattagttgc aattttaccc ccaggtgtga ctatcatgaa 130440
tgaccctttt gagtgagaga atggaagttt gcaattagca ctgaactttt ggctaatgaa 130500
actatgagat gcaccagaat caaacagaat taaagcaggt tgattataaa ctgaaaaggt 130560
accggtcatg atgggagctc cttctggcac ttcctctaga gcagtgaagt tgagcttccc 130620
ttgcctgact tgtaccttct gctttcttcc cttgtcttga tttggtgctg gcatctgcct 130680
ctgctggttc ctgggacaat tcttggcata gtggcccaca ttgccacaag tgaaacactt 130740
gttcccattg ccctggcgga actgctgctg ctgcggaggc tgattgtttc ttggggcggg 130800
agctggatag cggttgggtg ccggctgctg ctgctgctga ggtggcctga tcacccatct 130860
gcctgcctgc tgctgaaaac ccctgctctg attgtgagaa acaatccgga acctctgagc 130920
ctgagcggat ggtgctgcca ttggtgcctt tctcttcttc tctgcccggt gagcaacaat 130980
gcaatcctcc tgagagatgg ccatgttgac caactcattg aagctatcgg cccggacagt 131040
gttgagtcgt tcccgcagct tggtattgag acccctgcgg aagcgatccc tcttcttttc 131100
atcagaatca gcatgatacc ctgcatactg gcataagtcg ttgaaggctt gcgcatactg 131160
cagtaccgtg cgggttcctt gattgagggc caggaattcg ttcaacttcc gatcaagaat 131220
gccagctgga atgtggtgcc ctctgaaggc agtcttgaat tcctcccaag atacttcacg 131280
atcaccgggg agcatagcac ggaagtgatc ccaccaagtc cgagcagggc cgcgaagctg 131340
ctgtgcggcg aagcgagcct tggcctcatc agggcagtct cctgtgagga ggggaaactt 131400
ggactcgacg acgcgaagcc acacgtcggc gtccaatgga tcctctgcct tggtgaacaa 131460
gggcggctgc gtgctcagaa actcctggta tgttgccata gccggaggtc gctgatgctg 131520
gcctccacca ggatgctgag ggtggggctg gcgctgcaag agctgtcgca gaatctcatt 131580
ctgctgggcc atcagctcct gcactgtggg agctggagga ggtggcgggg gagcttgctc 131640
attttgcccg cgacgctgcc tcgctgccat ctgaaaacag agattgtcgc cattgttatc 131700
ccaattcaca tttccgaacg acaagatatc atctcatatg gaaggaaaat gccataatca 131760
taatattagg ttcgaatgaa gataacatgg tgacaaggat cccacagata tcaaaagttt 131820

```
acagggttac attaatcagg ggaaggtacc cacaagccta gtccaaaatg tgataccact 131880
aagctcgcat aggtttctat ccgcctaaaa atgtcaaagc gactgcttaa ccctgagcgg 131940
tggaagcgac actggatacg ggtgaaggag gtatcgcgga ggtagtccca ttggcaccag 132000
gggctggtcc tagctcctcg ggagcctctt ctccctcgct tcctgcttca ttggcctcca 132060
tctccaggtg gtgcatgtcc aagtggtcat ttgcttcctc gagttccctc tgcacgtcgt 132120
gaagctggtt ctccaagaca tcaatagtgt tatctcggat ctccacttgc tgctccaggg 132180
tggtaatacg ctggttcagc ctctccacct gcagatcctt ttccaccaac tctgtggata 132240
ggtcgaccac aaaatcttcc cgactgtcga gggtgagctt ggctgcctga gcggtattgg 132300
caagaagtgt catagcatcg ctctgaaggg cctgaaggcg gtacagcgca ctcatgcact 132360
gaacagtgac cctcccaacc aagtcaggat acattgccca cacatccttc acatggctca 132420
cgcggttaca ccacatggga tcatccttct tctcagcggg gaagagtccc aaggggtgca 132480
tcaccatctc caggggatgg tagccacaaa aagtcgtcag agtcttcatg gctgctgcct 132540
caacggtgtc gtccgtcctg agtccaatcg tctcagagtc aagagaacgc caacccggct 132600
gaaggggatg agcctccaaa gttagccaga cccgacaacg aggtacccga tgctcctcat 132660
acaactgcac cgtgtacaaa gggggcgtag ggtaaccggc ggaattaagc acttcccaca 132720
aaatggaagg gaagccatcg cgagaaagga agtcagaact gaaacgagag tctcctccac 132780
tggcgggggt gggtgaattc atctgcggaa gggaatcaaa gataaagatt atggtggaag 132840
gaaaaagaaa aagagagccc ggatgatttc gaagaaaagg gggttagctc aattttaatt 132900
cctctttatg ttttataatg catgcatgcg gaaagaaacg ttgcctctca aaaggaaaat 132960
agggtgcctt tttagggcat cctaaaatat aagtattggc ccacagggcc taattagtta 133020
gccacctatt tctccctcta tgcctaaggc ctttcgtcct aggtctagcg gtctagtcct 133080
gacgatccgt agtagcttct aggcaggttt tagattttga aaattggtat tcatggttta 133140
ttgcccttct ctgtggtgga atttgctctg ataccagctg tggcagaacc gcccgaatta 133200
ttccagctta agtgcctaag tcacgcctca ggggccgtaa cacacttaaa tcggaataac 133260
ccgtcagtcc ctcagatcta gtctgatgaa gccacttaac caggatcaaa tcccacaatc 133320
tcactcgaag gtgagtcaca gaagaaatac aataaaacag gaaacctcaa attaagtact 133380
gagttattac ataaatcgga gtttttgagt agcgaataaa gttcataaat taaagtgcag 133440
cggataatcg atgtcgtcgg taatgaggaa atgggcaagg cctagcccac tactcctcat 133500
gctcctctcc tgccggagca acatcccact cgaccgtcca acccggtggc agggtggtag 133560
gccaagtcac accatcaact acatcctgca tggtacctgc aaaaatggtg ccacaagcaa 133620
ggctgagtat actaatactc agctagactt aaccggtgtg aggagtctac tcctctacct 133680
ctagactatg cagctgtttg gctgaggggt ttggtttgcc aaaagcacta gctgtttcta 133740
aaatcaactt ttagcttttc aaattctacc atcattaact tagctagatt tgctccttct 133800
aagcatacat ggtaacaatc aattagttca gtcaacaagt tatctcatat aatccacatt 133860
tcacttctta ctcgatgcag tacaaggaat caagcagtct cattagctgc gagaagcaga 133920
cgattcgaat cgagttttta aaccttgcaa ggtaaaccta aacacacggc atgtcagggt 133980
actccgaccc cacacatgac aaccgtcccc atcgattccc cgttcgcgtc caggcctcac 134040
cgccttggca tacaatgctc cactgacccc gactgccgtc atgcagtggc cgcacttgta 134100
cccaccatag ctagcatggg agaccctgtc tcaggtcgca tgagggataa agtccgcgcc 134160
cggcttcact caggtactag gtttaccggt taccattttt cccggcatgt gcttagtacg 134220
```

ttcaaaagct tgactcaggt atccacacat taatccttaa ttcatttttc ccgtctcatg 134280
gacatggcat cctccctgga cccaagtcca cggactaaca tataccccat tatcaagatg 134340
aatacaatca attcctgacc tcgcgcgagt gctagaaaaa tcactcgact tctaccgaga 134400
tcctgattag caagcagcta ctcgacctag catactagta ttcatctcaa aaaggaatcc 134460
taagttcatg caactagagg tttcaagcaa ctcctacact taagtgcaca ttgcaatcct 134520
acaagcatta agtgtagtaa agtagcatat aataacatgg ttatgcataa aaccggggct 134580
tgccttcaat tgctggggct gcggggagat cctcaatagc agcctctgaa gcctgctcct 134640
ggtcctcctc ttggataggt ccttgctcag ggatgagcac gtactctccg tcggcaagat 134700
tacaatctaa tgaatgcaat gcgtaagata tatgcatgat atgatatgtg ctttagaatt 134760
tataacttta aagatgtatg atcttttgat ttaaaaccag ttaactttac ttatgtaaaa 134820
ccctttagtg gtatacttgg taaattgggt tagtcttatt gggatgaggt ttatttcttc 134880
ttctcttttc ttttattctc tttaatgttt tggagtaggt ttgaactaca agttgctttt 134940
ataaaattcc aaaaattctg caaaaattac agtggcttgt tactggtgta tggttctctg 135000
tctcaaaatt tggggttcag aaagtgaatg gttttctctg gacaaaatta ccaaatttta 135060
gggcagaagg ggtactttga actacaacta ttatttaata gtgggtaatt ctcaaaaact 135120
tatttttgct ggcttttagg tgttataaca tgacttgata caaatttcta gtcattaata 135180
ccctttaatt ctttccctaa gattttctta aggtttctag ccaaaggggt gctttctact 135240
accactatac ttgaaaaaca tcaaacaaca gagttcttat ttttcttagc tagtattttg 135300
tgcaagagca atcattctgg agtttggctt ccttttgcct aagggaaggg gtggtttgca 135360
ttatttgagc taaatggcct tcctcacaaa ttactagcaa aaggcatggg ttcacttctt 135420
tttcatgggt ttgtattttt ctctggtggt ttatctcatc atggacttag caaaattttg 135480
gttgcccatt atcacattat ttggggttgc tcatgattta gtgggaaaat gccttattat 135540
cattctgtat ttattttccc tacttaaaaa gttaggctgg ggtgctctgt atttttgtag 135600
tggggctctg gtggttataa gttcactgga tttttgttaa ccactttggt tatagttttg 135660
caattctaat aattgatttt cagtctacat aatgctaatt aaagcatctt aattagaaac 135720
tggtccaaat taatggtctc tgcatttttc ctaggttctc tgctgcataa gtaatctagg 135780
aaaaatatta ctaatcactg ttcattaatc tctaaggcct ttctgatttt ctctaagttt 135840
tggacaaaat ggctttaaat gaataactac atcataatct ctaatgctag ggctcctact 135900
atttttaaac agtgtctaat taaggtataa gcatctacaa atttcttaa gctcagcaca 135960 aaagaaaaac taattttcct taattaaaca aggtttaggg ggtttctgtt tttaatttta 136020
aactctaaaa tttagaacag aaagcatatg gttcactatt tttaaatgat aggtcataaa 136080
attccagagc tagcaaaatt ggtttgacag cttttcatta agatttcatc aagttatgga 136140
ttttctaagt tctctggtca ttttaaaaag aaataacaaa attgattaaa tggaaatcca 136200
ctttgcactg gggtccctgg cggttttcta agttttcctc gcaattcagt ccttaggtta 136260
ctattctcat gagtcgctga cattacgaaa aacccctcgg gttctacaga acctaacccg 136320
aggtccttct tctaccttaa acagtagccg cggcgaagaa aagggcggag gggcttaccg 136380
gcggcgagac tgttccggtg aagtggccga gggtgaaggg gaggtcgcgg ggatcacaac 136440
ggtgtgcgga acaccgtcgg agatggccgg agtcggtcgg tccacgcgcg caggcgggga 136500
tgctcgtcgg cggcgaggag accggcctgg tcgcggcgag atagttcaat caaataggtc 136560
atggaggtcc acgggatgcc agagaagaca tgagcgaaag gaatcgggcg ggagactcac 136620
tggatagctt ggtccacgcg cggcggcgga agaccgaagt ccggtgaggt tgattcttcg 136680
ggcctcccgg tgaagttccg gtcgggtccg agggcttggc aagcttcacg ggctactggc 136740
ggagctagcc gagcactggt tgggctggag ggtggctgga gtgggctggc cacggcggcc 136800
gtagttctgg cggcaatggc gggcggaaat gagctcgccg gagctaagga acagtggctg 136860
gccggtgagg gtgagtgcgg ggcgaagaga ggtgcgcccg gggaggcttt ataggcgcgg 136920
gcgggcacgg ccgagggcgt gggcgcgcgg cggacttgac cggacgccgg ggcgagcgcg 136980
cgcgcgggtt gggcgagctc tggcgtgccg accagggtcg aacacgtgtg cccgtgcgtt 137040
ctgcccaagc tctggcgcgt gtggtcgctc atccgagcct gctctcgcct tggtcagtgc 137100
acaaaacctc ttctcctccc tacaagctac cattcttgtg tggaggtcat aggattttgc 137160
ctactggttg cagagatatg gagccaggaa atctggtctg tctccctgcc caaacccgag 137220
gcaaatccca agttttgtcg tgtctagggc tcgcgtccca atgccatctt ctggcacaag 137280
acagaggggt tagttagaca caattttgtc aatggggcca ttaggattcg agttagggat 137340
caaggtgaac atccctgatc tttggctcaa ggtctgaatt tcagaattct gaaattcaga 137400
attcccaatg agtcccaaca aaagaagctt gatttggggg ttttcttgaa ttattttggc 137460
taagctttct caatctatct tgttgcttat caaatatact ttaacttata taattggctc 137520
aactcaaaat tttaaacttt tcattccctt ttgcttattt tcttgaattt tgttcatggg 137580
gttcacttag ggttcttaat tagggttgca cattcttatc ctttaagaga ctcaattgtc 137640
ttgatcatga cacttttaag catatacttg gtgaattctt tcttacttaa gttattttga 137700
tgctcatgct tactttggtt cacataaaat aatggtcctt ggtttggctt tttaagagaa 137760
accctaggtg acactggggt gtcacaggag gcacatacaa ggatgctgag cctcgacatg 137820
cgggcctagg agcataatgg aagaaataga ttatgtaaat aactaatgct gacagagtaa 137880
cgcatgacca aacttggagg cctggaccgt atatacaggg gtctggcatg ggttcggcac 137940
tctcctatgg gggtccggac tcactattga tgccttggag tacatcactt tctctggaca 138000
catggcggcc ccggacccgc ccatgtggtg gggtcaggtg ctgttgctgg cctagagtag 138060
tcgcccgagg ctagggcgag tcatggtttg gtcccacata cagctctttt accacgcgac 138120
taaagatagt cgcgtgggta ctgcgtattt atacagtagt aaggggtacc cttgtttcag 138180
ggtgccgaaa gtggcccccg gacccacctt aggggaggat gcgagcctgc atgtggggcc 138240
aaagcttgta ctttgcttca acgtgacctg atcggtgatt ggcatgccgt tttagcgcgt 138300
ctgcagacac gcccgctgtc aatccgcctt cagtcacgtc aactgccata tctgtctctg 138360
cagctgactg acccatggcc ccatgcctgg tggtttcgtc gggccacgcg tgggacgcct 138420
cgttgccgct gcataacctt ttgtcttctg cagcggcccc gaggaggtgc gctatcgtgc 138480
gcggcagttc gcatggcgat tcgctctttc cgcactcgaa atccagcaca caatctgtat 138540
gacttgtgga cccgggccac cgtgtcatag agtgggctgc ctgggtccta tgtgcgcatc 138600
gggcgagatt tcctgtggca attcaagggc gcacggaagg gtttccctga acaaggactc 138660
aggtttcctt gaaaaaggat tcaccccgcg tgcagcagtt accttttcgc attctctccc 138720
aatcgcctgc accccttgc cttcgtgctc ctctgttcca cgctcgcgcc gccgcacacg 138780
ccatggcctc gcttggtcat cctgactgct ttcagtctaa ggaggcgctc aacctggtgc 138840
gcggcctgct tggatggagc gcgccagggc tcgccggaag ttccgcgccg gcgccgtccc 138900
tcatggcgat ctcaccgccg gggagttcgt gctgttcacc tcctacatct tctacgggtt 138960

```
ggcgttgccg attctcgccc ttcttcttgc tgctgctgga ggagtttggg cttcagcttc 139020
aacacctcac accccactcc gtcctccagg cagccatctt cgtccacctc tgtgagatgt 139080
tcgtaggtgt ggccccctgt acttccctct tccgctgctt cttcgtgctg gtcaagttcg 139140
ggaagactag ggaccacatc ggtgcctact acttccagac gaggccagat ccagccgtcg 139200
tatacatccc cacctttggc ggtgcgaggt gggaaaactg gcgcaacgat tgggtgattg 139260
ccagcgccga ggccaacgac cgcctcgtcc tgccgagcga tgggccagcg ctcgaccgca 139320
agcagtggag gactaagccg tccctcttgc tagagttcct gcctgtattg gacagaatca 139380
agggcttggc tacgggcggc ctgccatcaa tgcacgtggt cggcgatctc ctgaagcacc 139440
ggatcgcgcc gctgcagagg agaccgcgta tgtgctgttg gttcaccggc ccaaacgaca 139500
tcgataggat ccaacgcagg ccgggcaccg ttctgtcctg ggacgagcta gcagtcctga 139560
tgggagggat tattggggaa acttttgtcc ctgagtccct gatactcccc cagaacatcc 139620
ctgcgctctg cgacgatcca ggcctgagga tggtgatctt ggccacgttg ccgaccctcg 139680
acgagagcgg catggcggtt cgctagaccg gtggccggga ccccctccgt gggatccaga 139740
tttctaatgc accgattgga ggttcccagc ccactggtgc ggctcccagc accaaccccg 139800
ccgtggcccc tagccccttg gacaaaggca aaggggctgc gagcagtgcc tccgccccag 139860
gtagctccga gggggtcgga ggaggagagg caacgcaggc catgtcgcgc tgatgggtcg 139920
ctcatttcgg agcccccccc agaagcgtca gagggctgca ggtggggccg aggaagctag 139980
ctcccaggcc cacggcgcgc agaggcgcgt cagtcctcac ccccaggggc accagcagca 140040
gcaacagcaa cagcaacagc gatagcaaca gcaggagcgg tgatcgcccc gcttccaggg 140100
tcactagaaa gtctagggcc ccaagtaagc gtagcccctt ttccatgagt ctaatcatca 140160
tgccgaccag ttttaaccca tcatctgttc gctagggctt cttccttcgc cgctcccaag 140220
gtcatgcctc ctccaccaga taccaggccc accgacgggt ctggctctca acagcaggaa 140280
cctgctgaga gtggtgccgg cggcccaccc ccagctgctg ccaagacagc accagcggct 140340
tctcatgccc cagccggggg tccggtggca gcgtcaggcg gcgtcgcagt ggcgaaggag 140400
gtcccagctg gggggatccgc gcccgctctc gacactgggg gtgacgcagt aggcatgtcc 140460
agctccaacc ccccgcctgc tccggaggag atggaggtgg tgtttgggcg gcgactccgg 140520
tcgggtgccg agcaagaagc ggcgccagtc cccctccctc gcataatgtc tcgtgcccac 140580
taggtcctta gtgacactgg ggcagcaatc ttgcgggagt gggaggcgct tgaggctgag 140640
caccagcgcc taagtgactg gcgcacccaa ctggaggagc gcaccagaac ggcgtcccaa 140700
caattcatct ccgagcggtc ccaactcgag caggaccata aggagtacaa gagggacctc 140760
cagagggtgt gcgccaggga gctggaggcg tcccggaggg agaagaaggt gaccaggaag 140820
gaggaggtcg tgacccagcg ggagaccctc acaacagagt accaggccaa gctgagtgcc 140880
ctggaccaga ctctggaagc ccagcgggcc cagcaggtca gggtcgtgga gaggctgcaa 140940
aagtggtagc aggagctcga gggcaaggct agcaatgcca ccctcgccga ggaaaatctt 141000
aaggcgaagg agcagtcctt ggaccggtgg gagacggacc tcgccaggca agagacggat 141060
ctcagcttca gggaagaaat gctcacccgg cgaggcgagt tgctggccaa gcacaagctc 141120
gaggcagagg agaaagagag gaagctggag gagcagatcc gctagttcaa tgcagcgcag 141180
gcggcaccgg gtccccaagc gatggaggcc accaggaagg cccttgaaga tctccaagcg 141240
gagcaccgcg tcgaggtcca gtgtattgtc gcgtgggccg gcgaggcaag cacggcacta 141300
```

-continued gtgccactag ggatgagccc catcccaatg tcggagctac cagcgtcgat ctctgatgcg 141360
ctcccggtgc tggactctac cgccgatcgc ctccgtcgcc tggatcagat cctcggggcc 141420
cgcctagagg cagagggcag caagctctgt cgggcagtgg ttgaataagt cctaacatgc 141480
ttccggagtc acgaccccac catatccttg gcgctagtga tcgctggtcc ggtagccgcc 141540
atagaagacg ccgcctggga gagtgtacaa gacgccgtgg agctggtggc cgagcgcttc 141600
cagcacgatc ctgctgacga cctatagaga caaagcaagg gttccactgg gaagcggttg 141660
taataacttt tgattttgta agatattata agaaccgcta atgaggtagc attggaactt 141720
aaacttattt gtatgttatt tgtccttgtt atgtgtagtg tcatcaactt ccccttggta 141780
cttggccccc tgggaggtag gctcgacgtg tcgaggctgg ataccagtat accaaagata 141840
aaattggtgg tccggcccct aggaggtagt ctctacagtt tgagactacc tactactgga 141900
ctgggacctg gacttgtaca cagcttcggc tttaaagtgt taggagcaca ccataggatc 141960
catcgtctgg tatctgccat cctttgattt atgcaacagg acctgcagga tttagcctgg 142020
gaagccaagc cgtatgcctg gacccatagg atcacagttc caaatactag ggcacccgtt 142080
atagagtggt ggagcatgca ggcttagggt acggaaccat gctaagcggc tacacaactc 142140
cggacccctc caggaggcta gcgcccattc tctagaactg gtccgcagtt tgccggaccc 142200
cctgtagcag taaaggggtc ttgaactgca agcctgtcta ctcaattcgg atgtcatcat 142260
accaacaagg gtgggaaact atatgggtgg gttagataaa aaataatgca tgtaaaccga 142320
agtagaataa aaccatcaca aaatcacatc taggggggtaa atcctttcct tataactcga 142380
tatacatggg tgtagaccaa cagatgggct tacgagggcg ggcctcaccg aattgacata 142440
cacatatgcg taacctagtt acaaaggaag aaaactcaac cccccagttt tgctattatg 142500
gatagaactt acagagatgc tctatattcc agggattggg aagaggcact ccttctgttg 142560
tggcaaggcg gacacaccat ggtcggcata tttctgtcac cttgaagggt ccttcccaac 142620
tgggggagag tttgtggagc ccttctcggt tcagtactcg ccttaggact aggtccccga 142680
ccctgagctc cctactatgc acaaaccgtt ggtggtagcg cctgagcgct tggttgtacc 142740
gtgcatttcg gatcaccgct tgccatctgc gttcgtcgat gaagtccatg tcctcacgtc 142800
gtagctattc ctgcatagac tcatcgaaag actggactca tggggagccc ataatgattt 142860
ccgggagaag gcaggcttcg gccccgtaga ccaagaagaa cggggtctcc ccggtagctc 142920
ggctgggtgt ggtccggttc cccccatagta cggacggaag ctcattggcc caattggcac 142980
catgcttttt taagcagtcg taggtgtgtg ccttgagtcc cctaaggatt tctgtgtttg 143040
ccctctcagc ctggtcgttg ctcctgggat gagacacaga tgtaaagcag agctgggtgc 143100
caatgccctc gcaatactct tggaagagtc gacttttgaa ctgggtccca ttgtccgtaa 143160
tgatatggct tgggacccca aatctgcata caatcgaatt gaggaaggca acagcagcac 143220
cttgggtgat actgaccata ggggtggcct ccgaccactt tatgaatttg tagatggcga 143280
caaagagaaa acggtacccg ccgacagccc taggaaatgg tcccaggata tccaccccccc 143340 atacggcgaa tggccaagag ggtggaatca tttgcagagc ctgagctggt gtgtgtgtgt 143400
gtctgctttg catgaaactg acatgcttcg caggacttca ccaactcggc tccctcctag 143460
agagcagttg gccagtagaa gccatgccag aagaacgaat caagctgatt ctcagagttg 143520
aaaannnnnn nnnnnnnnnn nnnnnnnnnn nnnnnnnnnn nnnnnnnnnn nnnnnnnnnn 143580
nnnnnnnnnn nnnnnnnnnn nnnnnnnnnn nnnnnnnnnn nnnnaattct tagaaaattc 143640
gtcctcaaac ccaagagaca ttaaagggat tcttgagacg ggctcaaaat gagttcggct 143700
taagggtcaa gaaaataaga agcgacaacg gaacggagtt caagaactct caaattgaaa 143760
gctttcttga ggaagaggga atcaagcatg agttctcttc tccctacacc cctcaacaaa 143820
atggtgtagt ggagaggaag aatcgaactc tattggacat ggcaaggacc atgctcgatg 143880
agtacaaaac ttcggatcgg ttttgggccg aggcggtcaa caccgcctgc tacgccatca 143940
accgattgta tctacaccga atcctcaaga agacatcata tgaactccta accggtaaaa 144000
agcccaacat ttcatacttt agagtttttg gtagcaaatg ctttattctt gttaaaagag 144060
gtagaaaatc taaatttgct cctaaaactg tagaaggttt tttacttggt tatgactcaa 144120
acacaagggc atatagggtc tttaacaagt ccactggact agttgaagtc tcatgtgacg 144180
ttgtgtttga tgaaactaac ggctctcaag tagagcaagt tgatcttgat gagataggtg 144240
atgaagaggc tccatgcatc gcattaagga acatgtccat tggggatgtg tgtcctaagg 144300
aatccgaaga gcctccaaat gcacaagatc aaccatcctc ctccatgcaa gcatctccac 144360
caactcaaga tgaggaagaa gctcaagtcg atgaagaaga agatcaatca aatgagccac 144420
ctcaagatga tggcaatgat caagggggag atgcaaataa tcaagaaaag gaggatgagc 144480
aagaaccaag ggcgccacac ccaagagtcc accaagcaat acaacgagat caccccgtcg 144540
acaccatcct cggcgacatt cataaggggg taacaactag atctcgtatt gcacattttt 144600
gtgaacatta ctcgtttgtt tcctctattg agccacacag ggtagaggaa gcactacaag 144660
attcggattg ggtggtggca atgcaagagg agctcaacaa cttcacaagg aatgaggtat 144720
ggcatttggt tccacgtcct aaccaaaatg ttgtaggaac caaatgggtc ttccgcaaca 144780
agcaagatga gcatggtgtg gtgacaagga acaaagctcg acttgtggcc aagggatact 144840
cccaagtcga aggtttggat ttcggtgaaa cctatgcacc cgtagctagg cttgagtcaa 144900
ttcgcatttt attggcatat gctacttacc atggctttaa gctttatcaa atggacgtga 144960
aaagtgcctt cctcaatgga ccaatcaagg aagaggtcta tgttgagcaa cctcccggct 145020
ttgaagacag tgagtaccct aaccatgtct ataggctctc taaggcgctt tatgggctca 145080
agcaagcccc aagagcatgg tatgaatgcc taagagattt ccttatttct aatagcttca 145140
aagtcggcaa ggccgatcct acactcttta ctaaaactct tgaaaatgac ttgtttgtat 145200
gccaaattta tgttgatgat attatatttg ggtctactaa cgagtctaca tgtgaagagt 145260
ttagtaggat tatgacacag aaattcgaga tgtctatgat gggggagttg aagtatttct 145320
taagatttca agtaaagcaa ctccaagagg gcactttcat tagccaaaca aagtacactc 145380
aagacatcct aagcaagttt ggaatgaagg atgccaagcc catcaaaaca cccatgggaa 145440
ccaatgggca tctcgacctc gacacgggag gtaagtccgt ggatcaaaag gtataccggt 145500
cgatgattgg ttcattgctt tatttatgtg catctcgacc ggacattatg ctctccgttt 145560
gcatgtgtgc aagattccaa tccgacccta aggaatccca ccttacggcc gtaaaacgaa 145620
tcttgagata tttggcttat acacctaagt ttgggctttg gtaccctcgg ggatccacgt 145680
ttgatttgat tggttattcg gatgccgatt gggcggggtg caaaattaat aggaagagca 145740
catcggggac ttgccagttc ttgggaagat ccttggtgtc ttgggcttca aagaagcaaa 145800
actcggtcgc tctttccacc gccgaagccg agtacattgc cgcaggacat tgttgcgcgc 145860
aattgctctg gatgaggcaa accctgcggg actatggtta caaattaacc aaagtccctt 145920
tgctatgtga taatgagagt gcaatcaaaa tggccgacaa tcccgtcgag catagccgca 145980
ctaagcacat agccattcgg tatcattttc ttagggatca ccaacaaaag gggatatcg 146040 agatttctta cattaatact aaagatcaat tagccgatat ctttaccaag ccacttgatg 146100
aacaatcttt taccagactt aggcatgagc tcaatattct tgattctaga aatttctttt 146160
gctagcttgc acacatagct catttgaata cccttgatca tatctctttt atatgctatg 146220
actaatgtgt tttcaagtct atttcaaacc aagtcatagg tatattggaa gggaattgga 146280
gtcttcggcg aagacaaagg cttccactcc gtaactcatc cttcgccatc actccaacca 146340
tctctctatt ctttgggggga gaaatgagca tcaaagaaaa ggacttcgtc tttggtataa 146400
tcttaactca tttacttatg accaaaggag aagaaattac ttcgagggct ctaatgattc 146460
cgtttttggc gattcatgcc aaaaaggggg agaaaggagc ccaaagcaaa aggaccgcac 146520
caccaccaat ttcaaaaact tagtgttttc caagaaatat ttatcaattg gcatcctatc 146580
gtgttcaaaa gggggagaaa gtagtatttc aaaaatgata tatcaaaacc ctcttgaaca 146640
ctaagaggag gatttaattt agggggagtt ttgtttagtc aaaggaaaag catttgaaac 146700
agggggagaa aacttcaaaa tcttgaaaat gctttgcaaa aatcttattc attcaccttt 146760
gactatttgc aaaagatctt tgaaatggac ttacaaaaga atttgcaaaa acaaaacatg 146820
tggtgcaaac gtggtccaaa atgctaaata aagaaagaaa cattccatgc atatcttgta 146880
agtagttata ttggctcaat tccaagcaac ctttacactt acattatgca aactagttca 146940
attatgcact tctatatttg ctttggtttg tgttggcatc aatcaccaaa aagggggaga 147000
ttgaaaggga attaggctta cacctagttc ctaaataatt ttggtggttg aattgcccaa 147060
cacaaatctt ttggactaac ttgtttgccc aagtgtatag tgtatacagg agtaaaaggt 147120
tcacactcag ccaataaaaa gaccaagttt tggattcaac aaaagagcaa aggggcaacc 147180
gaaggcaccc ctggtctggc gcaccggact gtccggtgtg ccaccggaca gtgaacagta 147240
cctgtccggt gcaccagggg actcagactc aaactcgcca ccttcgggaa tttctaaggc 147300
gactcggcta taattcaccg gactgtccgg tgtacaccgg acagtgtccg gtgcgccaag 147360
ggaggtcggc ctcaggaact cgctagcctc gggttcgcgc ggcagccgct ccgctaaaat 147420
tcaccggact gtccggtgtg caccggactg tccggtgtgc cagcggagca acggctccct 147480
gcggcgccaa cggctccctg cggtgcattt aatgcgcgcg cagcgcgcgc agacgccagg 147540
cacgcccata ccggtgcacc ggacatcaaa cagtacatgt ccggtgtgca ccggacaccc 147600
aggcgggccc acaagtcgga agcttcaacg gctagaatcc aacggcagtg atgacgtggc 147660
aggggcaccg gactgtccgg tgtgcaccgg actgtccggt gcgccatcga gcagacgcct 147720
ccagccaacg gtcaagtttg gtggttgggg ctataaatac cccaaccacc ccaccattca 147780
tagcatccaa gttttccact tcccaactac tacaagagct aggcattcaa ttctagacac 147840
atacaaagag atcaaatcct ctccaattca tcacaaagcc ctagtgacta gtgagagtga 147900
tttgtcgtgt tcatttgagc tcttgcgctt ggattgcttc ttttctttct cacttgttct 147960
tgagatcaaa actccattgt aatcaaggca agaggcacca attgtgtggt ggcccttgcg 148020
gggaagtttt gttcccggct ttgatttgag aagagaagct cactcgatcc gtggatcgtt 148080
tgagagaggg aagggttgaa agagacccgg cctttgtggc ctcctcaacg gggagtaggt 148140
ttgcaagaac cgaacctcgg taaaacaaat ctccgtgtct cacttgctca ttcgcttggg 148200
atttgttttg cgccctctct tgcggactca ttccttatta ctaacgctaa ccccggcttg 148260
tagttgtgtt tatatttgca aatttcagtt tcgccctatt caccccccctc taggcgacta 148320
tcaattggta tcggagcccg gtgcttcatt agagcctaac cgctcgaagt gatgtcggga 148380
gatcacgcca agaaggagat ggagaccggc gaaaggccca ctacaagcca cgggagcact 148440

```
tcatcggaag agtctcgcac caaaaggagg gagaagaaga agagctcctc caacaaaggg 148500
aaggagaaga aatcttcttc tcaccacaaa gagaagaagg aaaaatcttc ttcccacaag 148560
ccgcatcgga aaggcgacaa gcacaaaagg atgaggaagg tggtctacta cgagaccgac 148620
acttcatcaa catcgacctc cgactccgat gcgccctccg tcacttctaa gcgccaagag 148680
cgcaagaagt atagtaagat ccccctacgc taccctcgca tttccaaaca tacaccttta 148740
ctttccgtcc cattaggcaa accaccaact tttgatggtg aagattacgc taggtggagc 148800
gatttaatgc gatttcatct aacctcgctc cacaaaagca tatgggatgt tgttgagttt 148860
ggcgcgcagg taccatccgt aggggatgag gactatgatg aggatgaggt ggcccaaatc 148920
gagcacttca actctcaagc aacaacaata ctcctcgcct ctctaagtag agaggagtat 148980
aacaaagtac aagggttgaa gagcgccaag gagatttggg atgtactcaa aaccgcgcac 149040
gagggagacg agctcaccaa gatcaccaag cgggaaacga tcgagggggga gctcggtcgg 149100
ttccggcttc acaaaggaga ggagccacaa cacatgtaca accggctcaa gactttggtg 149160
aaccaagtgc gcaacctcgg gagcaagaag tgggacgatc acgaagtggt aaatgttatt 149220
ttaagatctc tcatttttct taatcccact caagttcaat tgattcgtgg taatcctaga 149280
tatactaaaa tgacccccga ggaagttatc gggcattttg taagttttga gtgcatgata 149340
gaaggctcga ggaaaatcaa cgagcttggc gactcatccg aagcccaacc cgttgcattc 149400
aaggcaacgg aggagaagaa ggaggagtct acaccaagtc gacaaccaat agacgcctcc 149460
aagcttgaca atgaggagat ggcgctcgtc attaagagct tccgccaaat cctcaaacaa 149520
aggaggggga aagactacaa gtcccgctcc aagaaggttt gctacaaatg tggtaagccc 149580
ggtcatttta ttgctaaatg tccaatatct agtgacagtg accgaggcga cgacaagaag 149640
gggagaagaa aggagaagaa gaggtattac aagaagaagg gcggcgatgc ccatgtttgt 149700
cgcaaatggg actccgacga gagctcaagc gactcctccg acgacgagga tgccgccaac 149760
atcgccgtca ccaagggact tctcttcccc aacgtcggcc acaagtgcct catggcaaag 149820
gacggcaaaa agaagaaggt taaatccaac tcctccacta aatatgaatc gtctagtgat 149880
gataatgcta gtgatgagga ggaaaatttg cgtatcctct ttgccaacct taacatagct 149940
caaaaggaaa aattaaatga attagtcagt gctattcatg aaaaggatga ccttttggat 150000
tcccaagagg attgtctaat taaagaaaac aagaaacatg ttaaggttag aaaggcttat 150060
gctctagaag ttgagaaatg tgaaaaattg tctagtgagc taagcacttg ccgtgagatg 150120
attgacaacc ttagaaatga aaatgctagt ttaaatgcta aggttgattc tcatatttgt 150180
aatgtttcaa ttcccaatcc tagagataat aatgatgagt tgcttgctag gattgaagaa 150240
ttaaacattt ctcttgctag ccttagatta gagaatgaaa atttgattgc taaggctaaa 150300
gattttgatg tttgcaaagt tacaatttcc gatcttagag ataagaatga tattcttcat 150360
gctaagattg ttgaacttaa ttcttgcaaa ccctctacat ctattgatga gcatgtatct 150420
atttgtacta gatgtagaga tgttgatgtt aatgctattc ttgatcatat ggctttaatt 150480
aaacaacaaa atgatcatat agcaaaatta gatgctaaaa ttgccgagca caacctagag 150540
aatgagaaat ttaaatttgc tcgtagcatg ctttataatg ggagacgccc tgacattaag 150600
gatggcattg gcttccaaag gggagacaat gtcaaactta atgcccctct taaaaacttg 150660
tctaactttg ttaagggcaa ggctcccatg cctcaggata acgagggtta cattttgtac 150720
cctgccggtt atcccgagag caaaattagg aaaattcatt ctaggaagtc tcactctggc 150780
```

```
cctaatcatg cttttatgta taagggtgag acatctagct ctaggcaacc aacccgtgcc 150840
aagttgccta gaaagaaaac tcctattgca tcaaatgatc atgctatttc atttaaaact 150900
tttgatgctt cttatgtgct tacaaacaaa tccggcaaag tagttgccaa atatgttggg 150960
ggcaagcaca aggggtcaaa gacttgtgtt tgggtaccca aagttattgt gtctaatgcc 151020
aaaggaccca aaaccatttg ggtacctaaa gtcaagaact aaatttgttt ttgtaggttt 151080
atgcatccgg gggctcaagt tggatactcg acagcgggtg cacaaaccca catgaccggg 151140
gagaaaagga tgttctcctc atatgagaaa aaccaagatc cccaacgagc tatcacattc 151200
ggggatggaa atcgaggttt ggtcaaagga ttgggtaaaa ttgctatatc acctgaccat 151260
actatttcca atgtttttct tgttgattca ttagattaca acttgctttc tgtttcccaa 151320
ttgtgtcaaa tgggctacaa ctgtcttttt actgatgtag gtgtcactgt ctttagaaga 151380
agtgacgatt caatagcatt taagggtgtg ttagagggtc agctatactt agtagatttt 151440
gatagagctg aactcgacac atgcttaatt gccaagacta acatgggttg gctctggcac 151500
cgccgactag cccatgttgg gatgaagaat cttcataagc ttctaaaggg agaacacatt 151560
ttaggattaa caaatgttca ttttgagaaa gacaggattt gtagcgcatg ccaagccggg 151620
aagcaagttg gcactcatca tccacacaag aacataatga caagtgacag gccactggag 151680
ctcctccaca tggatttatt cggcccgatc gcttacataa gtatcggcgg gagtaagtac 151740
tgtctagtta ttgtggatga ttattctcgc ttcacttggg tattcttttt acaggaaaaa 151800
tctctaaccc aagagacatt aaagggattc ttgagacggg ctcaaaatga gacgaatctc 151860
agatcgtctg tatagattan nnnnnnnnnn nnnnnnnnnn nnnnnnnnnn nnnnnnnnnn 151920
nnnnnnnnnn nnnnnnnnnn nnnnnnnnnn nnnnnnnnnn nnnnnnnnnn nnnnnnnnng 151980
catcttgcaa cctcacagac cgtggcgtgc tctggtcagg cgcggacggt cccagccttg 152040
ggcggacgtc cgagccttgg gtcggacggt ccgcgacctg ggcgaggagc ggtgtcttcc 152100
ctgcgtcaca ccggacgtcc gcagctctgg gccggacgtc cgcgacctgg cgacagggtc 152160
gtcttcctac tccttgctgg aatctagatc tcgtcccctg ggggaaagat cttaaggtgc 152220
tccgggtcga caggtcaccc ggggcgtccc cagacgacgt ggagtcgcct aggaattaag 152280
agatcaaatc gaggaagaag tcttggatgg acaactagat cttgcccccc ggaggggtga 152340
gatcctaggg tcgtcttggg atcggcaggc cacccaagac ggatctagac gacgtagagt 152400
tgaatagggg tggaggtgga tatgtggaag actacaacta gaactatgct acatctactc 152460
ctagggcagg aaaagtaaat aaggtaattg gttcgattgg aatgtgttcg ggggttctca 152520
atcggccgta cccctttata tttatagggg aggaggtctg gaccttttcc taagagatag 152580
ccaacaaact cccacgtgat tagatggata accacgcacg agataaggat aaacatccga 152640
gttaatctaa tctcgggaca cgcggaccgt ccgggcccat gggccggacc gtccgctcat 152700
tttggtgtcc aacatatgcc cccctgcctt ttggtggagc atggcgaacc aaaagcatta 152760
gcgaaaactt cggaaacaat tgacctcatg aggttttttt ttccgaagta aggactcagc 152820
tcgatgcaag tcatcggctc ttgcgatcag ataatataaa tacttgatgg gactttaatg 152880
cacagaggcc gtttcggatc gcatcctctt cagccatgtc tatctgatca acctgtcaat 152940
aggcaaaaac ttgtggtgcc ccccagccca aataagcaaa cggattgggc cagtaataca 153000
aattcatcgc cgtaccaccc cacacatgag taggacaaca catcggcgat ggatagaatg 153060
ggacgcacca tgctatccct ggaggaggat gataaggcga tattggttgt gctacccttt 153120
gggtccgttt agtcggcttt tgctttcgca cagatcgccc tattgacttt gtttgtttta 153180
```

ttggccggtt gtgtggaacg gccttcttca tatatttggc aagcaactga ccaaaagtag 153240
ggccgactct actgagtcgt ccagacgtct tagtagtgtt ttgtttccta acacttgtgt 153300
tggaacgttg tggtccgatg gtctgaggtt gctgcttctg accatctgcg gaccgtccgg 153360
ccatcatagc cggactgtcc gcgcctgtct cggactgttc ggccttagta cccggatcgt 153420
ccggcgtacg catgacaggc gaccgtgatc gggtgtccga tcgtgcttgc cccccggtgc 153480
ctccggtctt tcttttgtcc ggagccttca gagtaaccat tctgcgtgac atatttggtg 153540
tgcgaggatc accaatgacg atatttttat ttttactttt atcggccgca caaggccgaa 153600
ttatggcctt tttgctcatg ggctctaatg tggtgacagg aacaggtggc ctgtcaattt 153660
tcacctcttt ttgaaacctc aaccggcctt cgtttatagc cgattgtatt tgccgacgga 153720
agacggcaca atcattggtg ttatggagaa aggagccatg ccatttgcaa taaacacgcc 153780
cttttaattg ttcaaccgga ggaattacat gtgacaattt aatattacca tgtttaagca 153840
actcatcaaa tattttatca catttagtaa tattaaatgt gaacttaacc ttttcctttt 153900
gtttcgagtg cgggtaagag cgaacagaag gtttggcctt agtgggccaa acaagctcag 153960
ggacatgtga ctttttagt tcttggggct tgggtggccg attatattta tgtcggcctt 154020
ccgcactagg tggatcacag gtgacttctg gtgccccgga cggtccgact tgcacagtcg 154080
gacggtctgc gggtggatcg gacggtccgg tactatcctc ggacagtccg gtcacgtcag 154140
gcaacacctg tgacccttgt ggtgggctct gtgtaactcc agactgtccg gcgtagggtg 154200
ccggacggtc cgacagaggg ccggacggtc cgcaattgtg tgcggacggt ccggctgtgc 154260
ccagggttga ctcaccattt agcaaagatg gtgatgacgg tcgtcctaga tatgagtcca 154320
tcggcatacc agaatatggc tggggaaacc catttgccgc cgatgtgttt ggcgcaattg 154380
tttcatcgcc taatttatgt gataaaaaat taggcatgtg agtttttcct aatgcatgtg 154440
tcatcctctc tatatcctcc gtgatacttt taatccgatt atcaaaagaa attttaatag 154500
atggaatatc atcggctgac ctggcatcac ctattgtggg gagctgttgc agcacggcta 154560
acatatactc ggcgtttatc tccctctctt ggacggtctt ctggtggcag tctaccttga 154620
agtgcgagag gtaccacttg tccgccacct tgagcacctg atccttttgt cggtgggcct 154680
cctcgtctat tttcttcatg tcatcttcta attttttatg ctcagcggcc gataaattag 154740
tcagccttgt gttgctgttt ggagaagcac tgttgagatc tttagaatcg gccatgtaag 154800
cctgattttg tagatctgca acttcttccc cagcggagtc gccaaaaagt atgttgacgc 154860
ctttttggag cgccaaacac tcaacaagaa ccgtggcggt gccctctggt caggcgcgga 154920
cggtccgcag ccttgggccg gacggtccgc agccttgggc cggacggtcc gcgacctggg 154980
cgcaggagcg gtgtcttccc tgcgtcacac cggacggtcc gcagctctgg gccggacggt 155040
ccgcgacctg gcgacagggt cgtcttccta ctccttgctg gaatctagat ctcgtcccct 155100
gggggggaaag atcttaaggt gctccgggtc gacaggtcac ccggggcgtc cccagacgac 155160
gtggagtcgc ctaggaatta agagatcaaa tcgaggaaga agtcttggat ggacaactag 155220
atcttgcccc ccgggagggg tgagatccta gggtcgtctt gggatcggca ggccacccaa 155280
gacggatcta gacgacgtag agttgaatag gggtggaggt ggatatgtgg aagactacaa 155340
ctagaactat gctacatcta ctcctagggc aggaaaagta aataaggtaa ttggttcgat 155400
tggaatgtgt tcgggggttc tcaatcggcc gtaccccttt atatttatag gggaggaggt 155460
ctggaccttt tcctaagaga tagccaacaa actcccacgt gattagatgg ataaccacgc 155520

```
acgagataaa gaaaaacccc cnnnnnnnnn nnnnnnnnnn nnnnnnnnnn nnnnnnnnnn 155580
nnnnnnnnnn nnnnnnnnnn nnnnnnnnnn nnnnnnnnnn nnnnnnnnnn nnnnnnnnnn 155640
ngaattccaa gatttaaata gaagtctttt ataatgagag attaaataaa agaccctcat 155700
ataatttaaa ccaacccttg ttgaataaca tgattagaga tattctccaa aagaattaag 155760
cttaaaaaac cttaataaat actatacaca caaaaaaatc ctctatctta aaaattatga 155820
acataatttt aaatggacta tacattcaaa gaagtaattt ttactctatg tgtgtgcatt 155880
gcatacttaa aatatttgga taaaataaac aaaactaaac agatatatgt aattattgca 155940
tatcatgccg gagttttgga ttgagcattt agattagagt ttaaaataag ggaaagaaat 156000
atgaaaggga agataaaaca gaaaatcatt aaagaataaa gaaaaagggg aagctttctg 156060
cgctatgggc cggatctctg gcttctcggc ccagtttctt tccttcgtta gcgggcccaa 156120
ctctatttcc ctgctccggc gcagcccgct cctgcccact ctcgcgcctg cagccgcgtc 156180
tggcatgtgg gccatggccg tcaagtctat cctccccatg gcgatcctgc tcgtccgctg 156240
caagctcgcc tcctgtaaac tgtgcaacga ccttcgtgcc atggtgcacc cgcccactgc 156300
tagccgtacc cctggccata tataacggac gctccaacct cggccatggg tgcagctcta 156360
gtttcctctc cttcagcatc gtgggctacg ctcggtctgc cgatcgggag agaaggcgcc 156420
atcaccatcg tcgtaaggga gaaggagaac acagggggtg aattgccacc gacgggggtt 156480
cccgggcacg ccggtattgc ggtctcggcg tcgggttggg tcatccgtgg gacgcgtgca 156540
ggattctaga aggcacctcg tgcgagaaca acgaccagtg catgcttcgc tggtgacccg 156600
cggcgccacg gagcaactgc gtggtggggt caacacttga aacaccgtga tccttggtaa 156660
gaacagccct agcatacttg gagcctcctc ctctccgtga ttcacgtacc cacgctcgat 156720
actaggaaat ggggagccgg gcgggatatc actggtggtg tggtggggca tggccgcggc 156780
gtgcccgcac cagtgctctg ctttccgtcg tgaggtggaa ggaaatgcag cagccgttag 156840
atcatgggtg agcgatcacg atcagggcat ggctgggcct cgcgtgaacc gtggatctgg 156900
gaggtatcgg ctgtgattag atcacacgta acgtttcatc cgaatcgatc cgggtcgtct 156960
gatctggatc ttgcatatga ggatcgatct ctattatttt aagcgtgggc cgtttatcgt 157020
agatccgacg atctaggatg cgtaccggtt cggcgggcaa atcttctact ctgggcgctt 157080
ggctgatgat ccaaggaatt agtcacgtgt acccccttcac cgtgactaac ttataaaaga 157140
gaccccagac ttcttgcaaa tcagcccgca gtccgggtat aggtagaaat cattgcggat 157200
aagtcctaaa tattatatgg agccccctga tcttttatag aatagtgtcc ccaatccaga 157260
aatatttaat aattatagaa ttaaatccta aaacttaata aatacatatc tctttcattt 157320
taactctgat ttaatgtatt catgttgcgt tagcttcgta ataattttgc ctacgcttct 157380
gtaaaattat tttagcaaat agcatgtttc caaaaaataa atattcattt aatatatgct 157440
tagtagatta ttcctactaa tcaaagttag tttgtctatg attataaggt aactaaaata 157500
ttatgtctac tctagtatga tgtagattaa agttatttct ttaatatctt tatcacataa 157560
tttataaaat caacataaag acctagtctc atatttaatc acataggtct tccgaaaacc 157620
acatcttgtt aaccgtaact ccgaatttag tggttctcga acctaggatc tcgttgtggt 157680
gcgtagatca ttattatgca gtttgttctt tatgtttggt gtgatgttaa ttttgcctat 157740
accatgtttg tttgtattgc tatgattagc agcgaggtta cgagaatctt gaagaccaag 157800
ctggtaccta ggaatcttga gtctcagcca agttgtgccc ttgatcactt ttctttacct 157860
aataatgttc ctattaatca ctgtgacatg ctcaggttaa tttgatggga cccaataggt 157920
```

tttcctagta ttgtttatcc cctaccttgc aaacaaaagc actattgggt agtattgcta 157980
ttgctctacc tggttttggg aaattaatgt tacattatga tcatgttaca attcttttgt 158040
tattttaatt attgttcatg ataagattgc tatgttaatt ggaacatgga gcaaccaccc 158100
aggaaaacag tgctaccaca agggtggtat gggacgccct tggctgacta attaagaaag 158160
ctagtggaag actaccttac ccgaaagggg caagggcggt agaggagcat gcgtataggg 158220
aggttctcga gtcgatcatg ctgcgatggc tttttggacg agggattcct atattttcct 158280
tcttagaaac cgtagcgggt tttcggaagc tagtggaagt ttgtaaaggc ctcgtagtgg 158340
taacctacct tgtcttctcg gtagagatga atgagaagtc gcgatccctt ggcaaatagg 158400
taacatgact tgtgggtaaa gatgtgcaac ctgtgcagac tgtaaaactg ttatatcagc 158460
cgtgctcacg gtcatgagca gctcggaccc tcacatgagt aaattatgga actaaactta 158520
aattgtcata tgcattgcat tgtgggtgtt gttattaatt taatctctta tttatttggg 158580
tcggtatcta cttatactta gtaactgcta ataaaatttt gaccaacttt aaaagtcatg 158640
ctcatcttta cccatctcct ttggtaagcc ttacacttca catgagctcc cacctttggt 158700
gagttcatac acattattcc ccacaacttg ttgagcgatg aacgtatgtg agctcaccct 158760
tgctgtactc aaatccccct ggtcaagaac aggtaccgca agatgaggag catgaaggat 158820
gtcgcgatga gttcatgaga ggtctaggcc gtcgtctcac agtaaacttt gggttgatgg 158880
atcgtcgtca tcgtatgatg taattattta gttattttgt gcagaacttc tattatatag 158940
taaagatgtg acatttgttt ctataccatg agtcatcata tgtgtgagac tcgatcccag 159000
cacttggtga atttcgcgcc tgggttttgg acccctaaaa cccgggtgtg acatgctgct 159060
gttgagggaa ctgcctctgg aattgctact ggtgcgaaca ttggttctgg tgttggtatc 159120
cctgagggtg gatctacttg aactgctagg gtggattgcc agaaacggga gacgactgct 159180
gctcctggcc tagggtccac caatcttgcg cttttggtct tccatctcct ggcgcttcct 159240
ctcagtcatt attgccctat caatcagatg ttggaaggta gggaatgtgt ggttcatcaa 159300
ctagtagtgc aggggtcaac caaccctctc ggaaacctgt agtacctctt agcatcaatg 159360
ttgacatcct cgggtgcatt gtgagatagt tgcaggaatt tgtccatgta ctcactgaca 159420
gacaggggcc cttgcttcag tgccagaaat tcttccttcc tcactatcat caaaccttgt 159480
agaacgtggt acccgcagnn nnnnnnnnnn nnnnnnnnnn nnnnnnnnnn nnnnnnnnnn 159540
nnnnnnnnnn nnnnnnnnnn nnnnnnnnnn nnnnnnnnnn nnnnnnnnnn nnnnnnnncg 159600
cgcggaggcc ggtttgtcgg tgccggtttc tttcacgcaa cacgcccgct cctttttgcc 159660
tcggtgggtc ggcctgtcag cgcagaaccg ctcgttcgcg tattcaccct cgctggcaag 159720
cggaccccac ctgtcagcca cctccccttt ccctaaccac ccgctcgcgc accccgccgt 159780
ggatgcacac atgtcgcgtg tttttcggcc actcccccca cgcgcctgac ttttttggag 159840
cccacactca ctcgctcact cccctcgctc agtagcgtcc cacagccgac cccctcgcac 159900
ctctctctcg caccgagcgc acagccgtgg agcactgccg tagtccaccg tccgttccgt 159960
ggccgtcgtc gagttcctgt cgcgtccatt gccctactga tcttcgcctc ctcgccagca 160020
acacgagaca ccctctggtt ttccccagcc cctctatttc ccttggttcg ctcaccggac 160080
ctatcaccat gcagccgagt ctccgccacc gtccaccagg gccctcgcgg tgtcctcgcc 160140
gttgctcaag cgctctagag tcatctctcg acgtaaccaa cccacccatg cccttaattt 160200
cccatttact gccctgttgt ccatgcaatc gctcgccaga gttaagctgc gccgccgtgg 160260

```
ggctgctttg cctcggaccg tgctctctgg tgcctctacg ccggtgtcgt gcccatggct 160320

gagcccgccg tgtcaccctg agctcgcctg agccttttcc cagcgcccag accctcacca 160380

tggccgcgcc acgccgcgaa attgggcggc ggcgccatga gcagcctagc aaccccgccc 160440

gagcttgcca tcagatttca ggcatccatc tgagatctaa cgacctggct tcaattaaac 160500

tcgatctgat cccagctgtc cgatggagat ctggccactc ggatccgcca cctcacccgc 160560

gccctgcagc taggcccggc cagacagtcc gcctcgcccc taggtcgctg actatcctgg 160620

cccacctgtt agctcgtgct cgtgctcgcg ctcaaatcta atcctggccg ttgatctgtg 160680

atcatgcagt cgagatcagc tgatacccct ttgcgtggta gttttgttaa aaaggccctc 160740

ggctttctga gaatcaaccc atcgtccctg gttttcgcac gcatgcccct gtacttttgc 160800

agaaaggccc ctaatctttt aggttatcac ataattagac ctagttttgt attttgaatt 160860

ccaaaacttg tttatttcat atcttttgca tatgaactcc aaattgagtg attcaaattg 160920

caaaatgttt gtaaggttat tctctacctg tttaaattat aaccttttac tgtctgcatg 160980

tgctaatttt atgcctagac tataggttag tgtaactgat ggcttattta ttaataagaa 161040

ggataaaagg aaaaccataa tggtagttag atgtttaact ttgtgggtta ataatatgta 161100

atatatgaac ctatccctgg tataattctt ttgtctcatt aagataaatg aaattaagtt 161160

atgtaatcta ttgagataag taatacttag agaaccacaa acctatatgt gtattggtcc 161220

accctagacc ctaggcttcg cttgagtttg ttactttctt ttgaattagt gttcacttga 161280

ttgtatattt ttggtgtatt gtttctttat cattatcgaa atgtgttgaa tgcatgatcg 161340

ctttgcgtag acaacaagca gtctatggtt cctgagtgtg ttgccgaaga tcttcctggg 161400

caacaacctg gtgaaggcaa gtgtcctctg acctattatg tcctacttac ttcataattc 161460

actgtccccc tttacttaat tgaaacctaa ggtttgacta gtctgtattt atcttgtcct 161520

tgtttacctt ttgggttatt atggtaagct tcaagctatt gctccacttt aatcaacaaa 161580

catgatgcga atatttatga tatgatgttg ttattatgat tacgatgatg ttcttatggc 161640

actttaggag actcaggcta ttttcctgag tacctttcct ttggacctgc tcgttgagtg 161700

accacccgtg ataacagaac gaatcaagct gattcatcag cggccggg             161748
```

<210> SEQ ID NO 111
<211> LENGTH: 1348
<212> TYPE: DNA
<213> ORGANISM: Zea mays

<400> SEQUENCE: 111

```
tacaagaata ttgagacgtg agtacatagc attggcattt tcattagcaa gcatttcaaa     60

agaatttaat tttctcatag caatgtgata tctctcctca cgctcaattc tagttccttc    120

atgtagagca catatgtcca tccacaaatc atgacaattt ttatggtttc taactctatt    180

aaacacatct ttgcaaaggc ctctaaaaag ggtgtttttg gccttagcat tccatttctc    240

atagttcaac tcttcaccta caagatttgt gggatctcta ggttcgggga atctttgtgt    300

ggcggctttg tagacaccaa tgtctatagc ctctaaatat gcttccatac gaattttcca    360

atatggaaaa tcgtcaccat aaaaaacggg agaaggtcca tccccaccgg acatcgttac    420

tctagcggtt aagctaatct aagagcaaca aggctcttat accaattgaa aggatcacga    480

tgcccaagag ggggggttga attgggcttt tctaaaaatc aacactaact aaaatctaag    540

caagagccca acttcacccc gacaactagc actaagagaa taatactaga aatacaacaa    600

tgctaagata atacttcaaa tacttgctaa acaaatacac aatgtaaaat acttgaatta    660
```

-continued

```
agtgcggaat gtaaagcaag gtttagaaga ctcctccaat ttttctagag gtatcaaaga    720

gtcggcactc tcccctagtc ctcgttggag cacctgcgta agggtatcgc tctcccttgg    780

tcatcgcaag aaccaagtgc tcacaacgag atgatccttt gccactccgg cgcggtggat    840

ccctcacgac cgcttacaaa cttgagtcgg gtcaccaaca agatctccac ggtgatcacc    900

gagctcccaa cgccaccaag ccgtctaggt gatgccgatc accaagagta ataagccata    960

gactttcact tgaccaagag aagcctaatg catgcggtgt gtgctctagg tggctctcgc   1020

tagcgttaat gaggtccaaa tgcgggatta agattctcaa gtcacctcac taggctttgt   1080

ggtgcttgca atgctctacc aatgtgtagg agtaaatgtg ggcagcaaga ccatcaatat   1140

ggtaggtgga tggggtataa atagccctca cccaccaact agccattacc aggaatctgc   1200

tgcgcatggg cgcaccggac agtccggtgt gccaccggtg cgccaacggt cgactcaaac   1260

ggctagttct gacagctagc cgttggacag atggcatacc ggacagtccg atacgctgtc   1320

cggtgtgcct ctaaaattca actcacga                                      1348
```